United States Patent
Shah et al.

(10) Patent No.: US 12,042,502 B2
(45) Date of Patent: *Jul. 23, 2024

(54) ENHANCED PENETRATION OPHTHALMIC COMPOSITIONS OF BIMATOPROST AND TIMOLOL

(71) Applicant: Somerset Therapeutics, LLC, Hollywood, FL (US)

(72) Inventors: Mandar V. Shah, Rockaway, NJ (US); Veerappan Subramanian, Warren, NJ (US); Ilango Subramanian, Warren, NJ (US); Aman Trehan, Hillsborough, NJ (US)

(73) Assignee: SOMERSET THERAPEUTICS, LLC, Hollywood, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/187,471

(22) Filed: Mar. 21, 2023

(65) Prior Publication Data
US 2023/0293547 A1 Sep. 21, 2023

Related U.S. Application Data

(60) Provisional application No. 63/322,226, filed on Mar. 22, 2022, provisional application No. 63/322,223, filed on Mar. 22, 2022, provisional application No. 63/322,211, filed on Mar. 21, 2022.

(51) Int. Cl.
| | | |
|---|---|---|
| *A61K 31/5575* | (2006.01) | |
| *A61K 9/00* | (2006.01) | |
| *A61K 9/06* | (2006.01) | |
| *A61K 9/08* | (2006.01) | |
| *A61K 31/5377* | (2006.01) | |
| *A61K 47/02* | (2006.01) | |
| *A61K 47/18* | (2017.01) | |

(52) U.S. Cl.
CPC ........ *A61K 31/5575* (2013.01); *A61K 9/0019* (2013.01); *A61K 9/0048* (2013.01); *A61K 9/06* (2013.01); *A61K 9/08* (2013.01); *A61K 31/5377* (2013.01); *A61K 47/02* (2013.01); *A61K 47/186* (2013.01)

(58) Field of Classification Search
CPC .. A61K 31/5575; A61K 31/5377; A61K 9/08; A61K 47/186
See application file for complete search history.

(56) References Cited

U.S. PATENT DOCUMENTS

| | | |
|---|---|---|
| 6,646,001 B2 | 11/2003 | Hellberg |
| 7,851,504 B2 | 12/2010 | Chang |
| 8,309,605 B2 | 11/2012 | Chang |
| 8,338,479 B2 | 12/2012 | Chang |
| 8,343,949 B2 | 1/2013 | Lyons |
| 8,586,630 B2 | 11/2013 | Chang |
| 8,618,093 B2 | 12/2013 | Chen et al. |
| 8,629,140 B2 | 1/2014 | Chen et al. |
| 8,691,802 B2 | 4/2014 | Lyons |
| 8,906,907 B2 | 12/2014 | Chen et al. |
| 8,933,120 B2 | 1/2015 | Chang |
| 9,061,034 B2 | 6/2015 | Likitlersuang et al. |
| 9,078,854 B2 | 7/2015 | Likitlersuang et al. |
| 9,241,918 B2 | 1/2016 | Chang |
| 9,248,135 B2 | 2/2016 | Schiffman et al. |
| 9,474,760 B2 | 10/2016 | Chen et al. |
| 9,579,328 B2 | 2/2017 | Schiffman et al. |
| 9,763,958 B2 | 9/2017 | Likitlersuang et al. |
| 10,045,997 B2 | 8/2018 | Chen et al. |
| 10,058,560 B2 | 8/2018 | Likitlersuang et al. |
| 2007/0297990 A1* | 12/2007 | Shah ............... A61K 33/26 514/217.05 |
| 2013/0116254 A1* | 5/2013 | Pujara ............ A61K 31/498 514/236.2 |
| 2014/0088107 A1 | 3/2014 | Swatscheck et al. |
| 2015/0150880 A1* | 6/2015 | Chen ............... A61P 27/06 514/236.2 |
| 2019/0076442 A1 | 3/2019 | Karavas |

(Continued)

FOREIGN PATENT DOCUMENTS

| | | |
|---|---|---|
| WO | WO2010102078 | 9/2010 |
| WO | WO2016198434 | 12/2016 |

(Continued)

OTHER PUBLICATIONS

Hippalgaonkar, Journal of Ocular Pharmacology and Therapeutics, vol. 29, No. 2, 2013, pp. 216-228. (Year: 2013).*
Figus et al. (Eye (Lond). Apr. 2014; 28(4): 422-429) published online Jan. 17, 2014), (Year: 2014).*
Goldstein et al. ("Review Article", Eye (2022) 36:361-368) Published online Jul. 14, 2021. (Year: 2021).*
Giannico et al. "Eyelash Growth Induced by Topical Prostaglandin Analogues, Bimatoprost, Tafluprost, Travoprost, and Latanoprost in Rabbits." J Ocular Pharmacol Ther. 2013; 29(9): 817-820.
Johnson et al. "Thermal Stability of Bimatoprost, Latanoprost, and Travoprost Under Simulated Daily Use." Journal of Ocular Pharmacology and Therapeutics, Feb. 2011;27(1):51-9. doi: 10.1089/jop.2010.0115. Epub Nov. 30, 2010.

(Continued)

*Primary Examiner* — Jean P Cornet
(74) *Attorney, Agent, or Firm* — Len S. Smith; Julie E. Kurzrok; Transformative Legal LLC

(57) ABSTRACT

The present invention provides pharmaceutically acceptable and ophthalmologically suitable compositions comprising a therapeutically effective amount of a bimatoprost compound, a therapeutically effective amount of a timolol compound, benzalkonium chloride, and a penetration enhancer component other than benzalkonium chloride. In specific embodiments, compositions are provided as aqueous solutions. Further, in aspects, the invention also provides a process of preparing such compositions and methods of their use in treating ocular conditions, such as methods of reducing elevated intraocular pressure and/or treating glaucoma, such as open-angle glaucoma.

19 Claims, No Drawings

(56) References Cited

U.S. PATENT DOCUMENTS

2022/0409630 A1 12/2022 Chetoni
2023/0293541 A1 9/2023 Shah

FOREIGN PATENT DOCUMENTS

WO WO2018185788 10/2018
WO WO2020178672 9/2020

OTHER PUBLICATIONS

Inoue. "Managing adverse effects of glaucoma medications." Clin Ophthalmol, 2014; 8: 903-913.
Inoue et al. "Deepening of the upper eyelid sulcus caused by types of prostaglandin analogs." Glaucoma, 2013; 22(8): 626-631.
Inoue et al. "Adverse periocular reactions to five types of prostaglandin analogs." Eye, 2012; 26(11): 1465-1472.
Inoue et al. "Adverse reaction after use of latanoprost in Japanese glaucoma patients." Nihon Ganka Gakkai Zasshi, 2006; 110(8): 581-587. Abstract Only.
Baudouin, et al. "Preservatives in Eyedrops: The Good, the Bad and the Ugly." Progress in Retinal Eye Research. Jul. 2010; 29(4): 312-34. doi: 10.1016/j.preteyeres.2010.03.001. PMID: 20302969.
Honrubia et al. "Conjunctival Hyperaemia with the Use of Latanoprost Versus Other Prostaglandin Analogues in Patients with Ocular Hypertension or Glaucoma: Meta-Analysis of Randomized Clinical Trials." Br J Ophthalmol. 2009; 93(3): 316-321. Nov. 19, 2008.
Lumigan Specification Sheet. "Highlights of Prescribing Information." Allergan, Inc. Dated Aug. 2010, 9 pages.
Gandolfi, et al. "Effect of Bimatoprost on Patients with Primary Open-angle Glaucoma or Ocular Hypertension Who are Nonresponders to Latanoprost." American Academy of Ophthalmology. Mar. 2003; 110(3): 609-14.
Gandolfi S et al. "Three-Month Comparison of Bimatoprost and Latanoprost in Patients with Glaucoma and Ocular Hypertension." Advances in Therapy May-Jun. 2001 18(3): 110-21.
Ajanta Pharma. "Bimat LS TM Eye Drops." Last updated Jan. 5, 2021. https://www.1mg.com/medicines/bimat-ls-tm-54342.
Eisenberg, D. "Letters to the Editor; Latanoprost versus bimatoprost." Ophthalmology. 110(9): 1861-2. Dated Sep. 1, 2003.
Crichton, et al. "Ocular surface tolerability of prostaglandin analogues and prostamides in patients with glaucoma or ocular hypertension." Adv Ther. 2013; 20(3): 260-270.
Non-Final Office Action dated Jun. 2, 2023 for U.S. Appl. No. 18/187,507.
Inoue et al. "Ocular factors relevant to anti-glaucomatous eyedrop-related keratoepitheliopathy." J Glaucoma. 2003; 12(6): 480-485.
Reddy et al. "Tear Biomarkers in Latanoprost and Bimatoprost Treated Eyes." PLoS One, 13(8). Dated Aug. 6, 2018; 13 pages.
Yu, Man et al. "Travoprost and Latanoprost, but not Bimatoprost, Induced Nausea, Vomiting and Diarrhea." BMJ Case Rep. 2009: bcr08.2008.0618. Dated Feb. 26, 2009; 4 pages.

Pharmacia and Upjohn Company. "Xalatan latanoprost ophthalmic solution: Specification Sheet." Revised Aug. 2011, 14 pages.
Winkler et al. "Effects of Prostaglandin Analogues on Aqueous Humor Outflow Pathways." Journal of Ocular Pharmacology and Therapeutics, 2014; 30(2-3): 102-109. Mar. 1, 2014. doi: 10.1089/jop.2013.0179.
Wester et al. "Eyelash Growth from Application of Bimatoprost in Gel Suspension to the Base of the Eyelashes." Ophthalmology. 2010; 117(5): 1024-1031. doi:10.1016/j.ophtha.2009.10.017. Available in PMC May 1, 2011.
Physicians Total Care, Inc. "Travatanz Specification Sheet." Dated Sep. 2017, 7 pages.
Non-Final Office Action dated Jul. 17, 2023 for U.S. Appl. No. 18/187,487.
Karslioğlu MZ et al. "Periocular Changes in Topical Bimatoprost and Latanoprost Use." Turkish Journal of Medical Sciences, 2015;45(4):925-30. Accepted/Published Online: Oct. 27, 2014.
Shah et al. "A cross-sectional survey of the association between bilateral topical prostaglandin analogue use and ocular adnexal features." PLoS One. 2013; 8(5): e61638.
Li, X. et al. "Effects of Latanoprost and Bimatoprost on the Expression of Molecules Relevant to Ocular Inflow and Outflow Pathways." PLoS One. Mar. 24, 2016; 11(3): e0151644. doi: 10.1371/journal.pone.0151644. PMID: 27011234; PMCID: PMC4807090.
Rajendraprasad. "Carboxymethyl Cellulose versus Hydroxypropyl Methylcellulose Tear Substitutes for Dry Eye Due to Computer Vision Syndrome: Comparison of Efficacy and Safety." Int J Appl Basic Med Res. Jan.-Mar. 2021; 11(1): 4-8 (Year: 2021).
Priluck, J.C. et al. "Latisse-Induced Periocular Skin Hyperpigmentation." Small Case Series. Section Editor: W. Richard Green, MD. Ophthalmol. 2010; 128(6): 792-793.
Peplinski et al. "Deepening of lid sulcus from topical bimatoprost therapy." Optometry and Vision Science. 2004; 81(8): 574-577. doi: 10.1097.01.opx.0000141791.16683.4a.
Parrish et al. "A Comparison of Latanoprost, Bimatoprost, and Travoprost in Patients with Elevated Intraocular Pressure . . . " American Journal of Ophthalmology. May 2003; 135(5): 688-703. doi: 10.1016/s0002-9394(03)00098-9. PMID: 12719078.
Park et al. "Changes to upper orbital fat from use of topical bimatoprost, travoprost, and latanoprost." Japanese Opthalmological Society. 2011; 55(1): 22-27. doi: 10/1007/s10384-010-0904-z.
Merck & Company, Inc. "Zioptan Specification Sheet." Dated Sep. 2012, 12 pages.
Sherwood et al. "Six-Month Comparison of Bimatoprost Once-Daily and Twice-Daily with Timolol Twice-Daily in Patients with Elevated Intraocular Pressure." Survey of Ophthalmology, 2001; 45: S361-S368.
GANFORT® Summary of Product Characteristics.
GANFORT® Package leaflet: Information for the user.
Aptel, et. al., "Efficacy and tolerability of prostaglandin-timolol fixed combinations: a meta-analysis of randomized clinical trials," Eur J Ophthalmol. 2012;22(1):5-18.
Final Office Action dated Oct. 4, 2023 for U.S. Appl. No. 18/187,507.
Final Office Action dated Nov. 27, 2023 for U.S. Appl. No. 18/187,487.

* cited by examiner

ENHANCED PENETRATION OPHTHALMIC COMPOSITIONS OF BIMATOPROST AND TIMOLOL

RELATED APPLICATIONS/PRIORITY

This patent Applications claims priority to presently U.S. Provisional Patent Application No. 63/322,211 filed Mar. 21, 2022, entitled "ENHANCED PENETRATION OPHTHALMIC COMPOSITIONS OF BIMATOPROST AND TIMOLOL;" presently U.S. Provisional Patent Application No. 63/322,223 filed Mar. 22, 2022, entitled "METHOD OF TREATING OPHTHALMIC CONDITIONS WITH ENHANCED PENETRATION COMPOSITIONS OF BIMATOPROST AND TIMOLOL;" and presently U.S. Provisional Patent Application No. 63/322,226 filed Mar. 22, 2022, entitled "OPHTHALMIC GEL COMPOSITIONS OF BIMATOPROST AND TIMOLOL AND ASSOCIATED METHODS." This application claims the benefit of priority to, and incorporates by reference the entirety of, these above-referenced priority applications.

FIELD OF THE INVENTION

The invention primarily relates to ophthalmic compositions comprising a bimatoprost compound and a timolol compound for use in treating elevated intraocular pressure, and related methods of their manufacture and use.

BACKGROUND OF THE INVENTION

Glaucoma is a widespread, sight-threatening disease usually associated with an elevated intraocular pressure (IOP) which, if left untreated or treated unsuccessfully, can cause irreversible optic nerve and visual field damage. Management of glaucoma requires life-long treatment, typically by application of eye drops.

A large range of eye drops, containing beta-blockers, alpha-2 agonists, carbonic anhydrase inhibitors, and prostaglandins, are available for treating glaucoma. For over 20 years, prostaglandin analogues (often frequently referred to simply as "prostaglandins") have been successfully used as a first-line treatment in glaucoma patients. Developed and marketed prostaglandins used in treatment of eye conditions include latanoprost (initially developed and sold under the brand name XALATAN™), travoprost (sold as, e.g., TRAVATAN Z™) tafluprost (sold as, e.g., ZIOPTAN™), and bimatoprost (developed and sold under the brand name LUMIGAN®).

Despite overlapping and/or similar functionality and properties, prostaglandins have been repeatedly demonstrated to exhibit significant differences in both biological/cellular-level effects and physiological level effects, such as, e.g., with respect to irritation and other adverse effects. For example, pharmacologic and pharmacokinetic data suggest the existence of a unique bimatoprost receptor, distinct from the known FP receptors; however, this receptor is yet to be cloned, and bimatoprost has not been shown to work independent of FP receptor activation. See, e.g., Winkler N S et al. J Ocul Pharmacol Ther. 2014; 30 (2-3):102-109. doi: 10.1089/jop.2013.0179. Another study reports that bimatoprost appears to reduce the IOP of patients who are unresponsive to latanoprost, suggesting that the prostamide bimatoprost and the FP receptor agonist latanoprost stimulate different receptor populations. See, e.g., Gandolfi S A, Cimino L. Ophthalmology. 2003 March; 110(3):609-14. Cytokine expression studies relating to prostaglandins have also evidenced that these compounds stimulate different cytokine pathways. For example, MMP-9 expression was found to be higher in eyes receiving latanoprost, while the MMP-2 expression was higher in eyes receiving bimatoprost, with MMP1 protein levels being higher in the former. See, e.g., Reddy S et al. PLoS One. 2018 Aug. 6; 13 (8): e0201740. doi: 10.1371/journal.pone.0201740. PMID: 30080906; PMCID: PMC6078293. Differences in fibronectin expression and in aquaporin-1 expression in response to bimatoprost as compared to latanoprost also has been linked to variability in the IOP-lowering efficacy of the compounds in some studies. See, e.g., Li X et al. PLoS One. 2016 Mar. 24; 11 (3): e0151644. doi: 10.1371/journal.pone.0151644. PMID: 27011234; PMCID: PMC4807090. In terms of distribution, bimatoprost has been shown to reach target tissues differently than latanoprost, wherein intact bimatoprost has been identified in the target ciliary body indicating its direct involvement in the reduction of IOP, and further wherein bimatoprost has been linked with poor corneal penetration in comparison to latanoprost and travoprost. See, e.g., Eisenberg, D. Ophthalmology. 110(9): 1861-1862 (2003). Topical bimatoprost therapy has been demonstrated to cause more periocular changes than latanoprost therapy. See, e.g., Karslioğlu M Z et al. Turk J Med Sci. 2015; 45(4):925-30. PMID: 26422869. Prostaglandin products are associated with differences in active pharmaceutical ingredient (API) stability, as well, with bimatoprost shown to remain stable under certain conditions, with latanoprost and travoprost experiencing degradation under such conditions. See, e.g., Johnson T V et al. J Ocul Pharmacol Ther. 2011 February; 27(1):51-9. doi: 10.1089/jop.2010.0115. Epub 2010 Nov. 30. PMID: 21117945; PMCID: PMC3038126.

The prostaglandins have also been demonstrated to exhibit clinical differences. For example, see, e.g., Parrish R K et al. Am J Ophthalmol. 2003 May; 135(5):688-703. doi: 10.1016/s0002-9394 (03)00098-9. PMID: 12719078, wherein fewer latanoprost-treated patients reported ocular adverse events (P<0.001, latanoprost vs bimatoprost), fewer reported hyperemia (P=0.001, latanoprost vs bimatoprost), and average hyperemia scores were lower at week 12 (P=0.001, latanoprost vs bimatoprost), and, while latanoprost, bimatoprost, and travoprost have in some (other) studies been shown to be comparable in their ability to reduce IOP in OAG and OH patients, latanoprost exhibited greater ocular tolerability. That said, nausea, vomiting and sometimes diarrhea should be considered as adverse effects of travoprost and latanoprost. For example, according to the case report cited in Yu M et al. BMJ Case Rep. 2009; doi: 10.1136/bcr.08.2008.0618. Epub 2009 Feb. 26. PMID: 21686721; PMCID: PMC3028105, bimatoprost did not induce the same gastrointestinal adverse effects as travoprost and latanoprost, probably due to its different chemical structure and receptors. Still further, Gandolfi S et al. Adv Ther. 2001 May-June; 18(3):110-21. doi: 10.1007/BF02850299. PMID: 11571823 reports that conjunctival hyperemia was more commonly associated with bimatoprost therapy, while headache was more frequent with latanoprost in a three-month comparison of bimatoprost and latanoprost in patients with glaucoma and ocular hypertension. However, bimatoprost provided lower mean pressures than latanoprost at every time point studied and was statistically superior in achieving low target pressures. Id. Patients using travoprost or bimatoprost have been shown to have a significantly lower rate of adjunctive medication use compared to patients starting on latanoprost monotherapy (22.5%, 23.2%, and 30.2%, respectively), reflecting differences in overall efficacy of prostaglandins. See Covert D et al. Curr Med Res Opin. 2006 May; 22(5):971-6. doi: 10.1185/030079906x104777. PMID: 16709319.

Bimatoprost is specifically classified as prostamide and a synthetic analogue of prostaglandin F2a (PGF2a) with potent ocular hypotensive activity.

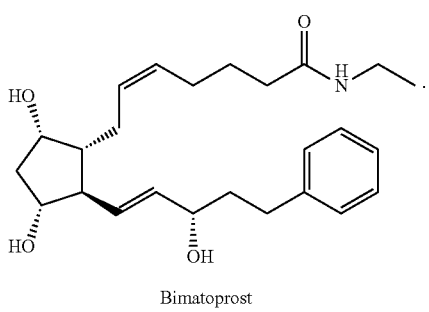 [SMILES: CCNC(=O)CCC/C=C\C[C@@H]1[C@@H](/C=C/[C@@H](O)CCc2ccccc2)[C@H](O)C[C@@H]1O]

Bimatoprost

Bimatoprost lowers IOP in patients with glaucoma or ocular hypertension by increasing outflow of aqueous humor through both the trabecular meshwork and uveoscleral routes.

The art is replete with both postulated and on-market (e.g., LUMIGAN®) bimatoprost ophthalmic bimatoprost compositions. Exemplary bimatoprost compositions disclosed in the patent art are described in, e.g., United States (US) Patent Numbers (Nos.) U.S. Pat. Nos. 6,646,001, 7,851,504, 8,309,605, 8,338,479, 8,343,949, 8,586,630, 8,691,802, 8,933,120, and 9,241,918; United States Patent Publication Number 2013/0245124; and, e.g., PCT Publication Numbers WO2009013434, WO2010102078, WO2016198434, WO2018185788, and WO2020178672. However, while a popular intraocular pressure reducing agent, bimatoprost is known in the art as causing increased side effects over other prostaglandin compounds.

For example, Inoue provides a compilation of the myriad of side effects patients must navigate when managing glaucoma treatment in the publication "Managing adverse effects of glaucoma medications," Clin Ophthalmol, 2014; 8:903-913. Therein, many publications are cited as disclosing the challenges presented by bimatoprost use. Honrubia, et. al., in "Conjunctival Hyperaemia with the Use of Latanoprost Versus Other Prostaglandin Analogues in Patients with Ocular Hypertension or Glaucoma: Meta-Analysis of Randomized Clinical Trials," (in Br J Ophthalmol. 2009; 93(3):316-321) discloses that conjunctival hyperemia occurred significantly less often with latanoprost than with travoprost or bimatoprost. Aptel, et. al., in "Efficacy and tolerability of prostaglandin analogs. A meta-analysis of randomized controlled clinical trials," (in J Glaucoma. 2008; 17(8):667-673) discloses that systematic reviews have shown conjunctival hyperemia to be more likely to occur with travoprost or bimatoprost use than latanoprost use. Crichton, et. al., in "Ocular surface tolerability of prostaglandin analogues and prostamides in patients with glaucoma or ocular hypertension," (in Adv Ther. 2013; 20(3):260-270) and Inoue, et. al., in "Adverse periocular reactions to five types of prostaglandin analogs," (in Eye. 2012; 26(11):1465-1472) disclose the reported incidence of conjunctival hyperemia differing between various prostaglandin analogs and occurring more often with bimatoprost use than with other prostaglandin analogs, and further report that the incidence of eyelash lengthening/bristling was demonstrated to be higher in bimatoprost than with other prostaglandins (travoprost, latanoprost, and tafluprost).

Eyelash growth-specific findings are further validated by Wester, et. al. (in Ophthalmology. 2010; 117(5):102-1031) wherein a gel formulation of bimatoprost is utilized specifically to promote eyelash growth. Similarly, Giannico, et. al., in "Eyelash Growth Induced by Topical Prostaglandin Analogues, Bimatoprost, Tafluprost, Travoprost, and Latanoprost in Rabbits," (in J Ocular Pharmacol Ther. 2013; 29(9):817-820) and Priluck J C et. al., (section editor Green) in "Latisse-Induced Periocular Skin Hyperpigmentation," (in Ophthalmol. 2010; 128(6):792-793) report that in a study of four types of prostaglandin analogs administered to rabbits, those receiving bimatoprost experienced significant eyelash growth. Still further complicating the use of bimatoprost, Priluck further discloses that eyelid skin hyperpigmentation can be a problem; an effect demonstrated by many other if not all prostaglandins, and further demonstrating the nuanced nature of ophthalmic bimatoprost product development and the care which may be taken to avoid unwanted side effects. While in certain circumstances, eyelash growth, or even, hypothetically, skin pigmentation may be desirable where such a targeted outcome is beneficial, such effect is likely very unwelcome in the target indication of glaucoma.

Even further, bimatoprost, when used in the treatment of glaucoma, has been reported as inducing iris pigment changes (inducing an increased pigment change over that of tafluprost); see, e.g., Inoue et. al., in "Adverse reaction after use of latanoprost in Japanese glaucoma patients," Nihon Ganka Gakkai Zasshi., 2006; 110(8):581-587. Deepening of the upper eye lid sulcus from topical application of bimatoprost during glaucoma treatment is yet an additional side effect resulting from bimatoprost treatment of glaucoma, often occurring more frequently in bimatoprost recipients than in those using alternative prostaglandins (see, e.g., Peplinski, et. al., in "Deepening of lid sulcus from topical bimatoprost therapy," (in Optom Vis Sci. 2004; 81(8):574-577); Park, et. al., in "Changes to upper eyelid orbital fat from use of topical bimatoprost, travoprost, and latanoprost," (in Jpn J Ophthalmol. 2011; 55(1):22-27); Inoue, et. al., in "Deepening of the upper eyelid sulcus caused by 5 types of prostaglandin analogs," (in J Glaucoma. 2013; 22(8):626-631); and Shah, et. al., in "A cross-sectional survey of the association between bilateral topical prostaglandin analogue use and ocular adnexal features," (in PLoS One. 2013; 8 (5): e61638).

The above effects are common in addition to the physical discomfort known to be common with bimatoprost use, including red and itchy eyelids, general ocular irritation and eye pain. Taken together, such effects could, still, arguably be endured if the alternative is the loss of eyesight due to uncontrolled intraocular pressure. While popular in their use, in a sub-population of patients with glaucoma or ocular hypertension, prostaglandins by themselves often do not produce sufficient pressure reduction to reach the desired target. As a result, many such patients require treatment with more than one medication, e.g., more than a single prostaglandin.

In an effort to increase efficacy, other classes of actives have been proposed in combination with prostaglandins such as bimatoprost. β-adrenoreceptor antagonists or β-blockers are often used as add-on therapy for patients who are already on a prostaglandin therapy. In certain cases where surgery is not indicated, β-blockers have traditionally been the drugs of choice for treating glaucoma. Topical β-blockers reduce the IOP by blockade of sympathetic nerve endings in the ciliary epithelium causing a fall in aqueous humor production. The compound timolol is one such β-blocker.

Timolol is a beta-adrenergic agent, chemically know as (−)-1-(tert-butylamino)-3-[(4-morpholino-1,2,5-thiadiazol-3-yl)-oxy]-2-propanol and having the following molecular structure:

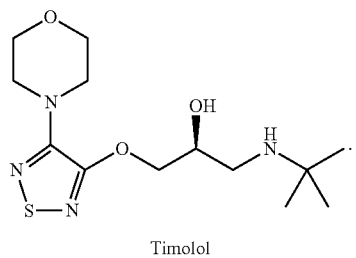 [SMILES: CC(C)(C)NC[C@H](O)COc1nsnc1N1CCOCC1]

Timolol

Timolol is available in the United States as single drug or as a fixed dose combination with drugs like dorzolamide or brimonidine for its ophthalmic use.

While having demonstrated IOP-reducing activity, like prostaglandins and especially bimatoprost, the use of timolol has come under scrutiny. Known side effects of timolol, e.g., timolol maleate, include temporary blurred vision, burning, stinging, itching, redness, watering, dryness, general irritation, and even headache. Inoue, et. al. in Ocular factors relevant to anti-glaucomatous eyedrop-related keratoepitheliopathy," (in J Glaucoma. 2003; 12(6):480-485) further describe that ocular adverse reactions to beta-blockers include conjunctival allergies, conjunctival injection, corneal epithelium disorders, blepharitis, and ocular pemphigoid, and goes one to describe a reduction in corneal sensitivity by such agents, leading to a reduction in reflective tearing and resulting in corneal epithelium disorders. Timolol is known to cause this effect and as reported by Inoue, was associated with a greater number of cases of corneal epithelium disorders than the use of carteolol.

Despite all such concerns related to each active individually, the market remains desperate for an efficacious treatment of glaucoma or at a minimum a sufficiently efficacious treatment short of surgical intervention, and, accordingly, the combination of timolol and bimatoprost specifically has been described in the patent literature.

U.S. Pat. Nos. U.S. Pat. Nos. 8,906,907, 8,629,140, 8,618,093, 9,474,760, and 10,045,997 describe composition(s) for, and related methods of, treating ocular hypertension including composition(s) comprising about 0.5% w/v timolol or pharmaceutically acceptable salts thereof and about 0.03% w/v bimatoprost.

U.S. Patent Publication No. 2019/0076442 describes preservative free ophthalmic pharmaceutical composition(s) for topical administration comprising bimatoprost or ophthalmological acceptable salts thereof and timolol or ophthalmological acceptable salts thereof for use in treating ocular hypertension and glaucoma.

U.S. Pat. Nos. 9,579,328 and 9,248,135 describes composition comprising a prostaglandin agent and a vasoconstrictor agent, wherein said vasoconstrictor agent is present in a sub-therapeutic amount. The said prostaglandin agent can be bimatoprost and the vasoconstrictor agent can be timolol and the sub-therapeutic amount is an amount less than about 0.25% w/w or less.

U.S. Pat. Nos. 9,061,034; 10,058,560, 9,763,958 and 9,078,854 also describe preservative free bimatoprost and timolol composition(s) for lowering intraocular pressure in a patient, wherein composition(s) comprises about 0.03% w/v bimatoprost and about 0.5% w/v timolol. Therein, it is disclosed that such composition(s) have an increased intraocular pressure lowering ability compared to the same composition preserved with benzalkonium chloride (BKC), a component which is discussed further elsewhere in this section.

U.S. Patent Publication No. US 2014/0088107 describes an aqueous ophthalmic preparation comprising a PGF2a analogue and at least one polyvinyl alcohol and the use thereof for the treatment of glaucoma and ocular hypertension. The PGF2a analogue disclosed in this art includes bimatoprost and the composition may further contain β-adrenergic receptor antagonists which includes timolol. Like the preceding references, a key aim of the invention disclosed in US 2014/0088107 is the provision of composition(s) which are essentially preservative-free. A specific example provided therein includes a combination of and timolol (see Table 2) wherein the bimatoprost is present in an amount representing about 0.03% of the composition and the composition is free of preservatives.

While there are no approved products available in the United States providing the combination of bimatoprost and timolol or pharmaceutically acceptable salts thereof at the time of this filing, the combination of bimatoprost 0.03% and timolol 0.5% is available outside of the United States, e.g., in countries such as Europe and India (see, e.g., GANFORT®), as composition(s) either with or without preservatives such as benzalkonium chloride. The combination of bimatoprost 0.01% and timolol maleate in an amount equivalent to 5 mg/mL (0.5% w/v) with 0.1 mg/mL (0.01% w/v) benzalkonium chloride as a preservative agent is available in India (Bimat LS™ Eye Drops by Ajanta Pharma).

Such-fixed dose combination therapies for the treatment of glaucoma themselves are often questioned, as has been reported by Aptel, et. al. in, "Efficacy and tolerability of prostaglandin-timolol fixed combinations: a meta-analysis of randomized clinical trials," (in Eur J Ophthalmol. 2012; 22(1):5-18). Therein Aptel describes that adverse reactions to the two main agents included in fixed-combination eye drops include those experienced when each agent is administered alone. However, because fixed-combination medications are often administered at lower frequencies, eye surface disorders caused by preservatives can occur in lower incidences, though certain combinations outperform others. A meta-analysis of the association between fixed-combination eye drop use and hyperemia conjunctiva showed that patients using bimatoprost plus timolol were 1.16 to 2.00 times more likely to develop the condition than patients using latanoprost plus timolol fixed-combination eye drops, and patients using travoprost plus timolol fixed-combination eye drops were 5.99 times more likely to develop the condition than patients using latanoprost plus timolol fixed-combination eye drops. Accordingly, the development of fixed-dose drug combinations has proven nuanced and unpredictable.

The incorporation of benzalkonium chloride as a preservative component of ophthalmic compositions provides its own challenges to product development. In 2001, the FDA approved LUMIGAN®, a sterile ophthalmic solution containing 0.03% bimatoprost ("LUMIGAN® 0.03%") developed by ALLERGAN, a leading, global ophthalmologic pharmaceutical company. While lacking a β-blocker, the LUMIGAN® 0.03% composition comprises benzalkonium chloride ("BKC") 0.05 mg/mL (0.005% or 50 ppm). LUMIGAN®0.03% is indicated for the reduction of elevated intraocular pressure in patients with open-angle glaucoma (OAG) or ocular hypertension (OH). LUMIGAN® 0.03% became a successful product, with 2011 sales of more than $600 million US dollars. However, LUMIGAN® 0.03% was known to also cause hyperemia (eye redness) that led many patients to discontinue use of the product. Vasodilatation in the conjunctiva, the most frequent adverse effect, led to about 3% of patients discontinuing therapy. See, e.g., Sherwood M, et al. Surv Ophthalmol. 2001; 45: S361-S368 and Hollo G. Exper Opin Drug Saf. 2007; 6:45-52. An increasing body of research also pointed to benzalkonium chloride (BKC) causing ophthalmological side effects. In fact, BKC was reported to consistently demonstrate toxic effects in laboratory, experimental, and clinical studies, causing tear film instability, loss of goblet cells, conjunctival squamous metaplasia and apoptosis, disruption of the corneal epithelium barrier, and damage to deeper ocular tissues. Baudouin C et al. Prog Retin Eye Res. 2010 July; 29(4): 312-34. doi: 10.1016/j.preteyeres.2010.03.001. PMID: 20302969. Such issues led to the conclusion that, "Care should therefore be taken to avoid the long-term use of preservatives, otherwise a less toxic alternative to benzalkonium chloride should be developed, as this weakly allergenic but highly toxic compound exerts dose- and time-dependent effects," (Baudoin, et. al., "Preservatives in eyedrops: the good, the bad and the ugly," Prog Retin Eye Res. 2010 July; 29(4):312-34). The authors further reported, "On the basis of all these experimental and clinical reports, it would be advisable to use benzalkonium-free solutions whenever possible . . . " Id. Patients can experience hypersensitivity reactions with BKC and BKC may be absorbed by soft contact lenses creating challenges for contact lens users. PCT Publication Number WO2018185788 is an example of the patent art advocating for the same BKC-free formulation approach. Attempts to replace benzalkonium chloride with other actives has proven challenging. For example, see the disclosure of US Patent Publication No. 2014/0088107 cited previously ("'107"), which discloses, "Due to the drawbacks of the use of benzalkonium chlorides, numerous attempts have been made to develop ophthalmic preparations comprising PGF2a analogues without the use of benzalkonium chlorides. One such product is sold under the trade name "TRAVATAN Z", wherein benzalkonium chloride is replaced by a complex system comprising polyoxyl 40 hydrogenated castor oil, boric acid, propylene glycol, sorbitol, and zinc chloride. A further preparation that is marketed as being preservative-free is sold in parts of Europe under the trade name "TAFLOTAN sine" and comprises disodium EDTA, glycerol and Polysorbate 80 in place of benzalkonium chloride. Despite the fact that both preservative-free" preparations do no longer contain benzalkonium chlorides, they now contain several other compounds instead, and, in particular, in both cases surfactants. The presence of multiple compounds obviously increases the chances of sensitization of a patient to one or several of the ingredients, as well as making the production thereof more expensive. Furthermore, the presence of surfactants might still lead to problems during long-term use." (See Paragraphs [0007]-[0008]). The '107 art proposes use of polyvinyl alcohol as a solution to the provision of a preservative free composition (solution) of a single PGF2α analogue. In another similar example provided by the prior cited art, U.S. Pat. No. 7,851,504 discloses incorporation of 100-200 ppm benzalkonium chloride which increased permeability of bimatoprost into ocular tissue (beyond preservation effect), while adding TPGS decreased permeability compared to 100-200 ppm BKC. Thus, while the art seeks to replace BKC, solutions sometimes still remain elusive.

The art provided above has been collected over the course of at least 20 years. Yet glaucoma sufferers continue to search for efficacious options to combat the debilitating disease, demonstrating that the development of new compositions and treatment regimens for the effective treatment of glaucoma require the application of inventive ingenuity.

Construction, Terms, and Acronyms

This section offers guidelines for reading this disclosure. The intended audience for this disclosure ("readers") are persons having ordinary skill in the practice of technologies discussed or used herein. Readers may also be called "skilled persons," and such technologies called "the art." Terms such as "understood," "known," and "ordinary meaning," refer to the general knowledge of skilled persons.

The term "uncontradicted" means not contradicted by this disclosure, logic, or plausibility based on knowledge of skilled persons.

Disclosed here are several different but related exemplary aspects of the invention (referred also to as, e.g., "cases," "facets," or "embodiments"). The invention encompasses all aspects, as described individually and as can be arrived at by any combination of such individual aspects. The breadth and scope of the invention should not be limited by any exemplary embodiment(s). No language in this disclosure should be construed as indicating any element/step is essential to the practice of the invention unless such a requirement is explicitly stated. Uncontradicted, any aspect(s) can be combined with any other aspect(s).

Uncontradicted, all technical/scientific terms used here generally have the same meanings as commonly understood by skilled persons, regardless of any narrower examples or descriptions provided here (including any term introduced initially in quotations). However, aspects characterized by the inclusion of elements, steps, etc., associated with specific descriptions provided here are distinct embodiments of the invention. Uncontradicted, disclosure of any aspect using known terms, which terms are narrowed by example or otherwise in this disclosure, implicitly discloses related aspects in which such terms are alternatively interpreted using the broadest reasonable interpretation of skilled persons.

Uncontradicted, "or" means "and/or" here, regardless of any occasional inclusion of "and/or" (e.g., phrases such as "A, B, or C" and "A, B, and/or C" simultaneously disclose aspects including (1) all of A, B, and C; (2) A and C; (3) A and B; (4) B and C; (5) only A; (6) only B; and (7) only C (and also support sub-groupings, such as "A or B," "A or C," etc.)).

Uncontradicted, "also" means "also or alternatively." Uncontradicted, "here" & "herein" mean "in this disclosure." The term "i.a." means "inter alia" or "among other things." "Also known as" is abbreviated "aka" or "AKA." "Elsewhere" means "elsewhere herein."

For conciseness, symbols are used where appropriate. E.g., "&" is used for "and," & "~" for "about." Symbols such as < and > are given their ordinary meaning (e.g., "≤" means "less than or equal to" & "≥" means "greater than or equal to"). A slash "/" can represent "or" ("A/B" means "A or B") or identify synonyms of an element, as will be clear from context.

The inclusion of "(s)" after an element or a step indicates that ≥1 of such an element is present, step performed, and the like. E.g., "element(s)" means both 1 element or ≥2 elements, with the understanding that each thereof is an independent aspect of the invention.

Use of the abbreviation "etc." (or "et cetera") in association with a list of elements/steps means any or all suitable combinations of the recited elements/steps or any known equivalents of such recited elements/steps for achieving the function(s) of such elements/steps that are known in the art. Terms such as "and combinations," or "or combinations" regarding listed elements/steps means any or all possible/ suitable combinations of such elements/steps.

Aspects may be described as suitable for use(s) disclosed herein. Uncontradicted, terms such as "suitability" means acceptable or appropriate for performing a particular function/achieving particular state(s)/outcome(s), and typically means effective, practical, and non-deleterious/harmful in the context the term is used. E.g., uncontradicted, the term "suitable" means appropriate, acceptable, or in contexts sufficient, or providing at least generally or substantially all of an intended function, without causing or imparting significant negative/detrimental impact.

Uncontradicted, heading(s) (e.g., "Construction, Terms . . . ") and subheadings are included for convenience and do not limit the scope of any aspect(s). Uncontradicted, aspect(s), step(s), or element(s) described under one heading can apply to other aspect(s) or step(s)/element(s) here.

Ranges of values are used to represent each value falling within such range that are within an order of magnitude of the smallest endpoint of the range without having to explicitly write each value of the range. E.g., a recited range of 1-2 implicitly discloses each of 1.0, 1.1, 1.2, . . . 1.9, and 2.0 and 10-100 implicitly discloses each of 10, 11, 12, . . . 98, 99, and 100). Uncontradicted, all ranges include the range's endpoints, regardless of how a range is described. E.g., "between 1-5" includes 1 and 5 in addition to 2, 3, and 4 (and all numbers between such numbers within an order of magnitude of such endpoints, e.g., 1.0, 1.1, . . . 4.9, and 5.0). For the avoidance of doubt, any number within a range, regardless of the order of magnitude of the number, is covered by the range (e.g., a range of 2-20 covers 18.593).

Terms of approximation (e.g., "about," "~", or "approximately") are used (1) to refer to a set of related values or (2) where a precise value is difficult to define (e.g., due to limits of measurement). Uncontradicted, all exact values provided here simultaneously/implicitly disclose corresponding approximate values and vice versa (e.g., disclosure of "about 10" provides explicit support for the use of 10 exactly in such aspect/description). Ranges described with approximate value(s) include all values encompassed by each approximate endpoint, regardless of presentation (e.g., "about 10-20" has the same meaning as "about 10-about 20"). The scope of value(s) encompassed by an approximate term typically depends on the context of the disclosure, criticality or operability, statistical significance, understanding in the art, etc. In the absence of guidance here or in the art for an element, terms such as "about" when used in connection with an element should be interpreted as ±10% of the indicated value(s) and implicitly disclosing ±5%, ±2%, ±1%, and ±0.5%.

Lists of aspects, elements, steps, and features are sometimes employed for conciseness. Unless indicated, each member of each list should be viewed as an independent aspect. Each aspect defined by any individual member of a list can have, and often will have, nonobvious properties vis-a-vis aspects characterized by other members of the list.

Uncontradicted, the terms "a" and "an" and "the" and similar referents encompass both the singular and the plural form of the referenced element, step, or aspect. Uncontradicted, terms in the singular implicitly convey the plural and vice versa herein (in other words, disclosure of an element/ step implicitly discloses corresponding use of such/similar elements/steps and vice versa). Hence, e.g., a passage regarding an aspect including X step supports a corresponding aspect including several X steps. Uncontradicted, any mixed use of a referent such as "a" in respect of one element/step or characteristic and "one or more of" with respect to another element/step or characteristic in a paragraph, sentence, aspect, or claim, does not change the meaning of such referents. Thus, for example, if a paragraph describes a composition comprising "an X" and "one or more Ys," the paragraph should be understood as providing disclosure of "one or more Xs" and "one or more Ys."

"Significant" and "significantly" mean results/characteristics that are statistically significant using ≥1 appropriate test(s)/trial(s) in the given context (e.g., p≤0.05/0.01). "Detectable" means measurably present/different using known detection tools/techniques. The acronym "DOS" (or "DoS") means "detectable(ly) or significant(ly)."

Uncontradicted, any value here that is not accompanied by a unit of measurement (e.g., a weight of 50 or a length of 20), any previously provided unit for the same element/step or the same type of element/step will apply, or, in cases where no such disclosure exists, the unit most commonly used in association with such an element/step in the art will apply.

Uncontradicted, the terms "including," "containing," "comprising," and "having" mean "including, but not limited to" or "including, without limitation." Uncontradicted, use of terms such as comprising and including regarding elements/steps means including any detectable number or amount of an element or including any detectable performance of a step/number of steps (with or without other elements/steps).

For conciseness, description of an aspect "comprising" or "including" an element, with respect to a collection/whole (e.g., a system, device, or composition), implicitly provides support for any detectable amount/number or ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the whole/ collection being made up of the element, or essentially all of the whole/collection being made up of the element (i.e., that the collection consists essentially of the referenced element). Similarly, a method described as including a step with respect to an effect/outcome implicitly provides support for the referenced step providing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the effect/outcome, representing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the steps/effort performed, or both. Explicit listing of percentages of elements/steps in connection with aspects does not limit or contradict such implicit disclosure.

Uncontradicted, terms such as "comprising" when used in connection with a step of a method provide implicit support for performing the step once, ≥2 times, or until an associated function/effect is achieved.

Uncontradicted, the term "one" means a single type, single iteration/copy/thing, of a recited element or step, or both, which will be clear from context. For example, the referent "one" used with a component of a composition can refer to one type of element (which may be present in numerous copies, as in the case of an ingredient in a composition), one unit of the element, or both. Similarly, "one" component, a "single" component, or the "only component" of a system typically means 1 type of element (which may be present in numerous copies), 1 instance/unit of the element, or both. Further, "one" step of a method typically means performing one type of action (step), one iteration of a step, or both. Uncontradicted, a disclosure of "one" element provides support for both, but uncontradicted, any claim to any "one" element means one type of such an element (e.g., a component of a composition/system).

The term "some" means ≥2 copies/instances or ≥5% of a listed collection/whole is, or is made up of, an element. Regarding methods, some means ≥5% of an effect, effort, or both, is made up of or is attributable to a step (e.g., as in "some of the method is performed by step Y") or indicates a step is performed ≥2 times (e.g., as in "step X is repeated some number of times"). "Predominately," "most," or "mostly," means detectably >50% (e.g., mostly comprises, predominately includes, etc., mean >50%) (e.g., a system that mostly includes element X is composed of >50% of element X). The term "generally" means ≥75% (e.g., generally consists of, generally associated with, generally comprises, etc., means ≥75%) (e.g., a method that generally consists of step X means that 75% of the effort or effect of the method is attributable to step X). "Substantially" or "nearly" means ≥95% (e.g., nearly all, substantially consists of, etc., mean ≥95%) (e.g., a collection that nearly entirely is made up of element X means that at least 95% of the elements in the collection are element X). Terms such as "generally free" of an element or "generally lacking" an element mean comprising ≤~25% of an element and terms such as "substantially free" of an element mean comprising ≤~5% of an element.

In certain embodiments describing API(s), excipient(s), or both present in amounts of "at least" or "greater than" a given amount or, e.g., present in amounts of "no more than" or "no greater than" or "less than" a given amount, the reader should interpret such disclosure as disclosing, e.g., encompassing and explicitly including, such undefined low or high amount(s) ranging to the opposite amount (high or low) that is maximally/minimally therapeutically effective, typically suitable, or both. For example, use of the phrase "at least" (and similar descriptors) in connection with an amount of a component of a formulation or of an entire formulation/composition can be interpreted as at least the amount described but that is no more than a maximally suitable or therapeutically effective amount (in the individual or in a population, such as determined in a clinical study). Similarly, phrases such as "less than" (and similar descriptors) an indicated amount can be interpreted referring to an amount that is still suitable (including, where appropriate, no amount, e.g., 0 units of the indicated component) or therapeutically effective (e.g., an amount that results in a DOS result in a significant number of individuals in a well-controlled and adequate study) but is less than the indicated amount.

Constituents herein are typically present in "effective amounts," and uncontradicted, any described class/type of, e.g., excipient (often referred to as a "component" herein—e.g., a "buffer component" may include one or more buffers) or specific excipient, or, e.g., in certain aspects active pharmaceutical ingredient(s) (API(s)) is understood to be present in the associated composition/formulation in an effective amount, which generally means, in this context, an amount that is effective for the described function(s) associated with the excipient/API (it being understood that some excipient or API compound(s)/ingredient(s) exhibit more than one effect). E.g., a tonicity agent will be understood to be present in a composition/formulation in an amount that is effective to impart an indicated tonicity effect, a tonicity effect that is required for suitability of the composition, or an effect that imparts a detectable or significant tonicity effect on a composition (with respect to a comparator composition lacking the compound(s)/ingredient(s)).

The phrase "substantially identical" may be used in certain contexts to reflect that tests that would be considered substantially identical by those of skill in the art (not differing meaningfully in terms of outcome) or that component(s) or step(s) can achieve the same result in a similar way as a referenced set of component(s)/step(s) so as to not meaningfully differ in intended result and manner of achieving such a result. It will be appreciated that the phrase "substantially identical" in such contexts comprises the use of identical amounts, identical formulations, and identical conditions, or, e.g., in other respects, composition(s) demonstrate an identical performance as a comparator.

Uncontradicted, any aspect described with respect to an optionally present element(s)/step(s) also provides implicit support for corresponding aspect(s) in which one, some, most, generally all, nearly all, essentially all, or all of such element(s) are lacking/step(s) not performed, in respect of the relevant aspect. E.g., disclosure of a system comprising element X implicitly also supports a system lacking element X.

Uncontradicted, changes to tense or presentation of terms (e.g., using "comprises predominately" in place of "predominately comprises") do not change the meaning of the corresponding term/phrase.

Uncontradicted, all methods provided here can be performed in any suitable order regardless of presentation (e.g., a method comprising steps A, B, and C, can be performed in the order C, B, and A; B and A and C simultaneously, etc.). Uncontradicted, elements of a composition can be assembled in any suitable manner by any suitable method. In general, any methods and materials similar or equivalent to those described here can be used in the practice of embodiments. Uncontradicted, the use of ordinal numbers such as "first," "second," "third," etc. is to distinguish respective elements rather than to denote a particular order of those elements.

Uncontradicted, any elements, steps, components, or features of aspects and all variations thereof, etc., are within the scope of the invention.

Elements associated with a function can be described as "means for" performing a function in a composition/device/system or a "step for" performing a part of a method, and parts of this disclosure refer to "equivalents," which means equivalents known in the art for achieving a referenced function associated with disclosed mean(s)/step(s). However, no element of this disclosure or claim should be interpreted as limited to a "means-plus-function" construction unless such intent is clearly indicated by the use of the terms "means for" or "step for." Terms such as "configured to" or "adapted to" do not indicate "means-plus-function" interpretation, but, rather, describe element(s)/step(s) configured to, designed to, selected to, or adapted to achieve a certain performance, characteristic, property, etc. using teachings provided here or in the art.

All references (e.g., publications, patent applications, and patents) cited herein are hereby incorporated by reference as if each reference were individually and specifically indicated to be incorporated by reference and set forth in its entirety herein. Uncontradicted, any suitable principles, methods, or elements of such references (collectively "teachings") can be combined with or adapted to aspects. However, citation/incorporation of patent documents is limited to the technical disclosure thereof and does not reflect any view regarding the validity, patentability, etc., thereof. In the event of any conflict between this disclosure and the teachings of such documents, the content of this disclosure controls regarding aspects of the invention. Numerous references are cited here to concisely incorporate known information and aid skilled persons in putting aspects into practice. While efforts have been made to include the most relevant references for such purposes, readers will understand that not every aspect of every cited reference will apply to every aspect of the invention.

All original claims contained in this disclosure when filed are incorporated into this specification as if they were a part of the description.

Additional Terms, Concepts, and Acronyms

The following description of certain terms and acronyms is provided to assist readers in understanding the invention. Additional acronyms may be only provided in other parts of this disclosure and acronyms that are well known in the art may not be provided here.

Uncontradicted, any description of weight is percent weight/volume ("% w/v").

Uncontradicted, the term "composition" as used herein, is interchangeable with pharmaceutical formulation, liquid composition, liquid formulation, and formulation, and refers to preparations comprising, e.g., a bimatoprost compound and a timolol compound in a form suitable for ophthalmic administration to a patient or subject. At times herein, the term "formulation" is used to describe a composition wherein exemplary ranges of composition constituents are provided, and "composition" is used where specific composition constituents are provided in specific exemplary amounts. Herein, uncontradicted, the term "constituent(s)" when referencing a composition or component of a composition refers to a compound/agent contained in the composition or component. A composition can have any suitable form, such as an ointment or a solution. In aspects, a composition is a solution, a gel, or both. Uncontradicted, disclosure of a composition, formulation, and the like, provides implicit support for any of the various specific types of compositions described herein as if separately stated (e.g., disclosure of a composition or formulation should be understood to disclose "a gel, a solution, or other type of composition . . . ").

The terms "treating," "treatment," and the like are generally understood. Uncontradicted, terms such as "treating" or "treatment" herein refer to any suitable type of treatment, and typically encompass any approach for obtaining measurable or significant beneficial or desired results in a subject's condition, including clinical results. Beneficial or desired clinical results can include, but are not limited to, alleviation or amelioration of one or more symptoms or conditions, diminishment of the extent of a disease, stabilizing (e.g., not worsening) the state of the disease or condition, slowing or delaying the progression of a disease or condition, amelioration or palliation of the disease state, diminishment of the reoccurrence of a disease or condition, and, e.g., remission, whether partial or total, and whether detectable or undetectable. In other words, uncontradicted, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of such effects. Readers will understand that each of the types of treatment described herein can represent separate and meaningfully different embodiments. Accordingly, the use of terms such as "treat" herein provide simultaneous implicit support for any of the particular forms of treatment described in this paragraph or elsewhere in this disclosure (e.g., stabilizing a condition, reducing the severity of a condition, reducing the duration of a condition, treating one or more particular conditions, etc.).

Except where explicitly indicated or clearly indicated by context, "improved" herein means detectably or significantly "increased." In aspects, "improved" means detectably or significantly "reduced," such as with respect to the toxicity of a composition. Uncontradicted, terms such as "enhanced," "improved," and the like are used synonymously herein.

"Pharmaceutical suitability", "pharmaceutically suitable", "ophthalmologically suitable" or "ophthalmological suitability" are phrases typically used to refer to compositions that are safe and effective for pharmaceutical administration and application, and particularly ophthalmological application(s), having sufficient potency, purity, strength, quality, and safety, stability, and tolerability, for pharmaceutical application, in cases specifically to the eye, as may be judged by regulatory authority review, and as established by, e.g., one or more well-controlled and adequate clinical studies performed in compliance with generally prevailing regulatory authority standards. Compositions described as "ophthalmologically suitable" should be interpreted to mean suitable for ophthalmic delivery when provided in a potency, purity, strength, or quality making it safe for ophthalmic use. Components described as "ophthalmologically suitable" should be interpreted in a similar manner. Uncontradicted, a description of "suitability" implicitly means that the referenced element, step, etc., is ophthalmologically/pharmaceutically suitable or otherwise medically suitable (e.g., safe and effective and otherwise suitable, such as tolerable in most, generally all, nearly all or essentially all recipients in one or more studies, or otherwise suitable for applications to the eye or treatment of eye conditions, as determined by proper nonclinical/clinical testing).

Excipients herein are typically present in "effective amounts," and uncontradicted, any described class/type of excipient (often referred to as a "component" herein—e.g., a "buffer component" may include one or more buffers) or specific excipient is understood to be present in the associated composition/formulation in an effective amount, which generally means, in this context, an amount that is effective for the described function(s) associated with the excipient (it being understood that some excipient compound(s)/ingredient(s) exhibit more than one effect). E.g., a tonicity agent will be understood to be present in a composition/formulation in an amount that is effective to impart an indicated tonicity effect, a tonicity effect that is required for suitability of the composition, or an effect that imparts a detectable or significant tonicity effect on a composition (with respect to a comparator composition lacking the compound(s)/ingredient(s)).

Similarly, active pharmaceutical ingredients (APIs), e.g., PACs, BACs, or AGACs (if present), typically individually or collectively are present in effective amounts. Pharmaceutical efficacy is understood in the art and, uncontradicted, such APIs can be effective in any one or more suitable modalities/ways. For example, an effective amount of an API is an amount that can detectably or significantly treat one or more aspects of a condition or disease (or, e.g., related symptom of such a condition or disease), such as may be established through one or more well-controlled and adequate clinical studies, bioequivalence, or other suitable means.

Aspects of the invention are described broadly and generically herein, as well as in narrower species and examples. Each of the narrower species, examples, and subgeneric groupings falling within the generic disclosure also form part of the invention. This includes the generic description of the invention with a proviso or negative limitation removing one or more specific matters from the genus, regardless of whether or not the excised (specifically excluded) material is specifically recited herein.

SUMMARY OF THE INVENTION

The inventions described and claimed herein have many attributes and aspects including, but not limited to, those set forth in, e.g., described or referenced in, this Summary. This Summary of the Invention ("Summary") is not intended to be all-inclusive, and the scope of the invention is not limited to or by the aspects, features, elements, or embodiments provided in this Summary, which is included for illustrative purposes only and not restriction. Any of the aspects described under this section can be combined with any other aspect described in this section or with any other aspect of this disclosure.

In aspects, disclosed herein are pharmaceutically acceptable and ophthalmologically suitable compositions comprising a therapeutically effective quantity of a prostaglandin analogue, such as, e.g., bimatoprost, such as bimatoprost base, and a beta-adrenergic receptor antagonist, such as, e.g., timolol or ophthalmological acceptable salt thereof, e.g., timolol maleate. In certain aspects, the invention provides ophthalmic compositions comprising bimatoprost base and timolol maleate. In aspects, the invention provides a process of preparing such compositions and associated methods of their use.

In aspects, the invention provides pharmaceutically acceptable and ophthalmologically suitable compositions comprising a therapeutically effective quantity of a prostaglandin analogue, such as, e.g., bimatoprost, e.g., bimatoprost base, and a beta-adrenergic receptor antagonist, such as, e.g., timolol or ophthalmological acceptable salt thereof, e.g., timolol maleate, wherein the composition is provided as a clear, aqueous solution.

In certain specific aspects, the invention provides a pharmaceutically acceptable and ophthalmologically suitable composition for treating an ocular condition in a mammalian eye comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; and (4) about 0.25% w/v-about 2.5% w/v of a penetration enhancer component, wherein the ratio of the quaternary ammonium salt to the penetration enhancer component is about 1: about 35-about 1: about 840, the ratio of the bimatoprost compound to the penetration enhancer component is about 1: about 12.5-about 1: about 500, the ratio of the timolol compound to the penetration enhancer component is between about 3.2: about 1-about 1: about 6.3, or any combination of such ratios are present.

In aspects, the invention provides a pharmaceutically acceptable and ophthalmologically suitable composition in the form of, e.g., a solution or a gel for treating an ocular condition, e.g., elevated intraocular pressure, glaucoma (e.g., open-angle glaucoma), or both, in a mammalian eye comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; and (4) about 0.25% w/v-about 2.5% w/v of a penetration enhancer component. In certain aspects, the inclusion of a penetration enhancer component is optional. In aspects, the inclusion of a penetration enhancer is excluded in certain compositions, such as, e.g., certain embodiments of compositions provided as a gel.

In aspects, compositions provided by the invention are characterized by one or more ratios of components or constituents therein. In aspects, the invention provides compositions wherein the ratio of a quaternary ammonium salt component of a composition to a penetration enhancer component of a composition (e.g., when such a penetration enhancer component is present) is about 1:35-about 1:840. In aspects, the invention provides compositions wherein the ratio of the bimatoprost compound to a penetration enhancer component of a composition is about 1:12.5-about 1:500. In aspects, the invention provides compositions wherein the ratio of the timolol compound to a penetration enhancer component is between about 3.2:1-1:6.3. In aspects, the invention provides compositions wherein the ratio of the total amount of API consisting of the bimatoprost compound and the timolol compound to a penetration enhancement component of a composition is about 3.2:1 to about 1:6.3.

In aspects, compositions provided by the invention are stable when stored under controlled room temperature conditions (e.g., temperature of about 15° C. to 25° C.+/−2° C.) for a period of at least about 1 months, such as, e.g., at least about 3 months, at least about 6 months, at least about 9 months, at least about 12 months, at least about 18 months, at least about 24 months, at least about 28 months, at least about 32 months, or, e.g., at least about 36 months.

In aspects, the invention provides methods of treatment using such compositions, such as methods of treating elevated intraocular pressure, glaucoma (e.g., open-angle glaucoma), or both. In aspects, the invention provides such methods wherein application of the methods results in an improvement in the target indication, e.g., a reduction in elevated intraocular pressure, which was unsatisfactorily responsive to prior treatment of the target indication with a topical beta-blocker administered alone, a prostaglandin analogue administered alone, or both.

In aspects, the invention provides methods of treatment using such compositions, such as methods of treating elevated intraocular pressure, glaucoma (e.g., open-angle glaucoma), or both. In aspects, application of such method(s) is clinically demonstrated to (1) be as effective or detectably or significantly more effective than treatment of the same or at least essentially the same, generally the same, or the same condition with about the same amount of the product approved as European Medicines Agency product number EMEA/H/C/000668 (presently sold under the trademark "GANFORT®") (having first received market approval in 2006) for the same or similar indication (e.g., reducing IOP) and for at least substantially the same administration period; (2) result in the user or an average population of users experiencing a reduction in frequency of adverse events (e.g., negative side effects) than those reported as adverse events (e.g., negative side effects) for the product approved as European Medicines Agency product number EMEA/H/C/000668 (GANFORT®) (having first received market approval in 2006); (3) result in a population of treated subjects, on average, maintaining a longer course of therapy than the course of therapy tolerated by a comparable population of treated subjects treated with the product approved as European Medicines Agency product number EMEA/H/C/000668 (GANFORT®) (having first received market approval in 2006) for the same or similar indication; or (4) any combination of (1), (2), and (3).

In additional aspects, the invention provides methods of using compositions disclosed herein in method(s) of treating elevated intraocular pressure, glaucoma, or both, in a mammalian eye.

In one specific aspect, the invention provides a method of treating elevated intraocular pressure, glaucoma, or both, in a mammalian eye, the method comprising administration of an effective amount of a composition comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; and (4) about 0.25% w/v-about 2.5% w/v of a penetration enhancer component, wherein the composition is further characterized by (a) the ratio of the quaternary ammonium salt to the penetration enhancer component is between about 1:35-about 1:840; (b) the ratio of the bimatoprost compound to the penetration enhancer component is about 1:12.5-about 1:500; (c) the ratio of the timolol compound to the penetration enhancer component is between about 3.2:1-1:6.3; or (d) any combination of (a) the ratio of the quaternary ammonium salt to the penetration enhancer component is between about 1:35-about 1:840; (b) the ratio of the bimatoprost compound to the penetration enhancer component is about 1:12.5-about 1:500; and (c) the ratio of the timolol compound to the penetration enhancer component is between about 3.2:1-1:6.3 are true.

In aspects, the invention provides methods of manufacturing compositions described in this Summary section, as well as kits for distributing and storing such compositions.

Exemplary Aspects of the Invention

The following is a non-limiting list of exemplary aspects of the invention, which illustrates embodiments of the invention in a summary form to aid readers in quickly understanding the overall scope of the invention. Similar to patent claims, listed aspects described in the paragraphs of this section may refer to (depend on/from) one or more other paragraphs. Readers will understand that such references mean that the features/characteristics or steps of such referenced aspects are incorporated into/combined with the referring aspect. E.g., if an aspect in a paragraph (e.g., a paragraph indicated by text at the end of the paragraph as aspect 2) refers to another aspect by one or more aspect numbers (e.g., aspect 1 or "any one of aspects 1-3"), it will be understood to include the elements, steps, or characteristics of such referenced aspects (e.g., aspect 1) in addition to those of the aspect in which the reference is made (e.g., if aspect 2 refers to aspect 1, it provides a description of a composition, method, system, device, etc., including the features of both aspect 1 and aspect 2).

Lists of aspects describing specific exemplary embodiments of the invention are sometimes employed for aiding the reader in understanding the invention. Such aspects can, within them, reference other exemplary aspects, either individually or as groups of aspects (e.g., via reference to a range within a list of numbered aspects when such aspects are provided as a numbered list). Reference to ranges of aspects should be interpreted as referencing all such aspects individually, each as unique embodiments of the invention, and in combination with one another as unique embodiment(s) of the invention, according to the presentation provided of such aspects unless such an aspect within such a referenced range is either contradictory or non-sensical. If contradicted, reference to the contradictory aspect should be excluded.

In one aspect, the invention provides a pharmaceutically acceptable and ophthalmologically suitable composition for treating an ocular condition in a mammalian eye comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; and (4) about 0.25% w/v-about 2.5% w/v of a penetration enhancer component, wherein the ratio of the quaternary ammonium salt to the penetration enhancer component is about 1:35-about 1:840 (aspect 1).

In one aspect, the invention provides the composition of aspect 1, wherein (1) the ratio of the bimatoprost compound to the penetration enhancer component is about 1:12.5-about 1:500; (2) the ratio of the timolol compound to the penetration enhancer component is between about 3.2:1-1:6.3 (e.g., ~3.2:1-~1:6.25); or (3) both (1) and (2) are true (aspect 2).

In one aspect, the invention provides a pharmaceutically acceptable and ophthalmologically suitable composition for treating an ocular condition in a mammalian eye comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; and (4) about 0.25% w/v-about 2.5% w/v of a penetration enhancer component, wherein the ratio of the bimatoprost compound to the penetration enhancer component is about 1:12.5-about 1:500 (aspect 3).

In one aspect, the invention provides the composition of aspect 3, wherein (1) the ratio of the quaternary ammonium salt to the penetration enhancer component is about 1:35-about 1:840, (2) the ratio of the timolol compound to the penetration enhancer component is between about 3.2:1-1:6.3 (e.g., ~3.2:1-~1:6.25), or (3) both (1) and (2) are true (aspect 4).

In one aspect, the invention provides a pharmaceutically acceptable and ophthalmologically suitable composition for treating an ocular condition in a mammalian eye comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; and (4) about 0.25% w/v-about 2.5% w/v of a penetration enhancer component, wherein the ratio of the timolol compound to the penetration enhancer component is between about 3.2:1-1:6.3 (e.g., ~3.2:1-~1:6.25) (aspect 5).

In one aspect, the invention provides the composition of aspect 5, wherein (1) the ratio of the bimatoprost compound to the penetration enhancer component is about 1:12.5-about 1:500, (2) the ratio of the quaternary ammonium salt to the penetration enhancer component is about 1:35-about 1:840, or (3) both (1) and (2) are true (aspect 6).

In aspects, the invention provides the composition of any one or more of aspects 1-6, wherein the penetration enhancer component comprises one or more constituents which provides both detectably or significantly increased penetration of the bimatoprost compound, the timolol compound, or both the bimatoprost and timolol compounds into corneal tissue, and wherein the penetration enhancer component comprises one or more of (1) a protein/peptide constituent, (2) a non-protein/peptide constituent, or (3) a combination of (1) and (2) (aspect 7).

In aspects, the invention provides the composition of any one or both of aspect 1 or aspect 7, wherein the penetration enhancer component comprises at least one constituent which provides detectable or significant activity as two or more of a penetration enhancer, a solubilizer, a demulcent, a buffer, a tonicity agent, a thickener, a chelator, a pH adjusting agent, a preservative, or a carrier (aspect 8).

In aspects, the invention provides the composition of any one or more of aspects 1-8, wherein the penetration enhancer component comprises at least one constituent which provides detectable or significant activity as a penetration enhancer, a solubilizer, a demulcent, or any combination of two or more thereof (aspect 9).

In aspects, the invention provides the composition of any one or more of aspects 1-9, wherein the penetration enhancer component comprises at least one constituent which provides detectable or significant activity as a penetration enhancer, a solubilizer, and a demulcent (aspect 10).

In aspects, the invention provides the composition of any one or more of aspects 1-5, wherein the penetration enhancer component comprises at least one constituent characterizable as a non-ionic surfactant having an HLB value of at least about 14.5, e.g., at least about 16.5 (aspect 11).

In aspects, the invention provides the composition of any one or more of aspects 1-11, wherein the penetration enhancer component comprises one or more of one or more polyoxyethylene sorbitan fatty acid ester(s), tocopheryl polyethylene glycol succinate (TPGS), poly-arginine, or polyserine (aspect 12).

In aspects, the invention provides the composition of any one or more of aspects 1-11, wherein the penetration enhancer component comprises one or more constituents characterizable as a protein/peptide (aspect 13). 1-13, wherein the penetration enhancer component comprises poly-arginine (aspect 14).

In aspects, the invention provides the composition of any one or more of aspects 1-14, wherein the penetration enhancer component comprises poly-serine (aspect 15).

In aspects, the invention provides the composition of any one or more of aspects 1-15, wherein the penetration enhancer component comprises one or more constituents characterizable as a non-protein/peptide (aspect 16).

In aspects, the invention provides the composition of any one or more of aspects 1-16, wherein the penetration enhancer component comprises one or more compounds selected from a group consisting of polyethylene sorbitan fatty acid esters, tocopherol polyethylene glycol succinate (TPGS), and polyoxyl hydrogenated castor oil (aspect 17).

In aspects, the invention provides the composition of any one or more of aspects 1-17, wherein the penetration enhancer component comprises a polyethylene sorbitan fatty acid ester selected from the group consisting of polyoxyethylene sorbitan laurate (polysorbate 20), polyoxyethylene sorbitan palmitate (polysorbate 40), a polyoxyethylene sorbitan stearate (polysorbate 60), a polyoxyethylene sorbitan tri stearate (polysorbate 65), or a polyoxyethylene sorbitan oleate/polyoxyethylene sorbitan mono-oleate ester (e.g., polysorbate 80), or a combination thereof (aspect 18).

In aspects, the invention provides the composition of any one or more of aspects 1-18, wherein the penetration enhancer component comprises polysorbate 20, polysorbate 80, or a combination of polysorbate 20 and polysorbate 80 (aspect 19).

In aspects, the invention provides the composition of any one or more of aspects 1-19, wherein the penetration enhancer component comprises polysorbate 20 (aspect 20).

In aspects, the invention provides the composition of any one or more of aspects 1-20, wherein the penetration enhancer component comprises polysorbate 80 (aspect 21).

In aspects, the invention provides the composition of any one or more of aspects 1-21, wherein the penetration enhancer component comprises TPGS (aspect 22).

In aspects, the invention provides the composition of any one or more of aspects 1-22, wherein the penetration enhancer component comprises a constituent characterizable as a polyoxyl hydrogenated castor oil (aspect 23).

In aspects, the invention provides the composition of any one or more of aspects 1-23, wherein the penetration enhancer component comprises polyoxyl 35 castor oil (cremophor EL) (aspect 24). 1-24, wherein the penetration enhancer component is present in an amount representing about 0.5% w/v-about 2% w/v of the composition (aspect 25).

In aspects, the invention provides the composition of any one or more of aspects 1-25, wherein the penetration enhancer component is present in an amount representing about 0.7% w/v-about 1.5% w/v of the composition (aspect 26).

In aspects, the invention provides the composition of any one or more of aspects 1-26, wherein the penetration enhancer component is present in an amount of between about 0.8% w/v-about 1.1% w/v of the composition (aspect 27).

In aspects, the invention provides the composition of any one or more of aspects 1-27, wherein the penetration enhancer component is present in an amount representing about 1% w/v of the composition (aspect 28).

In aspects, the invention provides the composition of any one or more of aspects 1-28, wherein the penetration enhancer component is present in an amount representing about 1.005% w/v of the composition (aspect 29).

In aspects, the invention provides the composition of any one or more of aspects 1-29, wherein the bimatoprost compound is bimatoprost (aspect 30).

In aspects, the invention provides the composition of any one or more of aspects 1-30, wherein the bimatoprost compound is present in an amount representing about 0.007% w/v-about 0.02% w/v of the composition (aspect 31)

In aspects, the invention provides the composition of any one or more of aspects 1-31, wherein the bimatoprost compound is present in an amount representing about 0.009% w/v-about 0.015% w/v of the composition (aspect 32).

In aspects, the invention provides the composition of any one or more of aspects 1-32, wherein the bimatoprost compound is present in an amount representing about 0.01% w/v of the composition (aspect 33).

In aspects, the invention provides the composition of any one or more of aspects 1-33, wherein the timolol compound is present as an ophthalmologically suitable salt of timolol (aspect 34).

In aspects, the invention provides the composition of any one or more of aspects 1-34, wherein the ophthalmologically suitable salt of timolol is timolol maleate (aspect 35). 1-35, wherein the composition comprises timolol maleate in an amount representing about 0.5% w/v-about 0.7% w/v of the composition (aspect 36).

In aspects, the invention provides the composition of any one or more of aspects 1-36, wherein the composition comprises timolol maleate in an amount representing about 0.6% w/v-about 0.7% w/v of the composition (aspect 37).

In aspects, the invention provides the composition of any one or more of aspects 1-37, wherein the composition comprises timolol maleate in an amount representing about 0.68% w/v (equivalent to about 0.5% timolol) of the composition (aspect 38).

In aspects, the invention provides the composition of any one or more of aspects 1-38, wherein the quaternary ammonium salt is a benzalkonium chloride compound (aspect 39).

In aspects, the invention provides the composition of any one or more of aspects 1-39, wherein the benzalkonium chloride compound is benzalkonium chloride (aspect 40).

In aspects, the invention provides the composition of any one or more of aspects 1-40, wherein the composition comprises benzalkonium chloride in an amount representing about 0.004% w/v-about 0.006% w/v of the composition (aspect 41).

In aspects, the invention provides the composition of any one or more of aspects 1-41, wherein the composition comprises benzalkonium chloride in an amount representing about 0.004% w/v-about 0.005% w/v of the composition (aspect 42).

In aspects, the invention provides the composition of any one or more of aspects 1-42, wherein the composition comprises benzalkonium chloride in an amount representing about 0.005% w/v of the composition (aspect 43).

In aspects, the invention provides the composition of any one or more of aspects 1-43, wherein the composition comprises a ratio of quaternary ammonium salt, e.g., benzalkonium chloride, to penetration enhancer component of about 1:100 to about 1:300 (aspect 44).

In aspects, the invention provides the composition of any one or more of aspects 1-44, wherein the ratio of quaternary ammonium salt, e.g., benzalkonium chloride, to penetration enhancer component is about 1:200 (aspect 45).

In aspects, the invention provides the composition of any one or more of aspects 1-45, wherein the ratio of the bimatoprost compound to the timolol compound is about 1:20 to about 1:160 (aspect 46). 1-46, wherein the ratio of the bimatoprost compound to the timolol compound is about 1:50 to about 1:100 (aspect 47).

In aspects, the invention provides the composition of any one or more of aspects 1-47, wherein the ratio of the bimatoprost compound to the timolol compound is about 1:68 (aspect 48).

In aspects, the invention provides the composition of any one or more of aspects 1-48, wherein the ratio of the bimatoprost compound to the quaternary ammonium salt, e.g., benzalkonium chloride, is about 6.7:1 to about 1:1.4 (aspect 49).

In aspects, the invention provides the composition of any one or more of aspects 1-49, wherein the ratio of the bimatoprost compound to the quaternary ammonium salt, e.g., benzalkonium chloride, is about 5:1 to about 1:1 (aspect 50).

In aspects, the invention provides the composition of any one or more of aspects 1-50, wherein the ratio of the bimatoprost compound to the quaternary ammonium salt, e.g., benzalkonium chloride, is about 2:1 (aspect 51).

In aspects, the invention provides the composition of any one or more of aspects 1-51, wherein the ratio of the bimatoprost compound to the penetration enhancer component is about 1:12.5 to about 1:500 (aspect 52).

In aspects, the invention provides the composition of any one or more of aspects 1-52, wherein the ratio of the bimatoprost compound to the penetration enhancer component is about 1:20 to about 1:200 (aspect 53).

In aspects, the invention provides the composition of any one or more of aspects 1-53, wherein the ratio of the bimatoprost compound to the penetration enhancer component is about 1:100 (aspect 54).

In aspects, the invention provides the composition of any one or more of aspects 1-54, wherein the ratio of the timolol compound to the quaternary ammonium salt, e.g., benzalkonium chloride, is about 57.1:1 to about 266.7:1 (aspect 55).

In aspects, the invention provides the composition of any one or more of aspects 1-55, wherein the ratio of the timolol compound to the quaternary ammonium salt, e.g., benzalkonium chloride, is about 90:1 to about 170:1 (aspect 56).

In aspects, the invention provides the composition of any one or more of aspects 1-56, wherein the ratio of the timolol compound to the quaternary ammonium salt, e.g., benzalkonium chloride, is about 136:1 (aspect 57). 1-57, wherein the ratio of the timolol compound to the penetration enhancer component is about 3.2:1 to about 1:6.3 (e.g., ~3.2:1-~1:6.25) (aspect 58).

In aspects, the invention provides the composition of any one or more of aspects 1-58, wherein the ratio of the timolol compound to the penetration enhancer component is about 2:1 to about 1:3 (aspect 59).

In aspects, the invention provides the composition of any one or more of aspects 1-59, wherein the ratio of the timolol compound to the penetration enhancer component is about 1:1.47 (aspect 60).

In aspects, the invention provides the composition of any one or more of aspects 1-60, wherein the ratio of the total amount of API consisting of the bimatoprost compound and the timolol compound to the quaternary ammonium salt, e.g., benzalkonium chloride, is about 57.9:1 to about 273.3:1 (aspect 61).

In aspects, the invention provides the composition of any one or more of aspects 1-61, wherein the ratio of the total amount of API consisting of the bimatoprost compound and the timolol compound to the quaternary ammonium salt, e.g., benzalkonium chloride, is about 100:1 to about 150:1 (aspect 62).

In aspects, the invention provides the composition of any one or more of aspects 1-62, wherein the ratio of the total amount of API consisting of the bimatoprost compound and the timolol compound to the quaternary ammonium salt, e.g., benzalkonium chloride, is about 138:1 (aspect 63).

In aspects, the invention provides the composition of any one or more of aspects 1-63, wherein the ratio of the total amount of API consisting of the bimatoprost compound and the timolol compound to the penetration enhancer component is about 3.28:1 to about 1:6.17 (aspect 64).

In aspects, the invention provides the composition of any one or more of aspects 1-64, wherein the ratio of the total amount of API consisting of the bimatoprost compound and the timolol compound to the penetration enhancer component is about 2:1-about 1:2 (aspect 65).

In aspects, the invention provides the composition of any one or more of aspects 1-65, wherein the ratio of the total amount of API consisting of the bimatoprost compound and the timolol compound to the penetration enhancer component is about 1:1.45 (aspect 66). 1-66, wherein the composition further comprises one or more excipients (aspect 67).

In aspects, the invention provides the composition of any one or more of aspects 1-67, wherein the composition further comprises one or more excipients present in the composition as a constituent of a one or more component(s) selected from the group consisting of a chelation component, a tonicity component, a preservation component, a solubilization component, a buffer component, a pH-adjusting component, and a carrier component (aspect 68).

In aspects, the invention provides the composition of any one or more of aspects 1-68, wherein the composition comprises a solubilization component comprising one or more constituents capable detectably or significantly increasing the solubilization of the bimatoprost compound, the timolol compound, or both the bimatoprost and timolol compounds (aspect 69).

In aspects, the invention provides the composition of any one or more of aspects 1-69, wherein the composition comprises a solubilization component comprising one or more constituents distinctly different from any compound providing detectably or significantly enhanced penetration of the bimatoprost compound, the timolol compound, or both the bimatoprost and the timolol compounds (aspect 70).

In aspects, the invention provides the composition of any one or more of aspects 1-70, wherein the composition comprises a solubilization component and wherein a constituent of the solubilization component is tromethamine (tris) (aspect 71).

In aspects, the invention provides the composition of any one or more of aspects 1-71, wherein the composition comprises tromethamine (tris) in an amount representing about 0.005% w/v-about 0.5% w/v of the composition (aspect 72).

In aspects, the invention provides the composition of any one or more of aspects 1-72, wherein the composition comprises tromethamine (tris) in an amount representing about 0.01% w/v-about 0.3% w/v of the composition (aspect 73).

In aspects, the invention provides the composition of any one or more of aspects 1-73, wherein the composition comprises tromethamine (tris) in an amount representing about 0.1% w/v-about 0.2% w/v of the composition (aspect 74).

In aspects, the invention provides the composition of any one or more of aspects 1-74, wherein the composition comprises sesame seed oil or oils having similar compositions and functional characteristics suitable for ophthalmic use (aspect 75).

In aspects, the invention provides the composition of any one or more of aspects 1-75, wherein the composition comprises a solubilization component, and wherein the solubilization component comprises one or more constituents which are also constituents of the penetration enhancer component, such that the one or more constituents provides both (1) detectably or significantly increased penetration of the bimatoprost compound, the timolol compound, or both the bimatoprost compound and the timolol compound into corneal tissue, and (2) detectably or significantly increased solubilization of the bimatoprost compound, the timolol compound, or both the bimatoprost compound and the timolol compound (aspect 76).

In aspects, the invention provides the composition of aspect 76, wherein the composition comprises a solubilization component, and wherein the solubilization component comprises any one or more of the constituents described in any one or more of aspects 8-29 (aspect 77).

In aspects, the invention provides the composition of any one or more of aspects 1-77, wherein the total amount of any constituent(s) of the penetration enhancer component, the solubilization component, or both the penetration enhancer component and the solubilization component in the composition represents about 0.1% w/v-about 5% w/v of the composition (aspect 78).

In aspects, the invention provides the composition of any one or more of aspects 1-78, wherein the composition comprises a tonicity component comprising one or more constituents which provides a detectable or significant impact on the osmolality of the composition (aspect 79).

In aspects, the invention provides the composition of any one or more of aspects 1-79, wherein the composition comprises a tonicity component and the tonicity component comprises one or more constituents present in an amount sufficient to establish the osmolality of the composition at between about 280 mOsm/Kg-about 370 mOsm/Kg (aspect 80).

In aspects, the invention provides the composition of any one or more of aspects 1-80, wherein the composition comprises a tonicity component and the tonicity component is present in the composition in an amount representing about 0.005% w/v-about 1% w/v of the composition (aspect 81).

In aspects, the invention provides the composition of any one or more of aspects 1-81, wherein the composition comprises a tonicity component and the tonicity component comprises sodium chloride (aspect 82).

In aspects, the invention provides the composition of any one or more of aspects 1-82, wherein the composition comprises sodium chloride in an amount representing about 0.5% w/v-about 1% w/v of the composition (aspect 83). 1-83, wherein the composition comprises sodium chloride in an amount representing about 0.7% w/v-about 0.9% w/v of the composition (aspect 84).

In aspects, the invention provides the composition of any one or more of aspects 1-84, wherein the composition comprises sodium chloride in an amount representing about 0.8% w/v of the composition (aspect 85).

In aspects, the invention provides the composition of any one or more of aspects 1-85, wherein the composition comprises a tonicity component and wherein the tonicity component does not comprise sodium chloride (aspect 86).

In aspects, the invention provides the composition of any one or more of aspects 1-86, wherein the composition comprises a tonicity component and wherein the tonicity component comprises mannitol (aspect 87).

In aspects, the invention provides the composition of any one or more of aspects 1-87, wherein the composition comprises mannitol in an amount representing about 2% w/v-about 6% w/v of the composition (aspect 88).

In aspects, the invention provides the composition of any one or more of aspects 1-88, wherein the composition comprises mannitol in an amount representing about 3% w/v-about 5% w/v of the composition (aspect 89).

In aspects, the invention provides the composition of any one or more of aspects 1-89, wherein the composition comprises mannitol in an amount representing about 4% w/v of the composition (aspect 90).

In aspects, the invention provides the composition of any one or more of aspects 1-90, wherein the composition comprises mannitol in an amount representing about 4.05% w/v of the composition (aspect 91).

In aspects, the invention provides the composition of any one or more of aspects 1-91, wherein the composition does not comprise mannitol (aspect 92).

In aspects, the invention provides the composition of any one or more of aspects 1-92, wherein the composition comprises a buffer component capable of maintaining the pH of the composition at about 6.2-about 7, or, e.g., about 6.9-about 7.5 (aspect 93).

In aspects, the invention provides the composition of any one or more of aspects 1-93, wherein the composition does not comprise a buffer component (aspect 94). 1-94, wherein the composition comprises a buffer component comprising at least one buffer component constituent (aspect 95).

In aspects, the invention provides the composition of any one or more of aspects 1-95, wherein the composition comprises a buffer component comprising at least two buffer component constituents (aspect 96).

In aspects, the invention provides the composition of any one or more of aspects 1-96, wherein the composition comprises a buffer component comprising a phosphate buffer constituent, a citrate buffer constituent, or both phosphate buffer and citrate buffer constituents (aspect 97).

In aspects, the invention provides the composition of any one or more of aspects 1-97, wherein the composition comprises a buffer component comprising a phosphate buffer in an amount representing about 0.1% w/v-about 0.4% w/v of the composition (aspect 98).

In aspects, the invention provides the composition of any one or more of aspects 1-98, wherein the composition comprises a buffer component comprising a phosphate buffer in an amount representing about 0.15% w/v-about 0.3% w/v of the composition (aspect 99).

In aspects, the invention provides the composition of any one or more of aspects 1-99, wherein the composition comprises a buffer component comprising a phosphate buffer in an amount representing about 0.2% w/v-about 0.3% w/v of the composition (aspect 100).

In aspects, the invention provides the composition of any one or more of aspects 1-100, wherein the composition comprises a buffer component comprising a phosphate buffer in an amount representing 0.268% w/v of the composition (aspect 101).

In aspects, the invention provides the composition of any one or more of aspects 1-101, wherein the composition comprises a buffer component comprising dibasic sodium phosphate (aspect 102).

In aspects, the invention provides the composition of any one or more of aspects 1-102, wherein the composition comprises a buffer component comprising a citrate buffer in an amount representing about 0.005% w/v-about 0.03% w/v of the composition (aspect 103).

In aspects, the invention provides the composition of any one or more of aspects 1-103, wherein the composition comprises a buffer component comprising a citrate buffer in an amount representing about 0.009% w/v-about 0.02% w/v of the composition (aspect 104). 1-104, wherein the composition comprises a buffer component comprising a citrate buffer in an amount representing about 0.01% w/v-about 0.02% w/v of the composition (aspect 105).

In aspects, the invention provides the composition of any one or more of aspects 1-105, wherein the composition comprises a buffer component comprising a citrate buffer in an amount representing about 0.014% w/v of the composition (aspect 106).

In aspects, the invention provides the composition of any one or more of aspects 1-106, wherein the composition comprises a buffer component comprising citric acid monohydrate (aspect 107).

In aspects, the invention provides the composition of any one or more of aspects 1-107, wherein the composition comprises a buffer component comprising a phosphate buffer in an amount of about 0.1% w/v-about 0.4% w/v of the composition and citrate buffer in an amount of about 0.005% w/v-about 0.03% w/v of the composition (aspect 108).

In aspects, the invention provides the composition of any one or more of aspects 1-108, wherein the composition comprises a buffer component comprising a phosphate buffer in an amount of about 0.2% w/v-about 0.3% w/v of the composition and citrate buffer in an amount of about 0.01% w/v-about 0.02% w/v of the composition (aspect 109).

In aspects, the invention provides the composition of any one or more of aspects 1-109, wherein the composition comprises a buffer component comprising a phosphate buffer in an amount of about 0.268% w/v of the composition and citrate buffer in an amount of about 0.014% w/v of the composition (aspect 110).

In aspects, the invention provides the composition of any one or more of aspects 1-110, wherein the composition comprises a viscosity enhancer component which detectably or significantly increases the viscosity of the composition (1) upon exposure to the environment of the mammalian eye to which it is administered, (2) upon exposure to temperatures of at least about 32 degrees Celsius (° C.), (3) upon exposure to an environment having an ionic strength detectably or significantly greater than that of one or more gelling agents present in the composition (e.g., gellan gum), (4) exposure to an environment having a pH of greater than about 6.2, or (5) any combination of (1)-(4), over the viscosity of the composition while stored prior to administration at a temperature of between about 15° C. to about 25° C.+/−2° C.) (aspect 111).

In aspects, the invention provides the composition of any one or more of aspects 1-111, wherein the composition does not comprise a viscosity enhancer component (aspect 112). 1-112, wherein the composition comprises gellan gum (aspect 113).

In aspects, the invention provides the composition of any one or more of aspects 1-113, wherein the composition comprises gellan gum in an amount representing about 0.4% w/v about 0.8% w/v of the composition (aspect 114).

In aspects, the invention provides the composition of any one or more of aspects 1-114, wherein the composition comprises gellan gum in an amount representing about 0.5% w/v-about 0.7% w/v of the composition (aspect 115).

In aspects, the invention provides the composition of any one or more of aspects 1-115, wherein the composition comprises gellan gum in an amount representing about 0.6% w/v of the composition (aspect 116).

In aspects, the invention provides the composition of any one or more of aspects 1-116, wherein the composition comprises a preservation component comprising one or more constituents which (1) prevents the detectable or significant degradation (e.g., loss of more than about 1%, about 2%, about 3%, about 4%, or loss of more than about 5%) of the bimatoprost compound, the detectable or significant degradation (e.g., loss of more than about 1%, about 2%, about 3%, about 4%, or loss of more than about 5%) of the timolol compound, or the detectable or significant degradation (e.g., loss of more than about 1%, about 2%, about 3%, about 4%, or loss of more than about 5%) of each of the bimatoprost compound and the timolol compound, (2) prevents detectable or significant microbial growth in the composition such that the composition becomes unsuitable (unsafe) for use, (3) prevents the accumulation of a detectable or significant level of impurities such that the composition becomes unsuitable for use, e.g., would fail to meet requirements for impurities established by a recognized regulatory body such as the United States Food and Drug Administration, or (4) any combination of (1)-(4) such that the composition remains suitable for use when stored at about 25° C.+/−2° C. and about 65% relative humidity, when stored at about 40° C.+/−2° C. and about 75% relative humidity, or when stored under either condition, or a sequential combination of such conditions, for at least about 1 month, such as at least about 3, 6, 9, or 12 months or more (aspect 117).

In aspects, the invention provides the composition of any one or more of aspects 1-117, wherein the composition comprises a preservation component comprising at least one constituent which provides detectable or significant preservation activity and detectable or significant penetration enhancement of the bimatoprost compound, the timolol compound, or both the bimatoprost compound and the timolol compound (aspect 118). 1-118, wherein the composition comprises a preservation component comprising one or more constituents which is not benzalkonium chloride, in addition to benzalkonium chloride present in the composition (aspect 119).

In aspects, the invention provides the composition of any one or more of aspects 1-120, wherein the only component of the preservation component is the benzalkonium chloride described in any one or more of aspects 41-43 (aspect 120).

In aspects, the invention provides the composition of any one or more of aspects 1-120, wherein the composition comprises a chelation component comprising one or more constituents providing detectable or significant chelation activity (aspect 121).

In aspects, the invention provides the composition of any one or more of aspects 1-121, wherein the composition does not comprise any constituent providing detectable or significant chelation activity (aspect 122).

In aspects, the invention provides the composition of any one or more of aspects 1-122, wherein the composition comprises a carrier component (aspect 123).

In aspects, the invention provides the composition of any one or more of aspects 1-123, wherein the composition comprises a carrier component and wherein the carrier component is at least substantially comprised of water (aspect 124).

In aspects, the invention provides the composition of any one or more of aspects 1-124, wherein the composition comprises water in an amount representing at least about 50% w/v of the composition (aspect 125).

In aspects, the invention provides the composition of any one or more of aspects 1-125, wherein the composition comprises water in an amount representing at least about 75% w/v of the composition (aspect 126).

In aspects, the invention provides the composition of any one or more of aspects 1-126, wherein the composition comprises water in an amount representing at least about 90% w/v of the composition (aspect 127).

In aspects, the invention provides the composition of any one or more of aspects 1-127, wherein the composition is characterizable as an aqueous composition (aspect 128).

In aspects, the invention provides the composition of any one or more of aspects 1-128, wherein the composition comprises a pH adjusting component comprising one or more constituents in sufficient amounts to establish the pH of the composition at about 6.2-about 7.8, such as, e.g., about 6.2-about 7, or, e.g., or about 6.9-about 7.5 (aspect 129). 1-129, wherein the composition comprises a pH adjusting component comprising one or both of sodium hydroxide and hydrochloric acid (aspect 130).

In aspects, the invention provides the composition of any one or more of aspects 1-130, wherein the composition comprises a pH adjusting component comprising one or both of sodium hydroxide and hydrochloric acid in an amount sufficient to establish the pH of the composition at about 6.2-about 7.8, such as, e.g., about 6.2-about 7 or, e.g., about 6.9-about 7.5 (aspect 131).

In aspects, the invention provides the composition of any one or more of aspects 1-131, wherein the composition comprises a pH adjusting component comprising hydrochloric acid in an amount sufficient to establish the pH of the composition at about 6.2-about 7.8, such as, e.g., about 6.2-about 7 or, e.g., about 6.9-about 7.5 (aspect 132).

In aspects, the invention provides the composition of any one or more of aspects 1-132, wherein the composition comprises a pH adjusting component comprising sodium chloride and hydrochloric acid in an amount sufficient to establish the pH of the composition at about 6.2-about 7.8, such as, e.g., about 6.2-about 7 or, e.g., about 6.9-about 7.5 (aspect 133).

In aspects, the invention provides the composition of any one or more of aspects 1-133, wherein the composition maintains a pH of about 6.2 to about 7.8, such as, e.g., about 6.2-about 7, or, e.g., about 6.9-about 7.5, when storage at about 15° C.-about 27° C. and about 60% relative humidity, after storage at about 38° C.-about 42° C. and 75% relative humidity, or after storage under either condition, or a sequential combination of such conditions, for at least about one month, such as 1-3 months, 2-6 months, 5-9 months, 8-12 months, 10-18 months, 12-24 months, 20-30 months, 28-36 months, or for more than 36 months (aspect 134).

In aspects, the invention provides the composition of any one or more of aspects 1-134, wherein the composition maintains a pH of about 6.2 to about 7.8, such as, e.g., about 6.2-about 7 or, e.g., 6.9-about 7.5 when storage at about 15° C.-about 27° C. and about 60% relative humidity, after storage at about 38° C.-about 42° C. and 75% relative humidity, or after storage under either condition, or a sequential combination of such conditions, for at least about one month, such as 1-3 months, 2-6 months, 5-9 months, 8-12 months, 10-18 months, 12-24 months, 20-30 months, 28-36 months, or for more than 36 months (aspect 135).

In aspects, the invention provides the composition of any one or more of aspects 1-135, wherein the composition maintains a pH of about 6.2-about 7 when storage at about 15° C.-about 27° C. and about 60% relative humidity, after storage at about 38° C.-about 42° C. and 75% relative humidity, or after storage under either condition, or a sequential combination of such conditions, for at least about one month, such as 1-3 months, 2-6 months, 5-9 months, 8-12 months, 10-18 months, 12-24 months, 20-30 months, 28-36 months, or for more than 36 months (aspect 136).

In aspects, the invention provides the composition of any one or more of aspects 1-136, wherein the composition maintains a pH of about 6.9 to about 7.5 or, e.g., about 7.1 to about 7.3 when storage at about 15° C.-about 27° C. and about 60% relative humidity, after storage at about 38° C.-about 42° C. and 75% relative humidity, or after storage under either condition, or a sequential combination of such conditions, for at least about one month, such as 1-3 months, 2-6 months, 5-9 months, 8-12 months, 10-18 months, 12-24 months, 20-30 months, 28-36 months, or for more than 36 months (aspect 137).

In aspects, the invention provides the composition of any one or more of aspects 1-137, wherein the composition has a pH of about 6.2-about 7.8 (aspect 138).

In aspects, the invention provides the composition of any one or more of aspects 1-138, wherein the composition has a pH of about 6.2-about 7.5 (aspect 139).

In aspects, the invention provides the composition of any one or more of aspects 1-139, wherein the composition has a pH of about 6.2-about 7 (aspect 140).

In aspects, the invention provides the composition of any one or more of aspects 1-140, wherein the composition has a pH of about 6.9-about 7.5 (aspect 141).

In aspects, the invention provides the composition of any one or more of aspects 1-141, wherein the composition has a pH of about 7.0-about 7.4 (aspect 142).

In aspects, the invention provides the composition of any one or more of aspects 1-141, wherein the composition has a pH of about 7.1-about 7.3 (aspect 143).

In aspects, the invention provides the composition of any one or more of aspects 1-143, wherein the composition has an osmolality of between about 270-about 370 mOsm/Kg (aspect 144).

In aspects, the invention provides the composition of any one or more of aspects 1-144, wherein the composition has an osmolality of between about 280-about 330 mOsm/Kg (aspect 145).

In aspects, the invention provides the composition of any one or more of aspects 1-145, wherein the composition is suitable for use in methods of treating one or more ocular conditions selected from the group consisting of glaucoma, elevated intraocular pressure, elevated intraocular pressure associated with glaucoma (such as, e.g., associated with open-angle glaucoma), visual impairment associated with elevated intraocular pressure, or any combination thereof (aspect 146).

In aspects, the invention provides the composition of any one or more of aspects 1-146, wherein the composition is suitable for use in methods of treating elevated intraocular pressure such as elevated intraocular pressure associated with glaucoma, e.g., open-angle glaucoma (aspect 147).

In aspects, the invention provides the composition of any one or more of aspects 1-147, wherein the composition is distributed into single-dose or multidose containers (aspect 148).

In aspects, the invention provides the composition of any one or more of aspects 1-148, wherein the composition is distributed into single-dose containers (aspect 149).

In aspects, the invention provides the composition of any one or more of aspects 1-148, wherein the composition is distributed into multidose containers (aspect 150).

In aspects, the invention provides the composition of any one or more of aspects 1-150, wherein the composition maintains at least about 97% of the bimatoprost compound and at least 97% of the timolol compound when stored at about 25° C.+/−2° C. and about 65% relative humidity, when stored at about 40° C.+/−2° C. and about 75% relative humidity, or when stored under either condition, or a sequential combination of such conditions, for at least about one month, e.g., at least about 2 months, at least about 3 months, at least about 2-about 6 months, about 3-about 9 months, about 6-about 12 months, about 9-about 18 months, about 12-about 24 months, about 18-about 30 months, about 24-about 36 months, or, e.g., for at least about 36 months (aspect 151).

In aspects, the invention provides the composition of any one or more of aspects 1-151, wherein the composition maintains at least about 98% of the bimatoprost compound and at least 97% of the timolol compound when stored at about 25° C.+/−2° C. and about 65% relative humidity, when stored at about 40° C.+/−2° C. and about 75% relative humidity, or when stored under either condition, or a sequential combination of such conditions, for at least about one month, e.g., at least about 2 months, at least about 3 months, at least about 2-about 6 months, about 3-about 9 months, about 6-about 12 months, about 9-about 18 months, about 12-about 24 months, about 18-about 30 months, about 24-about 36 months, or, e.g., for at least about 36 months (aspect 152). 1-152, wherein the composition maintains at least about 99% of the bimatoprost compound and at least 97% of the timolol compound when stored at about 25° C.+/−2° C. and about 65% relative humidity, when stored at about 40° C.+/−2° C. and about 75% relative humidity, or when stored under either condition, or a sequential combination of such conditions, for at least about one month, e.g., at least about 2 months, at least about 3 months, at least about 2-about 6 months, about 3-about 9 months, about 6-about 12 months, about 9-about 18 months, about 12-about 24 months, about 18-about 30 months, about 24-about 36 months, or, e.g., for at least about 36 months (aspect 153).

In aspects, the invention provides the composition of any one or more of aspects 1-156, wherein the composition comprises less than about 2.5% total impurities after storage at about 15° C.-about 27° C. and about 60% relative humidity, after storage at about 38° C.-about 42° C. and 75% relative humidity, or after storage under either condition, for a sequential combination of such conditions, or a period of at least about 1 month, e.g., at least about 2 months, at least about 3 months, at least about 2-about 6 months, about 3-about 9 months, about 6-about 12 months, about 9-about 18 months, about 12-about 24 months, about 18-about 30 months, about 24-about 36 months, or, e.g., for at least about 36 months (aspect 154).

In one aspect, the invention provides a pharmaceutically acceptable and ophthalmologically suitable composition for treating an ocular condition in a mammalian eye comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; (4) about 0.25% w/v-about 2.5% w/v of a penetration enhancer component; and (5) optionally one or more excipients, wherein the ratio of the quaternary ammonium salt to the penetration enhancer component is between about 1:35-about 1:840, and wherein the composition is stable when stored at about 25° C.+/−2° C. and about 65% relative humidity, when stored at about 40° C.+/−2° C. and about 75% relative humidity, or when stored under either condition, or a sequential combination of such conditions, for at least about 1 month, e.g., at least about 2 months, at least about 3 months, at least about 2-about 6 months, about 3-about 9 months, about 6-about 12 months, about 9-about 18 months, about 12-about 24 months, about 18-about 30 months, about 24-about 36 months, or, e.g., for at least about 36 months (aspect 155).

In one aspect, the invention provides a pharmaceutically acceptable and ophthalmologically suitable composition for treating an ocular condition in a mammalian eye comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; and (4) about 0.25% w/v-about 2.5% w/v of a penetration enhancer component, wherein the ratio of the bimatoprost compound to the penetration enhancer component is about 1:12.5-about 1:500, wherein the composition is stable when stored at about 25° C.+/−2° C. and about 65% relative humidity, when stored at about 40° C.+/−2° C. and about 75% relative humidity, or when stored under either condition, or a sequential combination of such conditions, for at least about 1 month, e.g., at least about 2 months, at least about 3 months, at least about 2-about 6 months, about 3-about 9 months, about 6-about 12 months, about 9-about 18 months, about 12-about 24 months, about 18-about 30 months, about 24-about 36 months, or, e.g., for at least about 36 months (aspect 156).

In one aspect, the invention provides a pharmaceutically acceptable and ophthalmologically suitable composition for treating an ocular condition in a mammalian eye comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; and (4) about 0.25% w/v-about 2.5% w/v of a penetration enhancer component, wherein the ratio of the timolol compound to the penetration enhancer component is between about 3.2:1-1:6.3 (e.g., ~3.2:1-~1:6.25), wherein the composition is stable when stored at about 25° C.+/−2° C. and about 65% relative humidity, when stored at about 40° C.+/−2° C. and about 75% relative humidity, or when stored under either condition, or a sequential combination of such conditions, for at least about 1 month, e.g., at least about 2 months, at least about 3 months, at least about 2-about 6 months, about 3-about 9 months, about 6-about 12 months, about 9-about 18 months, about 12-about 24 months, about 18-about 30 months, about 24-about 36 months, or, e.g., for at least about 36 months (aspect 157).

In aspects, the invention provides the composition of any one or more of aspects 155-157, wherein the composition further comprises any one or more of the characteristics described in any one or more of aspects 1-154 (aspect 158).

In aspects, the invention provides the composition of any one or more of aspects 1-154, wherein the composition is provided in the form of a solution, suspension, ointment, gel, emulsion, oil, or other dosage form suitable for topical administration to the mammalian eye (aspect 159).

In aspects, the invention provides the composition of any one or more of aspects 1-159, wherein the composition is provided in the form of a solution (aspect 160). 1-159, wherein the composition is provided in the form of a gel (aspect 161).

In one aspect, the invention provides a pharmaceutically acceptable and ophthalmologically suitable composition in the form of a solution for treating an ocular condition in a mammalian eye comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; and (4) about 0.25% w/v-about 2.5% w/v of a penetration enhancer component, wherein the ratio of the quaternary ammonium salt to the penetration enhancer component is between about 1:36-about 1:834 (aspect 162).

In one aspect, the invention provides a pharmaceutically acceptable and ophthalmologically suitable composition in the form of a solution for treating an ocular condition in a mammalian eye comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; (4) about 0.25% w/v-about 2.5% w/v of a penetration enhancer component; and (5) optionally one or more excipients, wherein the ratio of the quaternary ammonium salt to the penetration enhancer component is between about 1:36-about 1:834, and wherein the composition is stable when stored at about 25° C.+/−2° C. and about 65% relative humidity, when stored at about 40° C.+/−2° C. and about 75% relative humidity, or when stored under either condition, or a sequential combination of such conditions, for at least about 1 month, e.g., at least about 2 months, at least about 3 months, at least about 2-about 6 months, about 3-about 9 months, about 6-about 12 months, about 9-about 18 months, about 12-about 24 months, about 18-about 30 months, about 24-about 36 months, or, e.g., for at least about 36 months (aspect 163).

In one aspect, the invention provides a pharmaceutically acceptable and ophthalmologically suitable composition in the form of a gel for treating an ocular condition in a mammalian eye comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; and (4) about 0.25% w/v-about 2.5% w/v of a penetration enhancer component, wherein the ratio of the quaternary ammonium salt to the penetration enhancer component is between about 1:36-about 1:834 (aspect 164).

In one aspect, the invention provides a pharmaceutically acceptable and ophthalmologically suitable composition in the form of a gel for treating an ocular condition in a mammalian eye comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; (4) about 0.25% w/v-about 2.5% w/v of a penetration enhancer component; and (5) optionally one or more excipients, wherein the ratio of the quaternary ammonium salt to the penetration enhancer component is between about 1:25-about 1:2500, and wherein the composition is stable when stored at about 25° C.+/−2° C. and about 65% relative humidity, when stored at about 40° C.+/−2° C. and about 75% relative humidity, or when stored under either condition, or a sequential combination of such conditions, for at least about 1 month, e.g., at least about 2 months, at least about 3 months, at least about 2-about 6 months, about 3-about 9 months, about 6-about 12 months, about 9-about 18 months, about 12-about 24 months, about 18-about 30 months, about 24-about 36 months, or, e.g., for at least about 36 months (aspect 165).

In aspects, the invention provides the compositions of any one or both of aspects 164-165, wherein the ratio of bimatoprost compound, e.g., bimatoprost base, to the viscosity enhancer component is about 1:2 to about 1:1000 (aspect 166).

In aspects, the invention provides the composition of aspect 166, wherein the ratio of bimatoprost compound, e.g., bimatoprost base, to the viscosity enhancer component is about 1:1 to about 1:500 (aspect 167).

In aspects, the invention provides the compositions of aspect 167, wherein the ratio of bimatoprost compound, e.g., bimatoprost base, to the viscosity enhancer component is about 1:1 to about 1:100 (aspect 168).

In aspects, the invention provides the composition of aspect 168, wherein the ratio of bimatoprost compound, e.g., bimatoprost base, to the viscosity enhancer component is about 1:60 (aspect 169).

In aspects, the invention provides any one or more of the compositions of aspects 164-169, wherein the ratio of timolol compound, e.g., a salt of timolol, e.g., timolol maleate, to the viscosity enhancer component is about 10:1 to about 1:10 (aspect 170).

In aspects, the invention provides the composition of aspect 170, wherein the ratio of timolol compound, e.g., a salt of timolol, e.g., timolol maleate, to the viscosity enhancer component is about 5:1 to about 1:5 (aspect 171).

In aspects, the invention provides the composition of aspect 171, wherein the ratio of timolol compound, e.g., a salt of timolol, e.g., timolol maleate, to the viscosity enhancer component is about 2:1 to about 1:2 (aspect 172).

In aspects, the invention provides the composition of aspect 172, wherein the ratio of timolol compound, e.g., a salt of timolol, e.g., timolol maleate, to the viscosity enhancer component is about 1.13:1 (aspect 173).

In aspects, the invention provides the composition of any one or more of aspects 164-173, wherein the composition comprises a viscosity enhancer component and wherein the ratio of the total amount of API consisting of the bimatoprost compound, e.g., bimatoprost base, and the timolol compound, e.g., salt of timolol, e.g., timolol maleate, to the viscosity enhancer component is about 10.5:1 to about 1:9.9 (aspect 174).

In aspects, the invention provides the composition of aspect 174, wherein the ratio of the total amount of API consisting of the bimatoprost compound, e.g., bimatoprost base, and the timolol compound, e.g., salt of timolol, e.g., timolol maleate, to the viscosity enhancer component is about 5:1 to about 1:5 (aspect 175).

In aspects, the invention provides the composition of aspect 175, wherein the ratio of the total amount of API consisting of the bimatoprost compound, e.g., bimatoprost base, and the timolol compound, e.g., salt of timolol, e.g., timolol maleate, to the viscosity enhancer component is about 3:1 to about 1:2 (aspect 176).

In aspects, the invention provides the composition of aspect 176, wherein the ratio of the total amount of API consisting of the bimatoprost compound, e.g., bimatoprost base, and the timolol compound, e.g., salt of timolol, e.g., timolol maleate, to the viscosity enhancer component is about 1:1.15 (aspect 177).

In aspects, the invention provides the composition of any one or more of aspects 164-177, wherein the composition further comprises any one or more of the characteristics described in any one or more of aspects 1-154 (aspect 178).

In one aspect, the invention provides a pharmaceutically acceptable and ophthalmologically suitable gel composition for treating an ocular condition in a mammalian eye comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt, and (4) about 0.1% w/v-about 1% w/v of a viscosity enhancing component, wherein the viscosity of the composition detectably or significantly increases (a) upon exposure to the environment of the mammalian eye to which it is administered, (b) upon exposure to temperatures of at least about 32 degrees Celsius (° C.), (c) upon exposure to an environment having an ionic strength detectably or significantly greater than that of one or more gelling agents present in the composition (e.g., gellan gum), (d) exposure to an environment having a pH of greater than about 6.2, or (e) any combination of (a)-(d), over the viscosity of the composition while stored prior to administration at a temperature of between about 15° C. to about 25° C.+/−2° C.) (aspect 179).

In one aspect, the invention provides a pharmaceutically acceptable and ophthalmologically suitable gel composition for treating an ocular condition in a mammalian eye comprising (1) about 0.005% w/v-about 0.02% w/v of a bimatoprost compound; (2) about 0.4% w/v-about 0.8% w/v of a timolol compound; and (3) about 0.003%-about 0.007% of a quaternary ammonium salt, wherein the viscosity of the composition detectably or significantly increases (a) upon exposure to the environment of the mammalian eye to which it is administered, (b) upon exposure to temperatures of at least about 32 degrees Celsius (° C.), (d) upon exposure to an environment having an ionic strength detectably or significantly greater than that of one or more gelling agents present in the composition (e.g., gellan gum), (d) exposure to an environment having a pH of greater than about 6.2, or (e) any combination of (a)-(d), over the viscosity of the composition while stored prior to administration at a temperature of between about 15° C. to about 25° C.+/−2° C.), wherein the composition is stable when stored at about 25° C.+/−2° C. and about 65% relative humidity, when stored at about 40° C.+/−2° C. and about 75% relative humidity, or when stored under either condition, or a sequential combination of such conditions (aspect 180).

In one aspect, the invention provides the composition of aspect 180, wherein the composition further comprises about 0.1% w/v-about 1% w/v of a viscosity enhancing component (aspect 181).

In one aspect, the invention provides a pharmaceutically acceptable and ophthalmologically suitable gel composition for treating an ocular condition in a mammalian eye comprising (1) about 0.005% w/v-about 0.02% w/v of a bimatoprost compound, and (2) about 0.4% w/v-about 0.8% w/v of a timolol compound (aspect 182).

In one aspect, the invention provides a pharmaceutically acceptable and ophthalmologically suitable gel composition for treating an ocular condition in a mammalian eye comprising (1) about 0.005% w/v-about 0.02% w/v of a bimatoprost compound, and (2) about 0.4% w/v-about 0.8% w/v of a timolol compound, wherein (a) upon exposure to the environment of the mammalian eye to which it is administered, (b) upon exposure to temperatures of at least about 32 degrees Celsius (° C.), (d) upon exposure to an environment having an ionic strength detectably or significantly greater than that of one or more gelling agents present in the composition (e.g., gellan gum), (d) exposure to an environment having a pH of greater than about 6.2, or (e) any combination of (a)-(d), over the viscosity of the composition while stored prior to administration at a temperature of between about 15° C. to about 25° C.+/−2° C.), wherein the composition is stable when stored at about 25° C.+/−2° C. and about 65% relative humidity, when stored at about 40° C.+/−2° C. and about 75% relative humidity, or when stored under either condition, or a sequential combination of such conditions (aspect 183).

In aspects, the invention provides the composition of any one or both of aspect 182 or aspect 183, wherein the composition further comprises a preservative component (aspect 184).

In aspects, the invention provides the composition of aspect 184, wherein the preservative component comprises one or more quaternary ammonium salts (aspect 185).

In aspects, the invention provides the composition of aspect 185, wherein the preservative component is at least substantially comprised of benzalkonium chloride (aspect 186).

In aspects, the invention provides the composition of aspect 186, wherein the composition comprises benzalkonium chloride in an amount representing about 0.003% w/v-about 0.007% w/v of the composition (aspect 187).

In aspects, the invention provides the composition of any one or more of aspects 182-187, wherein the composition comprises a penetration enhancer component (aspect 188).

In aspects, the invention provides the composition of aspect 188, wherein the penetration enhancer component is present in the composition in an amount of between about 0.25% w/v-about 2.5% w/v of the composition (aspect 189).

In aspects, the invention provides the composition of aspect 189, wherein the penetration component is at least substantially comprised of one or more compounds selected from a group consisting of polyethylene sorbitan fatty acid esters, tocopherol polyethylene glycol succinate (TPGS), and polyoxyl hydrogenated castor oil (aspect 190).

In aspects, the invention provides the composition of aspect 190, wherein the penetration enhancer component is at least substantially comprised of a polyethylene sorbitan fatty acid ester selected from the group consisting of polyoxyethylene sorbitan laurate (polysorbate 20), polyoxyethylene sorbitan palmitate (polysorbate 40), a polyoxyethylene sorbitan stearate (polysorbate 60), a polyoxyethylene sorbitan tri stearate (polysorbate 65), or a polyoxyethylene sorbitan oleate/polyoxyethylene sorbitan mono-oleate ester (e.g., polysorbate 80), or a combination thereof (aspect 191).

In aspects, the invention provides the composition of aspect 191, wherein the penetration enhancer component is at least substantially comprised of polysorbate 20, polysorbate 80, or a combination of polysorbate 20 and polysorbate 80 (aspect 192).

In aspects, the invention provides the composition of aspect 192, wherein the penetration enhancer component is at least substantially comprised of polysorbate 80 (aspect 193).

In aspects, the invention provides the composition of aspect 190, wherein the penetration enhancer component is at least substantially comprised of TPGS (aspect 194).

In aspects, the invention provides the composition of aspect 190, wherein the penetration enhancer component is at least substantially comprised of a constituent characterizable as a polyoxyl hydrogenated castor oil (aspect 195).

In aspects, the invention provides the composition of aspect 195, wherein the penetration enhancer component is at least substantially comprised of polyoxyl 35 castor oil (cremophor EL) (aspect 196).

In aspects, the invention provides the composition of any one or more of aspects 188-196, wherein the composition comprises both a preservative component comprising a quaternary ammonium salt (e.g., benzalkonium chloride) and a penetration enhancer component, wherein the ratio of the quaternary ammonium salt (e.g., benzalkonium chloride) to the penetration enhancer component is about 1: about 35 to about 1: about 840 (aspect 197).

In aspects, the invention provides the composition of aspect 197, wherein the ratio of the quaternary ammonium salt (e.g., benzalkonium chloride) to the penetration enhancer component is about 1: about 100 to about 1: about 300 (aspect 198).

In aspects, the invention provides the composition of aspect 198, wherein the ratio of the quaternary ammonium salt (e.g., benzalkonium chloride) to the penetration enhancer component is about 1: about 200 (aspect 199).

In aspects, the invention provides the composition of any one or more of aspects 179-199, wherein the composition further comprises at least one constituent characterizable as a solubilizer, e.g., tromethamine (aspect 200).

In aspects, the invention provides the composition of aspect 200, wherein the composition comprises a penetration enhancer component and wherein the penetration enhancer component comprises at least one constituent which detectably or significantly increases the solubilization of one or more active pharmaceutical ingredients in the composition (e.g., bimatoprost compound, timolol compound, or both), such that the composition comprises at least two solubilization constituents which each provide detectable or significant solubilization effect (e.g., each detectably or significantly increase the solubilization of one or more active pharmaceutical ingredients such as bimatoprost compound, timolol compound, or both) (aspect 201).

In aspects, the invention provides the compositions of any one or more of aspects 179-201, wherein the ratio of bimatoprost compound, e.g., bimatoprost base, to the viscosity enhancer component, when present in the composition, is about 1:2 to about 1:1000 (aspect 202).

In aspects, the invention provides the composition of aspect 202, wherein the ratio of bimatoprost compound, e.g., bimatoprost base, to the viscosity enhancer component, when present in the composition, is about 1:1 to about 1:500 (aspect 203).

In aspects, the invention provides the compositions of aspect 203, wherein the ratio of bimatoprost compound, e.g., bimatoprost base, to the viscosity enhancer component, when present in the composition, is about 1:1 to about 1:100 (aspect 204).

In aspects, the invention provides the composition of aspect 204, wherein the ratio of bimatoprost compound, e.g., bimatoprost base, to the viscosity enhancer component is about 1:60 (aspect 205).

In aspects, the invention provides any one or more of the compositions of aspects 179-205, wherein the ratio of timolol compound, e.g., a salt of timolol, e.g., timolol maleate, to the viscosity enhancer component, when present in the composition, is about 10:1 to about 1:10 (aspect 206).

In aspects, the invention provides the composition of aspect 206, wherein the ratio of timolol compound, e.g., a salt of timolol, e.g., timolol maleate, to the viscosity enhancer component is about 5:1 to about 1:5 (aspect 207).

In aspects, the invention provides the composition of aspect 207, wherein the ratio of timolol compound, e.g., a salt of timolol, e.g., timolol maleate, to the viscosity enhancer component is about 2:1 to about 1:2 (aspect 208).

In aspects, the invention provides the composition of aspect 208, wherein the ratio of timolol compound, e.g., a salt of timolol, e.g., timolol maleate, to the viscosity enhancer component is about 1.13:1 (aspect 209).

In aspects, the invention provides any one or more of the compositions of aspects 179-209, wherein the ratio of the total amount of API consisting of the bimatoprost compound, e.g., bimatoprost base, and the timolol compound, e.g., salt of timolol, e.g., timolol maleate, to the viscosity enhancer component is about 10.5:1 to about 1:9.9, such as, e.g., about 5:1 to about 1:5 or about 3:1 to about 1:2, e.g., about 1:1.15 (aspect 210).

In aspects, the invention provides the composition of any one or more of aspects 179-210, wherein the composition further comprises any one or more of the characteristics described in any one or more of aspects 1-154 (aspect 211).

In aspects, the invention provides the composition of any one or more of aspects 182-211, wherein the composition comprises about 0.1% w/v-about 1% w/v of a viscosity enhancing component (aspect 212).

In aspects, the invention provides a method of treating elevated intraocular pressure, glaucoma, or both, in a mammalian eye, the method comprising administration of an effective amount of a composition comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; and (4) about 0.25% w/v-about 2.5% w/v of a penetration enhancer component, wherein (1) the ratio of the quaternary ammonium salt to the penetration enhancer component is between about 1:35-about 1:840; (2) the ratio of the bimatoprost compound to the penetration enhancer component is about 1:12.5-about 1:500; (3) the ratio of the timolol compound to the penetration enhancer component is between about 3.2:1-1:6.3 (e.g., ~3.2:1-~1:6.25); or (4) any combination of (1), (2), and (3) are true (aspect 213).

In aspects, the invention provides a method of treating elevated intraocular pressure, glaucoma, or both, in a mammalian eye, the method comprising administration of an effective amount of a composition provided in the form of a solution comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; and (4) about 0.25% w/v-about 2.5% w/v of a penetration enhancer component, wherein (1) the ratio of the quaternary ammonium salt to the penetration enhancer component is between about 1:36-about 1:834; (2) the ratio of the bimatoprost compound to the penetration enhancer component is about 1:12.5-about 1:500; (3) the ratio of the timolol compound to the penetration enhancer component is between about 3.2:1-1:6.3 (e.g., ~3.2:1-~1:6.25); or (4) any combination of (1), (2), and (3) are true (aspect 214).

In aspects, the invention provides a method of treating elevated intraocular pressure, glaucoma, or both, in a mammalian eye, the method comprising administration of an effective amount of a gel composition comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; and (4) about 0.25% w/v-about 2.5% w/v of a penetration enhancer component, wherein (1) the ratio of the quaternary ammonium salt to the penetration enhancer component is between about 1:36-about 1:834; (2) the ratio of the bimatoprost compound to the penetration enhancer component is about 1:12.5-about 1:500; (3) the ratio of the timolol compound to the penetration enhancer component is between about 3.2:1-1:6.3 (e.g., ~3.2:1-~1:6.25); or (4) any combination of (1), (2), and (3) are true (aspect 215).

In aspects, the invention provides a method of treating elevated intraocular pressure, glaucoma, or both, in a mammalian eye, the method comprising administration of an effective amount of a gel composition comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt, and (4) wherein the viscosity of the composition detectably or significantly increases (1) upon exposure to the environment of the mammalian eye to which it is administered, (2) upon exposure to temperatures of at least about 32 degrees Celsius (° C.), (3) upon exposure to an environment having an ionic strength detectably or significantly greater than that of one or more of gelling agents present in the composition (e.g., gellan gum), (4) exposure to an environment having a pH of greater than about 6.2, or (5) any combination of (1)-(4), over the viscosity of the composition while stored prior to administration at a temperature of between about 15° C. to about 25° C.+/−2° C.), wherein the composition is stable when stored at about 25° C.+/−2° C. and about 65% relative humidity, when stored at about 40° C.+/−2° C. and about 75% relative humidity, or when stored under either condition, or a sequential combination of such conditions, for at least one month (aspect 216).

In aspects, the invention provides the method of any one or more of aspects 213-216, wherein the method is clinically demonstrated to be as effective or detectably or significantly more effective than treatment of the same or at least essentially the same, generally the same, or the same condition with about the same amount of a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide, and water for the same or similar indication (e.g., reducing IOP) and for at least substantially the same administration period as determined by one or more well-controlled and adequate clinical studies performed in compliance with generally prevailing regulatory authority standards (aspect 217).

In aspects, the invention provides the method of any one or more of aspects 213-217, wherein the method is clinically demonstrated to be as effective or detectably or significantly more effective than treatment of the same or at least essentially the same, generally the same, or the same condition with about the same amount of the product approved as European Medicines Agency product number EMEA/H/C/000668 for the same or similar indication (e.g., reducing IOP) and for at least substantially the same administration period (aspect 218).

In aspects, the invention provides the method of any one or more of aspects 213-218, wherein the method is clinically demonstrated to be as effective or detectably or significantly more effective than treatment of the same or at least essentially the same, generally the same, or the same condition with about the same amount of a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water for the same or similar indication (e.g., reducing IOP) and for at least substantially the same administration period (aspect 219).

In aspects, the invention provides the method of any one or more of aspects 1-219, wherein performance of the method results in a significantly lower level of any one or more of the adverse events reported in section 4.8 ("Undesirable Effects") of the product information sheet for the product approved as European Medicines Agency product number EMEA/H/C/000668 (GANFORT®), having first received market approval on May 19, 2006, first published on May 3, 2010, and available on the Web at: ema.europa.eu/en/documents/product-information/ganfort-epar-product-information_en.pdf (aspect 220).

In aspects, the invention provides the method of any one or more of aspects 213-220, wherein the effective amount is 1-2 drops of the composition administered once or twice daily over an effective treatment period, and wherein the method results in detectably or significantly reduced frequency of ocular redness compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 221).

In aspects, the invention provides the method of any one or more of aspects 213-221, wherein the effective amount is 1-2 drops of the composition administered once or twice daily over an effective treatment period, and wherein the method results in detectably or significantly reduced frequency of ocular burning compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 222).

In aspects, the invention provides the method of any one or more of aspects 213-222, wherein the effective amount is 1-2 drops of the composition administered once or twice daily over an effective treatment period, and wherein the method results in detectably or significantly reduced frequency of ocular itching compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 223).

In aspects, the invention provides the method of any one or more of aspects 213-223, wherein the effective amount is 1-2 drops of the composition administered once or twice daily over an effective treatment period, and wherein the method results in detectably or significantly reduced frequency of ocular stinging compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 224).

In aspects, the invention provides the method of any one or more of aspects 213-224, wherein the effective amount is 1-2 drops of the composition administered once or twice daily over an effective treatment period, and wherein the method results in detectably or significantly reduced frequency of conjunctival irritation (irritation of the conjunctiva) compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 225).

In aspects, the invention provides the method of any one or more of aspects 213-225, wherein the effective amount is 1-2 drops of the composition administered once or twice daily over an effective treatment period, and wherein the method results in detectably or significantly reduced frequency of sensitivity to light compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 226).

In aspects, the invention provides the method of any one or more of aspects 213-226, wherein the effective amount is 1-2 drops of the composition administered once or twice daily over an effective treatment period, and wherein the method results in detectably or significantly reduced frequency of eye pain compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 227).

In aspects, the invention provides the method of any one or more of aspects 213-227, wherein the effective amount is 1-2 drops of the composition administered once or twice daily over an effective treatment period, and wherein the method results in detectably or significantly reduced frequency of sticky eye(s) compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 228).

In aspects, the invention provides the method of any one or more of aspects 213-228, wherein the effective amount is 1-2 drops of the composition administered once or twice daily over an effective treatment period, and wherein the method results in detectably or significantly reduced frequency of dry eye(s) compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 229).

In aspects, the invention provides the method of any one or more of aspects 213-229, wherein the effective amount is 1-2 drops of the composition administered once or twice daily over an effective treatment period, and wherein the method results in detectably or significantly reduced frequency of the sensation that something is in the recipient's eye(s) compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 230).

In aspects, the invention provides the method of any one or more of aspects 213-230, wherein the effective amount is 1-2 drops of the composition administered once or twice daily over an effective treatment period, and wherein the method results in detectably or significantly reduced frequency of detectable or significant breaks in the surface of the eye either with or without associated inflammation compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 231).

In aspects, the invention provides the method of any one or more of aspects 213-231, wherein the effective amount is 1-2 drops of the composition administered once or twice daily over an effective treatment period, and wherein the method results in detectably or significantly reduced frequency of detectable or significant reduction in clear vision compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 232).

In aspects, the invention provides the method of any one or more of aspects 213-232, wherein the effective amount is 1-2 drops of the composition administered once or twice daily over an effective treatment period, and wherein the method results in detectably or significantly reduced frequency of redness and itching of the eyelid(s) compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 233).

In aspects, the invention provides the method of any one or more of aspects 213-233, wherein the effective amount is 1-2 drops of the composition administered once or twice daily over an effective treatment period, and wherein the method results in detectably or significantly reduced frequency of hair growth around treated eye(s) compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 234).

In aspects, the invention provides the method of any one or more of aspects 213-234, wherein the effective amount is 1-2 drops of the composition administered once or twice daily over an effective treatment period, and wherein the method results in detectably or significantly reduced frequency of darkening of the eyelid(s) compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 235).

In aspects, the invention provides the method of any one or more of aspects 213-235, wherein the effective amount is 1-2 drops of the composition administered once or twice daily over an effective treatment period, and wherein the method results in detectably or significantly reduced frequency of darkening of the skin color around the treated eye(s) compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 236).

In aspects, the invention provides the method of any one or more of aspects 213-236, wherein the effective amount is 1-2 drops of the composition administered once or twice daily over an effective treatment period, and wherein the method results in detectably or significantly reduced frequency of eyelash lengthening compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 237).

In aspects, the invention provides the method of any one or more of aspects 213-237, wherein the effective amount is 1-2 drops of the composition administered once or twice daily over an effective treatment period, and wherein the method results in detectably or significantly reduced frequency of ocular irritation compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 238).

In aspects, the invention provides the method of any one or more of aspects 213-238, wherein the effective amount is 1-2 drops of the composition administered once or twice daily over an effective treatment period, and wherein the method results in detectably or significantly reduced frequency of eye watering compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 239).

In aspects, the invention provides the method of any one or more of aspects 213-239, wherein the effective amount is 1-2 drops of the composition administered once or twice daily over an effective treatment period, and wherein the method results in detectably or significantly reduced frequency of swollen eyelid(s) compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 240).

In aspects, the invention provides the method of any one or more of aspects 213-240, wherein the effective amount is 1-2 drops of the composition administered once or twice daily over an effective treatment period, and wherein the method results in detectably or significantly reduced frequency of reduced vision compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 241).

In aspects, the invention provides the method of any one or more of aspects 213-241, wherein the effective amount is 1-2 drops of the composition administered once or twice daily over an effective treatment period, and wherein the method results in detectably or significantly reduced frequency of runny nose compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 242).

In aspects, the invention provides the method of any one or more of aspects 213-242, wherein the effective amount is 1-2 drops of the composition administered once or twice daily over an effective treatment period, and wherein the method results in detectably or significantly reduced frequency of headache compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 243).

In aspects, the invention provides the method of any one or more of aspects 213-243, wherein the effective amount is 1-2 drops of the composition administered once or twice daily over an effective treatment period, and wherein the method results in detectably or significantly reduced frequency of abnormal sensation(s) in the eye(s) compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a composition reference consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 244).

In aspects, the invention provides the method of any one or more of aspects 213-244, wherein the effective amount is 1-2 drops of the composition administered once or twice daily over an effective treatment period, and wherein the method results in detectably or significantly reduced frequency of iris inflammation compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 245).

In aspects, the invention provides the method of any one or more of aspects 213-245, wherein the effective amount is 1-2 drops of the composition administered once or twice daily over an effective treatment period, and wherein the method results in detectably or significantly reduced frequency of swollen conjunctiva compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 246).

In aspects, the invention provides the method of any one or more of aspects 213-246, wherein the effective amount is 1-2 drops of the composition administered once or twice daily over an effective treatment period, and wherein the method results in detectably or significantly reduced frequency of painful eyelid(s) compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 247).

In aspects, the invention provides the method of any one or more of aspects 213-247, wherein the effective amount is 1-2 drops of the composition administered once or twice daily over an effective treatment period, and wherein the method results in detectably or significantly reduced frequency of tired eye(s) compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 248).

In aspects, the invention provides the method of any one or more of aspects 213-248, wherein the effective amount is 1-2 drops of the composition administered once or twice daily over an effective treatment period, and wherein the method results in detectably or significantly reduced frequency of ingrown (in-growing) eyelash(es) compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 249).

In aspects, the invention provides the method of any one or more of aspects 213-249, wherein the effective amount is 1-2 drops of the composition administered once or twice daily over an effective treatment period, and wherein the method results in detectably or significantly reduced frequency of darkening iris color compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 250).

In aspects, the invention provides the method of any one or more of aspects 213-251, wherein the effective amount is 1-2 drops of the composition administered once or twice daily over an effective treatment period, and wherein the method results in detectably or significantly reduced frequency of sunken eye appearance compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 251).

In aspects, the invention provides the method of any one or more of aspects 213-251, wherein the effective amount is 1-2 drops of the composition administered once or twice daily over an effective treatment period, and wherein the method results in detectably or significantly reduced frequency of separation of the eyelid from the surface of the eye compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 252).

In aspects, the invention provides the method of any one or more of aspects 213-252, wherein the effective amount is 1-2 drops of the composition administered once or twice daily over an effective treatment period, and wherein the method results in detectably or significantly reduced frequency of eyelash darkening compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 253).

In aspects, the invention provides the method of any one or more of aspects 213-253, wherein the effective amount is 1-2 drops of the composition administered once or twice daily over an effective treatment period, and wherein the method results in detectably or significantly reduced frequency of shortness of breath compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 254).

In aspects, the invention provides the method of any one or more of aspects 213-254, wherein the effective amount is 1-2 drops of the composition administered once or twice daily over an effective treatment period, and wherein the method results in detectably or significantly reduced frequency of one or more of conjunctival hyperemia, tear film instability, loss of goblet cells, conjunctival squamous metaplasia and apoptosis, disruption of the corneal epithelium barrier, damage to deep ocular tissue, cystoid macular oedema (retinal swelling leading to worsening vision), eye swelling, blurred vision, ocular discomfort, difficulty breathing/wheezing, symptoms of allergic reaction (swelling, redness of the eye and rash of the skin) or hypersensitivity, changes in taste sensation, dizziness, slowing of heart rate, high blood pressure, difficulty sleeping, nightmare, asthma, hair loss, periocular skin discoloration, and tiredness, or detectably or significantly reduced absorption of BKC by soft contact lenses, compared to treatment of the same or at least essentially the same, generally the same, or the same condition with about the same amount of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; or (4) any combination thereof, for at least substantially the same administration period (aspect 255).

In aspects, the invention provides the method of any one or more of aspects 213-255, wherein the method comprising the administration of a reference composition consisting of both the bimatoprost compound and the timolol compound is capable of reducing elevated intraocular pressure in a recipient suffering therefrom but who was previously demonstrated as being insufficiently responsive to a topical beta-blocker administered alone, a prostaglandin analogue administered alone, or both (aspect 256).

In aspects, the invention provides the method of any one or more of aspects 213-256, wherein the effective amount is 1-2 drops of the composition administered to a mammalian eye once or twice daily over an effective treatment period, and the method is optionally repeated for a number of times demonstrated to provide a significant clinical effect in a significant number of patients in a well-controlled and adequate study or that is shown to be bioequivalent to a product that has been demonstrated to achieve the at least substantially the same, generally the same, or effectively the same clinical effect (aspect 257).

In aspects, the invention provides the method of any one or more of aspects 213-257, wherein the effective amount is 1 drop of the composition administered to a mammalian eye once or twice daily over an effective treatment period, and the method is optionally repeated for a number of times demonstrated to provide a significant clinical effect in a significant number of patients in a well-controlled and adequate study or that is shown to be bioequivalent to a product that has been demonstrated to achieve the at least substantially the same, generally the same, or effectively the same clinical effect (aspect 258).

In aspects, the invention provides the method of any one or more of aspects 213-258, wherein the effective amount is 1 drop of the composition administered to a mammalian eye once daily over an effective treatment period, and the method is optionally repeated for a number of times demonstrated to provide a significant clinical effect in a significant number of patients in a well-controlled and adequate study or that is shown to be bioequivalent to a product that has been demonstrated to achieve the at least substantially the same, generally the same, or effectively the same clinical effect (aspect 259).

In aspects, the invention provides the method of any one or more of aspects 213-259, wherein the method comprises the administration of the composition to each affected eye, both eyes, or only the dominant eye of the recipient over the course of an effective treatment period (aspect 260).

In aspects, the invention provides the method of any one or more of aspects 213-260, wherein the method comprises the administration of 1-2 drops of the composition to each affected eye, both eyes, or the dominant eye of the recipient once or twice daily over the course of an effective treatment period (aspect 261).

In aspects, the invention provides the method of any one or more of aspects 213-261, wherein the method comprises the administration of 1 drop of the composition to each affected eye, both eyes, or the dominant eye of the recipient once or twice daily over the course of an effective treatment period (aspect 262).

In aspects, the invention provides the method of any one or more of aspects 213-262, wherein the method comprises the administration of 1 drop of the composition to each affected eye, both eyes, or the dominant eye of the recipient once daily over the course of an effective treatment period (aspect 263).

In aspects, the invention provides the method of any one or more of aspects 260-263, wherein the effective treatment period is a period of time lasting between about 1 day and about 5 years (aspect 264).

In aspects, the invention provides the method of any one or more of aspects 260-264, wherein the effective treatment period is a period of time lasting between about 1 day and about 3 years (aspect 265).

In aspects, the invention provides the method of any one or more of aspects 260-265, wherein the effective treatment period is a period of time lasting between about 1 day and about 1 year (aspect 266).

In aspects, the invention provides the method of any one or more of aspects 260-266, wherein the effective treatment period is a period of time lasting between about 1 day and about 6 months (aspect 267).

In aspects, the invention provides the method of any one or more of aspects 260-267, wherein the effective treatment period is a period of time lasting between about 1 day and about 3 months (aspect 268).

In aspects, the invention provides the method of any one or more of aspects 260-268, wherein the effective treatment period is a period of time lasting between about 1 day and about 1 month (aspect 269).

In aspects, the invention provides the method of any one or more of aspects 260-269, wherein the effective treatment period is a period of time lasting between about 1 day and about 5 days (aspect 270).

In aspects, the invention provides the method of any one or more of aspects 260-270, wherein the effective treatment period is a period of time lasting between about 1 day and about 1 week (aspect 271).

In aspects, the invention provides the method of any one or more of aspects 260-271, wherein the effective treatment period is a period of time lasting between about 5 days and about 1 month (aspect 272).

In aspects, the invention provides the method of any one or more of aspects 260-272, wherein the effective treatment period is a period of time lasting between about 2 weeks and about 3 months (aspect 273).

In aspects, the invention provides the method of any one or more of aspects 260-273, wherein the effective treatment period is a period of time lasting between about 1 month and about 6 months (aspect 274).

In aspects, the invention provides the method of any one or more of aspects 260-274, wherein the effective treatment period is a period of time lasting between about 3 months and about 9 months (aspect 275).

In aspects, the invention provides the method of any one or more of aspects 260-275, wherein the effective treatment period is a period of time lasting between about 6 months and about 12 months (aspect 276).

In aspects, the invention provides the method of any one or more of aspects 260-276, wherein the effective treatment period is a period of time lasting between about 9 months and about 18 months (aspect 277).

In aspects, the invention provides the method of any one or more of aspects 260-277, wherein the effective treatment period is a period of time lasting between about 12 months and about 24 months (aspect 278).

In aspects, the invention provides the method of any one or more of aspects 260-278, wherein the effective treatment period is a period of time lasting between about 18 months and about 30 months (aspect 279).

In aspects, the invention provides the method of any one or more of aspects 260-279, wherein the effective treatment period is a period of time lasting between about 24 months and about 36 months (aspect 280).

In aspects, the invention provides the method of any one or more of aspects 260-280, wherein the method comprises chronic treatment, wherein the effective treatment period is a period of time lasting more than about 3 years (aspect 281).

In aspects, the invention provides the method of any one or more of aspects 260-281, wherein the method comprises chronic treatment, wherein the effective treatment period is a period of time lasting more than about 5 years (aspect 282).

In aspects, the invention provides the method of any one or more of aspects 213-281, wherein the method results in the user maintaining a longer course of therapy than the course of therapy tolerated by use of (1) the product approved as European Medicines Agency product number EMEA/H/C/000668; (2) a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide; (3) a reference composition consisting of 0.1 mg/mL (0.01% w/v) bimatoprost, 6.8 mg/mL (0.68% w/v) timolol maleate (an amount equivalent to 5 mg/mL or 0.5% w/v timolol), 0.05 mg (0.001% w/v) benzalkonium chloride, sodium chloride, sodium phosphate dibasic heptahydrate, citric acid monohydrate, hydrochloric acid and/or sodium hydroxide; (4) an ophthalmic composition demonstrating essentially the same, generally the same, or the same intraocular pressure reduction capability, (5) ophthalmic compositions comprising a higher amount of benzalkonium chloride, bimatoprost compound, timolol compound, or any combination thereof, or (6) any combination thereof (aspect 283).

In aspects, the invention provides a method of manufacturing any one or more of the compositions of any one or more of aspects 1-212, wherein the method comprises (1) preparation of a bulk composition, (2) offline filtration of the bulk composition, (3) online filtration of the bulk composition, and (4) final packaging of the composition (aspect 284).

In aspects, the invention provides a method of manufacturing any one or more of the compositions of any one or more of aspects 1-212, wherein the method comprises (1) preparation of a bulk composition comprising (a) the preparation of a polymer phase solution; (b) the preparation of a drug phase solution; and (c) filtration of the drug phase solution into the polymer phase solution; (2) filtration of the bulk composition; and (3) final packaging of the composition (aspect 285).

In aspects, the invention provides the method of manufacturing of any one or both of aspect 284 or aspect 285, wherein the composition(s) resulting from the method are used in any one or more of the methods of treatment in any one or more of aspects 213-283 (aspect 286).

In aspects, the invention provides a kit comprising a composition according to any one or more of aspects 1-212, and a device suitable for facilitating the delivery of the composition to a recipient eye (aspect 287).

In aspects, the invention provides the kit of aspect 287, wherein the device is suitable for facilitating the delivery of the composition to a recipient eye is a container capable of delivering compositions held therein in a drop-by-drop manner (e.g., a dropper bottle) (aspect 288).

In aspects, the invention provides the kit any one or both of aspect 287 or aspect 288, wherein the composition is provided within the delivery device/container (aspect 289).

In aspects, the invention provides the kit of any one or more of aspects 287-289, wherein the kit comprises multiple doses of composition provided as a plurality of single-dose containers, a single multi-dose container, or a plurality of multi-dose containers (aspect 290).

In aspects, the invention provides the kit of any one or more of aspects 287-290, wherein the composition is a composition manufactured according to any one or more of the methods of manufacturing described in aspects 284-286 (aspect 291).

In aspects, the invention provides the kit of any one or more of aspects 287-291, wherein the kit is used in the method of treatment of any one or more of aspects 213-283 (aspect 292).

In aspects, the invention provides a composition comprising at least one bimatoprost compound, at least one timolol compound, and at least one compound capable of detectably or significantly enhancing the penetration of the bimatoprost compound, the timolol compound, or both the bimatoprost and the timolol compound into a tissue of the eye, wherein the composition has any one or more of the characteristics described in any one or more of aspects 1-212, wherein (1) the composition is utilized in any one or more of the methods of any one or more of aspect 213-283, (2) the composition is manufactured according to a method described in any one or more of aspects 284-286, (3) the composition is present as a part of a kit according to any one or more of 287-292, or (4) any combination of (1)-(3) (aspect 293).

In aspects, the invention provides a composition in the form of a gel comprising at least one bimatoprost compound and at least one timolol compound wherein the composition has any one or more of the characteristics described in any one or more of aspects 1-212, wherein (1) the composition is utilized in any one or more of the methods of any one or more of aspect 213-283, (2) the composition is manufactured according to a method described in any one or more of aspects 284-286, (3) the composition is present as a part of a kit according to any one or more of 287-292, or (4) any combination of (1)-(3) (aspect 294).

DETAILED DESCRIPTION OF THE INVENTION

For convenience, both combinations of elements/steps and individual elements/steps may be described in this section of this disclosure. Despite the inclusion of passages focused on specific elements/steps, any aspect, facet, embodiment, or other description of particular step(s) or element(s) can be applied to any general description of the compositions/methods of the invention, or any other recited element(s)/step(s) thereof, which are provided in any part of this disclosure.

As used herein, the word "exemplary" means "serving as an example, instance, or illustration." The following detailed description is merely exemplary in nature and is not intended to limit application and uses. Any embodiment described herein as "exemplary" is not necessarily to be construed as preferred or advantageous over other embodiments.

Compositions

In aspects, the invention provides pharmaceutically acceptable and ophthalmologically suitable compositions comprising a prostaglandin analogue component (PAC), comprising, e.g., a synthetic analogue of prostaglandin F2α (PGF2α), and a beta-adrenoreceptor antagonist ("β-blocker") component (BBC), and one or more excipients. In aspects, such compositions are suitable for ophthalmic administration, e.g., for the treatment of one or more conditions of the eye, such as elevated intraocular pressure (IOP), such as elevated IOP associated with glaucoma, e.g., open-angle glaucoma. In aspects, such compositions are suitable for the treatment of impaired vision (improving vision or reducing impaired vision) associated with elevated IOP. In aspects, the PAC and the BBC represent the only active pharmaceutical ingredients (APIs) in the composition.

Prostaglandin Analogue Component (PAC)

In aspects, compositions provided by the invention comprise a prostaglandin analogue component ("PAC") in addition to a beta-adrenoreceptor antagonist (β-blocker) component (BBC). In aspects, the PAC comprises one or more prostaglandin analogue compounds, e.g., one or more synthetic analogue(s) of prostaglandin F2α. In aspects, the term "prostaglandin analogue" used herein refers compounds which bind to a prostaglandin receptor, and which mimic the function of (e.g., demonstrate at least essentially the same, at least generally the same, at least substantially the same, or the same biological function) as naturally occurring prostaglandins. More specifically, in aspects, the term "prostaglandin analogue" is used to describe a synthetic analogue of prostaglandin F2α (PGF2α).

In aspects, the PAC can comprise any pharmaceutically acceptable and ophthalmologically suitable prostaglandin analogue agent/drug. In aspects, examples of suitable PAC constituents include, e.g., ophthalmologically suitable forms of latanoprost, travoprost, bimatoprost, tafluprost, latanoprostene bunod, alprostadil, dinoprostone, epoprostenol, treprostinil, iloprost, trimoprostil, rioprostil, cloprostenol, fluprostenol, luprostiol, etiproston, tiaprost, unoprostone and its derivatives such as, e.g., unoprostone isopropyl, misoprostol, sulfoprostone, gemeprost, alfaprostol, and delprostenate compound(s), etc. In certain aspects, the PAC comprises one or more bimatoprost compound(s).

Bimatoprost Compounds

In aspects, the PAC of compositions provided by the invention comprises one or more bimatoprost compounds (compounds that comprise bimatoprost, including derivatives thereof, or that include another compound that is a pharmaceutically acceptable analog of bimatoprost that exhibits at least similar physiological/therapeutic effects as bimatoprost).

Analogs of bimatoprost may be suitable in compositions/methods of the invention, such analogs being generated, e.g., by application of routine methods. However, in aspects, certain compounds or groups of compounds may offer one or more different properties, such that each such compound can be considered its own aspect or to define a category of aspects of the invention. In aspects, the PAC does not include analogs of bimatoprost, only bimatoprost, bimatoprost derivatives (a molecule comprising a bimatoprost core and additional groups), or a related compound (e.g., a salt of either or both thereof). In aspects, a PAC only comprises bimatoprost or a related compound, such as a salt thereof.

As disclosed above, bimatoprost ((Z)-7-[(1R, 2R, 3R, 5S)-3, 5-Dihydroxy-2-[(1E, 3S)-3-hydroxy-5-phenyl-1-pentenyl]cyclopentyl]-5-N-ethylheptenamid) is a synthetic analogue of prostaglandin F2a (PGF2a) with a molecular weight of 415.58 g/mol and demonstrating ocular hypotensive activity, having the structure provided below.

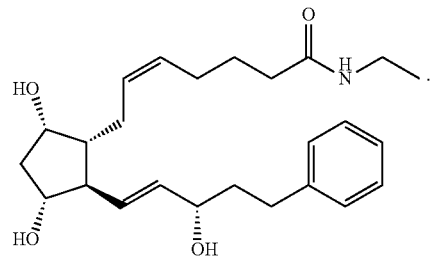

Bimatoprost

In aspects, the bimatoprost compound can be any pharmaceutically acceptable and ophthalmologically suitable bimatoprost compound, such as, e.g., any pharmaceutically acceptable and ophthalmologically suitable salt(s), pharmaceutically acceptable and ophthalmologically suitable solvate(s) (e.g., if identified/identifiable), pharmaceutically acceptable and ophthalmologically suitable hydrate(s), pharmaceutically acceptable and ophthalmologically suitable enantiomer(s), pharmaceutically acceptable and ophthalmologically suitable derivative(s), pharmaceutically acceptable and ophthalmologically suitable polymorph(s), and pharmaceutically acceptable and ophthalmologically suitable prodrug(s) thereof. In aspects, a bimatoprost compound is limited to one or some of these types of compound(s) but excludes other type(s) of any such compounds. E.g., in aspects, a bimatoprost compound does not include a polymorph, but does include a salt of bimatoprost.

In aspects, exemplary salts of bimatoprost can include, e.g., the tromethamine salt of bimatoprost or bimatoprost salts disclosed in the art, such as, e.g., those disclosed in US20140316009A1 (Hughes).

In aspects, exemplary hydrates of bimatoprost can include, e.g., those disclosed in the art at the time of this filing, such as those disclosed in, e.g., CN104981450A (Wu).

In aspects, exemplary enantiomers of bimatoprost can include, e.g., enantiomers of bimatoprost compounds (e.g., bimatoprost derivatives) disclosed in the art at the time of this filing, such as those disclosed in, e.g., WO2012112451, or disclosed by, e.g., Dams, et. al. in "A novel convergent synthesis of the antiglaucoma PGF2α analogue bimatoprost," Chirality. 2013 March; 25(3):170-9.

In aspects, exemplary derivatives of bimatoprost can include, e.g., bimatoprost derivatives disclosed in the art at the time of this filing, such as, e.g., those disclosed in WO2012112451 (Woodward) or, e.g., WO2009136281A1 (Benedini).

In aspects, exemplary polymorphs of bimatoprost can include, e.g., bimatoprost polymorphs disclosed in the art at the time of this filing, such as, e.g., those disclosed in, e.g., US2009163596 (Gutman) or, e.g., U.S. Pat. No. 9,855,232 (Wu).

In aspects, the bimatoprost compound is not a prodrug. In alternative aspects, a prodrug of bimatoprost or another bimatoprost compound is incorporated into a composition or used in a method. Prodrugs may be known or developed where practical. Bimatoprost itself may or may not act as a prodrug. To the extent that bimatoprost acts as a prodrug or any other bimatoprost compound encompassed by this disclosure acts as a prodrug, readers will understand that any suitable metabolite of any such prodrug is simultaneously and implicitly provided by this disclosure and, uncontradicted, such metabolites are encompassed by the scope of bimatoprost compounds.

In aspects, compositions of the invention can comprise bimatoprost in any ophthalmologically acceptable form, such as for example bimatoprost in amorphous or crystalline forms (including polymorphic forms thereof); a pharmaceutically acceptable salt of bimatoprost (e.g., a tromethamine salt thereof); or any mixtures thereof suitable for ophthalmic use. Accordingly, uncontradicted, the term "bimatoprost" or "bimatoprost compound", as used herein, can in aspects be interpreted as referring to any bimatoprost compound; that is, bimatoprost or any related compound above, e.g., one or more of its pharmaceutically acceptable salts, pharmaceutically acceptable solvates (if identified/identifiable), pharmaceutically acceptable hydrates, pharmaceutically acceptable enantiomers, pharmaceutically acceptable derivatives, pharmaceutically acceptable polymorphs and pharmaceutically acceptable prodrugs thereof. Uncontradicted, in aspects "bimatoprost" or "bimatoprost compound" can refer to any metabolite, analog, or a derivative of bimatoprost capable of exhibiting functional and physical responses that are significantly similar to that of bimatoprost, e.g., such functional and physical responses similar to those of prostaglandins and/or metabolites, or analogs or derivatives of bimatoprost exhibiting prostaglandin receptor activity. Uncontradicted, in aspects "bimatoprost" or "bimatoprost compound" refers to bimatoprost in hydrolyzed form. Uncontradicted, in aspects "bimatoprost" or "bimatoprost compound" refers to bimatoprost in free form or free acid form. In aspects, the bimatoprost of the composition is limited to only one, two, or some larger combination of the various types of bimatoprost compounds described herein or their equivalents known in the art. In aspects, the bimatoprost component of a composition is limited to one form of bimatoprost. In aspects, the PAC comprises bimatoprost base (bimatoprost base compound). In aspects, the only constituent of the PAC is bimatoprost base.

PAC (Amount)

In aspects, the invention provides compositions comprising a therapeutically effective amount of a PAC comprising one or more constituents. In aspects, the effective amount is an amount capable of inducing a statistically significant improvement in one or more conditions, such as reducing IOP, treating glaucoma, etc. In aspects, compositions comprise an amount of a PAC capable of detectably or significantly lowering intraocular pressure ("IOP"), either alone or in conjunction with one or more additional active pharmaceutical ingredients (APIs) in recipient(s) (patient(s)) with ocular hypertension (e.g., as often experienced by glaucoma patients). In aspects, compositions comprise an amount of a PAC capable of detectably or significantly increasing outflow of aqueous humor through the trabecular meshwork, uveoscleral, or both the trabecular meshwork and uveoscleral routes.

In aspects, the PAC is present in compositions provided by the invention in an amount representing about 0.001% w/v-about 0.05% w/v of the composition, such as, e.g., ~0.001% w/v-~0.045% w/v, ~0.001% w/v-~0.04% w/v, ~0.001% w/v-~0.035% w/v, ~0.001% w/v-~0.03% w/v, ~0.001% w/v-~0.025% w/v, ~0.001% w/v-~0.02% w/v, ~0.001% w/v-~0.015% w/v, or, e.g., ~0.001% w/v-~0.01% w/v of the composition. Note that herein, the phrase, "in an amount representing about" can be interpreted as such an amount provided "making up about" that amount (e.g., percentage, such as % w/v) of the composition; for example, disclosure of component or constituent [X] present in an amount representing about [Y]% w/v of a composition can be interpreted as component or constituent [X] making up about [Y]% w/v of the composition.

In aspects, the PAC is present in compositions provided by the invention in an amount representing ~0.002% w/v-~0.05% w/v, ~0.004% w/v-~0.05% w/v, ~0.006% w/v-~0.05% w/v, ~0.008% w/v-~0.05% w/v, or, e.g., ~0.01% w/v-~0.05% w/v of the composition.

In aspects, the PAC is present in compositions provided by the invention in an amount representing ~0.002% w/v-about 0.045% w/v of the composition, such as, e.g., ~0.005% w/v-~0.03% w/v, ~0.005% w/v-~0.025% w/v, ~0.005% w/v-~0.02% w/v, ~0.007% w/v-~0.02% w/v, ~0.009% w/v-~0.015% w/v, or, e.g., about 0.01% w/v of the composition.

In aspects, compositions provided herein comprise a PAC (e.g., such as, e.g., a bimatoprost compound, such as bimatoprost base) present in an amount representing no more than about 0.05% w/v, no more than about 0.04% w/v, no more than about 0.03% w/v, no more than about 0.02% w/v, or no more than about 0.01% w/v of the composition(s).

In aspects, the PAC comprises two or more PAC constituents, wherein the total amount of such constituents is represented by the concentrations/amounts provided above. In aspects, compositions comprise a PAC comprising a single PAC constituent, wherein the total amount of such single constituent is represented by the concentrations/amounts provided above. In aspects, the PAC comprises a pharmaceutically acceptable and ophthalmologically suitable bimatoprost compound, such as, e.g., bimatoprost base. In aspects, the PAC comprises a single constituent which is a bimatoprost compound, e.g., bimatoprost base. In aspects, the single bimatoprost compound constituent, e.g., bimatoprost base, is present in compositions in the above-identified amounts. In aspects, bimatoprost base is present in compositions in the above-identified amounts.

In aspects, the PAC, e.g., in aspects the bimatoprost compound, is present in compositions provided by the invention in an amount representing ~0.001% w/v-~0.01% w/v of the composition, ~0.005% w/v-0.015% w/v of the composition, or e.g., ~0.007% w/v-about 0.025% w/v of the composition. In aspects, advantages of such compositions can include, e.g., a reduction in the number or severity of one or more side effects known to be caused by bimatoprost compared to compositions comprising a higher concentration of a bimatoprost compound, e.g., compositions comprising greater than about 0.01% w/v, ≥~0.02% w/v, ≥~0.03% w/v, ≥~0.04% w/v, or, e.g., ≥~0.05% w/v of a bimatoprost compound.

In aspects, such amounts of a PAC, PAC constituents, or both, disclosed in this section represent an effective amount of a PAC, PAC constituent, or both.

Beta-Adrenoreceptor Antagonist (β-Blocker) Component (BBC)

In aspects, compositions provided by the invention comprise a beta-adrenoreceptor antagonist (β-blocker) (component ("BBC") in addition to a prostaglandin analogue component (PAC). In aspects, the BBC comprises one or more β-blocker compounds. In aspects, the term "β-blocker compound" used herein refers compounds which demonstrate competitive antagonistic action on beta-adrenoreceptors (e.g., beta-adrenoreceptors B1, B2, and B3).

In aspects, the BBC can comprise any pharmaceutically acceptable and ophthalmologically suitable β-blocker compound. In aspects, examples of suitable PAC constituents include, e.g., timolol, betaxolol, carteolol, levobunolol, befunolol, metipranolol and mepindolol compound(s), etc. In certain aspects, the BBC comprises one or more timolol compound(s).

Timolol Compounds

In aspects, the BBC of compositions provided by the invention comprises one or more timolol compounds (compounds that comprise timolol, including derivatives thereof, or that include another compound that is a pharmaceutically acceptable analog of timolol that exhibits at least similar physiological/therapeutic effects as timolol).

Analogs of timolol may be suitable in compositions/methods of the invention, such analogs being generated, e.g., by application of routine methods. However, in aspects, certain compounds or groups of compounds may offer one or more different properties, such that each such compound can be considered its own aspect or to define a category of aspects of the invention. In aspects, the BBC does not include analogs of timolol, only timolol, timolol derivatives (a molecule comprising a timolol core and additional groups), or a related compound (e.g., a salt of either or both thereof). In aspects, a BBC only comprises timolol or a related compound, such as a salt thereof.

As disclosed above, timolol ((−)-1-(tert-butylamino)-3-[(4-morpholino-1,2,5-thiadiazol-3-yl)-oxy]-2-propanol) is a beta-adrenergic agent with a molecular weight of 316.421 g/mol and having the structure provided below.

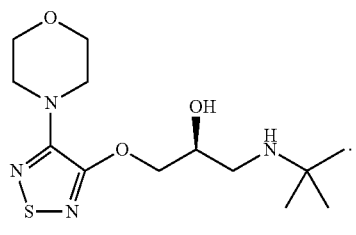

Timolol

In aspects, the timolol compound can be any pharmaceutically acceptable and ophthalmologically suitable timolol compound, such as, e.g., any pharmaceutically acceptable and ophthalmologically suitable salt(s), pharmaceutically acceptable and ophthalmologically suitable solvate(s), pharmaceutically acceptable and ophthalmologically suitable hydrate(s), pharmaceutically acceptable and ophthalmologically suitable enantiomer(s), pharmaceutically acceptable and ophthalmologically suitable derivative(s), pharmaceutically acceptable and ophthalmologically suitable polymorph(s), and pharmaceutically acceptable and ophthalmologically suitable prodrug(s) thereof. In aspects, a timolol compound is limited to one or some of these types of compound(s) but excludes other type(s) of any such compounds. E.g., in aspects, a timolol compound does not include a polymorph, but does include a salt of timolol.

In aspects, compositions of the invention can comprise timolol in any ophthalmologically acceptable form, such as for example timolol in a derivatized form, a base form, or mixtures thereof suitable for ophthalmic use. Accordingly, uncontradicted, the term "timolol" or "timolol compound", as used herein, can in aspects be interpreted as referring to any timolol compound; that is, timolol or any related compound above, e.g., one or more of its pharmaceutically acceptable salts, pharmaceutically acceptable solvates, pharmaceutically acceptable hydrates, pharmaceutically acceptable enantiomers, pharmaceutically acceptable derivatives, pharmaceutically acceptable polymorphs and pharmaceutically acceptable prodrugs thereof. Uncontradicted, in aspects "timolol" or "timolol compound" can refer to any metabolite, analog, or a derivative of timolol capable of exhibiting functional and physical responses that are significantly similar to that of timolol, e.g., such functional and physical responses similar to those of β-blockers and/or metabolites, or analogs or derivatives of timolol exhibiting beta-adrenoreceptor antagonist activity. In aspects, the timolol of the compositions is limited to only one, two, or some larger combination of the various types of timolol compounds described herein or their equivalents known in the art. In aspects, the timolol component of a composition is limited to one form of timolol. In aspects, the BBC of the compositions provided by the invention comprise a salt of timolol, such as, e.g., timolol maleate.

Timolol Maleate

Timolol maleate (the maleate salt form of timolol), is a non-selective beta-adrenergic receptor blocking agent, having the chemical name is (−)-1-(tert-butylamino)-3-[(4-morpholino-1,2,5-thiadiazol-3-yl) oxy]-2-propanol maleate (1:1) (salt). Timolol maleate is a white to almost white, odorless powder with a molecular weight of 432.5 g/mol.

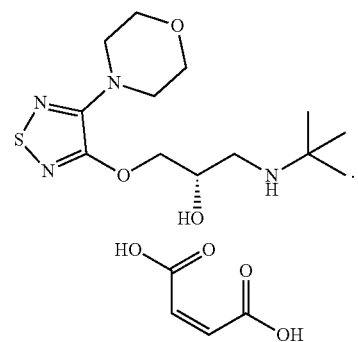

Timolol maleate

BBC (Amount)

In aspects, the invention provides compositions comprising a therapeutically effective amount of a BBC comprising one or more constituents. In aspects, the effective amount is an amount capable of inducing a statistically significant improvement in one or more conditions, such as reducing IOP, treating glaucoma, etc. In aspects, compositions comprise an amount of a BBC capable of detectably or significantly lowering intraocular pressure ("IOP"), either alone or in conjunction with one or more additional active pharmaceutical ingredients (APIs) in recipient(s) (patient(s)) with ocular hypertension (e.g., as often experienced by glaucoma patients). In aspects, compositions comprise an amount of a BBC capable of detectably or significantly reducing the rate of aqueous humor formation through reduction of flow to the ciliary process.

In aspects, the BBC is present in compositions provided by the invention in an amount representing about 0.1% w/v-about 1% w/v of the composition, such as, e.g., ~0.15% w/v-~1% w/v, ~0.2% w/v-~1% w/v, ~0.25% w/v-~1% w/v, ~0.3% w/v-~1% w/v, ~0.35% w/v-~1% w/v, ~0.4% w/v-~1% w/v, ~0.45% w/v-~1% w/v, or, e.g., ~0.5% w/v-~1% w/v of the composition.

In aspects, the BBC is present in compositions provided by the invention in an amount representing ~0.1% w/v-~0.9% w/v, ~0.1% w/v-~0.8% w/v, ~0.1% w/v-~0.7% w/v, ~0.1% w/v-~0.6% w/v, or, e.g., ~0.1% w/v-~0.5% w/v of the composition.

In aspects, the PAC is present in compositions provided by the invention in an amount representing ~0.15% w/v-about 0.9% w/v of the composition, such as, e.g., ~0.2% w/v-~0.85% w/v, ~0.25% w/v-~0.8% w/v, ~0.3% w/v-~0.75% w/v, ~0.35% w/v-~0.7% w/v, ~0.4% w/v-~0.7% w/v, ~0.45% w/v-~0.7% w/v, ~0.5% w/v-~0.7% w/v, ~0.55% w/v-~0.7% w/v, or, e.g., about 0.5% w/v of the composition or, e.g., ~0.68% w/v of the composition. In aspects, the PAC comprises a timolol compound, e.g., a salt of timolol, e.g., timolol maleate in an amount representing about 0.68% of the composition. In aspects, 0.68% w/v timolol maleate (or about 6.8 mg of timolol maleate) is equivalent to about 0.5% w/v timolol free base (or about 5 mg timolol free base). Such a conversion can be applied elsewhere as applicable herein, as is routinely understood in the art.

In aspects, the BBC comprises two or more BBC constituents, wherein the total amount of such constituents is represented by the concentrations/amounts provided above. In aspects, compositions comprise a BBC comprising a single BBC constituent, wherein the total amount of such single constituent is represented by the concentrations/amounts provided above. In aspects, the BBC comprises a pharmaceutically acceptable and ophthalmologically suitable timolol compound, such as, e.g., a salt of timolol, e.g., timolol maleate. In aspects, the BBC comprises a single constituent which is a timolol compound, e.g., a salt of timolol, e.g., timolol maleate. In aspects, the single timolol compound constituent, e.g., the salt of timolol, e.g., timolol maleate, is present in compositions in the above-identified amounts.

In aspects, the BBC, e.g., in aspects the timolol compound, e.g., salt of timolol, e.g., timolol maleate, is present in compositions provided by the invention in an amount representing ~0.1% w/v-~0.07% w/v of the composition, ~0.4% w/v-0.8% w/v of the composition, or e.g., ~0.5% w/v-about 1% w/v of the composition. In aspects, advantages of such compositions can include, e.g., a reduction in the number or severity of one or more side effects known to be caused by timolol compared to compositions comprising a higher concentration of a timolol compound, e.g., compositions comprising greater than about 0.7% w/v, ≥~0.8% w/v, ≥~0.9% w/v, or, e.g., ≥~1% w/v of timolol maleate. In aspects, advantages of such compositions can include, e.g., an increase in the efficacy of the timolol compound in providing a detectably or significant therapeutic effect, such as, a reduction in intraocular pressure, compared to compositions comprising a lower concentration of a timolol compound, e.g., compositions comprising less than about 0.5% w/v, ≤~0.4% w/v, ≤~0.3% w/v, ≤~0.2% w/v, or ≤~0.1% w/v of a timolol compound, or compared to compositions comprising a sub-therapeutic amount of a timolol compound.

In aspects, such amounts of a BBC, BBC constituents, or both, disclosed in this section represent an effective amount of a BBC, BBC constituent, or both.

Alternative or Additional Anti-Glaucoma Agent(s) Component (AGAC)

In certain aspects, compositions provided by the invention comprise a PAC comprising one or more constituents, e.g., a bimatoprost compound, and second component (the "alternative or additional anti-glaucoma agent(s) component" ("AGAC")) comprising one or more antiglaucoma agents not characterizable as a beta-adrenoreceptor antagonist, such as, for example, one or more pharmaceutically acceptable and ophthalmologically suitable carbonic anhydrase inhibitor(s), one or more pharmaceutically acceptable and ophthalmologically suitable alpha-adrenergic agonist(s), or both. In aspects, suitable carbonic anhydrase inhibitor(s) include, e.g., a brinzolamide compound, e.g., brinzolamide acetazolamide, a methazolamide compound, a dorzolamide compound, a diclofenamide compound, an ethoxzolamide compound, a zonisamide compound, etc. In aspects, suitable alpha-adrenergic agonist(s) include, e.g., a brimonidine compound, a clonidine compound, an apraclonidine compound, a dexmedetomidine compound, a fadolmidine compound, etc.

In aspects, an AGAC can be present in compositions described herein as an alternative to the BBC or in addition to the BBC. In aspects, an AGAC can comprise one or more constituents and be present in compositions described herein in therapeutically effective amounts (e.g., in amounts providing a detectable or therapeutic effect in treating glaucoma as determined by an appropriately conducted clinical trial).

Typically, an AGAC, combination of AGACs, or constituent(s) of one or more AGACs, are individually or collectively present in an effective amount. In such context, an effective amount can be an amount that detectably or significantly enhances or modifies the therapeutic capability/potential of the associated product or method. For example, an AGAC can detectably or significantly improve the treatment of one or more conditions, e.g., glaucoma (such as open-angle glaucoma) or other elevated intraocular pressure-related conditions.

In certain aspects, compositions do not comprise an AGAC component, and the only APIs of the composition are present as a constituent of PAC or BBC.

Bimatoprost & Timolol Compound Combinations

In aspects, compositions provided by the invention comprise a pharmaceutically acceptable and ophthalmologically suitable PAC (e.g., a bimatoprost compound, such as, e.g., bimatoprost base) and a pharmaceutically acceptable and ophthalmologically suitable BBC (e.g., a timolol compound, e.g., a salt of timolol, e.g., timolol maleate) in combination with one another (within a single composition). Such combination compositions can be referred to as "fixed dosage" combination products. Uncontradicted, the term "fixed dose" (AKA, "fixed-dose") is understood in the art as referring to a combination of two or more active ingredients (API(s)) within a single form of pharmaceutical administration and does not necessarily impart any limitation on the relationship of dose(s) of such active ingredients, etc.). See, e.g., Goodman et al. Expert Review of Pharmacoeconomics & Outcomes Research, 20:1, 1-26. Nonetheless, in aspects, fixed-dose combinations provided herein are characterized by specific amounts of APIs or relationships (e.g., ratios) of APIs, such ratio discussed elsewhere herein.

In one aspect, the pharmaceutically acceptable and ophthalmologically suitable compositions provided herein comprise both a bimatoprost compound, e.g., bimatoprost base, and a timolol compound, e.g., a salt of timolol, e.g., timolol maleate, which are capable of detectably or significantly reducing elevated intraocular pressure in a recipient, e.g., adult patient(s), such as a recipient diagnosed with glaucoma (e.g., open-angle glaucoma) who are insufficiently responsive to topical beta-blockers alone or prostaglandin analogues alone.

In aspects, compositions provided by the invention comprise a pharmaceutically acceptable and ophthalmologically suitable fixed-dose combination of a PAC and a BBC. In aspects, the PAC and the BBC comprise, e.g., a bimatoprost compound (e.g., bimatoprost base) and a timolol compound, respectively. In aspects, compositions provided by the invention comprise, e.g., about 0.001% w/v-about 0.05% w/v of a PAC, e.g., ~0.001% w/v-0.04% w/v, ~0.001% w/v-0.03% w/v, ~0.001% w/v-0.02% w/v, or ~0.001% w/v-0.01% w/v (such as, in aspects, no more than about 0.05% w/v, no more than about 0.04% w/v, no more than about 0.03% w/v, no more than about 0.02% w/v, or no more than about 0.01% w/v) of a PAC, such as, e.g., a bimatoprost compound, such as bimatoprost base. In aspects, compositions provided by the invention further comprise, e.g., about 0.1% w/v-about 1% w/v of a BBC, such as, e.g., ~0.2% w/v-~0.9% w/v, ~0.3% w/v-~0.8% w/v, ~0.4% w/v-~0.7% w/v, or, e.g., ~0.5% w/v-~0.7% w/v, such as, e.g., about 0.5% w/v or about 0.68% w/v of a BBC, such as, e.g., a timolol compound, such as a salt of timolol, e.g., timolol maleate.

In aspects, compositions provided by the invention comprise a total amount of API (such as, e.g., a total amount of a bimatoprost compound, e.g., bimatoprost base, and timolol compound, e.g., a salt of timolol, e.g., timolol maleate) which represents about 0.1% w/v-about 1.5% w/v of the composition, such as, e.g., ~0.1% w/v-~1.2% w/v, ~0.1% w/v-~1% w/v, ~0.1% w/v-~0.9% w/v, ~0.1% w/v-~0.8% w/v, or, e.g., ~0.1% w/v-~0.7% w/v of the composition.

In aspects, compositions provided by the invention comprise a total amount of API (such as, e.g., a total amount of a bimatoprost compound, e.g., bimatoprost base, and timolol compound, e.g., a salt of timolol, e.g., timolol maleate) which represents about 0.1% w/v-about 1.5% w/v of the composition, such as, e.g., ~0.2% w/v-~1.5% w/v, ~0.3% w/v-~1.5% w/v, ~0.4% w/v-~1.5% w/v, ~0.5% w/v-~1.5% w/v, ~0.6% w/v-~1.5% w/v, or, e.g., ~0.7% w/v-~1.5% w/v of the composition.

In aspects, compositions provided by the invention comprise a total amount of API (such as, e.g., a total amount of a bimatoprost compound, e.g., bimatoprost base, and timolol compound, e.g., a salt of timolol, e.g., timolol maleate) which represents about 0.2% w/v-about 1.2% w/v of the composition, such as, e.g., ~0.2% w/v-~1% w/v, ~0.3% w/v-~9% w/v, ~0.4% w/v-~8% w/v, or, e.g., ~0.5% w/v-~0.7% w/v, such as for example about 0.7% w/v or about 0.69% w/v of the composition.

In aspects, such amounts of total API disclosed in this section represent an effective amount of total API, e.g., an effective amount of PAC and BBC, e.g., an effective amount of bimatoprost compound and timolol compound.

Excipients

According to certain aspects, compositions provided by the invention comprise one or more excipients, which are a type of, or alternatively can be characterized as, a composition constituent/component or ingredient. In aspects, the one or more excipients can be any pharmaceutically acceptable and ophthalmologically acceptable excipients provided that the excipient(s) does/do not detectably or significantly interfere with the activity or stability of the PAC, the BBC, the AGAC (in aspects where an AGAC is present), or the activity or stability of any other excipient(s). Most, generally all, or all of the excipients of compositions are typically characterized by one or more classes or components, which typically are defined by the function of such ingredient or component. Examples of the types of components/ingredients that can be present in compositions of the invention are described in turn in the following sections, but readers will understand that these disclosures can be combined in accordance with more general descriptions provided in the Summary, Exemplary Aspects, or other portions of this disclosure.

Preservative Component (Preservation Agent(s))

In aspects, compositions provided by the invention comprise a preservative component (which may also be referred to herein as a preservation component). In aspects, the preservative component comprises any one or more pharmaceutically acceptable and ophthalmologically suitable constituents (e.g., pharmaceutically acceptable and ophthalmologically suitable compounds) which detectably or significantly increase the stability of the composition, detectably or significantly decrease the degradation of one or more other constituents of the composition (over a period of time/under storage conditions—as exemplified elsewhere herein and as is known in the art), detectably or significantly increase the period of time that the composition is considered safe and efficacious for use, detectably or significantly increases or extends shelf life by maintaining an amount of active pharmaceutical ingredient above a threshold, e.g., a PAC, e.g., bimatoprost base, or a BBC constituent, e.g., timolol maleate, within desirable or acceptable limits, maintaining the level of any one or more impurities below an acceptable/suitable level, detectably or significantly impeding/inhibiting or preventing/restricting growth of bacteria or other microorganisms in the composition, or any such similar measures of composition stability/preservation, or any combination of some or all thereof. For example, in aspects, a preservative component comprises one or more pharmaceutically acceptable and ophthalmologically suitable constituents (e.g., pharmaceutically acceptable and ophthalmologically suitable compounds) which aid in maintaining, e.g., via reducing or preventing microbial contamination, at least about 95%, 95%, 97%, 98% or more of the API(s) of the composition, such as, e.g., a bimatoprost compound, a timolol compound, or both a bimatoprost compound and a timolol compound, when stored at about 25° C.+/−2° C. and about 40%+/−5% relative humidity; about 40° C.+/−2° C.

and not more than about 25% relative humidity; about 15° C.-about 27° C. and about 60% relative humidity; about 38° C.-about 42° C. and 75% relative humidity; or when stored under any such condition, or a sequential combination of such conditions, for a period of at least about 1, 3, 6, 9, 12, 18, 24, or, e.g., at least about 36 months. As another example, in aspects, a preservative component comprises one or more pharmaceutically acceptable and ophthalmologically suitable constituents (e.g., pharmaceutically acceptable and ophthalmologically suitable compounds) which aid, e.g., via reducing or preventing microbial contamination, the composition in maintaining a level of total impurities which is less than about 2.5% after storage at about 25° C.+/−2° C. and about 40%+/−5% relative humidity; about 40° C.+/−2° C. and not more than about 25% relative humidity; about 15° C.-about 27° C. and about 60% relative humidity; about 38° C.-about 42° C. and 75% relative humidity; or when stored under any such condition, or a sequential combination of such conditions, for a period of at least about 1, 3, 6, 9, 12, 18, 24, or, e.g., at least about 36 months.

In aspects, the preservation component can comprise any one or more pharmaceutically acceptable or ophthalmologically suitable compounds capable of demonstrating any one or more of the above-described effects (e.g., to a detectable or significant level). In aspects, compositions herein comprise one or more preservative agents as constituents of a penetration component which maintain the composition in a state (e.g., with regard to maintenance of the amount of API(s), with regard to the level of impurities, or both) which meets requirements for safety and stability established by a recognized regulatory body such as, e.g., the United States Food and Drug Administration, when stored at about 25° C.+/−2° C. and about 40%+/−5% relative humidity; about 40° C.+/−2° C. and not more than about 25% relative humidity; about 15° C.-about 27° C. and about 60% relative humidity; about 38° C.-about 42° C. and 75% relative humidity; or when stored under any such condition, or a sequential combination of such conditions, for a period of at least about 1, 3, 6, 9, 12, 18, 24, or, e.g., at least about 36 months.

In aspects, one or more preservative agents of a preservation component provide one or more other detectably or significant functional activities, such as for example, providing detectable or significant penetration enhancement activity, such as, e.g., detectably or significantly enhancing the penetration of one or more PAC constituents, e.g., a bimatoprost compound, e.g., bimatoprost base, detectably or significantly enhancing the penetration of one or more BBC constituents, e.g., a timolol compound, e.g., a salt of timolol, e.g., timolol maleate, or both a bimatoprost compound and a timolol compound into an ocular tissue. In aspects, one or more preservative agents of a preservation component provide detectable or significant solubilization activity, such as, e.g., detectably or significantly enhancing the solubilization of, or detectably or significantly maintaining the solubilization of, one or more composition constituents, e.g., one or more PAC constituents, e.g., a bimatoprost compound, e.g., bimatoprost base, one or more BBC constituents, e.g., a timolol compound, e.g., a salt of timolol, e.g., timolol maleate, or, e.g., detectably or significantly maintaining the solubilization of both one or more PAC constituents and one or more BBC constituents.

In aspects, the pharmaceutically acceptable and ophthalmologically suitable compositions provided by the invention comprise a preservative component comprising one or more preservation agents present in anti-microbially effective amounts, e.g., an amount capable of detectably or significantly inhibiting microbial growth. In aspects, a preservation component of a composition can comprise any ophthalmologically suitable and pharmaceutically acceptable preservative which does not detectably or significantly interfere with the required functionality of any one or more other composition constituents. In aspects, exemplary constituents of a preservative component comprise, e.g., hydrogen peroxide; sorbic acid; biquanides; quaternary ammonium salts such as benzalkonium chloride(s) (abbreviated herein as BKC, though in other literature other abbreviations such as BAC, BAK, or BZK may be used) and benzethonium chloride; cationic compounds such as chlorhexidine gluconate; p-hydroxybenzoates such as methyl p-hydroxybenzoate, ethyl p-hydroxybenzoate, propyl p-hydroxybenzoate and butyl p-hydroxybenzoate; alcohol compounds such as chlorobutanol and benzyl alcohol; sodium dehydroacetate; thiomersal, etc. In aspects, a preservative component can comprise benzalkonium chloride(s) (BKC), wherein the BKC provides detectable or significant penetration enhancement activity, detectable or significant preservation activity, detectable or significant solubilization effect(s), or any combination thereof. Benzalkonium chlorides, a class of quaternary ammonium compounds suitable for use in compositions herein, include, e.g., known as alkyl dimethyl benzyl ammonium chlorides (or ADBAC), alkyl dimethyl (phenylmethyl) chlorides, and ammonium alkyl dimethyl benzyl chlorides.

In aspects, compositions provided by the invention comprise a preservation component comprising one or more preservation agents, wherein the preservation component is present in the composition in a concentration representing about 0.0001% w/v to about 0.02% w/v, such as, e.g., ~0.001% w/v–~0.015% w/v, ~0.001% w/v–~0.01% w/v, or ~0.001% w/v–~0.008% w/v, ~0.002% w/v–~0.02% w/v, ~0.004% w/v–~0.02% w/v, or ~0.006% w/v–~0.02% w/v, e.g., ~0.0005% w/v–~0.015% w/v, ~0.001% w/v–~0.01% w/v, ~0.002% w/v–~0.009% w/v, ~0.004% w/v–~0.008% w/v, or ~0.004% w/v–~0.007% w/v, such as, e.g., about 0.005% w/v of the composition. In certain aspects, benzalkonium chloride can be present in such amounts. In certain aspects, compositions lack benzalkonium chloride. In certain aspects, compositions provided by the invention lack any preservative component. In certain aspects, compositions comprise a preservative component which does not comprise benzalkonium chloride as a constituent. In aspects, such amounts represent an effective amount of a preservative/preservation component.

In aspects, a preservation component can comprise a quaternary ammonium salt, e.g., benzalkonium chloride, present in the formulation in a concentration of about 0.0001% w/v to 0.02% w/v, such as about 0.003% w/v to about 0.02% w/v, such as about 0.004% w/v to about 0.02% w/v, or for example about 0.005% w/v. In some aspects, compositions provided by the invention comprise benzalkonium chloride in an amount of less than about 0.01% w/v. In some aspects, compositions provided by the invention comprise benzalkonium chloride in an amount greater than about 0.001% w/v, greater than about 0.002% w/v, greater than about 0.003% w/v, or, e.g., greater than about 0.004% w/v of the composition. In aspects, such amounts as disclosed here are advantageous in that such amount(s) (1) provides sufficient preservative activity to maintain the stability of the compositions according to the composition stability characteristics described elsewhere herein; (2) provides a detectable or significant enhancement in the penetration of a PAC constituent (e.g., a bimatoprost compound, e.g., bimatoprost base), a BBC constituent (e.g., a timolol compound, such as a salt of timolol, e.g., timolol maleate), or both a PAC constituent and a BBC constituent, such penetration enhancement detectable as an increased amount of API penetrating a corneal tissue, detectable as an increased rate of API penetrating a corneal tissue, or both; or both (1) and (2). In aspects, such amounts as disclosed here are advantageous in that such amount(s) provide sufficient preservation effect, provide detectable penetration enhancement effect, do not cause a level of ocular irritation upon administration/use by a recipient to cause the recipient to stop use of the composition, or any combination thereof.

In certain aspects, the invention provides compositions suitable for use in methods of reducing elevated intraocular pressure, such as, e.g., reducing intraocular pressure associated with glaucoma (e.g., open-angle glaucoma), comprising a reduced amount of benzalkonium chloride (e.g., an amount of no more than about 0.005% w/v), as benzalkonium chloride is recognized in the art as a potentially irritating preservative and incorporating one or more non-irritating compounds or compounds in non-irritating amounts such as polysorbate 80 to compensate for the reduction in benzalkonium chloride concentration. In aspects, the invention provides compositions advantageously capable of achieving a comparable, detectably improved, or significantly improved level of intraocular pressure reduction using no more than about 0.005% w/v of benzalkonium chloride, such as, e.g., about 0.005% w/v benzalkonium chloride (50 ppm BKC), compared to compositions containing 200 ppm BKC.

In aspects, antimicrobial effective amounts of a preservative may be determined by performing preservative efficacy tests or antimicrobial effectiveness tests. These tests are inter alia described in Chapter 51 of the United States Pharmacopeia 29-National Formulary 24 (USP 29-NF 24). In aspects, preservative agents of a preservation component are used in an amount within the concentration ranges described in standard reference books like Remington's Pharmaceutical Sciences and Handbook of Pharmaceutical Excipients (e.g., the $23^{rd}$ Edition thereof—Published in 2020).

In certain aspects, the preservation component comprises two or more constituents wherein the total concentration/amount of the two or more preservation component constituents is represented by the concentrations/amounts provided above. In aspects, the preservation component comprises a single constituent wherein the single constituent is present in an amount represented by the concentrations/amounts provided above, such as, e.g., benzalkonium chloride in amounts provided above.

In this and any other ingredient aspect of the invention, the invention also can be characterized as comprising a "means" for providing a recited function, here imparting/providing an effective, detectable, or significant preservation effect (e.g., increased stability of one or more constituents of the composition, maintenance of an acceptable level of impurities during composition storage, increased composition shelf life, etc.) of compositions. In such a respect, any known equivalents of such named agents can also be, e.g., are, incorporated into compositions or methods of the invention. As with other sections similarly described herein, any of the components of the invention can be, where suitable, described as means (e.g., the above-described preservation agents/compounds or components can be described as preservation means or means for providing effective, detectable, or significant preservation activity/characteristics to the composition or one or more constituents of the composition.)

Penetration Enhancer Component (Penetration Enhancer(s))

In certain aspects, compositions provided by the invention comprise a penetration enhancer component (a part of the composition that comprises one or more penetration enhancer(s)/penetration-enhancing compound(s) in effective amounts for detectably or significantly enhancing penetration of other constituents, such as the PAC or one or more compound(s) thereof, the BBC or one or more compound(s) thereof, the AGAC (in aspect where such a component is present) or one or more compound(s) thereof, or one or more constituents of each of the PAC, BBC, and AGAC components).

In aspects, a penetration enhancer component comprises any one or more pharmaceutically acceptable and ophthalmologically suitable penetration enhancer(s) (which can be referred to as penetration agents or penetration enhancing agents/constituents), which provide detectable or significant penetration enhancement effect of any one or more constituents of the PAC, one or more constituents of the BBC, or one or more constituents of each of both the PAC and the BBC. In aspects, the penetration enhancer component (e.g., constituent(s) of the penetration enhancer component) is any pharmaceutically acceptable and ophthalmologically suitable compound(s) capable of (when present in a suitable amount and under suitable conditions) (1) detectably or significantly increasing the amount of a PAC constituent, e.g., a bimatoprost compound, such as bimatoprost base, which penetrates eye tissue in a given period of time (e.g., the period of time between doses, such as within a 24-hour period); (2) detectably or significantly increasing the amount of a BBC constituent, e.g., a timolol compound, such as a salt of timolol, e.g., timolol maleate, or both a PAC constituent and a BBC constituent which penetrates eye tissue in a given period of time (e.g., the period of time between doses, such as within a 24-hour period); or (3) detectably or significantly increases the amount of a PAC constituent and a BBC constituent which penetrates eye tissue in a given period of time (e.g., the period of time between doses, such as within a 24-hour period). In aspects, the penetration enhancer component or constituent(s) thereof is/are pharmaceutically acceptable and ophthalmologically suitable compound(s) which detectably or significantly increase the amount of a PAC constituent (e.g., bimatoprost base), BBC constituent (e.g., timolol maleate), or both, penetrating eye tissue within a 24-hour, 22-hour, 20-hour, 18-hour, 16-hour, 14-hour, 12-hour, 10-hour, 8-hour, 6-hour, 4-hour, 2-hour, or 1-hour period of time, such that a detectably or significantly greater amount of the PAC constituent(s) (e.g., a bimatoprost compound, e.g., bimatoprost base), BBC constituent(s), (e.g., a timolol compound, such as a salt of timolol, e.g., timolol maleate), or both, is available within the eye tissue for treating the condition of the eye to which the treatment is directed. In aspects, the presence of a penetration enhancer component detectably or significantly increases the amount of a PAC constituent (e.g., bimatoprost base), a BBC constituent (e.g., a timolol compound, e.g., a salt of timolol, e.g., timolol maleate), or both, which penetrates eye tissue over the amount of the same PAC constituent, BBC, or both, present in the same amount in a comparable composition lacking the penetration enhancer component.

In aspects, the penetration enhancer component or constituent(s) of the penetration enhancer component is or are any pharmaceutically acceptable and ophthalmologically suitable compound(s) capable of (1) detectably or significantly increasing the rate of penetration into an eye tissue of a PAC constituent, e.g., a bimatoprost compound, such as bimatoprost base, (2) detectably or significantly increasing the rate of penetration into an eye tissue of a BBC constituent, e.g., a timolol compound, such as a salt of timolol, e.g., timolol maleate, or (3) detectably or significantly increasing the rate of penetration into an eye tissue of both a PAC constituent and a BBC constituent. In aspects, a constituent of the penetration enhancer component detectably or significantly increases the amount of a PAC constituent, BBC constituent, or both a PAC constituent and a BBC constituent penetrating eye tissue per unit time compared to the amount per unit time of the same PAC constituent, BBC constituent, or both the same PAC constituent and the same BBC constituent present in the same amount in a comparable composition lacking the penetration component.

In aspects, a penetration enhancer component constituent is a compound or composition capable of detectably or significantly enhancing penetration of an active pharmaceutical ingredient, e.g., a PAC constituent (e.g., a bimatoprost compound, e.g., bimatoprost base), a BBC constituent (e.g., a timolol compound, e.g., a salt of timolol, e.g., timolol maleate) or both a PAC constituent and a BBC constituent, in mammalian eye tissue (e.g., in human eye tissue, such as in the tissue of human patients). In some respects, a penetration enhancer component constituent can be any ophthalmologically suitable compound or mixture of compounds capable of exerting the effect of increasing the speed of penetration of an API present in the formulation (e.g., a bimatoprost compound, a timolol compound, or both) into ocular cells, e.g., corneal cells, or improving (e.g., increasing) the uptake or retention of an API present in the formulation (e.g., a bimatoprost compound, a timolol compound, or both) into ocular tissue or ocular cells. In aspects, a penetration enhancer detectably or significantly enhances penetration of an API, e.g., a bimatoprost compound, e.g., bimatoprost base, or, e.g., a timolol compound, e.g., timolol maleate, or both a bimatoprost compound and a timolol compound, into ocular tissue by at least about 10%, at least about 20%, at least about 30%, at least about 40%, at least about 50%, at least about 60%, at least about 70%, at least about 80%, at least about 90%, or by at least about 100%, such as at least approximately 120%, at least approximately 140%, at least approximately 160%, at least approximately 180%, or at least approximately 200% or even more, over similar (e.g., at least generally the same, at least substantially the same, at least essentially the same, essentially the same, or the same) formulations (in terms of the presence of API(s), excipient(s), amount(s) of any or all thereof or combinations of such characteristic(s)) lacking such a penetration enhancer. In aspects, penetration can be measured or reflect the amount of API(s) in a tissue, such as ocular tissue; can reflect the penetration of the API(s) throughout the tissue (e.g., the average amount throughout an entire tissue, the minimum amount throughout the tissue, or both, such as any of the amounts described herein or the presence of significant or detectable amount(s) of the API(s) as distributed through the tissue); or both.

In one aspect, the invention provides a pharmaceutically acceptable and ophthalmologically suitable composition comprising a bimatoprost compound, a timolol compound, and benzalkonium chloride, wherein, e.g., the concentration of the bimatoprost compound is about 0.005% w/v to about 0.02% w/v, the concentration of the timolol compound is about 0.25% w/v to about 0.5% w/v, and the concentration of the benzalkonium chloride is about 0.003% w/v to about 0.007% w/v. In one specific exemplary aspect, the invention provides such a composition wherein the composition further comprises a penetration enhancer component separate from any penetration enhancement effect provided by the benzalkonium chloride, e.g., a penetration enhancer component comprising at least one constituent other than benzalkonium chloride. In further exemplary aspects, such a penetration enhancer component represents at least about 0.1% w/v, ≥~0.2% w/v, ≥~0.3% w/v, ≥~0.4% w/v, ≥~0.5% w/v, ≥~0.6% w/v, ≥~0.7% w/v, ≥~0.8% w/v, ≥~0.9% w/v, or, e.g., ≥~1% w/v of the composition.

In certain aspects, compositions herein do not comprise a penetration enhancer component. In certain aspects, a composition provided herein is provided in the form of a gel. In some aspects, the gel composition comprises a penetration enhancer component. In alternative aspects, a composition provided in the form of a gel does not comprise a penetration enhancer component. In aspects, a penetration enhancer component can comprise one or more constituents which is not benzalkonium chloride. In aspects, a penetration enhancer component can comprise one or more constituents which is not benzalkonium chloride, however benzalkonium chloride is present in the composition, and the benzalkonium chloride may in present in the composition in a sufficient amount so as to provide detectable or significant penetration enhancement effect, such that the benzalkonium chloride can also be considered a constituent of the penetration enhancer component.

In aspects, a penetration enhancer component of a composition can comprise any ophthalmologically suitable and pharmaceutically acceptable penetration enhancing agent which does not detectably or significantly interfere with the required functionality of any one or more other composition constituents, such as any one or more APIs or one or more excipients. In aspects, a penetration enhancer component can comprise at least one constituent characterizable as a non-ionic surfactant having an HLB value of at least about 12, such as ≥~12.5, ≥~13, ≥~13.5, ≥~14, ≥~14.5, ≥~15, ≥~15.5, ≥~16, ≥~16.5, ≥~17, ≥~17.5, or, e.g., ≥~18. In aspects, the penetration enhancer component comprises at least one agent selected from a group comprising a polyoxyl-n-castor oil, a polyoxyethylene, a polyoxypropylene, and/or any combination or block polymer thereof. In aspects, the penetration enhancer component can comprise, mostly comprise, generally consist of, substantially consist of, consist essentially of, or consist of a non-ionic penetration enhancer constituent (e.g., polysorbate 80).

In aspects, exemplary constituents of a penetration enhancer component can comprise, e.g., a protein/peptide penetration enhancing agent (e.g., poly-arginine or polyserine). In aspects, exemplary constituents of a penetration enhancer component can comprise, e.g., a non-protein/peptide penetration enhancing agent. In aspects, exemplary constituents of a penetration enhancer component comprise, e.g., one or more of (e.g., in aspects a combination of two or more of pharmaceutically acceptable and ophthalmologically suitable polyoxyethylene sorbitan fatty acid ester(s), tocopheryl polyethylene glycol succinate (TPGS), poly-arginine, polyserine, tromethamine (tris), sesame seed oil or oils having similar compositions and functional characteristics suitable for ophthalmic use, etc. Exemplary polyoxyethylene sorbitan fatty acid esters include but not limited to polyoxyethylene sorbitan laurate (polysorbate 20), polyoxyethylene sorbitan palmitate (polysorbate 40), a polyoxyethylene sorbitan stearate (polysorbate 60), a polyoxyethylene sorbitan tri stearate (polysorbate 65). In some aspects the polyoxyethylene sorbitan fatty acid ester can be a polyoxyethylene sorbitan oleate polyoxyethylene sorbitan monooleate ester (e.g., polysorbate 80). In certain aspects, compositions provided by the invention can comprise a penetration enhancer component comprising effective amounts of one or more of one or more polyoxyethylene sorbitan fatty acid ester(s), tocopheryl polyethylene glycol succinate (TPGS), poly-arginine, or polyserine. In certain aspects, compositions provided by the invention can comprise a penetration enhancer component comprising effective amounts of one or more of one or more of the compounds selected from the group consisting of polyoxyethylene sorbitan fatty acid ester(s), tocopheryl polyethylene glycol succinate (TPGS), poly-arginine, and polyserine.

In aspects, additional compounds suitable for use in the present invention for increasing the penetration of an API of the composition within ocular tissue also can include quaternary ammonium compounds, such as, e.g., an ophthalmologically suitable quaternary ammonium salt. Quaternary ammonium compounds include ammonium salts in which organic radicals have been substituted for all four hydrogens of the original ammonium cation. Such compounds typically have a structure comprising a central nitrogen atom which is joined to four organic radicals and one acid radical. The organic radicals may be alkyl, aryl, or aralkyl, and the nitrogen can be part of a ring system. Examples of such compounds include benzalkonium chloride (e.g., CAS RN: 8001-54-5); benzethonium chloride CAS 121-54-0; cetalkonium chloride (e.g., CAS 122-18-9); cetrimide (e.g., CAS 8044-71-1); cetrimonium bromide (e.g., CAS 57-09-0); cetylpyridinium chloride (e.g., CAS 123-03-5); and stearalkonium chloride (e.g., CAS 122-19-0), provided that typically the quaternary ammonium compound included in any composition provided herein is of a nature and amount that is ophthalmologically safe. Such compounds can, e.g., in aspects also provide a detectably or significant preservation effect as described above. Therefore, in aspects, such a compound may be both a constituent of a preservative component and a penetration enhancer component.

In aspects, a penetration enhancer component can comprise benzalkonium chloride, benzethonium chloride, benzyltrimethylammonium chloride (also known as Triton B or trimethylbenzylammonium hydroxide), or lauryltrimethylammonium chloride (also known as dodecyltrimethylammonium chloride). In some embodiments, the ophthalmic formulations of the invention lack any quaternary ammonium salt.

In some aspects, formulations described herein also or alternatively comprise polyoxyl n castor oils (n=35-40) or polyoxyl hydrogenated castor oils, such as for example polyethoxylated castor oils, e.g., polyoxyl 35 castor oil (e.g., Cremophor EL), polyoxyl 40 castor oil (e.g., Marlowet 40, Emulgin RO 40), a polyoxyethylene hydrogenated castor oil (such as, e.g., polyoxyethylene hydrogenated castor oil 10/polyoxyl 10 hydrogenated castor oil, polyoxyethylene hydrogenated castor oil 40/polyoxyl 40 hydrogenated castor oil (Cremophor RH 40), polyoxyethylene hydrogenated castor oil 50/polyoxyl 50 hydrogenated castor oil, and polyoxyethylene hydrogenated castor oil 60/polyoxyl 60 hydrogenated castor oil (Cremophor RH 60)). In aspects, one suitable polyoxyl castor oil is polyoxyl-35-castor oil. The term "cremophor" can be used in this disclosure as a convenient reference to mean any such type of castor oil-related compounds/compositions, groups of two or more (as a class), combinations thereof, and equivalents thereof.

In aspects, a penetration enhancer component can comprise, e.g., a polyoxyethylene polyoxypropylene glycol, e.g., a polyoxyethylene (160) polyoxypropylene (30) glycol (Pluronic F68), a polyoxyethylene (42) polyoxypropylene (67) glycol (Pluronic P123), a polyoxyethylene (54) polyoxypropylene (39) glycol (Pluronic P85); a polyoxyethylene (196) polyoxypropylene (67) glycol (Pluronic F127) and a polyoxyethylene (20) polyoxypropylene (20) glycol (Pluronic L-44); or a polyethyleneglycol fatty acid ester, such as mono-lauric acid polyethyleneglycol, monostearin acid ethylene glycol, monostearin acid polyethyleneglycol, the mono-oleic acid polyethyleneglycol, monostearin acid ethylene glycol, an ethylene glycol distearate, the distearic acid polyethyleneglycol, and diiso stearic-acid polyethyleneglycol. In aspects, a suitable compound is polyoxyl 40 stearate. In other aspects, a penetration enhancer component can comprise tyloxapol. In further aspects, poloxamers (block copolymers) of certain examples above, such as a polyoxyethylene-polyoxypropylene block copolymer (e.g., Pluronic F-68 from BASF) and polaxamines (copolymers of three long chains of ethylene oxide and a single chain of propylene oxide that are used as nonionic surfactants) are compounds suitable for penetration enhancer components of compositions herein. In certain aspects, compositions lack any constituent characterizable as a poloxamer, e.g., characterizable as a block copolymer (e.g., in certain aspects, compositions lack any poloxamer/block copolymer).

As noted above, any ingredient/constituent/excipient described herein typically is present in an effective amount (an amount that alone or in combination with other present agents provides a measurable or significant desired effect, such as penetration enhancement). Any ingredient/constituent described here with respect a component/composition comprising that ingredient/component, again, provides implicit support for corresponding aspects in which the described component mostly comprises, generally consists of, substantially consists of, consists essentially of, or consists only of the recited constituent, type of constituent, etc.

In aspects, compositions provided by the invention comprise a penetration enhancer component comprising one or more penetration enhancing agents, wherein the penetration enhancer component is present in the composition in a concentration representing about 0.01% w/v-about 1% w/v, such as, e.g., ~0.05% w/v-~0.5% w/v, ~0.7% w/v-~0.3% w/v, or, e.g., ~0.1% w/v-~0.2% w/v such as, e.g., ~0.185% w/v of the composition.

In aspects, compositions provided by the invention comprise a penetration enhancer component comprising one or more penetration enhancing agents, wherein the penetration enhancer component is present in the composition in a concentration representing about 0.05% w/v to about 5% w/v of the composition, such as, e.g., ~0.1% w/v-~5% w/v, ~0.15% w/v-~5% w/v, ~0.2% w/v-~5% w/v, or ~0.25% w/v-~5% w/v, such as ~0.05% w/v-~5% w/v, ~0.05% w/v-~4.5% w/v, ~0.05% w/v-~4% w/v, ~0.05% w/v-~3.5% w/v, ~0.05% w/v-~3% w/v, ~0.05% w/v-~2.5% w/v, ~0.05% w/v-~2% w/v, ~0.05% w/v-~1.5% w/v, or ~0.05% w/v-~1% w/v, such as ~0.1% w/v-~4% w/v, ~0.15% w/v-~3% w/v, ~0.2% w/v-~2.5% w/v, ~0.25% w/v-~2.5% w/v, ~0.2% w/v-~1% w/v, or ~0.2% w/v-~0.5% w/v, such as for example about 0.25% w/v of the composition, about 0.5% w/v of the composition, or, e.g., about 1% w/v of the composition. In aspects, such amounts represent an effective amount of a penetration enhancer component.

In aspects, compositions provided by the invention comprise a penetration enhancer component comprising one or more penetration enhancing agents, wherein the penetration enhancer component is present in the composition in a concentration representing about 0.005% w/v to about 0.01% w/v of the composition, such as, e.g., ~0.005% w/v-~0.009% w/v, or ~0.005% w/v-~0.008% w/v, such as, e.g., ~0.006% w/v-~0.01% w/v or ~0.007% w/v-~0.01% w/v, as in, e.g., about ~0.006% w/v-~0.009% w/v or ~0.007% w/v-~0.008% w/v of the composition, such as, e.g., ~0.005% w/v of the composition. In aspects, such amounts represent an effective amount of a penetration enhancer component.

In aspects, compositions provided by the invention comprise a penetration enhancer component comprising one or more penetration enhancing agents, wherein the penetration enhancer component is present in the composition in a concentration representing about 0.25% w/v-about 5% w/v of the composition, such as, e.g., ~0.25% w/v-~2.5% w/v of the composition, e.g., ~0.5% w/v-~2% w/v, ~0.5% w/v-~1.5% w/v, or, e.g., ~0.8% w/v-~1.1% w/v of the composition, such as for example ~1% w/v of the composition. In aspects, such amounts represent an effective amount of a penetration enhancer component.

In certain aspects, the penetration enhancer component comprises two or more constituents wherein the total concentration/amount of the two or more penetration enhancer component constituents is represented by the concentrations/amounts provided above. For example, in some exemplary aspects, compositions comprise a penetration enhancer component comprising, e.g., polysorbate 80, cremophor EL, or, e.g., TPGS, present in an amount representing ~0.05% w/v-~5% w/v, ~0.1% w/v-~4% w/v, ~0.15% w/v-~3% w/v, ~0.2% w/v-~2% w/v, ~0.2% w/v-~1% w/v, or ~0.2% w/v-~0.5% w/v, such as for example about 1% w/v of the composition, and, optionally further, a benzalkonium chloride in an amount representing about 0.001% w/v to about 0.01% w/v of the composition, such as, e.g., ~0.002% w/v-~0.008% w/v or ~0.004% w/v-~0.006% w/v of the composition, such as ~0.005% w/v of the composition. In aspects, compositions can comprise a penetration enhancer component comprising two or more constituents, such as, e.g., one of polysorbate 80, tromethamine (tris), cremophor EL, poly-arginine, or polyserine. and benzalkonium chloride, wherein the penetration component comprises about 0.05% w/v to about 2% w/v, such as about 0.1% w/v-~1.8% w/v, such as, e.g., about 0.1% w/v-~0.5% w/v, about 0.2% w/v and about 1.4% w/v of the composition, such as, e.g., about 0.2% w/v or about 1% w/v of the composition or about 1.005% w/v of the composition. This principle can be applied to combinations of any of the specific penetration enhancers described herein, any combination of classes of penetration enhancers, or any mixture thereof, and can include three or more of such compounds/classes of compounds. For example, compositions can comprise polysorbate 80, benzalkonium chloride, and, e.g., cremophor, wherein each provide, or the combination thereof provides, or both, detectable or significant penetration enhancement effect(s). In another example, compositions can comprise, e.g., one or more of polysorbate 80, cremophor, or TPGS, along with benzalkonium chloride. In another example, compositions can comprise, e.g., one or more of polysorbate 80, cremophor, or TPGS, along with benzalkonium chloride and tromethamine (tris). In aspects, such amounts provided in this paragraph represent an effective amount of a penetration enhancer component.

In aspects, the penetration enhancer component comprises/consists essentially of/consists of a single constituent wherein, in aspects, the single constituent is present in an amount represented by the concentrations/amounts provided above.

In certain aspects, the penetration enhancer component comprises/consists essentially of (and, of course, by implication, alternatively consists of) two or more polyoxyethylene sorbitan fatty acid esters wherein the total amount of the two or more polyoxyethylene sorbitan fatty acid esters is represented by the concentrations/amounts above.

In aspects, the penetration enhancer component comprises/consists essentially of a single polyoxyethylene sorbitan fatty acid ester, wherein the total amount of the single polyoxyethylene sorbitan fatty acid ester is represented by the concentrations/amounts provided above. In certain aspects, the penetration enhancer component comprises a single constituent, the single constituent being a polyoxyethylene sorbitan fatty acid ester, such as, e.g., polysorbate 80, wherein the single polyoxyethylene sorbitan fatty acid ester, e.g., polysorbate 80, is, e.g., present in an amount representing ~0.05% w/v-~5% w/v, ~0.1% w/v-~4% w/v, ~0.15% w/v-~3% w/v, ~0.2% w/v-~2% w/v, ~0.2% w/v-~1.5% w/v, or ~0.5% w/v-~1.2% w/v, such as for example about 1% w/v of the composition. In aspects, such amounts represent an effective amount of a penetration enhancer component constituent.

In aspects, a single constituent of the penetration enhancer component is/consists essentially of polysorbate 80. In aspects, a single constituent of the penetration enhancer component is/consists essentially of cremophor EL. In aspects, a single constituent of the penetration enhancer component is/consists essentially of TPGS. In aspects, the penetration enhancer component is/consists essentially of polysorbate 80, cremophor EL, or TPGS in combination with benzalkonium chloride. In some embodiments, the penetration enhancer component of compositions further comprises tromethamine (tris).

In certain alternative aspects, the penetration enhancer component comprises a single constituent, wherein the single constituent is a quaternary ammonium compound, e.g., a quaternary ammonium salt, e.g., benzalkonium chloride, e.g., being present in an amount representing about 0.001% w/v to about 0.01% w/v of the composition, such as, e.g., ~0.002% w/v-~0.009% w/v, ~0.003% w/v-~0.008% w/v, ~0.004% w/v-~0.007% w/v, or ~0.004% w/v-~0.006% w/v of the composition, e.g., ~0.005% w/v of the composition. In aspects, such amounts represent an effective amount of benzalkonium chloride. In aspects, the compositions provided by the invention comprise no penetration enhancer component. In aspects, the compositions provided by the invention comprise no penetration enhancer component other than benzalkonium chloride. In aspects, compositions provided by the invention comprise benzalkonium chloride in an amount which does not provide detectable or significant penetration enhancer activity. According to certain aspects of the invention, compositions can comprise at least one additional ophthalmologically suitable quaternary ammonium salt, selected from a group comprising benzethonium chloride, benzyltrimethylammonium chloride, lauryl trimethyl ammonium chloride, or any combination thereof which each alone or in combination provide a detectable or significant increase in penetration of a PAC constituent, a BBC constituent, or one or more constituents of each of the PAC and the BBC. In another aspect, compositions are free of any penetration enhancer(s) other than benzalkonium chloride characterizable as a quaternary ammonium salt. In certain aspects, compositions are free of any penetration enhancer(s) characterizable as a quaternary ammonium salt.

In aspects, one or more constituents of the penetration enhancer component can further provide one or more additional detectable or significant functionalities to a formulation/composition, such as, for example, a detectable or significant solubilization effect (such as is described elsewhere herein), detectable or significant demulcent effect, detectable or significant preservation effect, or any combination thereof. In aspects, one or more constituents of the penetration enhancer component can further provide a preservation/preservative effect. In one aspect, a penetration enhancing agent of the penetration enhancer component also provides a detectable or significant solubilization effect. In one aspect, a penetration enhancing agent of the penetration enhancer component also provides a detectable or significant demulcent effect. In one aspect, a penetration enhancing agent of the penetration enhancer component also provides both a detectable or significant solubilization enhancement effect and a detectable or significant demulcent effect. In one aspect, a penetration enhancing agent of the penetration enhancer component also provides a detectable or significant preservation effect and a detectable or significant solubilization effect. In certain aspects, a penetration enhancing agent of the penetration enhancer component does not provide a solubilization effect, does not provide a preservation effect, does not provide a demulcent effect, or does not provide any combination of such additional effects. That is, in aspects, a penetration enhancer and a solubilizing agent, or a penetration enhancer and a demulcent, or, e.g., a penetration agent and a preservation agent can be differing compounds.

As stated above, in aspects, compositions provided by the invention can comprise one or more penetration enhancers (e.g., penetration enhancer component constituents) in an amount of about, e.g., 0.001% w/v-about 2.7% w/v, about 1% w/v-about 3% w/v, or, e.g., about 2% w/v-about 5% w/v. In aspects, such amounts represent an effective amount of a penetration enhancer. In aspects, such amounts are advantageous in that such an amount provides a detectable or significant increase in the amount of API, e.g., the amount of a bimatoprost compound (e.g., bimatoprost base), the amount of a timolol compound (e.g., a salt of timolol, e.g., timolol maleate), or both the amount of a bimatoprost compound and timolol compound, which penetrates ocular tissue per administration or also or alternatively the rate at which such one or more compounds penetrates ocular tissue upon administration. In aspects, such amounts are advantageous in that such an effect can be achieved without the user experiencing one or more side effects which cause the use to discontinue use of the composition.

In this and any other ingredient aspect of the invention, the invention also can be characterized as comprising a "means" for providing a recited function, here imparting/providing an effective, detectable, or significant penetration effect to one or more constituents of composition(s) of the invention. In such a respect, any known equivalents of such named agents can also be, e.g., are, incorporated into compositions or methods of the invention. As with other sections similarly described herein, any of the components of the invention can be, where suitable, described as means (e.g., the above-described penetration enhancement agents/compounds or components can be described as penetration enhancer means (or penetration means) or means for providing effective, detectable, or significant penetration activity/characteristics to one or more constituents of the composition).

Solubilization Component (Solubilizing Agent(s))

In aspects, compositions provided by the invention comprise a solubilization component. In aspects, the solubilization component comprises any one or more pharmaceutically acceptable and ophthalmologically suitable constituents (e.g., pharmaceutically acceptable and ophthalmologically suitable compounds) which detectably or significantly increase the solubilization of one or more other constituents of the composition, detectably or significantly increase the period of time that one or more other constituents of the composition remain solubilized, or both. In aspects, the solubilization component can comprise any one or more pharmaceutically acceptable or ophthalmologically suitable compounds capable of demonstrating such an effect. In aspects, a solubilizing agent of a solubilization component can be a surfactant, e.g., demonstrating detectable or significant surfactant properties/functions, e.g., in the context of the associated composition/formulation. In aspects, a solubilization component of a composition (e.g., a surfactant) can comprise any ophthalmologically suitable and pharmaceutically acceptable solubilizing agent (or, e.g., surfactant) which does not detectably or significantly interfere with the required functionality of any one or more other composition constituents.

In aspects, one or more constituents of the solubilization component can further provide one or more additional detectable or significant functionalities, such as, for example, detectable or significant penetration enhancement effect(s) (such as is described elsewhere herein), detectable or significant demulcent effect(s), or both. In one aspect, a solubilizing agent of the solubilizing component also provides detectable or significant penetration enhancement effect(s). In one aspect, a solubilizing agent of the solubilizing component also provides detectable or significant demulcent effect(s). In one aspect, a solubilizing agent of the solubilizing component also provides both detectable or significant penetration enhancement effect and detectable or significant demulcent effect. In certain aspects, a solubilizing agent of the solubilizing component does not provide either a penetration enhancement effect or a demulcent effect. In aspects, a penetration enhancer and a solubilizing agent, or a penetration enhancer and a demulcent, can be different compounds, or a combination of all three agents can be present due to the inclusion of two compounds or three separate compounds in the composition, in the former case where such a compound is a dual class excipient (e.g., as is the case with a penetration enhancer that also is a preservative).

In aspects, compositions comprise a penetration enhancer component comprising one or more constituents which provide detectable or significant solubilizing activity. Therefore, in aspects, compositions can comprise a plurality of solubilizing agents, such as, for example, a first solubilizing agent which further provides detectable or significant penetration enhancement activity (e.g., a polyoxyethylene sorbitan fatty acid ester, such as polysorbate 80), TPGS, or also or alternatively a polyoxyl hydrogenated castor oils, such as for example one or more polyethoxylated castor oils, such as cremophor EL, in addition to a second solubilizing agent, such as, e.g., tromethamine.

In aspects, exemplary constituents of a solubilization component comprise, e.g., one or more of pharmaceutically acceptable and ophthalmologically suitable polyoxyethylene sorbitan fatty acid esters, tocopheryl polyethylene glycol succinate (TPGS), poly-arginine, polyserine, tromethamine (tris), sesame seed oil or oils having similar compositions and functional characteristics suitable for ophthalmic use, etc. Exemplary polyoxyethylene sorbitan fatty acid esters include polyoxyethylene sorbitan laurate (polysorbate 20), polyoxyethylene sorbitan palmitate (polysorbate 40), a polyoxyethylene sorbitan stearate (polysorbate 60), a polyoxyethylene sorbitan tri stearate (polysorbate 65). In some aspects the polyoxyethylene sorbitan fatty acid ester can be a polyoxyethylene sorbitan oleate/polyoxyethylene sorbitan mono-oleate ester (e.g., polysorbate 80). In certain aspects, constituents of a solubilization component can comprise, e.g., one or more polyethoxylated castor oils, such as, e.g., polyethoxylated castor oils characterizable as cremophor(s).

In aspects, one or more compounds provided in the section entitled "Penetration Enhancer Component (Penetration Enhancer(s))" also have solubilization properties, and, thus, may be considered a constituent of a solubilization component.

In aspects, compositions provided by the invention comprise a solubilization component comprising one or more solubilizing agents, wherein the solubilization component is present in the composition in a concentration representing about 0.05% w/v to about 5% w/v of the composition, such as, e.g., ~0.1% w/v-~5% w/v, ~0.15% w/v-~5% w/v, ~0.2% w/v-~5% w/v, or, e.g., ~0.25% w/v-~5% w/v of the composition.

In aspects, compositions provided by the invention comprise a solubilization component comprising one or more solubilizing agents, wherein the solubilization component is present in the composition in a concentration representing about 0.05% w/v to about 5% w/v of the composition, such as, e.g., ~0.05% w/v-~4.5% w/v, ~0.05% w/v-~4% w/v, ~0.05% w/v-~3.5% w/v, ~0.05% w/v-~3% w/v, ~0.05% w/v-~2.5% w/v, ~0.05% w/v-~2% w/v, ~0.05% w/v-~1.5% w/v, or ~0.05% w/v-~1% w/v of the composition.

In aspects, compositions provided by the invention comprise a solubilization component comprising one or more solubilizing agents, wherein the solubilization component is present in the composition in a concentration representing about 0.05% w/v to about 5% w/v of the composition, such as, e.g., ~0.1% w/v-~4% w/v, ~0.15% w/v-~3% w/v, ~0.2% w/v-~2% w/v, ~0.3% w/v-~1.5% w/v, or ~0.4% w/v-~1% w/v, such as for example about 0.1% w/v, ~0.2% w/v, ~0.3% w/v, ~0.4% w/v, ~0.5% w/v, ~0.6% w/v, ~0.7% w/v, ~0.8% w/v, ~0.9% w/v, ~1% w/v, ~1.1% w/v, or, e.g., ~1.2% w/v of the composition.

In certain aspects, the solubilization component comprises two or more constituents wherein the total concentration/amount of the two or more solubilization component constituents is represented by the concentrations/amounts provided above. For example, in some aspects, compositions an comprise a solubilization component comprising a constituent characterizable as a polyethoxylated castor oil and tromethamine. In aspects, compositions can comprise, e.g., a polyethoxylated castor oil, e.g., cremophor, TPGS, or, e.g., polysorbate 80 in an amount representing about 0.1% w/v to about 5% w/v, such as, e.g., ~0.5% w/v-~4% w/v, or ~1% w/v-~3% w/v, such as, e.g., about 0.25% w/v-about 2.5% w/v of the composition, e.g., ~1% w/v of the composition or also or alternatively, e.g., tromethamine (tris) in an amount representing ~0.1% w/v-0.2% w/v, e.g., ~0.185% w/v of the composition. In aspects, compositions can comprise, e.g., tromethamine (tris), in an amount representing about 0.1% w/v to about 0.5% w/v, such as, e.g., ~0.1% w/v-~0.4% w/v, ~0.1% w/v-~0.3% w/v, or ~0.1% w/v-~0.2% w/v, such as, e.g., about 0.185% w/v of the composition. In aspects, compositions can comprise a solubilization component comprising at least two solubilization constituents, wherein the total amount of the at least two solubilization constituents represents about 0.2% w/v to about 5% w/v of the composition, such as, e.g., ~0.3% w/v-~4% w/v, ~0.4% w/v-~3% w/v, ~0.5% w/v-~2% w/v, or, e.g., ~1% w/v-~1.5% w/v, e.g., ~1.185% w/v of the composition.

In aspects, the solubilization component comprises a single constituent wherein the single constituent is present in an amount represented by the concentrations/amounts provided above. In certain aspects, the solubilization component comprises two or more polyoxyethylene sorbitan fatty acid esters wherein the total amount of the two or more polyoxyethylene sorbitan fatty acid esters is represented by the concentrations/amounts provided above (or alternatively each is present in the amounts provided above). In aspects, the solubilization component comprises a single polyoxyethylene sorbitan fatty acid ester, wherein the total amount of the single polyoxyethylene sorbitan fatty acid ester is represented by the concentrations/amounts provided above. In certain aspects, the solubilization component comprises a single constituent which further provides detectable or significant penetration enhancement activity, the single constituent being a polyoxyethylene sorbitan fatty acid ester, such as, e.g., polysorbate 80, wherein, in aspects, the single polyoxyethylene sorbitan fatty acid ester, e.g., polysorbate 80, is present in an amount representing ~0.05% w/v-~5% w/v, ~0.1% w/v-~4% w/v, ~0.15% w/v-~3% w/v, ~0.25% w/v-~2.5% w/v, ~0.2% w/v-~2% w/v, ~0.2% w/v-~1.5% w/v, or ~0.2% w/v-~0.5% w/v, such as for example about 1% w/v of the composition. In aspects, the solubilization component further comprises a single constituent, e.g., an additional single constituent, wherein the single constituent is present in an amount represented by the concentrations/amounts provided above, such as, e.g., tromethamine in an amount of about 0.01% w/v-about 1% w/v, such as, e.g., ~0.05% w/v-~0.5% w/v, ~0.7% w/v
~0.3% w/v, or, e.g., ~0.1% w/v-~0.2% w/v such as, e.g., ~0.185% w/v of the composition.

In aspects, such amounts of a solubilization component, solubilization component constituents, or both, disclosed in this section represent an effective amount of a solubilization component, solubilization component constituent, or both. In certain aspects, composition(s) herein lack a solubilization component.

In this and any other ingredient aspect of the invention, the invention also can be characterized as comprising a "means" for providing a recited function, here imparting/providing an effective, detectable, or significant solubilization effect (e.g., increased solubilization) to one or more constituents of composition(s) of the invention. In such a respect, any known equivalents of such named agents can also be, e.g., are, incorporated into compositions or methods of the invention. As with other sections similarly described herein, any of the components of the invention can be, where suitable, described as means (e.g., the above-described solubilization agents/compounds or components can be described as solubilization means or means for providing effective, detectable, or significant solubilization activity/characteristics to one or more constituents of the composition.)

Combination Solubilization/Penetration Enhancer Component (Solubilizing Agent(s)/Penetration Enhancer(s))

In certain aspects, a single ingredient of compositions provided by the invention can be a constituent of both a penetration enhancer component and a solubilization component. E.g., in aspects, a single ingredient of compositions provided by the invention can be characterized as capable of providing both detectable and significant solubilization effect and detectable and significant penetration enhancement effect, such affects being described above in each of the solubilization component and penetration enhancer component sections, respectively. Therefore, in aspects, one or more compounds provided in the section entitled "Penetration Enhancer Component (Penetration Enhancer(s))," having penetration enhancing effect(s), can, in aspects be interpreted as being repeated in the section entitled "Solubilization Component (Solubilizing Agent(s))," having solubilization effect(s). Further, in aspects, one or more compounds provided in the section entitled "Solubilization Component (Solubilizing Agent(s))," having solubilization effect(s), can, in aspects, be interpreted as being repeated in the section entitled "Penetration Enhancer Component (Penetration Enhancer(s))," having penetration enhancing effect(s). In certain aspects, a constituent of the penetration enhancer component can act as only a penetration enhancer and provide no detectable or significant solubilization effect. Similarly, in aspects, a constituent of the solubilization component can act as only a solubilizer and provide no detectable or significant penetration enhancement effect.

In aspects, one or more ingredients providing both a detectable or significant penetration enhancing effect and a detectable or significant solubilization effect can further provide detectable or significant demulcent effect. In certain aspects, an ingredient providing both a detectable or significant penetration enhancing effect and a detectable or significant solubilization effect does not provide detectable or significant demulcent effect. That is, in aspects, a single ingredient providing both penetration enhancer functionality and solubilizing functionality, and a demulcent, can be different/differing compounds.

Exemplary combination solubilizer and penetration enhancer compounds include, e.g., one or more of pharmaceutically acceptable and ophthalmologically suitable polyoxyethylene sorbitan fatty acid esters, tocopheryl polyethylene glycol succinate (TPGS), poly-arginine, polyserine, tromethamine (tris), sesame seed oil or oils having similar compositions and functional characteristics suitable for ophthalmic use, etc. Exemplary polyoxyethylene sorbitan fatty acid esters include but not limited to polyoxyethylene sorbitan laurate (polysorbate 20), polyoxyethylene sorbitan palmitate (polysorbate 40), a polyoxyethylene sorbitan stearate (polysorbate 60), or a polyoxyethylene sorbitan tri stearate (polysorbate 65). In some aspects the polyoxyethylene sorbitan fatty acid ester can be a polyoxyethylene sorbitan oleate/polyoxyethylene sorbitan mono-oleate ester (e.g., polysorbate 80). Other exemplary combination solubilizer and penetration enhancer compounds include, e.g., polyethoxylated castor oil(s), e.g., a cremophor (such as, e.g., cremophor EL).

In some aspects, compositions comprise, e.g., benzalkonium chloride and one or more of, e.g., polysorbate 80, cremophor EL, and TPGS.

In some aspects, compositions comprise, e.g., benzalkonium chloride; one or more of, e.g., polysorbate 80, cremophor EL, and TPGS; and tromethamine (tris).

In aspects, compositions provided by the invention comprise a single ingredient providing both penetration enhancement and solubilization functionality, wherein the single ingredient is present in the composition in a concentration representing about 0.05% w/v to about 5% w/v of the composition, such as, e.g., ~0.1% w/v-~5% w/v, ~0.15% w/v-~5% w/v, ~0.2% w/v-~5% w/v, or ~0.25% w/v-~5% w/v, such as ~0.05% w/v-~5% w/v, ~0.05% w/v-~4.5% w/v, ~0.05% w/v-~4% w/v, ~0.05% w/v-~3.5% w/v, ~0.05% w/v-~3% w/v, ~0.05% w/v-~2.5% w/v, ~0.05% w/v-~2% w/v, ~0.05% w/v-~1.5% w/v, or ~0.05% w/v-~1% w/v, such as ~0.1% w/v-~4% w/v, ~0.15% w/v-~3% w/v, ~0.2% w/v-~2% w/v, ~0.2% w/v-~1% w/v, or ~0.2% w/v-~0.5% w/v, such as for example about 1% w/v of the composition. In certain aspects, the single ingredient is a polyoxyethylene sorbitan fatty acid ester, such as, e.g., polysorbate 80, wherein the single polyoxyethylene sorbitan fatty acid ester, e.g., polysorbate 80, is present in an amount representing ~0.05% w/v-~5% w/v, ~0.1% w/v-~4% w/v, ~0.15% w/v-~3% w/v, ~0.2% w/v-~2% w/v, or ~0.2% w/v-~1% w/v, such as for example about 0.25% w/v-2.5% w/v of the composition, e.g., about 1% w/v of the composition. In certain aspects, the single ingredient is TPGS, and TPGS is present in an amount representing ~0.05% w/v-~5% w/v, ~0.1% w/v-~4% w/v, ~0.15% w/v-~3% w/v, ~0.2% w/v-~2% w/v, or ~0.2% w/v-~1% w/v, such as for example about 0.25% w/v-2.5% w/v of the composition, e.g., about 1% w/v of the composition. In certain aspects, the single ingredient is a polyethoxylated castor oil, e.g., cremophor EL, wherein the polyethoxylated castor oil, e.g., cremophor EL, is present in an amount representing ~0.05% w/v-~5% w/v, ~0.1% w/v-~4% w/v, ~0.15% w/v-~3% w/v, ~0.2% w/v-~2% w/v, or ~0.2% w/v-~1% w/v, such as for example about 0.25% w/v-2.5% w/v of the composition, e.g., about 1% w/v of the composition, wherein the cremophor provides both detectable or significant solubilization and penetration enhancement activity. In aspects, compositions can comprise both a polyethoxylated castor oil, e.g., a cremophor, and a polyoxyethylene sorbitan fatty acid ester, e.g., polysorbate 80, wherein a combination solubilization/penetration enhancer component comprises the two compounds in an amount representing about 0.1% w/v to about 2% w/v of the composition, such as, e.g., about 0.5% w/v to about 1.5% w/v, e.g., about 1% w/v, ~1.5% w/v, or, e.g., ~2% w/v of the composition. In aspects, such a composition can further comprise one or more constituents which provide detectable or significant penetration enhancement activity (e.g., a penetration enhancing agent) or detectable or significant solubilization activity (e.g., a solubilization agent).

In aspects, the single constituent of the solubilization component is polysorbate 80. In aspects, the single ingredient, e.g., the single polyoxyethylene sorbitan fatty acid ester, e.g., polysorbate 80, further provides detectable or significant demulcent effect.

Demulcent Component (Demulcent(s))

In aspects, compositions provided by the invention comprise a demulcent component. In aspects, the demulcent component comprises any one or more pharmaceutically acceptable and ophthalmologically suitable constituents (e.g., pharmaceutically acceptable and ophthalmologically suitable compounds) which detectably or significantly increase the soothing effect of the composition; detectably or significantly reduce the degree of, or prevent, irritation caused by the composition or caused by one or more other constituents of the composition; detectably or significantly reduce the degree of, or prevent, inflammation caused by the composition or caused by one or more other constituents of the composition; or a combination thereof. In aspects, the demulcent component can comprise any one or more pharmaceutically acceptable or ophthalmologically suitable compounds capable of demonstrating such an effect.

In aspects, one or more constituents of the demulcent component can further provide one or more additional detectable or significant functionalities, such as, for example, detectable or significant penetration enhancement effect, detectable or significant solubilization effect, detectable or significant viscosity enhancing effect/thickening effect, or a combination thereof (such as is described for each such effect elsewhere herein). That is, in one aspect, a demulcent constituent of the demulcent component also provides detectable or significant penetration enhancement effect. In one aspect, a demulcent constituent of the demulcent component also provides detectable or significant solubilization effect. In one aspect, a demulcent constituent of the demulcent component also provides detectable or significant viscosity enhancing/thickening effect. In one aspect, a demulcent constituent of the demulcent component also provides both detectable or significant penetration enhancement effect and detectable or significant solubilization effect. In one aspect, a demulcent constituent of the demulcent component also provides detectable or significant viscosity enhancing/thickening effect. In certain aspects, a demulcent constituent of the demulcent component does not provide a penetration enhancement effect, a solubilization effect, or a viscosity enhancing/thickening effect. That is, in aspects, a penetration enhancer and a demulcent, a solubilizer and a demulcent, or, e.g., a demulcent and a thickening agent can be differing compounds.

In aspects, a demulcent component of a composition can comprise any ophthalmologically suitable and pharmaceutically acceptable demulcent which does not detectably or significantly interfere with the required functionality of any one or more other composition constituents, such as, e.g., a PAC constituent, a BBC constituent, or both constituents of the PAC and the BBC. In aspects, exemplary constituents of a demulcent component comprise, e.g., a constituent that also provides detectable or significant penetration enhancement activity, solubilization activity, or both penetration enhancement activity and solubilization activity, such as, e.g., polysorbate 80. In some aspects the polyoxyethylene sorbitan fatty acid ester can be a polyoxyethylene sorbitan oleate/polyoxyethylene sorbitan mono-oleate ester (e.g., polysorbate 80). In some aspects, exemplary constituents of a demulcent component comprise, e.g., one or more polyols (sugar-like hydrogenated carbohydrates; sometimes referred to as polyhydric alcohols), e.g., polyols in liquid form, such as for example glycerin, polyethylene glycol 300, polyethylene glycol 400, polysorbate 80 as described previously, propylene glycol, etc.

In aspects, exemplary constituents of a demulcent component comprise, e.g., one or more of pharmaceutically acceptable and ophthalmologically suitable cellulose derivatives, such as, e.g., carboxymethylcellulose sodium, hydroxyethyl cellulose, hypromellose, methylcellulose, etc.

In alternative aspects, an exemplary constituent of a demulcent component is, e.g., a high-molecular-weight polysaccharide, e.g., dextran 70. In still further aspects, an exemplary constituent of a demulcent component is, e.g., gelatin. In yet further aspects, an exemplary constituent of a demulcent component is, e.g., polyvinyl alcohol (PVA). In some aspects, an exemplary constituent of a demulcent component is, e.g., povidone.

In aspects, compositions provided by the invention comprise a demulcent component comprising one or more demulcent constituents, wherein the demulcent component is present in the composition in a concentration representing about 0.01% w/v to about 5%, about 0.05% w/v to about 5% w/v, or another detectably, physiologically effective, or significant amount of the composition, such as, e.g., ~0.1% w/v-~5% w/v, ~0.15% w/v-~5% w/v, ~0.2% w/v-~5% w/v, or ~0.25% w/v-~5% w/v, such as ~0.05% w/v-~5% w/v, ~0.05% w/v-~4.5% w/v, ~0.05% w/v-~4% w/v, ~0.05% w/v-~3.5% w/v, ~0.05% w/v-~3% w/v, ~0.05% w/v-~2.5% w/v, ~0.05% w/v-~2% w/v, ~0.05% w/v-~1.5% w/v, or ~0.05% w/v-~1% w/v, such as ~0.1% w/v-~4% w/v, ~0.15% w/v-~3% w/v, ~0.2% w/v-~2% w/v, ~0.2% w/v-~1% w/v, or ~0.2% w/v-~0.5% w/v, such as for example about 0.25% w/v, about 0.5% w/v, or, e.g., about 1% w/v of the composition.

In certain aspects, the demulcent component comprises two or more constituents wherein the total concentration/amount of the two or more demulcent component constituents is represented by the concentrations/amounts provided above. In aspects, the demulcent component comprises a single constituent wherein the single constituent is present in an amount represented by the concentrations/amounts provided above. In certain aspects, the demulcent component comprises two or more of polyoxyethylene sorbitan fatty acid esters wherein the total amount of the two or more polyoxyethylene sorbitan fatty acid esters is represented by the concentrations/amounts provided above. In aspects, the demulcent component comprises a single polyoxyethylene sorbitan fatty acid ester, wherein the total amount of the single polyoxyethylene sorbitan fatty acid ester is represented by the concentrations/amounts provided above. In certain aspects, the demulcent component comprises a single constituent, the single constituent being a polyoxyethylene sorbitan fatty acid ester, such as, e.g., polysorbate 80, wherein the single polyoxyethylene sorbitan fatty acid ester, e.g., polysorbate 80, is present in an amount representing ~0.05% w/v-~5% w/v, ~0.1% w/v-~4% w/v, ~0.15% w/v-~3% w/v, ~0.2% w/v-~2% w/v, ~0.2% w/v-~1% w/v, or ~0.2% w/v-~0.5% w/v, such as for example about 0.25% w/v, about 0.5% w/v, or, e.g., about 1% w/v of the composition. In aspects, the single constituent of the demulcent component is polysorbate 80.

In certain alternative aspects, compositions comprise a demulcent component wherein the demulcent component comprises a cellulose derivative in an amount of about 0.2% w/v-about 2.5% w/v of the composition, typically in an amount of less than or equal to about 1% w/v. In aspects, compositions comprise a demulcent component wherein the demulcent component comprises dextran 70 in an amount of about 0.1% w/v of the composition. In aspects, a demulcent component comprising dextran 70 further comprises one or more additional demulcent constituents. In aspects, compositions comprise a demulcent component wherein the demulcent component comprises gelatin in an amount of about 0.01% w/v of the composition. In aspects, compositions comprise a demulcent component wherein the demulcent component comprises polyvinyl alcohol (PVA) in an amount of about 0.1% w/v-about 4% w/v of the composition. In aspects, compositions comprise a demulcent component wherein the demulcent component comprises povidone in an amount of about 0.1% w/v-about 2% w/v of the composition.

In certain aspects, compositions comprise a demulcent component representing about 0.01% w/v-about 2% w/v, such as, e.g., about 1% w/v-about 3% w/v, or, e.g., about 2% w/v-about 5% w/v. In aspects, treatment of an ophthalmic condition/ocular condition with compositions provided by the invention comprising a demulcent component, e.g., comprising polysorbate-80 or one or more other demulcents of a demulcent component, detectably or significantly reduce or prevent inflammation, irritation, or both, over (as compared to) similar compositions (compositions comprising about the same or the same amount of most, generally all, substantially all, or all of the otherwise same ingredients), not comprising a demulcent. In aspects, such amount(s) disclosed here of a demulcent component is advantageous in that it provides a detectable or significant demulcent effect compared to essentially the same, generally the same, or the same composition(s) lacking such a demulcent component, making use, e.g., repeated use or prolonged use (e.g., use for a sufficient period of time so as to result in a detectable or significant clinical effect on the target indication, such as, e.g., elevated intraocular pressure, glaucoma, or both) tolerable to the user. In aspects, such amount(s) of a demulcent is advantageous as such amounts can in aspects be provided without causing detectable or significant interference with any one or more other components. In aspects, a demulcent component can bolster the effect of one or more other components (e.g., by further providing a detectable or significant contribution to the solubility of one or more constituents of the composition (e.g., one or more constituents of a PAC, BBC, or both) or by enhancing the penetration into ocular tissue of one or more constituents of the composition (e.g., amount of the constituent penetrating ocular tissue, rate of constituent penetrating ocular tissue, or both). Thus, in aspects, such amount(s) of a demulcent component is/are advantageous in that the demulcent component can detectably or significantly contribute to the efficacy, stability, or both efficacy and stability of compositions comprising such a demulcent component.

In aspects, such amounts of a demulcent component, demulcent component constituents, or both, disclosed in this section represent an effective amount of a demulcent component, demulcent component constituent, or both. According to certain aspects, composition(s) provided herein lack any constituent demonstrating detectable or significant demulcent activity(ies).

In this and any other ingredient aspect of the invention, the invention also can be characterized as comprising a "means" for providing a recited function, here imparting/providing an effective, detectable, or significant demulcent effect (e.g., soothing, or reduced irritation effect) to one or more constituents of composition(s) of the invention. In such a respect, any known equivalents of such named agents can also be, e.g., are, incorporated into compositions or methods of the invention. As with other sections similarly described herein, any of the components of the invention can be, where suitable, described as means (e.g., the above-described demulcent agents/compounds or components can be described as demulcent means or means for providing effective, detectable, or significant demulcent activity/characteristics to one or more constituents of the composition.)

Buffer Component (Buffer(s))

In aspects, compositions provided by the invention comprise a buffer component. In aspects, the buffer component comprises any one or more pharmaceutically acceptable and ophthalmologically suitable constituents (e.g., pharmaceutically acceptable and ophthalmologically suitable compounds) which provide detectable or significant pH buffering effect, such that, e.g., the compositions maintain a pH within the pH ranges described herein for extended periods of time (e.g., a pH of about 6-about 8, e.g., ~6-~7.8, ~6-~7.6, or ~6-~7.4, such as, e.g., ~6.2-~8, ~6.4-~8, ~6.6-~8, ~6.8-~8, ~7-~8, ~7.2-~8, or ~7.4-~8, such as, e.g., ~6.2-~7.8, or, e.g., ~7-~7.5) when stored at about 25° C.+/-2° C. and about 40%+/-5% relative humidity; about 40° C.+/-2° C. and not more than about 25% relative humidity; about 15° C.-about 27° C. and about 60% relative humidity; about 38° C.-about 42° C. and 75% relative humidity; or when stored under any such condition, or a sequential combination of such conditions, for a period of at least about 1 month, e.g., ≥~3, ≥~6, ≥~9, ≥~12, ≥~18, ≥~24, or, e.g., at least about 36 months.

According to some aspects, compositions described herein do not comprise a buffer component. In aspects, compositions provided by the invention do not comprise any constituent characterizable as a buffer.

In aspects, compositions described herein can comprise one or more buffers or pH-adjusting agents (such agents described in more detail elsewhere herein) used to adjust or maintain the pH within a target pH range, such as, e.g., from about 6 to about 8, e.g., ~6.2-~7.8 or ~7-~7.5. In aspects, one or more constituents of the buffer component can further provide one or more additional detectable or significant functionalities, such as, for example, detectable or significant pH adjusting effects. In some aspects, a constituent of a buffer component can contribute the tonicity of the composition. In aspects, a buffer component can be selected (or characterized by), at least in part, to aid in or adding in (detectably or significantly promoting) the establishment of a target tonicity. Therefore, in some embodiments, one or more buffers and one or more tonicity agents can combine to contribute to the osmolality of a composition. In aspects, a buffer component can be selected or characterized by, at least in part, based upon the presence of one or more other constituents of the composition and, e.g., their concentration(s) (such as, e.g., contemplating the tonicity contribution of one or more other composition constituents).

In aspects, a buffer component of a composition can comprise any ophthalmologically suitable and pharmaceutically acceptable buffer which does not detectably or significantly interfere with the required functionality of any one or more other composition constituents. In aspects, exemplary constituents of a buffer component comprise, e.g., one or more of a phosphate buffer (e.g., sodium phosphate, e.g., monobasic or dibasic sodium phosphate), citrate buffer (e.g., sodium citrate compound, e.g., sodium citrate dihydrate), tris buffer, carbonate buffer (e.g., ammonium carbonate, sodium carbonate or sodium bicarbonate), succinate buffer, maleate buffer, a borate buffer, combinations of sodium hydroxide, potassium hydroxide, hydrochloric acid, lactic acid, phosphoric acid, sulfuric acid, etc. or combinations thereof. In specific aspects, compositions provided by the invention do not comprise a borate buffer, e.g., compositions do not comprise boric acid or sodium borate. Here, disclosures of aspects based on "not comprising" an element provide simultaneous support for having very low amounts of an element, lacking an effective amount of an element, or lacking any detectable amount of such an element, etc.

In aspects, compositions provided by the invention comprise a buffer component comprising one or more buffering agents, wherein the buffer component is present in the composition in a concentration representing about 0.005% w/v to about 1.5% w/v of the composition, such as, e.g., ~0.01% w/v-~0.5% w/v, ~0.015% w/v-~0.5% w/v, or ~0.02% w/v-~0.5% w/v, e.g., ~0.01% w/v-~0.4% w/v, ~0.01% w/v-~0.3% w/v, ~0.01% w/v-~0.2% w/v, ~0.01% w/v-~0.1% w/v, or ~0.01% w/v-~0.05% w/v of the composition.

In aspects, compositions provided by the invention comprise a buffer component comprising one or more buffering agents, wherein the buffer component is present in the composition in a concentration representing about 0.01% w/v to about 1.5% w/v of the composition, such as, e.g., ~0.05% w/v-~1.5% w/v, ~0.1% w/v-~1.5% w/v, ~0.2% w/v-~1.5% w/v, ~0.3% w/v-~1.5% w/v, ~0.4% w/v-~1.5% w/v, or ~0.5% w/v-~1.5% w/v of the composition.

In aspects, compositions provided by the invention comprise a buffer component comprising one or more buffering agents, wherein the buffer component is present in the composition in a concentration representing about 0.05% w/v to about 1.5% w/v of the composition, such as, e.g., ~0.06% w/v-~1.2% w/v, ~0.08% w/v-~1% w/v, ~0.1% w/v-~0.8% w/v, ~0.12% w/v-~0.7% w/v, ~0.14% w/v-~0.6% w/v, ~0.16% w/v-~0.4% w/v, ~0.18% w/v-~0.3% w/v, or, e.g., ~0.2% w/v-~0.3% w/v.

In one exemplary aspect, compositions comprise a citrate buffer, e.g., citric acid monohydrate, in an amount of ~0.005% w/v-~0.09%, e.g., ~0.01% w/v-~0.05% w/v, 0.01% w/v-~0.04% w/v, 0.01% w/v-~0.03% w/v, or 0.01% w/v-~0.02% w/v, such as about 0.014% w/v of the composition.

In another exemplary aspect, compositions comprise a phosphate buffer, e.g., dibasic sodium phosphate USP (heptahydrate) in an amount of ~0.01% w/v-~0.5% w/v of the composition, e.g., ~0.02% w/v-~0.5% w/v, ~0.04% w/v-~0.5% w/v, ~0.06% w/v-~0.5% w/v, ~0.08% w/v-~0.5% w/v, ~0.1% w/v-~0.5% w/v, ~0.15% w/v-~0.5% w/v, or ~0.2% w/v-~0.5% w/v, e.g. ~0.01% w/v-~0.45% w/v, ~0.01% w/v-~0.4% w/v, ~0.01% w/v-~0.35% w/v, or ~0.01% w/v-~0.3% w/v, such as ~0.05% w/v-~0.4% w/v, ~0.1% w/v-~0.35% w/v, ~0.15% w/v-~0.3% w/v, or ~0.3% w/v-~0.3% w/v, such as, e.g., ~0.268% w/v of the composition.

In aspects, compositions comprise a buffer component comprising two or more buffer constituents. For example, in aspects, compositions comprise a citrate buffer, e.g., citric acid monohydrate, in an amount of ~0.005% w/v-~0.09% w/v, e.g., ~0.01% w/v-~0.05% w/v, 0.01% w/v-~0.04% w/v, ~0.01% w/v-~0.03% w/v, or ~0.01% w/v-~0.02% w/v, such as about 0.014% w/v of the composition, and a phosphate buffer, e.g., dibasic sodium phosphate USP (heptahydrate) in an amount of ~0.01% w/v-~0.5% w/v of the composition, e.g., such as ~0.05% w/v-~0.4% w/v, ~0.1% w/v-~0.35% w/v, ~0.15% w/v-~0.3% w/v, or ~0.3% w/v-~0.3% w/v, such as, e.g., ~0.268% w/v of the composition.

In aspects, such amounts of a buffer component, buffer component constituents, or both, disclosed in this section represent an effective amount of a buffer component, buffer component constituent, or both.

In this and any other ingredient aspect of the invention, the invention also can be characterized as comprising a "means" for providing a recited function, here imparting/providing an effective, detectable, or significant pH buffering effect. In such a respect, any known equivalents of such named agents can also be, e.g., are, incorporated into compositions or methods of the invention. As with other sections similarly described herein, any of the components of the invention can be, where suitable, described as means (e.g., the above-described buffering agents/compounds or components can be described as buffering means/buffer means or means for providing effective, detectable, or significant pH buffering activity/characteristics to the composition.)

Tonicity Component (Tonicity Agent(s))

In aspects, compositions provided by the invention comprise a tonicity component. In aspects, the tonicity component comprises any one or more pharmaceutically acceptable and ophthalmologically suitable constituents (e.g., pharmaceutically acceptable and ophthalmologically suitable compounds) which detectably or significantly modify or aid in the establishment of the tonicity of the composition. In aspects, the tonicity component can comprise any one or more pharmaceutically acceptable or ophthalmologically suitable compounds capable of demonstrating such an effect. In aspects, the tonicity agents/constituents of the tonicity component are suitable for establishing compositions having a targeted isotonic range, e.g., an osmolality of about 171 mOsm/Kg-about 1711 mOsm/K, e.g., ~200 mOsm/Kg-~1000 mOsm/K, ~250 mOsm/Kg-~500 mOsm/Kg, or, e.g., ~280 mOsm/Kg to ~370 mOsm/Kg.

In aspects, a tonicity component of a composition can comprise any ophthalmologically suitable and pharmaceutically acceptable tonicity agent which does not detectably or significantly interfere with the required functionality of any one or more other composition constituents. In aspects, exemplary constituents of a tonicity component comprise, e.g., any one or more pharmaceutically acceptable and ophthalmologically suitable tonicity agents including, e.g., sodium chloride, potassium chloride, dextrose, glucose, glycerin, glycerol, mannitol, sorbitol, other electrolytes, etc. In certain aspects, compositions comprise a tonicity component wherein the tonicity component does not comprise any constituent which may detectably or significantly promote microbial growth.

In aspects, compositions provided by the invention comprise a tonicity component comprising one or more tonicity agents, wherein the tonicity component is present in the composition in a concentration representing about 0.005% w/v to about 1% w/v of the composition, such as, e.g., ~0.005% w/v-~0.95% w/v, ~0.005% w/v-~0.9% w/v, ~0.005% w/v-~0.85% w/v, or ~0.005% w/v-~0.8% w/v, such as, e.g., ~0.05% w/v-~1% w/v, ~0.1% w/v-~1% w/v, ~0.2% w/v-~1% w/v, ~0.3% w/v-~1% w/v, ~0.4% w/v-~1% w/v, ~0.5% w/v-~1% w/v, ~0.6% w/v-~1% w/v, ~0.7% w/v-~1% w/v, or ~0.8% w/v-~1% w/v. In aspects, the tonicity component is present in compositions provided by the invention in an amount of about 0.5% w/v and about 1% w/v of the composition, such as in an amount of about 0.8% w/v.

In certain aspects, compositions provided by the invention comprise a tonicity component comprising one or more tonicity agents, wherein the tonicity component is present in the composition in a concentration representing about 2% w/v to about 6% w/v of the composition, such as, e.g., ~2.5% w/v-~6% w/v, ~3% w/v-~6% w/v, ~3.5% w/v-~6% w/v, ~4% w/v-~6% w/v, or ~4.5% w/v-~6% w/v, e.g., ~2% w/v-~5.5% w/v, or ~2% w/v-~4.5% w/v, such as, e.g., ~2.5% w/v-~5.5% w/v, ~3% w/v-~5% w/v, ~3.5% w/v-~5% w/v, or ~4% w/v-~5% w/v, such as, e.g., ~4.05% w/v.

In certain aspects, the tonicity component comprises two or more constituents wherein the total concentration/amount of the two or more tonicity component constituents is represented by any of the applicable concentrations/amounts provided above or combinations thereof (e.g., a single constituent present in an amount of about 0.005% w/v to about 1% w/v of the composition, and a single constituent present in an amount of about 2% w/v to about 6% w/v, for a total buffer component amount representing about 1.005% w/v-about 7% w/v of the composition).

In aspects, the tonicity component comprises a single tonicity constituent wherein the single constituent is present in an amount represented by the concentrations/amounts provided above. In certain aspects, the tonicity component comprises a single constituent, the single constituent being sodium chloride. In aspects, sodium chloride is present in an amount representing about 0.005% w/v to about 1% w/v of the composition, such as, e.g., ~0.005% w/v-~0.95% w/v, ~0.005% w/v-~0.9% w/v, ~0.005% w/v-~0.85% w/v, or ~0.005% w/v-~0.8% w/v, e.g., ~0.006% w/v-~0.84% w/v, ~0.007% w/v-~0.83% w/v, ~0.008% w/v-~0.82% w/v, ~0.009% w/v-~0.81% w/v, such as, e.g., ~0.01% w/v-~0.8% w/v, or, e.g., ~0.05% w/v-~1% w/v, ~0.1% w/v-~1% w/v, ~0.2% w/v-~1% w/v, ~0.3% w/v-~1% w/v, ~0.4% w/v-~1% w/v, ~0.5% w/v-~1% w/v, ~0.6% w/v-~1% w/v, ~0.7% w/v-~1% w/v, or ~0.8% w/v-~1% w/v of the composition, such as, e.g., in an amount of about 0.8% w/v of the composition. In certain aspects, the tonicity component comprises a single constituent, the single constituent being mannitol, wherein the mannitol is present in an amount representing about 2% w/v to about 6% w/v, e.g., ~2.5% w/v-~5.5% w/v, ~3% w/v-~5% w/v, or ~3.5% w/v-~5% w/v, e.g., ~4% w/v-~5% w/v such as about 4.5% w/v.

Any aspect described herein as comprising a single element of a composition are to be understood as implicitly simultaneously disclosing compositions that consist essentially of such an element, at least in respect of any applicable component/function. Thus, for example, the preceding paragraph implicitly discloses a composition that comprising a tonicity constituent that consists essentially of sodium chloride (and, thus, can include other elements that do not materially modify, e.g., detract from or impair, the novel characteristics of the element, here sodium chloride, in the provided context).

In some aspects, compositions provided by the invention comprise no more than about 0.1% w/v of a tonicity agent. In some aspects, compositions provided by the invention comprise no more than about 0.1% w/v sodium chloride. In some aspects, compositions provided by the invention comprise no more than about 4.1% w/v of a tonicity agent. In some aspects, compositions provided by the invention comprise no more than about 4.05% w/v mannitol.

In aspects, such amounts of a tonicity component, tonicity component constituents, or both, disclosed in this section represent an effective amount of a tonicity component, tonicity component constituent, or both. In certain aspects, composition(s) provided herein lack any constituent providing detectable or significant tonicity-modifying activity(ies).

In this and any other ingredient aspect of the invention, the invention also can be characterized as comprising a "means" for providing a recited function, here imparting/providing an effective, detectable, or tonicity effect (e.g., establishment of a target osmolality or osmolality range). In such a respect, any known equivalents of such named agents can also be, e.g., are, incorporated into compositions or methods of the invention. As with other sections similarly described herein, any of the components of the invention can be, where suitable, described as means (e.g., the above-described tonicity agents/compounds or components can be described as tonicity means or means for providing effective, detectable, or tonicity characteristics to the composition.)

Viscosity Enhancer Component (Viscosity Enhancing Agent(s), Thickening Agent(s), Gelling Agent(s))

In aspects, compositions provided by the invention comprise a viscosity enhancer component (also referred to as a thickening component or gelling/gel component). In aspects, certain constituents of such a component may provide viscosity enhancement without forming a gel. In aspects, as is described herein, a viscosity enhancer component comprises a constituent which only increases the viscosity of the composition after administration, e.g., after exposure to an environment associated with administration to a mammalian eye.

Herein, in aspects, constituents of the composition which impart a viscosity enhancing effect, e.g., an increase in viscosity compared to the same composition without the constituent, or, e.g., an increase in viscosity after administration to a mammalian eye compared to the composition prior to administration to the mammalian eye, can be a constituent of the viscosity enhancer component. In aspects, the viscosity enhancer component comprises any one or more pharmaceutically acceptable and ophthalmologically suitable constituents (e.g., pharmaceutically acceptable and ophthalmologically suitable compounds) which detectably or significantly increase the viscosity, thickness, or gelling characteristics of the composition or of one or more other constituents of the composition. In certain aspects, one or more constituents of a viscosity enhancing component change from under certain conditions so as to modify the viscosity of the composition (such as, e.g., a gel forming agent of a composition). In a specific example, one or more constituents of a viscosity enhancing component gels when the ionic environment changes (e.g., increases) (e.g., the ionic environment is sufficiently increased), such that, e.g., the composition comprising the constituent is liquid when packaged, prior to administration (e.g., when in its final packaging), however when administered to/delivered to a mammalian eye, the composition thickens, e.g., gels. In certain aspects, the invention provides composition(s) specifically characterizable as a gel. In some aspects, compositions comprising a thickening component are gel compositions.

In aspects, one or more constituents of a thickening component can modify the viscosity of the composition after administration, such as, e.g., it/they do not detectably or significantly increase the viscosity of the composition prior to administration compared to an at least substantially similar composition lacking such constituent(s), but upon administration to a mammalian eye cause the detectable or significant increase in viscosity of the composition. In aspects, events upon administration which can cause a thickening agent constituent to increase the viscosity of the composition can be or include, e.g., (1) exposure to the environment of a mammalian eye to which the composition may be administered (or an environment, such as a test solution/media, that is substantially similar or the same in some, most, generally all, or all material respects), (2) exposure to an environment of at least about 28 degrees Celsius (° C.), such as the temperature of a mammalian eye to which it is administered, such as ≥~29° C. or ≥~30° C., e.g., ≥~31° C., ≥~32° C., ≥~33° C., ≥~34° C., or ≥~35° C., (3) exposure to an environment having an ionic strength that is detectably or significantly greater than that of one or more gelling agents present in the composition (e.g., gellan gum, or, e.g., guar gum); (4) exposure to an environment having a pH of greater than, about 6.2, e.g., ≥~6.4, ≥~6.6, ≥~6.8, ≥~7, or, e.g., ≥~7.2, or, e.g., combinations of any of (1)-(4). In aspects, upon exposure to such exemplified environments, a constituent can aid in or cause the formation of a viscoelastic gel. In aspects, the formation of such a gel in-situ (1) detectably or significantly increases the residence time of the APIs of the composition, (2) detectably or significantly enhances the bioavailability of the APIs of the composition, (3) detectably or significantly reduces the frequency of required dosing to achieve an at least generally equivalent, substantially equivalent, effectively equivalent, or equivalent efficacy in treatment of the target condition, (4) improves patient compliance with administration regimen(s), or (5) any combination thereof, compared to an at least generally equivalent, at least substantially equivalent, at least effectively equivalent, or equivalent composition lacking such a gelation in-situ.

According to certain aspects, the invention provides compositions comprising a viscosity enhancer component, wherein at least one constituent of the viscosity enhancer component is a gelling agent, wherein the gelling agent detectably or significantly increases the viscosity of the composition upon administration to the mammalian eye over the viscosity of the composition immediately prior to the administration of the composition to the mammalian eye within no more than about 20 seconds of making contact with the mammalian eye, such as, e.g., within ≤~18 seconds, ≤~16 seconds, ≤~14 seconds, ≤~12 seconds, ≤~10 seconds, ≤~8 seconds, ≤~6 seconds, ≤~4 seconds, or, ≤~2 seconds, such as within ≤~1 second of making contact with the mammalian eye.

In aspects, constituent(s) of a viscosity enhancer component detectably or significantly improve the form of the formulation for convenient administration (e.g., make the composition easier for a user to apply). In aspects, constituent(s) of a viscosity enhancer component detectably or significantly improve, e.g., increase, contact of the composition with eye tissue, or e.g., detectably or significantly increase the length of time the composition maintains contact with eye tissue following administration. In aspects, constituent(s) of a viscosity enhancer component detectably or significantly improves (e.g., detectably or significantly increases) bioavailability of active pharmaceutical ingredient(s) of the composition, such as, e.g., constituents of the PAC, such as a bimatoprost compound, e.g., bimatoprost base, constituents of the BBC, such as a timolol compound, e.g., a salt of timolol, e.g., timolol maleate, or, e.g., constituents of both the PAC and BBC. In aspects, one or more constituents of the viscosity enhancer component can further provide one or more additional detectable or significant functionalities, such as, e.g., a detectable or significant demulcent effect.

In aspects, the viscosity enhancer component can comprise any one or more pharmaceutically acceptable or ophthalmologically suitable compounds capable of demonstrating such effect(s). In aspects, a viscosity enhancer component of a composition can comprise any ophthalmologically suitable and pharmaceutically acceptable viscosity enhancing agent which does not detectably or significantly interfere with the required functionality of any one or more other composition constituents.

In aspects, exemplary constituents of a viscosity enhancer component comprise, e.g., polymers containing, mostly composed, generally consisting of, or consisting of, hydrophilic groups such as monosaccharides and polysaccharides, ethylene oxide groups, hydroxyl groups, carboxylic acids, or other charged functional groups.

In aspects, exemplary polymer constituents of a viscosity enhancer component are high molecular weight polymers, e.g., polymers having a molecular weight of at least about 15,000 Daltons ("Da"), such as, e.g., ≥~20,000 Da, ≥~30,000 Da, ≥~40,000 Da, or, e.g., ≥~50,000 Da, e.g., about 15,000 Da to about 50,000 Da.

In aspects, exemplary polymer constituents of a viscosity enhancer component have a molecular weight of at least about 50,000 Da, such as, e.g., ≥~60,000 Da, ≥~70,000 Da, ≥~80,000 Da, ≥~90,000 Da, or, e.g., ≥~100,000 Da, such as, e.g., ~50,000 Da to ~100,000 Da.

In aspects, exemplary polymer constituents of a viscosity enhancer component have a molecular weight of at least about 100,000 Da, such as, e.g., ≥~110,000 Da, ≥~120,000 Da, ≥~130,000 Da, ≥~140,000 Da, ≥~150,000 Da, ≥~160,000 Da, ≥~170,000 Da, ≥~180,000 Da, ≥~190,000 Da or, e.g., ≥~200,000 Da, such as, e.g., ~100,000 Da to ~200,000 Da.

In aspects, exemplary polymer constituents of a viscosity enhancer component have a molecular weight of at least about 200,000 Da, such as, e.g., ≥~210,000 Da, ≥~220,000 Da, ≥~230,000 Da, ≥~240,000 Da, ≥~250,000 Da, ≥~260,000 Da, ≥~270,000 Da, ≥~280,000 Da, ≥~290,000 Da, or ≥~300,000 Da, such as, e.g., ~200,000 Da–~300,000 Da.

In aspects, exemplary polymer constituents of a viscosity enhancer component have a molecular weight of at least about 300,000 Da, such as, e.g., ≥~310,000 Da, ≥~320,000 Da, ≥~330,000 Da, ≥~340,000 Da, ≥~350,000 Da, ≥~360,000 Da, ≥~370,000 Da, ≥~380,000 Da, ≥~390,000 Da, or, e.g., ≥~400,000 Da, such as, e.g., ~300,000 Da–~400,000 Da.

In aspects, exemplary polymer constituents of a viscosity enhancer component have a molecular weight of at least about 400,000 Da, such as, e.g., ≥~410,000 Da, ≥~420,000 Da, ≥~430,000 Da, ≥~440,000 Da, ≥~450,000 Da, ≥~460,000 Da, ≥~470,000 Da, ≥~480,000 Da, ≥~490,000 Da, or ≥~500,000 Da, such as, e.g., ~410,000 Da–~500,000 Da.

In certain aspects, exemplary polymer constituents of a viscosity enhancer component have a molecular weight of at least about 500,000 Da, such as ~500,000 Da–~1,500,000 Da, e.g., 500,000 Da–~1,250,000 Da, 500,000 Da–~1,000,000 Da, or 500,000 Da–~750,000 Da, e.g., 750,000 Da–~1,500,000 Da, 1,000,000 Da–~1,500,000 Da, or 1,250,000 Da–~1,500,000 Da. In certain aspects, exemplary polymer constituents of a viscosity enhancer component have a molecular weight of greater than 1,500,000 Da.

In certain aspects, exemplary polymer constituents of a viscosity enhancer component provide a detectable or significant increase in viscosity compared to the composition without the constituent(s), such as, e.g., an increase in viscosity over the composition without the constituent(s) either (1), while packaged, prior to use, (2) after administration to a mammalian eye (e.g., upon being placed under detectably or significantly different tonicity conditions), or (3) both (1) and (2), of at least about 0.5%, ≥~1%, ≥~3%, ≥~5%, ≥~10%, ≥~15%, ≥~20%, ≥~25%, ≥~30%, ≥~35%, ≥~40%, ≥~45%, or, e.g., ≥~50%.

In aspects, examples of suitable viscosity-enhancing agents include, e.g., sodium carboxymethylcellulose, hydroxypropylmethylcellulose, povidone, polyvinyl alcohol, polyethylene glycol, and gellan gum. In certain aspects, examples of suitable viscosity-enhancing agents include, e.g., agents capable of forming a gel in-situ, such as, e.g., a polymer such as a triblock copolymer poly (ethylene oxide)-b-poly (propylene oxide)-b-poly (ethylene oxide) (PEO-PPO-PEO) (e.g., pluronics or poloxamers), such as, e.g., the poloxamers 188 (F-68), 237 (F-87), 338 (F-108) and 407 (F-127), Pluronic F-127 (F-127) or Poloxamer 407 (P407) (copolymer PEO106-PPO70-PEO106); gellan gum, guar gum, xanthan gum, chitosan, xyloglucan (often referred to as tamarind seed polysaccharide (TSP), polyacrylic acid polymers (e.g., Carbopol), alginate (alginic acid), e.g., calcium alginate, sodium alginate, etc., pectin, carrageenan, cellulose derivatives such as, e.g., methyl cellulose, hydroxyethyl cellulose, hydroxypropyl methylcellulose (HPMC), sodium carboxymethyl cellulose (NaCMC), etc. In aspects, combinations of such agents can provide gelation activity, such as, e.g., a Carbopol and HPMC, or a Carbopol and chitosan, or, e.g., calcium alginate and HPMC, gellan gum with xanthan gum, HPMC, or Carbopol, gellan gum and carrageenan, etc. In aspects, a single agent can be present, such as, e.g., guar gum or, e.g., gellan gum. In one aspect, compositions are free of carbomer type gelling agent.

In certain aspects, formulations described herein lack any viscosity enhancer component, e.g., lack any thickening (e.g., viscosity-enhancing) compounds or agents/constituents.

In aspects, compositions provided by the invention comprise a viscosity enhancer component comprising one or more viscosity enhancing agents, wherein the viscosity enhancer component is present in the composition in a concentration representing about 0.1% w/v to about 1% w/v of the composition, such as, e.g., ~0.1% w/v-~0.9% w/v, ~0.1% w/v-~0.8% w/v, ~0.1% w/v-~0.7% w/v, or ~0.1% w/v-~0.6% w/v, e.g., ~0.2% w/v-~1% w/v, ~0.3% w/v-~1% w/v, ~0.4% w/v-~1% w/v, ~0.5% w/v-~1% w/v, or ~0.6% w/v-~1% w/v, such as, e.g., ~0.2% w/v-~9% w/v, ~0.3% w/v-~0.8% w/v, ~0.4% w/v-~0.7% w/v, ~0.5% w/v-~0.7% w/v, or, e.g., about 0.6% w/v of the composition.

In certain aspects, the thickening component comprises two or more constituents wherein the total concentration/amount of the two or more thickening component constituents is represented by the concentrations/amounts provided above. In aspects, the solubilization component comprises a single constituent wherein the single constituent is present in an amount represented by the concentrations/amounts provided above. In certain aspects, the solubilization component comprises a single constituent, the single constituent being gellan gum, wherein the gellan gum, is present in an amount representing ~0.2% w/v-~9% w/v, ~0.3% w/v-~0.8% w/v, ~0.4% w/v-~0.7% w/v, ~0.5% w/v-~0.7% w/v, or, e.g., about 0.6% w/v of the composition.

In aspects, such amounts of a viscosity enhancer component, viscosity enhancer component constituents, or both, disclosed in this section represent an effective amount of a viscosity enhancer component, viscosity enhancer component constituent, or both.

In this and any other ingredient aspect of the invention, the invention also can be characterized as comprising a "means" for providing a recited function, here imparting/providing an effective, detectable, or significant viscosity enhancing, thickening, or gelling effect to composition(s) of the invention. In such a respect, any known equivalents of such named agents can also be, e.g., are, incorporated into compositions or methods of the invention. As with other sections similarly described herein, any of the components of the invention can be, where suitable, described as means (e.g., the above-described viscosity enhancing agents/compounds or components can be described as viscosity enhancing, thickening, or gelling means or means for providing effective, detectable, or significant viscosity enhancing, thickening, or gelling activity/characteristics to the composition.)

Chelation Component (Chelating Agent(s))

In aspects, compositions provided by the invention comprise a chelation component. In aspects, the chelation component comprises any one or more pharmaceutically acceptable and ophthalmologically suitable constituents (e.g., pharmaceutically acceptable and ophthalmologically suitable compounds) which detectably or significantly increase chelation within the composition, detectably or significantly supplement or enhance preservative efficacy, or a combination thereof, by forming stable water-soluble complexes (chelates) with alkaline earth and heavy metal ions, by sequestering divalent or polyvalent metal cations, or both. In aspects, constituent(s) of a chelation component remain effective at a pH of between about 6.5 and 8.0. In aspects, the chelation component can comprise any one or more pharmaceutically acceptable or ophthalmologically suitable compounds capable of demonstrating such an effect. In aspects, a chelation component of a composition can comprise any ophthalmologically suitable and pharmaceutically acceptable chelating agent which does not detectably or significantly interfere with the required functionality of any one or more other composition constituents. In certain aspects, compositions provided herein do not comprise compound(s) providing detectable or significant chelating activity(ies).

In aspects, exemplary constituents of a chelation component comprise, e.g., one or more of cromolyn, monomeric polyacids such as EDTA, cyclohexanediamine tetraacetic acid (CDTA), hydroxyethylethylenediamine triacetic acid (HEDTA), diethylenetriamine pentaacetic acid (DTPA), dimercaptopropane sulfonic acid (DMPS), dimercaptosuccmic acid (DMSA), aminotrimethylene phosphonic acid (ATPA), citric acid, any ophthalmologically acceptable salts thereof, and/or combinations of any two or more such compounds. In other aspects, a chelating agent can be a phosphate, such as, e.g., pyrophosphates, tripolyphosphates, and, hexametaphosphates; a chelating antibiotic such as chloroquine and tetracycline; a nitrogen-containing chelating agent containing two or more chelating nitrogen atoms within an imino group or in an aromatic ring (e.g., diimines, 2,2'-bipyridines, etc.); or for example a polyamine such as cyclam (1,4,7,11-tetraazacyclotetradecane), N—($C_1$-$C_{30}$ alkyl)-substituted cyclams (e.g., hexadecyclam, tetramethylhexadecylcyclam), diethylenetriamine (DETA), spermine, diethylnorspermine (DENSPM), diethylhomospermine (DEHOP), and deferoxamine (N'-[5-[[4-[[5-(acetylhydroxyamino) pentyl]amino]-1,4-dioxobutyl]hydroxyamino]pentyl]-N'-(5-aminopentyl)-N-hydroxybutanediamide; also known as desferrioxamine B and DFO).

In certain aspects, a chelation component of compositions provided by the invention comprise EDTA or an ophthalmologically suitable EDTA salt such as, e.g., diammonium EDTA, disodium EDTA, dipotassium EDTA, triammonium EDTA, trisodium EDTA, tripotassium EDTA, or calcium disodium EDTA.

In aspects, compositions provided by the invention comprise a chelation component comprising one or more chelating agents, wherein the chelation component is present in the composition in a concentration representing about 0.001% w/v-about 0.1% w/v, such as, e.g., about 0.002% w/v-0.1% w/v, about 0.004% w/v-about 0.1% w/v, about 0.006% w/v-about 0.1% w/v, about 0.008% w/v-about 0.1% w/v, or for example about 0.01% w/v-about 0.1% w/v or, e.g., comprising another detectably, physiologically effective, or significant amount.

In certain aspects, the chelation component comprises two or more constituents wherein the total concentration/amount of the two or more chelation component constituents is represented by, e.g., any of the applicable concentrations/amounts provided above. In aspects, the chelation component comprises a single constituent wherein the single constituent is present in an amount represented by the concentrations/amounts provided above, such as, e.g., edetate disodium in amounts provided above.

In aspects, such amounts of a chelation component, chelation component constituents, or both, disclosed in this section represent an effective amount of a chelation component, chelation component constituent, or both.

In this and any other ingredient aspect of the invention, the invention also can be characterized as comprising a "means" for providing a recited function, here imparting/providing an effective, detectable, or significant chelating effect (e.g., forming stable water-soluble complexes (chelates) with alkaline earth and heavy metal ions) of compositions. In such a respect, any known equivalents of such named agents can also be, e.g., are, incorporated into compositions or methods of the invention. As with other sections similarly described herein, any of the components of the invention can be, where suitable, described as means (e.g., the above-described chelating agents/compounds or components can be described as chelation means or means for providing effective, detectable, or significant chelation activity/characteristics to the composition or one or more constituents of the composition.)

pH Adjusting Component (pH Adjusting Agent(s))

In aspects, compositions provided by the invention comprise a pH adjusting component. In aspects, the pH adjusting component comprises any one or more pharmaceutically acceptable and ophthalmologically suitable constituents (e.g., pharmaceutically acceptable and ophthalmologically suitable compounds) which detectably or significantly alter or aid in the establishment of a target pH of the composition, such as a pH of between about 6 to about 8, such as a pH of about 6.2 to about 7 or, e.g., a pH of about 6.9 to about 7.5. In aspects, the pH adjusting component can comprise any one or more pharmaceutically acceptable or ophthalmologically suitable compounds capable of demonstrating such an effect. In aspects, a pH adjusting component of a composition can comprise any ophthalmologically suitable and pharmaceutically acceptable pH adjusting agent which does not detectably or significantly interfere with the required functionality of any one or more other composition constituents.

In aspects, one or more constituents of the pH adjusting component can further provide one or more additional detectable or significant functionalities, such as, for example, detectable or significant buffering effects (as described elsewhere herein). In aspects, a pH adjusting agent of a composition can be a compound that is different from a buffer/buffering agent of the composition. In some aspects, a constituent of a pH adjusting component can contribute the tonicity of the composition. Therefore, in some embodiments, one or more pH adjusting component constituents and one or more tonicity agents can combine to contribute to the osmolality of a composition.

In aspects, exemplary constituents of a buffer component comprise, e.g., one or more of sodium hydroxide, sodium carbonate, sodium bicarbonate, potassium hydroxide, ammonium carbonate, hydrochloric acid, lactic acid, phosphoric acid, sodium phosphate, sulfuric acid, etc. In aspects, such agents can be used to adjust the pH to a desirable/target range, such as, e.g., to about 6 to about 7.2, such as ~6.1-~7.1, ~6.1-~7, or ~6.2-~7, or, e.g., to about 6.5 to about 8, such as ~6.6-~7.8, ~6.8-~7.6, or ~7-~7.5, such as ~71-~7.3. In aspects, the pH of the compositions, e.g., compositions comprising a bimatoprost compound, e.g., bimatoprost base, and a timolol compound, e.g., timolol maleate, can be adjusted in any suitable manner by means of the addition of pH adjusting agents in an amount sufficient to establish and maintain a composition pH of, e.g., from about 6-about 7.5, such as, e.g., about 6.2-about 7, or, e.g., about 6.9-about 8, e.g., ~6.9-~7.5, for example by addition of aqueous hydrochloric acid solutions or aqueous sodium hydroxide solutions. Such pH adjusting solutions can be diluted or concentrated in any suitable manner to achieve a desired effect/state. E.g., in aspects, suitable pH adjusting agents include 0.01 molar (M) hydrochloric acid ("HCl"), 0.1M HCl, 1M HCl, 2M HCl, 3M HCl, 4M HCl, 5M HCl, 6M HCl (e.g., a 0.01-6 M, such as 0.1-5 M, e.g., 0.25-5 M, or 0.2-4 M HCl), 0.01M sodium hydroxide ("NaOH"), 0.1M NaOH, 1M NaOH, 2M NaOH, 3M NaOH, 4M NaOH, 5M NaOH (e.g., 0.01 M-5 5M NaOH, such as 0.2-5 M, 0.25-4 M, or 0.3-6M or 0.3-3M NaOH), and 6M NaOH. In one aspect, suitable pH adjusting agents include either one of or a combination of HCl or NaOH, e.g., 1M HCl or 1M NaOH, which, in aspects, alternatively can be added to a composition to achieve a desired pH range.

In aspects, compositions provided by the invention can comprise a pH adjusting component comprising one or more pH adjusting agent(s), wherein the pH adjusting component is present in the compositions provided by the invention in an amount effective in providing the target pH. In aspects, such an amount can be considered a "trace amount," e.g., less than ~0.005% w/v, <0.004% w/v, <~0.003% w/v, <0.002% w/v, e.g., <~0.001% w/v. In aspects, such an amount can be an amount representing about 0-about 0.01% w/v. In aspects, one or more pH adjusting agent(s) can be present in the compositions provided by the invention in an amount effective in providing the target pH, such amounts representing about 0% w/v-about 0.1% w/v, such as, e.g., about 0.01% w/v, ~0.02% w/v, ~0.03% w/v, ~0.04% w/v, ~0.05% w/v, ~0.06% w/v, ~0.07% w/v, ~0.08% w/v, or, e.g., ~0.09% w/v.

In certain aspects, the pH adjusting component comprises two or more constituents wherein the total concentration/amount of the two or more pH adjusting component constituents within one or more ranges provided above. In aspects, the pH adjusting component comprises a single constituent wherein the single constituent is present in an amount within one or more ranges provided above. In aspects, compositions comprise NaOH, HCl, or both NaOH and HCl only in sufficient amounts to adjust pH during the manufacturing process (e.g., in an amount of less than 0.1% w/v, or, e.g., less than ~0.005% w/v).

In aspects, such amounts of a pH adjusting component, pH adjusting component constituents, or both, disclosed in this section represent an effective amount of a pH adjusting component, pH adjusting component constituent, or both.

In this and any other ingredient aspect of the invention, the invention also can be characterized as comprising a "means" for providing a recited function, here imparting/providing an effective, detectable, or significant pH adjustment effect (e.g., pH establishment) to/of composition(s) of the invention. In such a respect, any known equivalents of such named agents can also be, e.g., are, incorporated into compositions or methods of the invention. As with other sections similarly described herein, any of the components of the invention can be, where suitable, described as means (e.g., the above-described pH adjusting agents/compounds or components can be described as pH adjusting means or means for providing effective, detectable, or significant pH adjustment activity/characteristics to the composition). In such aspects, it is understood that known equivalents to the recited elements provided herein also can be utilized/present in the place of such specifically named elements.

Antioxidant Component (Antioxidant(s))

In aspects, compositions comprise antioxidant(s) in effective amount(s). An "antioxidant" is typically understood as referring to a substance that preferentially reacts with oxygen, thereby detectably or significantly protecting other components of a composition to which it is added from premature degradation due to oxidation (e.g., protecting APIs that is known to be detectably/significantly susceptible to oxidation).

According to aspects, one or more antioxidant compounds can be present in composition(s) of the invention as an antioxidant component, which detectably or significantly improve API stability or reduce the amount of impurities, such as, e.g., providing for a composition which is stable under room temperature storage conditions, e.g., retains at least about 97% of the one or more PAC constituents, e.g., bimatoprost compound(s), retains at least about 97% of the one or more BBC constituents, e.g., timolol compound(s), or retains at least about 97% of one or more PAC constituents and one or more BBC constituents when stored at about 15° C.-about 27° C. and about 60% relative humidity, when stored at about 38° C.-about 42° C. and 75% relative humidity, or when stored under either condition or a sequential combination of such conditions, for at least about one month such as ≥~2 months or such as ≥~3 months, ≥~6 months, ≥~12 months, or, e.g., ≥~18 months, ≥~24 months, or ≥~36 months.

For example, composition(s) provided by the invention can comprise an antioxidant component comprising one or more antioxidant agents which detectably improve the stability of the one or more bimatoprost compound(s), one or more timolol compound(s), or both one or more bimatoprost compound(s) and one or more timolol compound(s), reduces the amount of composition impurities, enhances preservative effectiveness, or any or all thereof, at a period of at least 2 weeks post manufacturing, such as at a period ≥~3 weeks, ≥~1 month, ≥~6 weeks, ≥~2 months, ≥~10 weeks, ≥~3 months, ≥~14 weeks, ≥~4 months, ≥~18 weeks, ≥~5 months, ≥~22 weeks, ≥~6 months, or for even longer periods (e.g., 3-24, 3-18, 3-12, 3-36, 4-12, 4-24, 4-36, 6-12, 6-18, 6-24, or 6-36 months).

In aspects, the invention provides composition(s) comprising one or more pharmaceutically acceptable and ophthalmologically suitable antioxidant agents as constituents of an antioxidant component effective at pH range of, e.g., ~6.2-~7, or, e.g., ~6.9-~7.5. In aspects, antioxidant compound(s) of the composition(s) herein do not detectably or significantly negatively impact any other component of the formulation, such as, e.g., they do not detectably or significantly reduce the efficacy of any one or more API(s), e.g., bimatoprost compound(s), timolol compound(s), or both.

In aspects any ophthalmologically suitable and pharmaceutically acceptable antioxidant can be used in methods of the invention/incorporated in compositions of the invention, in any suitably effective amount(s). In aspects, exemplary antioxidant(s) in a composition described herein can comprise, e.g., sodium ascorbate, ascorbic acid, thiamine, pyridoxine, histidine, cysteine, glutathione, sodium bisulphite, sodium sulphite, sodium metabisulphite, sodium thiosulphite, sodium formaldehyde sulphoxylate, acetylcysteine, cysteine, thioglycerol, thioglycollic acid, thiolactic acid, thieurea, dihithreitol, propyl gallate, butylated hydroxyanisole, butylated hydroxytoluene, tertiary butyl hydroquinone, ascorbyl palmitate, nordihydroguaiaretic acid and alpha-tocopherol, any ophthalmologically acceptable salts thereof, or combinations of any two or more such compounds. In aspects, one or more antioxidant compound(s)/agent(s) can be present in the compositions provided by the invention in an amount representing about 0.001% w/v-about 2% w/v of the composition, such as, e.g., ~0.001% w/v-~1.8% w/v, ~0.001% w/v-~1.6% w/v, ~0.001% w/v-~1.4% w/v, ~0.001% w/v-~1.2% w/v, ~0.08% w/v-~1% w/v, e.g., ~0.05-~1% w/v of the composition, or another detectably, physiologically effective, or significant amount.

In aspects, such amounts of an antioxidant component, antioxidant component constituents, or both, disclosed in this section represent an effective amount of an antioxidant component, antioxidant component constituent, or both. In certain aspects, composition(s) provided herein lack any constituent providing detectable or significant antioxidant activity(ies).

In this and any other ingredient aspect of the invention, the invention also can be characterized as comprising a "means" for providing a recited function, here imparting/providing an effective, detectable, or significant antioxidant effect to/of composition(s) of the invention. In such a respect, any known equivalents of such named agents can also be, e.g., are, incorporated into compositions or methods of the invention. As with other sections similarly described herein, any of the components of the invention can be, where suitable, described as means (e.g., the above-described antioxidant agents/compounds or components can be described as antioxidant means or means for providing effective, detectable, or significant antioxidant activity/characteristics to the composition.)

Carrier Component (Carrier Agent(s))

In aspects, compositions provided by the invention comprise a carrier component. In aspects, this component may be referenced as vehicle component. In aspects, the carrier component comprises any one or more pharmaceutically acceptable and ophthalmologically suitable constituents (e.g., pharmaceutically acceptable and ophthalmologically suitable carriers) which detectably or significantly maintain all constituents of the composition in deliverable form, such as in the form of a liquid, e.g., a solution, or, e.g., a gel. In aspects, the carrier component can comprise any one or more pharmaceutically acceptable or ophthalmologically suitable carriers capable of performing such a function. In aspects, a carrier component of a composition can comprise any ophthalmologically suitable and pharmaceutically acceptable carrier which does not detectably or significantly interfere with the required functionality of any one or more other composition constituents.

In aspects, exemplary constituents of a carrier component comprise, e.g., one or more of a pharmaceutically acceptable and ophthalmologically suitable lipid (e.g., establishing a lipid carrier/vehicle), a gel (e.g., establishing a gel carrier/vehicle), an oil-based carrier (establishing an oil-based carrier/vehicle), a carrier in the form of an emulsion (establishing an emulsion carrier/vehicle), an emulsifier-containing carrier that forms an emulsion when mixed with other components, or, a carrier forming a solution carrier/vehicle, e.g., water to form an aqueous solution carrier/vehicle. In aspects, the carrier is an aqueous carrier. In aspects, the carrier is mostly, generally only, essentially only, substantially only, or only composed of water, e.g., water for injection (WFI) (a sterile, solute-free preparation of distilled water). In alternative aspects, other ophthalmologically suitable aqueous carriers which do not adversely affect the stability of the composition(s) may be used, such as, e.g., deionized water.

In aspects, compositions provided by the invention comprise a carrier component comprising one or more carriers, wherein the carrier component is present in a concentration representing at least about 60% w/v of the composition, such as, e.g., ≥~65% w/v, ≥~70% w/v, ≥~75% w/v, ≥~80% w/v, ≥~85% w/v, ≥~90% w/v, or ≥~95% w/v of the composition.

In certain aspects, the carrier component comprises two or more constituents wherein the total concentration/amount of the two or more carrier component constituents is represented by the concentrations/amounts provided above. In aspects, the carrier component comprises a single constituent wherein the single constituent is present in an amount represented by the concentrations/amounts provided above. In certain aspects, the carrier component comprises a single constituent, the single constituent being water, or, e.g., water for injection (WFI), wherein the water is present in an amount representing ≥~70% w/v, ≥~75% w/v, ≥~80% w/v, ≥~85% w/v, ≥~90% w/v, or ≥~95% w/v of the composition. In aspects, the pharmaceutically acceptable and ophthalmologically suitable compositions are aqueous compositions. In aspects, compositions provided by the invention typically comprise at least about 70% w/v water, and even more typically at least about 85% w/v-about 95% w/v water.

In common aspects, compositions are aqueous solutions or aqueous gels. In aspects, such aqueous compositions can be easily administered to the recipient such as by means of instilling one to two drops of the solutions in affected eye(s). In aspects, the bimatoprost compound(s) and timolol compound(s) compositions are aqueous solutions. In aspects, the bimatoprost compound(s) and timolol compound(s) compositions are aqueous gel composition. In aspects, the aqueous compositions, whether provided as a solution or gel, are comprised of more than ~50% w/v water, e.g., more than ~75% w/v, or, e.g., more than ~90% w/v water and generally all, or all components of the formulation are fully dissolved such that a clear, aqueous composition is provided.

In aspects, such amounts of a carrier component, carrier component constituents, or both, disclosed in this section represent an effective amount of a carrier component, carrier component constituent, or both.

In this and any other ingredient aspect of the invention, the invention also can be characterized as comprising a "means" for providing a recited function, here imparting/providing an effective, detectable, or significant carrier function (e.g., vehicle) to/of composition(s) of the invention. In such a respect, any known equivalents of such named agents can also be, e.g., are, incorporated into compositions or methods of the invention. As with other sections similarly described herein, any of the components of the invention can be, where suitable, described as means (e.g., the above-described carriers or components can be described as carrier means or means for providing effective, detectable, or significant carrier or vehicle activity/characteristics to the composition.)

Compositions Do Not Include/Are Not Provided As/Are Specifically Provided As

In aspects, compositions provided by the invention comprises at least two active pharmaceutical ingredients, e.g., at least one API belonging to a PAC and at least one API belonging to a BBC. For example, in aspects, compositions do not comprise a sole PAC, e.g., a sole bimatoprost compound, or a sole BBC, e.g., a sole timolol compound. In aspects, compositions comprise no other API other than a bimatoprost compound and a timolol compound. In aspects, compositions comprise no more than two APIs, such as no API other than a PAC constituent (e.g., a bimatoprost compound) and a BBC constituent (e.g., a timolol compound). For example, in certain aspects, compositions do not comprise a third API such as, e.g., travoprost or e.g., latanoprost. In aspects, compositions provided by the invention do not comprise an alpha-adrenergic agonist. In aspects, each API of the compositions provided by the invention are provided in an amount capable of resulting in a detectable or significant therapeutic effect, e.g., are provided in therapeutic amounts. In aspects, compositions comprise a bimatoprost compound in an amount less than 0.03% w/v, such as less than 0.02% w/v. In aspects, compositions comprise a timolol compound in an amount equal to or greater than at least about 0.3% w/v, such as greater than at least about 0.4% w/v. In aspects, compositions comprise a timolol compound in an amount equal to or greater than about 0.5% w/v. In aspects, compositions comprise a timolol compound in an amount equal to or greater than about 0.6% w/v. In aspects, compositions comprise a bimatoprost compound in an amount no greater than about 0.02% w/v, such as an amount no greater than about 0.015% w/v, e.g., no greater than about 0.01% w/v.

In aspects, compositions comprise an amount of sodium chloride greater than at least about 0.5% w/v, such as greater than about 0.6% w/v, greater than about 0.7% w/v, or, e.g., greater than 0.8% w/v. In aspects, compositions comprise an amount of sodium chloride greater than or equal to about 0.8% w/v.

In certain aspects, compositions comprise at least one preservative compound, e.g., at least one compound demonstrating detectable or significant preservative property(ies) described herein. In aspects, composition(s) provided by the invention are not characterizable as preservative-free. In aspects, compositions specifically comprise a benzalkonium chloride preservative. In certain aspects, compositions comprise benzalkonium in an amount greater than at least about 0.001% w/v, such as at least greater than about 0.002% w/v, 0.003% w/v, or at least greater than about 0.004% w/v. In certain aspects, compositions comprise a preservative compound, e.g., benzalkonium chloride, in an amount not greater than about 0.007% w/v of the composition.

In aspects, compositions provided by the invention comprise at least one penetration enhancing agent (providing detectable or significant increased penetration into ocular tissue of at least one constituent of a PAC, at least one constituent of a BBC, or both). In aspects, compositions comprise at least one penetration agent which is not benzalkonium chloride. In aspects, compositions comprise at least one penetration agent in addition to benzalkonium chloride.

In aspects, compositions provided by the invention comprise at least one agent providing detectable or significant increased penetration into ocular tissue of at least one constituent of a PAC, at least one constituent of a BBC, or both which further provides detectable solubilization effect. In aspects, compositions further comprise at least one additional agent providing detectable solubilization effect, such that the composition(s) comprise at least two agents providing detectable solubilization of a PAC constituent, BBC constituent, or both.

In aspects, compositions do not comprise an antioxidant component (e.g., a compound providing detectable or significant antioxidant activity).

In aspects, compositions do not comprise EDTA. In aspects, compositions do not comprise a chelation component (e.g., a compound providing detectable or significant chelating activity).

In aspects, compositions do not comprise glycerol.

In aspects, compositions do not comprise more than 0.009% w/v of a polyvinyl alcohol. In aspects, compositions comprise no polyvinyl alcohol. In aspects, compositions do not comprise, e.g., Mowiol, e.g., Mowiol 4-88, Mowiol 8-88, or, e.g., Mowiol 18-88.

In aspects, compositions do not comprise a combination of compounds comprising polyoxyl 40 hydrogenated castor oil, boric acid, propylene glycol, sorbitol, and zinc chloride. In aspects, compositions do not comprise a combination of compounds comprising disodium EDTA, glycerol, and polysorbate 80.

In aspects, a composition provided by the invention does not comprise an amount of free monosaccharide that results in a detectable or significant increase in bacterial growth or detectably or significant increase in the tonicity of the composition (e.g., osmolality). In aspect, a composition does not comprise more than about, e.g., 0.01% w/v, 0.001% w/v, 0.0001% w/v, 0.00001% w/v, 0.000001% w/v, or, e.g., 0.0000001% w/v of a free monosaccharide, e.g., glucose. In aspects, compositions can be characterized as essentially free or free (to the limits of detection) of any of the compounds described in this paragraph or section. In aspects, compositions do not comprise more than about, e.g., 0.01% w/v, 0.001% w/v, 0.0001% w/v, 0.00001% w/v, 0.000001% w/v, or, e.g., 0.0000001% w/v of a free monosaccharide not characterizable as a sugar alcohol. In aspects, a tonicity component does not comprise any such amount of a constituent characterizable as a glucose compound, e.g., D-glucose (dextrose).

In certain aspects, compositions do not comprise a surfactant. In certain aspects, compositions do not comprise any component characterizable as a surfactant other than polysorbate 80. In aspects, compositions do not comprise one or more of chlorbutano thimerosal, phenylmercuric acetate phenylmurcuric nitrate, chloride components (e.g., stabilized chloride dioxide, etc.) or, e.g., mixtures thereof. In aspects, compositions do not comprise one or more of polyvinyl alcohol, povidone (polyvinyl pyrrolidone), hydroxypropylmethyl cellulose (also presented as "hydroxypropyl methylcellulose" or "hydroxylpropyl methyl cellulose"), polyxamers, carboxymethyl cellulose, hydroxyethyl cellulose, or cyclodextrin.

Ratios

In aspects, one way to characterize compositions provided by the invention is by the ratios of one or more components or constituents of the composition(s).

According to aspects, any component(s) or compound(s)/agent(s) described herein can be present in composition(s) in therapeutically effective amount(s), compositionally compatible amount(s), or both. In aspects, any single component or compound/agent provided herein can be present in a relationship with, such as, e.g., in a ratio with, any one or more other single component or compound/agent. In aspects, any combination of component(s) or compound(s)/agent(s) provided herein can be present in a ratio with any other combination of component(s) or compound(s)/agent(s). In aspects, ratio(s) between such component(s) or compound(s)/agent(s) or combinations thereof can be established using any provided amounts for each disclosed herein, including, e.g., values within ranges of such amounts disclosed herein. To exemplify this disclosure, the following table is provided. Table 1 below, e.g., illustrating a ratio array, demonstrates the types of ratios which the reader should understand to be encompassed by the disclosure herein. As one example, a "PEC", or "penetration enhancement component" can be present in composition(s) herein in a ratio with a "PAC", or "prostaglandin analogue component", such a ratio established by the amounts cited in the relevant disclosure for each of the penetration enhancement component and prostaglandin analogue component herein. Further, as a PAC can be represented by a single compound, e.g., bimatoprost, and as a penetration enhancement component can be represented by a single compound, e.g., polysorbate 80, such a ratio can represent the relationship between such two compounds. Further, as a penetration enhancement component may be represented by a plurality of compounds, for example in aspects benzalkonium chloride and polysorbate 80, such a ratio can represent the relationship between, e.g., bimatoprost and the sum of the two penetration enhancement component constituents, wherein the values for such a ration are established by the amounts cited in the relevant disclosure for each constituent herein.

TABLE 1

Exemplary component/constituent ratios.

|  | PAC | BIM | BBC | TIM | AAC | BTC | PVC | PEC | SZC | DCC | BFC | TCC | VEC | CHC | PHC | AXC | CRC |
|---|---|---|---|---|---|---|---|---|---|---|---|---|---|---|---|---|---|
| PAC | — | BIM: PAC | BBC: PAC | TIM: PAC | AAC: PAC | BTC: PAC | PVC: PAC | PEC: PAC | SZC: PAC | DCC: PAC | BFC: PAC | TCC: PAC | VEC: PAC | CHC: PAC | PHC: PAC | AXC: PAC | CRC: PAC |
| BIM | PAC: BIM | — | BBC: BIM | TIM: BIM | AAC: BIM | BTC: BIM | PVC: BIM | PEC: BIM | SZC: BIM | DCC: BIM | BFC: BIM | TCC: BIM | VEC: BIM | CHC: BIM | PHC: BIM | AXC: BIM | CRC: BIM |
| BBC | PAC: BBC | BIM: BBC | — | TIM: BBC | AAC: BBC | BTC: BBC | PVC: BBC | PEC: BBC | SZC: BBC | DCC: BBC | BFC: BBC | TCC: BBC | VEC: BBC | CHC: BBC | PHC: BBC | AXC: BBC | CRC: BBC |
| TIM | PAC: TIM | BIM: TIM | BBC: TIM | — | AAC: TIM | BTC: TIM | PVC: TIM | PEC: TIM | SZC: TIM | DDC: TIM | BFC: TIM | TCC: TIM | VEC: TIM | CHC: TIM | PHC: TIM | AXC: TIM | CRC: TIM |
| AAC | PAC: AAC | BIM: AAC | BBC: AAC | TIM: AAC | — | BTC: AAC | PVC: AAC | PEC: AAC | SZC: AAC | DDC: AAC | BFC: AAC | TCC: AAC | VEC: AAC | CHC: AAC | PHC: AAC | AXC: AAC | CRC: AAC |
| BTC | PAC: BTC | BIM: BTC | BBC: BTC | TIM: BTC | AAC: BTC | — | PVC: BTC | PEC: BTC | SZC: BTC | DDC: BTC | BFC: BTC | TCC: BTC | VEC: BTC | CHC: BTC | PHC: BTC | AXC: BTC | CRC: BTC |
| PVC | PAC: PVC | BIM: PVC | BBC: PVC | TIM: PVC | AAC: PVC | BTC: PVC | — | PEC: PVC | SZC: PVC | DDC: PVC | BFC: PVC | TCC: PVC | VEC: PVC | CHC: PVC | PHC: PVC | AXC: PVC | CRC: PVC |
| PEC | PAC: PEC | BIM: PEC | BBC: PEC | TIM: PEC | AAC: PEC | BTC: PEC | PVC: PEC | — | SZC: PEC | DDC: PEC | BFC: PEC | TCC: PEC | VEC: PEC | CHC: PEC | PHC: PEC | AXC: PEC | CRC: PEC |
| SZC | PAC: SZC | BIM: SZC | BBC: SZC | TIM: SZC | AAC: SZC | BTC: SZC | PVC: SZC | PEC: SZC | — | DDC: SZC | BFC: SZC | TCC: SZC | VEC: SZC | CHC: SZC | PHC: SZC | AXC: SZC | CRC: SZC |
| DCC | PAC: DCC | BIM: DCC | BBC: DCC | TIM: DCC | AAC: DCC | BTC: DCC | PVC: DCC | PEC: DCC | SZC: DCC | — | BFC: DCC | TCC: DCC | VEC: DCC | CHC: DCC | PHC: DCC | AXC: DCC | CRC: DCC |
| BFC | PAC: BFC | BIM: BFC | BBC: BFC | TIM: BFC | AAC: BFC | BTC: BFC | PVC: BFC | PEC: BFC | SZC: BFC | DDC: BFC | — | TCC: BFC | VEC: BFC | CHC: BFC | PHC: BFC | AXC: BFC | CRC: BFC |

TABLE 1-continued

Exemplary component/constituent ratios.

|  | PAC | BIM | BBC | TIM | AAC | BTC | PVC | PEC | SZC | DCC | BFC | TCC | VEC | CHC | PHC | AXC | CRC |
|---|---|---|---|---|---|---|---|---|---|---|---|---|---|---|---|---|---|
| TCC | PAC:<br>TCC | BIM:<br>TCC | BBC:<br>TCC | TIM:<br>TCC | AAC:<br>TCC | BTC:<br>TCC | PVC:<br>TCC | PEC:<br>TCC | SZC:<br>TCC | DDC:<br>TCC | BFC:<br>TCC | — | VEC:<br>TCC | CHC:<br>TCC | PHC:<br>TCC | AXC:<br>TCC | CRC:<br>TCC |
| VEC | PAC:<br>VEC | BIM:<br>VEC | BBC:<br>VEC | TIM:<br>VEC | AAC:<br>VEC | BTC:<br>VEC | PVC:<br>VEC | PEC:<br>VEC | SZC:<br>VEC | DDC:<br>VEC | BFC:<br>VEC | TCC:<br>VEC | — | CHC:<br>VEC | PHC:<br>VEC | AXC:<br>VEC | CRC:<br>VEC |
| CHC | PAC:<br>CHC | BIM:<br>CHC | BBC:<br>CHC | TIM:<br>CHC | AAC:<br>CHC | BTC:<br>CHC | PVC:<br>CHC | PEC:<br>CHC | SZC:<br>CHC | DDC:<br>CHC | BFC:<br>CHC | TCC:<br>CHC | VEC:<br>CHC | — | PHC:<br>CHC | AXC:<br>CHC | CRC:<br>CHC |
| PHC | PAC:<br>PHC | BIM:<br>PHC | BBC:<br>PHC | TIM:<br>PHC | AAC:<br>PHC | BTC:<br>PHC | PVC:<br>PHC | PEC:<br>PHC | SZC:<br>PHC | DDC:<br>PHC | BFC:<br>PHC | TCC:<br>PHC | VEC:<br>PHC | CHC:<br>PHC | — | AXC:<br>PHC | CRC:<br>PHC |
| AXC | PAC:<br>AXC | BIM:<br>AXC | BBC:<br>AXC | TIM:<br>AXC | AAC:<br>AXC | BTC:<br>AXC | PVC:<br>AXC | PEC:<br>AXC | SZC:<br>AXC | DDC:<br>AXC | BFC:<br>AXC | TCC:<br>AXC | VEC:<br>AXC | CHC:<br>AXC | PHC:<br>AXC | — | CRC:<br>AXC |
| CRC | PAC:<br>CRC | BIM:<br>CRC | BBC:<br>CRC | TIM:<br>CRC | AAC:<br>CRC | BTC:<br>CRC | PVC:<br>CRC | PEC:<br>CRC | SZC:<br>CRC | DDC:<br>CRC | BFC:<br>CRC | TCC:<br>CRC | VEC:<br>CRC | CHC:<br>CRC | PHC:<br>CRC | AXC:<br>CRC | — |

ABBREVIATIONS: PAC (prostaglandin analogue component);
BIM (bimatoprost compound);
BBC (beta-adrenoreceptor antagonist (B-blocker) component);
TIM (timolol compound);
AAC (alternative or additional anti-glaucoma agent(s) component, also referred to herein as an AGAC);
PVC (preservative component);
PEC (penetration enhancer component);
SZC (solubilization component);
DDC (demulcent component);
BFC (buffer component);
TCC (tonicity component);
VEC (viscosity enhancer component);
CHC (chelation component);
PHC (pH adjusting component);
AXC (antioxidant component),
CRC (carrier component).

Provided in Table 2 are exemplary amounts of exemplary component(s)/ingredient(s), which, in aspects, can be/are present in composition(s) provided by the invention in a ratio with any one or more other component(s)/compound(s) disclosed, wherein such ratios can, in aspects, be in a ratio formed by such disclosed amounts.

TABLE 2

Exemplary Ingredients and Exemplary Amounts from Which Ratio(s) Can be Derived.

| Component/Compound Description | Exemplary Compound(s) (if component provided) | Exemplary Amount(s) (% w/v) |
|---|---|---|
| Prostaglandin Analogue Component | Bimatoprost compound, e.g., bimatoprost base | 0.005-0.02 |
| Beta-Adrenoreceptor Antagonist (β-Blocker) Component | Timolol compound, e.g., timolol maleate | 0.4-0.8 |
| Preservative Component | Benzalkonium Chloride | 0.003-0.007 |
| Penetration Enhancer Component | Polysorbate 80, TPGS, Cremophor EL, Tromethamine (TRIS) | 0.25-2.5 |
| Solubilization Component | Polysorbate 80, TPGS, Cremophor EL, Tromethamine (TRIS) | 0.25-2.5 |
| Demulcent Component | Polysorbate 80 | 0.25-2.5 |
| Buffer Component | Dibasic sodium phosphate, citric acid monohydrate | 0.005-0.6 |
| Tonicity Component | Mannitol, Sodium Chloride | 0.005-6 (e.g., 0.005-1, 2-6) |
| Viscosity Enhancer Component | Gellan Gum | 0.1-1 |
| Bimatoprost Compound | Bimatoprost base | 0.005-0.02 |
| Timolol Compound | Timolol maleate | 0.4-0.8 |
| Polysorbate 80 | — | 0.25-2.5 |
| TPGS | — | 0.25-2.5 |
| Cremophor EL | — | 0.25-2.5 |
| Benzalkonium Chloride | — | 0.003-0.007 |
| Sodium Chloride | — | 0.05-1.5 |
| Dibasic Sodium Phosphate | — | 0.01-0.5 |
| Citric Acid Monohydrate | — | 0.005-0.09 |
| Tromethamine | — | 0.05-1 |
| Mannitol | — | 2-6 |
| Gellan Gum | — | 0.1-1 |

Note:
In aspects, values in Table 2 represent the amounts of each respective component/ingredient's representative percentage by weight/volume (% w/v) of the composition(s). In other aspects, values in Table 3 represent the amounts of each respective component/ingredient's representative percentage by weight/weight (wt. %) of the composition(s).

In aspects, compositions provided by the invention comprise a ratio of quaternary ammonium salt, e.g., benzalkonium chloride, to penetration enhancer component of about 1:2 to about 1:2500, e.g., ~1:100 to ~1:300 or ~1:35 to ~1:840, or, e.g., ~1:200.

In aspects, compositions provided by the invention comprise a ratio of bimatoprost compound, e.g., bimatoprost base, to timolol compound, e.g., salt of timolol, e.g., timolol maleate, of about 1:2 to about 1:200, such as ~1:2 to ~1:100 or ~1:20 to ~1:160, e.g., ~1:20-~1:100, ~1:30-~1:90, ~1:40-~1:80, ~1:50-~1:70, ~1:60-~1:70, ~1:65-~1:70, or, e.g., about 1:68.

In aspects, compositions provided by the invention comprise a ratio of bimatoprost compound, e.g., bimatoprost base, to quaternary ammonium salt, e.g., benzalkonium chloride, of about 1:2 to about 200:1, such as, e.g., ~1:2-~100:1, ~1:1-~50:1, ~1:1-~20:1, ~1:1-~10:1, ~1:1-~5:1, or ~6.7:1 to ~1:1.4, e.g., about 2:1.

In aspects, compositions provided by the invention comprise a ratio of bimatoprost compound, e.g., bimatoprost base, to penetration enhancement component of about 1:1 to about 1:500, ~1:10-~1:500, ~1:12.5-~1:500, such as ~1:20 to ~1:200, ~1:30-~1:180, ~1:40-~1:160, ~1:50:~1:140, ~1:60-~1:120, ~1:70-~1:110, ~1:80-~1:110, ~1:90-~1:105, or, e.g., about 1:12.5-about 1:500, e.g., about 1:100.

In aspects, compositions provided by the invention comprise a ratio of timolol compound to quaternary ammonium salt, e.g., benzalkonium chloride, of about 40:1 to about 1000:1, e.g., ~50:1-~500:1, ~50:1-~400:1, ~60:1-~300:1, ~70:1-~200:1, or, e.g., such as about 100:1 to about 500:1 or about 57:1-about 267:1, e.g., ~100:1-~150:1, ~120:1-~140:1, such as, e.g., about 136:1.

In aspects, compositions provided by the invention comprise a ratio of timolol compound, e.g., salt of timolol, e.g., timolol maleate, to penetration enhancer component of about 4:1 to about 1:6.25, such as, e.g., ~3:1-~1:6, ~2:1-~1:5, ~1:1-~1:4, ~1:1-~1:3, or, e.g., ~1:1-~1:2, such as, e.g., about 1:1-about 1:5, or ~3:1-~1:6.5, ~3.2-~1:6.3, or ~3.2:1 to about 1:6.25, e.g., about 2:1-about 1:3, e.g., about 1:1.5, or, e.g., about 1:1.47.

In aspects, compositions provided by the invention comprise a ratio of the total amount of API consisting of the bimatoprost compound, e.g., bimatoprost base, and the timolol compound, e.g., salt of timolol, e.g., timolol maleate, to quaternary ammonium salt, e.g., benzalkonium chloride, of about 120:1 to about 4005:1, such as, e.g., ~120:1-~2000:1, ~120:1-~1000:1, ~120:1-~500:1, ~120:1-~400:1, ~120:1-~300:1, ~120:1-~200:1, or, e.g., ~120:1-~150:1, such as, e.g., ~57:1 to ~274:1, e.g., ~140:1 or ~138:1.

In aspects, compositions provided by the invention comprise a ratio of the total amount of API consisting of the bimatoprost compound, e.g., bimatoprost base, and the timolol compound, e.g., salt of timolol, e.g., timolol maleate, to penetration enhancement component of about 16:1 to about 1:2.1, such as, e.g., ~10:1-~1:2, ~5:1-~1:2, or, e.g., ~2:1-~1:2, e.g., ~1:1 to ~1:10, ~1:1-~1:7, ~1:1-~1:6, ~1:1-~1:5, ~1:2-~1:5, or, e.g., ~1:3-~1:5, such as ~3.3:1 to ~1:6.2, e.g., ~1:1.5 or ~1:1.45.

In aspects, compositions provided by the invention comprise a ratio of bimatoprost compound, e.g., bimatoprost base, to the viscosity enhancer component of about 1:2 to about 1:1000, such as, e.g., ~1:2-~1:500, ~1:2-~1:400, ~1:2-~1:300, ~1:2-~1:200, or, e.g., ~1:2-~1:100, such as, e.g., ~1:5-~1:100, ~1:10-~1:100, ~1:20-~1:30-~1:100, ~1:40-~1:90, ~1:50-~1:80, or, e.g., ~1:50-~1:70, as in, e.g., ~1:1 to ~1:500 or ~1:1 to ~1:100, such as, e.g., about 1:60.

In aspects, compositions provided by the invention comprise a ratio of timolol compound, e.g., a salt of timolol, e.g., timolol maleate, to the viscosity enhancer component of about 10:1 to about 1:10, such as, e.g., ~5:1 to ~1:5, ~4:1-~1:4, ~3:1-~1:3, or ~2:1 to ~1:2, such as, e.g., about 1.1:1 to about 1.15:1, or about 1.13:1.

In aspects, compositions provided by the invention comprise a ratio of the total amount of API consisting of the bimatoprost compound, e.g., bimatoprost base, and the timolol compound, e.g., salt of timolol, e.g., timolol maleate, to the viscosity enhancer component is about 10:1 to about 1:10, such as, e.g., ~5:1 to ~1:5, ~4:1-~1:4, ~3:1-~1:3, or ~2:1 to ~1:2, such as, e.g., as in, e.g., ~2:1-~1:1, ~1.5:1-~1:1, ~1.4:1-~1:1, ~1.3:1-~1:1, or, e.g., ~1.2:1-~1:1, such as, e.g., ~1.15:1.

Additional Means/Steps for Performing Functions

In aspects, compositions provided by the invention comprise one or more means for performing one or more specific functions and methods of the invention include steps for performing functions. In general, any element described herein as a "means" for performing a function can also, wherever suitable, serve as a "step for" performing a function in the context of methods of the invention, and vice versa. E.g., a component described herein as a means for preserving a composition also simultaneously and implicitly supports a method of making such a composition comprising a step of preserving a composition and a kit comprising a means for delivering a composition implicitly and simultaneously provides a step for delivering the composition comprising the use of such delivery means.

In one aspect, compositions provided by the invention comprise means for preserving the composition(s), e.g., detectably or significantly inhibiting microbial growth, in aspects detectably or significantly reducing the number of impurities or detectably or significantly improving the stability of the compositions such that compositions remain safe and suitable for administration after storage of at least about 1 month, e.g., ~2 months, or e.g., ~3 months or more after manufacturing at room temperature (e.g., about 25° C. and about 60% relative humidity or, e.g., about 25° C.+/−2° C. and about 40%+/−5% relative humidity) ("preservation means"). Support for preservation means can be found in, e.g., the section entitled "Preservative Component (Preservation Agent(s))."

In one aspect, compositions provided by the invention comprise means for enhancing penetration of one or more composition constituents, in aspects such means for penetration enhancement detectably or significantly improving the penetration into an eye tissue of one or more active pharmaceutical ingredients, e.g., PAC constituent, BBC constituent, or both, e.g., bimatoprost compound, e.g., bimatoprost base, timolol compound, e.g., salt of timolol, e.g., timolol maleate, or both ("penetration enhancement means"). Support for penetration enhancement means can be found in, e.g., the section entitled "Penetration Enhancer Component (Penetration Enhancer(s))."

In one aspect, compositions provided by the invention comprise means for solubilization of one or more composition constituents, in aspects such means for solubilization detectably or significantly improving the solubilization of one or more composition constituents, e.g., one or more active pharmaceutical ingredients, e.g., PAC constituent, BBC constituent, or both, e.g., bimatoprost compound, e.g., bimatoprost base, timolol compound, e.g., salt of timolol, e.g., timolol maleate, or both, detectably or significantly maintaining the solubilization of one or more composition constituents for a detectably or significantly longer period of time, or both ("solubilization means"). Support for solubilization means can be found in, e.g., the section entitled "Solubilization Component (Solubilizing Agent(s))."

In one aspect, compositions provided by the invention comprise means for solubilization of one or more composition constituents; in aspects, such means for solubilization detectably or significantly improving the solubilization of one or more composition constituents, e.g., one or more active pharmaceutical ingredients, e.g., PAC constituent, BBC constituent, or both, e.g., bimatoprost compound, e.g., bimatoprost base, timolol compound, e.g., salt of timolol, e.g., timolol maleate, or both; in aspects, such means detectably or significantly maintaining the solubilization of one or more composition constituents for a detectably or significantly longer period of time (than substantially similar or identical compositions lacking such means—substantially similar in this respect and in some aspects typically meaning either about the same amount, same amount, or significantly similar amount of most, generally all, essentially all or all relevant ingredients), or both; and, further or alternatively, in aspects, detectably or significantly improving the penetration into an eye tissue of one or more active pharmaceutical ingredients, e.g., PAC constituent, BBC constituent, or both, e.g., bimatoprost compound, e.g., bimatoprost base, timolol compound, e.g., salt of timolol, e.g., timolol maleate, or both ("penetration enhancement and solubilization means"). Support for penetration enhancement and solubilization means can be found in, e.g., the section entitled "Combination Solubilization/Penetration Enhancer Component (Solubilizing Agent(s)/Penetration Enhancer(s))."

In one aspect, compositions provided by the invention comprise means for soothing irritation caused by one or more composition constituents, such means for soothing detectably or significantly reducing or preventing irritation or inflammation caused by one or more composition constituents ("demulcent means"). Support for demulcent means can be found in, e.g., the section entitled "Demulcent Component (Demulcent(s))."

In aspects, compositions provided by the invention comprise a means of buffering a composition, in aspects such a means capable of maintaining the pH of compositions between ~6 and ~8, such as, e.g., ~6.2-~7 or, e.g., ~6.9-~7.5, for an extended period of time, e.g., at least about 1 month, ~3 months, ~6 months, ~12 months, ~18 months, ~24 months, or, e.g., at least about 36 months when stored at about 15° C. to about 25° C.+/−2° C. In certain aspects, compositions provided by the invention lack such a means of buffering pH ("buffering means"). In aspects, such buffering means are described in, e.g., the section entitled "Buffer Component (Buffer(s))."

In one aspect, compositions provided by the invention comprise means for providing a suitable tonicity of the composition(s), providing a suitable osmolality of the composition(s), e.g., means for providing composition(s) which, in aspects, do not cause detectable or significant ocular irritation due to tonicity when provided according to instructions ("tonicity means"). Support for tonicity means can be found in, e.g., the section entitled "Tonicity Component (Tonicity Agent(s))."

In one aspect, compositions provided by the invention comprise means for increasing viscosity, such means for viscosity enhancement in aspects detectably or significantly increasing the thickness or viscosity of a composition, or, e.g., detectably or significantly modifying the nature of the composition such as, e.g., providing the composition as a gel ("viscosity enhancer means" or "thickening means"). In aspects, such means for increasing viscosity only do so (1) upon exposure to the environment of the mammalian eye to which it is administered, (2) upon exposure to temperatures of at least about 32 degrees Celsius (° C.), (3) upon exposure to an environment having an ionic strength detectably or significantly greater than that of one or more gelling agents present in the composition (e.g., gellan gum), (4) exposure to an environment having a pH of greater than about 6.2, or (5) any combination of (1)-(4), over the viscosity of the composition while stored prior to administration at a temperature of about 15° C. to about 25° C.+/−2° C.). Support for viscosity enhancer/thickening means can be found in, e.g., the section entitled "Viscosity Enhancer/Thickening Component (Viscosity Enhancing Agent(s)/Thickening Agent(s))."

In one aspect, compositions provided by the invention comprise means for chelation, in aspects such means for chelation detectably or significantly improving the stability of one or more active pharmaceutical ingredients, e.g., one or more PAC constituents, BBC constituents, or both, e.g., bimatoprost compound, e.g., bimatoprost base, timolol compound, e.g., salt of timolol, e.g., timolol maleate, or both, detectably enhancing the effectiveness of one or more preservatives, or any combination thereof ("chelation means"). Support for chelation means can be found in, e.g., the section entitled "Chelation Component (Chelating Agent(s))."

In one aspect, compositions provided by the invention comprise means for adjusting the pH of the composition(s), in aspects providing a suitable or target pH of the composition(s) of, e.g., about 6-about 8, e.g., about 6.2-about 7, or, e.g., about 6.9-about 7.5 ("pH adjusting means"). Support for pH adjusting means can be found in, e.g., the section entitled "pH Adjusting Component (pH Adjusting Agent(s)).

In one aspect, compositions provided by the invention comprise means for protecting API(s) from oxidation, e.g., means for providing antioxidant protection of API(s), such means for antioxidant protection of API(s) which in aspects detectably or significantly improving the stability of the one or more bimatoprost compound(s), timolol compound(s), or both, detectably or significantly reducing impurities detected at time points 2 weeks, 1 months, 2 months, or 3 months or more (e.g., 6, 12, 18, 24, or 36 months) after manufacturing, or any combination thereof ("antioxidant means"). Support for antioxidant means can be found in, e.g., the section entitled "Antioxidant Component (Antioxidant(s))."

In one aspect, compositions provided by the invention comprise means for providing compositions of the invention as liquid compositions (e.g., solutions, gels, etc.), e.g., providing a carrier for the API(s) and any one or more other excipients of the composition(s) ("carrier means"). Support for carrier means can be found in, e.g., the section entitled "Carrier Component (Carrier Agent(s))."

Composition Characteristics

Ready-To-Use

In aspects, compositions provided by the invention are provided in ready-to-use (RTU) form, and do not require dilution or further modification prior to administration. In such compositions, the composition, in aspects, is stored in a healthcare setting, and is ready for immediate administration to a subject, such as a human patient. In such compositions, the composition, in aspects, is stored in a home setting, and is ready for immediate administration, e.g., self-administration, to a subject.

pH

As used herein, the term "pH" is the conventional measurement unit of hydrogen ion activity in a solution at room temperature (about 25° C.) unless another temperature is specified. In aspects, compositions provided by the invention have a pH of between about 6 and about 8.

In aspects, compositions provided by the invention have a pH of about 6 to about 8, such as about 6 to about 7 or about 6 to about 7.5, such as, e.g., ~6-~7.4, ~6-~7.3, ~6-~7.2, ~6-~7.1, or ~6-~7, e.g., ~6.1-~8, ~6.2-~8, ~6.3-~8, ~6.4-~8, ~6.5-~8, ~6.6-~8, ~6.7-~8, ~6.8-~8, ~6.9-~8, or, e.g., ~7-~8, for example ~6.1-~7.5, or ~6.2-~7.8, ~6.2-~7.5, or ~6.2-~7.3 such as, e.g., ~6.1-~7.4, ~6.2-~7.2, or, e.g., about 6.2 to ~7, such as, e.g., ~6.3, ~6.4, ~6.4, ~6.6, ~6.7, ~6.8, or, e.g., ~6.9.

In aspects, compositions provided by the invention have a pH of about 6 to about 8, such as ~6.5-~8, or, e.g., about 6.9 to about 7.5, such as, e.g., ~6.9-~7.4, ~6.9-~7.3, or ~6.9-~7.2, e.g., ~7-~7.5, ~7.1-~7.5, or, e.g., ~7.1-~7.3.

In aspects, the pH of the compositions provided by the invention, such as, e.g., bimatoprost and timolol compound compositions, will be affected by the concentration of each of the ingredients during manufacturing. Hence, in aspects, the pH of the compositions can be adjusted during the manufacturing to attain the target pH ranges described above, such as, e.g., ~6.2-~7, or alternatively ~6.9-~7.5, e.g., ~7.1-~7.3. In aspects, the pH of the compositions provided by the invention is maintained from the time of establishment during manufacturing and the time of packaging to the time of administration to the mammalian eye when stored at controlled room temperature, e.g., at a temperature of about 15° C. to 25° C.+/−2° C. or a temperature of about 25° C.+/−2° C. and about 40%+/−5% relative humidity, for a period of at least about 1 month, such as, e.g., for a period of about 1-about 36 months or more.

Osmolality

In aspects, compositions provided by the invention are characterizable as isotonic. In aspects, compositions provided by the invention have an osmolality of about 171 milliosmoles per kilogram (mOsm/Kg) to about 1171 mOsm/Kg, such as, e.g., ~171 mOsm/Kg-~1100 mOsm/Kg, ~171 mOsm/Kg-~1000 mOsm/Kg, ~171 mOsm/Kg-~900 mOsm/Kg, ~171 mOsm/Kg-~800 mOsm/Kg, ~171 mOsm/Kg-~700 mOsm/Kg, ~171 mOsm/Kg-~600 mOsm/Kg, ~171 mOsm/Kg-~500 mOsm/Kg, or ~171 mOsm/Kg-~400 mOsm/Kg.

In some aspects, compositions provided by the invention have an osmolality of about 180 mOsm/Kg-about 1171 mOsm/Kg, such as, e.g., ~200 mOsm/Kg-~1171 mOsm/Kg, ~220 mOsm/Kg-~1171 mOsm/Kg, ~240 mOsm/Kg-~1171 mOsm/Kg, ~260 mOsm/Kg-~1171 mOsm/Kg, ~280 mOsm/Kg-~1171 mOsm/Kg, ~300 mOsm/Kg-~1171 mOsm/Kg, ~320 mOsm/Kg-~1171 mOsm/Kg, ~340 mOsm/Kg-~1171 mOsm/Kg, ~360 mOsm/Kg-~1171 mOsm/Kg, ~380 mOsm/Kg-~1171 mOsm/Kg, or, e.g., ~400 mOsm/Kg-~1171 mOsm/Kg, e.g., ~200 mOsm/Kg-~1000 mOsm/Kg.

In aspects, compositions provided by the invention have an osmolality of about 200 mOsm/Kg to about 500 mOsm/Kg, or, e.g., about 200 mOsm/Kg to about 400 mOsm/Kg, such as, e.g., ~250 mOsm/Kg-~400 mOsm/Kg, ~260 mOsm/Kg-~390 mOsm/Kg, ~270 mOsm/Kg-~380 mOsm/Kg, or, e.g., ~280 mOsm/Kg-~370 mOsm/Kg, for example ~210 mOsm/Kg-~390 mOsm/Kg, ~220 mOsm/Kg-~380 mOsm/Kg, ~230 mOsm/Kg-~370 mOsm/Kg, ~240 mOsm/Kg-~360 mOsm/Kg, or, e.g., ~250 mOsm/Kg-~350 mOsm/Kg or ~280 mOsm/Kg-~370 mOsm/Kg.

In aspects, the invention provides compositions comprising a tonicity agent component such that the composition comprises an isotonic range (e.g., an osmolality) within a range provided herein. In aspects, the osmolality of the pharmaceutically acceptable and ophthalmologically suitable formulations provided by the invention are advantageous in that such isotonicity can be important to composition efficacy and patient comfort, thus contributing to continued use of the composition, e.g., tolerability of the composition for a longer period of time than a composition comprising an osmolality either higher than or lower than that of the compositions described herein.

Viscosity

In aspects, compositions provided by the invention, after manufacture and while in storage at about 15° C.-about 27° C., have a viscosity of less than about 75 cps, e.g., in aspects, a viscosity of less than about 70 cps, less than about 65 cps, less than about 60 cps or less than about 50 cps. In aspects, compositions provided by the invention formulated such that they are capable of forming a gel comprise a viscosity after manufacture and while in storage at about 15° C.-about 27° C. have a viscosity which is detectably or significantly less than the viscosity of the composition after administration to a mammalian eye. That is, in aspects, compositions provided by the invention, when provided in the form of a composition capable of forming a gel, form a gel having a viscosity after administration to a mammalian eye which is detectably or significantly greater than the viscosity of the composition after manufacture and while in storage of about 15° C.-about 27° C., prior to administration. In aspects, compositions after administration to a mammalian eye can comprise a viscosity of greater than about 15 cps, such as, e.g., ≥~20 cps, ≥~30 cps, ≥~40 cps, ≥~50 cps, ≥~60 cps, ≥~70 cps, ≥~80 cps, ≥~90 cps, or, e.g., ≥~100 cps. In aspects, compositions have at least generally the same, at least substantially the same, at least essentially the same, essentially the same, or the same viscosity after administration to a mammalian eye as prior to administration (e.g., after manufacture and during storage at, e.g., about 15° C.-about 27° C.). In certain aspects, at any time during storage at about 15° C.-about 27° C. and after administration to mammalian eye, the composition has a viscosity of between about 1 and about 150 cps, e.g., ~1 cps-~140 cps, ~1 cps-~130 cps, ~1 cps-~120 cps, ~1 cps-~110 cps, or, e.g., in aspects,-1 cps-~100 cps. In aspects, higher viscosity compositions can be advantageous (e.g., in tolerability, effectiveness, stability, ease of administration or use, etc.). In aspects, a composition having a detectably or significantly higher viscosity than the composition in aqueous solution form when stored at about 15° C.-about 27° C. can be advantageous. In aspects, such advantages may be, e.g., providing a detectable or significant improvement in the ease of convenient administration, (e.g., make the composition easier for a user to apply), detectably or significantly increasing contact of the composition with eye tissue, or e.g., detectably or significantly increasing the length of time the composition maintains contact with eye tissue following administration. In aspects, a detectable or significant difference in viscosity is achieved after a composition is applied to the eye. In aspects, compositions in the form of a gel detectably or significantly increase in viscosity upon contact with the eye over the viscosity of the composition prior to administration, e.g., when stored at about 15° C.-about 27° C., such as increasing in viscosity by at least about 10%, ≥~20%, ≥~30%, ≥~40%, ≥~50%, ≥~60%, ≥~70%, ≥~80%, ≥~90%, or ≥~100% or more, such as ≥~125%, ≥~150%, ≥~175%, ≥~200%, or even more, such as, e.g., ≥~400%, ≥~600%, ≥~800%, or, for example, ≥~1000% or more. In aspects, such an increased viscosity is advantageous for the reasons provided in this paragraph or, e.g., elsewhere herein.

Stability

Uncontradicted, the term "stable" or "stable composition" as used herein, refers to a composition comprising both a PAC (e.g., comprising a bimatoprost compound, e.g., bimatoprost base) and a BBC (e.g., comprising a timolol compound, e.g., a salt of timolol, e.g., timolol maleate) provided by the invention having sufficient physical and chemical stability to allow storage at a convenient temperature, such as between about 0° C. and about 50° C. for a commercially reasonable or relevant period of time.

In aspects, compositions of the invention are stable. In aspects, compositions of the invention exhibit physical stability, chemical stability, or both, over any of the periods of storage described herein. The term "physical stability" typically refers to maintenance of color, dissolved oxygen level, head space oxygen level, and particulate matter, and the term "chemical stability" typically relates to formation of drug-related impurities in terms of total impurity, single maximum individual impurity, and maximum individual unknown impurity. For the purpose of the present invention chemical stability also includes maintenance of pH of the finished formulation. In aspects, compositions provided by the invention demonstrate stability required for commercially relevant times after manufacturing, such as for at least about 1, 3, 6, 9, 12, 18, 24 or 36 months, during which composition(s) is/kept in its/their original packaging under specified storage condition. The term "shelf life" refers to the amount of time the ophthalmic composition may be stored without detectable or significant loss of potency and/or dissolution profile. Preferably, the shelf life refers to the amount of time the ophthalmic composition may be stored without a loss of more than 2%, 5%, 8% or 10% of the potency and/or loss of suitable dissolution. Compositions of the invention, in aspects, exhibit such shelf-life characteristic. Herein, uncontradicted, the term "room temperature" refers to controlled room temperature as about 15° C. to 25° C.+/−2° C.

In one aspect, the invention provides pharmaceutically acceptable and ophthalmologically suitable compositions comprising less than about 2.5% of total impurities, such as, e.g., ≤~2% total impurities, ≤~1.5%, ≤~1%, or ≤~0.5% total impurities. The term "impurity" refers to an undesired substance in a composition which may be present in an initial composition and/or may be formed after a certain period of shelf life of a composition. These impurities may, e.g., be formed via degradation of one or more components of the composition. Sources of degradation can include, but are not limited to, oxidation, light, ultraviolet light, moisture, heat, changes in pH, and composition component interactions.

In aspects, the invention provides compositions described herein, wherein the composition comprises less than about 2.5% total impurities, e.g., less than about 2%, less than about 1.5%, less than about 1%, or, e.g., less than about 0.5% total impurities after storage at about 25° C.+/−2° C. and about 40%+/−5% relative humidity; about 40° C.+/−2° C. and not more than about 25% relative humidity; about 15° C.-about 27° C. and about 60% relative humidity; about 38° C.-about 42° C. and 75% relative humidity; or when stored under any such condition, or a sequential combination of such conditions, for a period of at least about 1 month, e.g., ~3 months, ≥~6 months, ≥~9 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months.

In one aspect, the invention provides pharmaceutically acceptable and ophthalmologically suitable compositions which remain stable and retain at least about 90%, such as, e.g., ≥~92%, ≥~94%, ≥~96%, ≥~98%, or even ≥~99% of the labelled concentration of bimatoprost compound, e.g., bimatoprost base, the labelled concentration of timolol compound, e.g., timolol maleate, or both the labelled concentration of bimatoprost and timolol compounds after storage under typical and/or accelerated conditions.

In aspects, the invention provides compositions as described herein, wherein the composition maintains at least about 98%, e.g., at least about 99%, of the bimatoprost compound, the timolol compound, or both when stored at about 25° C.+/−2° C. and about 40%+/−5% relative humidity; about 40° C.+/−2° C. and not more than about 25% relative humidity; about 15° C.-about 27° C. and about 60% relative humidity; about 38° C.-about 42° C. and 75% relative humidity; or when stored under any such condition, or a sequential combination of such conditions, for at least about one month, such as, e.g., ≥~3 months, ≥~6 months, ≥~9 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months.

Dosage Forms & Administration Rates

In aspects, compositions provided by the invention are pharmaceutically acceptable and ophthalmologically suitable compositions provided as a topically applied composition. In aspects, pharmaceutically acceptable and ophthalmologically suitable compositions provided by the invention can be provided as, e.g., formulated as, solutions, suspensions, ointments, creams, gels, sprays, and other dosage forms suitable for topical ophthalmic administration. In aspects, compositions herein are provided as topically applied solution compositions. In aspects, compositions herein are provided as topically applied gel compositions, or, e.g., compositions which form a gel upon administration (e.g., upon exposure to a sufficient amount of heat, e.g., body or ophthalmic temperature(s)). In some aspects, compositions provided by the invention are injectable compositions or are formulated to be suitable for administration by injection. In aspects, compositions provided by the invention can be suitable for topical delivery as drops or implantation in or on a subject's eye or tissue surrounding the eye, e.g., suitable for implantation into a subconjunctival space, naso-lacrimal duct, or vitreous body of the subject.

In aspects, compositions provided by the invention are aqueous solutions. In aspects, compositions provided as aqueous solutions provide ease of use of such compositions including as a patient's ability to easily administer such compositions by means of instilling a suitable dose of the solutions to affected eye(s). In aspects, aqueous compositions provided by the invention are typically more than about 50% w/v, e.g., ≥~55% w/v, ≥~60% w/v, ≥~65% w/v, ≥~70% w/v, ≥~75% w/v, ≥~80% w/v, ≥~85% w/v, or ≥~90% w/v water, and at least generally all, substantially all, or all components of the formulation are fully dissolved such that a clear, aqueous solution (or, in aspects, e.g., a clear, aqueous gel) is provided.

In aspects, pharmaceutically acceptable and ophthalmologically suitable compositions provided by the invention are provided as a liquid solution, wherein compositions are administered as drops to affected eye(s). In aspects, compositions are administered as about 1 to about 3 drops, such as, e.g., about 1 to about 2 drops, e.g., about 1, about 2, or about 3 drops of the composition to each affected eye per dose/administration. Typically, a single administration comprises no more than about 2 drops of composition, such as about 1 or about 2 drops of composition per administration. In aspects, exact amounts to be administered can be determined by an overseeing physician, e.g., optometrist. In aspects, a typical drop size is between about 5 μL and about 100 μL, such as, e.g., ~5 μL-~75 μL, or ~5 μL-about 50 μL, such as, e.g., ~10 μL-~100 μL or, e.g., ~25 μL-~100 μL, for example ~25 μL-~70 μL, or, e.g., ~20 μL-~60 μL.

In aspects, compositions provided herein can be administered in doses of 1-3 drops, such as no more than 3 drops, no more than 2 drops, or, e.g., no more than 1 drop one or twice per day (e.g., once or twice per 24-hour period). In aspects, compositions herein are administered as 1-2 drops once or twice daily. In aspects, compositions herein are administered as 1-2 drops once daily (e.g., once per 24-hour period). In aspects, compositions herein are administered as a single drop once or twice daily. In aspects, compositions herein are administered as a single drop once daily (e.g., once per 24-hour period). In aspects, compositions comprising bimatoprost and timolol compounds are administered to the mammalian eye once daily as 1-2 drops, e.g., as a single drop, either in the morning or in the evening.

In certain aspects, pharmaceutically acceptable and ophthalmologically suitable compositions provided by the invention are provided as a gel. In aspects, compositions provided as a gel increase the amount of time the composition contacts eye tissue, leading to, in aspects, an increased bioavailability of active ingredient(s) contained therein (i.e., a detectable or significant improvement in bioavailability of the API(s)).

In aspects, pharmaceutically acceptable and ophthalmologically suitable compositions provided by the invention as gel compositions are administered as drops to affected eye(s). In aspects, compositions are administered as about 1 to about 3 drops, such as, e.g., about 1 to about 2 drops, e.g., about 1, about 2, or about 3 drops of the composition to each affected eye per dose/administration. Typically, a single administration comprises no more than about 2 drops of composition, such as about 1 or about 2 drops of composition per administration. In aspects, exact amounts to be administered can be determined by an overseeing physician, e.g., optometrist. In aspects, a typical drop size is between about 5 μL and about 100 μL, such as, e.g., ~5 μL-~75 μL, or ~5 μL-about 50 μL, such as, e.g., ~10 μL-~100 μL or, e.g., ~25 μL-~100 μL, for example ~25 μL-~70 μL, or, e.g., ~20 μL-~60 μL.

According to certain aspects, pharmaceutically acceptable and ophthalmologically suitable compositions provided by the invention are controlled release compositions, such as, e.g., characterizable as slow-release compositions.

In some aspects, compositions are administered as a single administration. In other aspects, compositions are administered as a plurality of administrations, such as, e.g., 5, 10, 20, 30, 40, or 50 or more administrations, such as, e.g., daily administration for a period of days, weeks, months, or years (e.g., 1, 2, 3, 4, or 5 years or longer). In aspects, multiple administrations are separated from one another by a period of at least about 1 minute, such as at least about 30 minutes or longer, such as, e.g., at least about 1 hour or longer, or such as 24 hours or longer.

In aspects, an effective treatment period is a period of about 1 day, about 1 day-about 1 week, about 5 days to about 1 month, about 1 week to about 3 months, about 2 weeks to about 3 months, about 1 month to about 6 months, about 3 months to about 9 months, about 6 months to about 12 months (1 year), about 9 months to about 18 months, about 12 months to about 24 months, about 18 months to about 30 months, about 24 months to about 36 months, or about 1 year to about 3 years, or longer, e.g., a period of greater than about 1 year, greater than about 2 years, greater than about 3 years, greater than about 4 years, or greater than about 5 years. In certain aspects, compositions provided by the invention are used as a chronic treatment, e.g., in treating a chronic condition, such that the effective treatment period is ongoing with no defined end point. In aspects, compositions provided by the invention are used in treatment of a chronic condition, wherein treatment is for a period of at least about 1 year or longer, e.g., ≥~2 years, ≥~3 years, ≥~4 years, or ≥~5 years or longer, e.g., ≥~5, ≥~10, ≥~15, ≥~20, or ≥~25 years or more.

In aspects, ophthalmic compositions described herein can be applied to each affected eye; to both eyes; or, e.g., the dominant eye of the recipient over the course of an effective treatment period. Exact application may, in aspects, vary depending on the target indication, the tolerance or goals of the recipient, the aim of the attending physician/treatment provider, or any combination thereof.

Methods of Use

In aspects, the invention provides methods of using any one or more of the compositions described herein in methods of treating one or more ocular conditions, one or more symptoms related to one or more ocular conditions, or any combination thereof. Exemplary methods are provided here. In aspects, performance of one or more methods described herein results in a significant reduction in elevated intraocular pressure in a treated mammalian eye.

In aspects, the invention provides any one or more of the methods described in this section, wherein the administration of the composition, when administered in an effective amount (e.g., amounts disclosed herein), for an effective treatment period (e.g., treatment periods described herein), results in a detectable or significant improvement in vision; detectable or significant modulation of one or more physiological properties of the eye; detectable or significant reduction in intraocular pressure; detectable or significant treatment of glaucoma, e.g., open-angle glaucoma or any one or more symptoms related to glaucoma described herein, or any combination of such results.

Method of Improving Vision

In one aspect, the invention provides pharmaceutically acceptable and ophthalmologically suitable compositions comprising a bimatoprost compound and a timolol compound and methods for their use in improving vision, reducing visual impairment, treating a vision-related ophthalmic condition, or combinations thereof. In aspects, such an effect is attained via the detectable or significant reduction in intraocular pressure. In aspects, compositions provided by the invention and methods of their use described herein can be provided to or for any patient in need thereof or suffering from a condition benefiting from the provision of compositions or methods described herein. In aspects, a suitable patient is a patient, e.g., a mammal, such as, e.g., a human, suffering from elevated intraocular pressure, glaucoma (e.g., open-angle glaucoma), elevated intraocular pressure associated with glaucoma, or combination(s) thereof. In aspects, a suitable patient is a patient for whom prior treatment with one or more single prostaglandin analogues has proven insufficient to treat their condition. In aspects, a suitable patient is a patient for whom prior treatment with one or more single beta-adrenoreceptor antagonists (β-blockers) has proven insufficient to treat their condition.

In aspects, compositions provided by the invention are suitable for administration to any subject benefiting from the administration thereof, e.g., any mammal with an ophthalmic condition benefitting from the receipt of a suitable amount of such compositions. In aspects, a suitable recipient is an adult human. In aspects, a suitable patient is a patient for whom prior treatment with one or more single prostaglandin analogues and one or more single beta-adrenoreceptor antagonists has proven insufficient.

In aspects, compositions provided by the invention are suitable for administration to children (in this and similar other aspects, "suitability" or "suitable for" in regards to characteristics of a composition refers to, i.a., the characteristic of demonstrated suitability in terms of efficacy and safety, e.g., demonstrated through clinical trials to be sufficiently suitable (safe and effective) to treat the indicated condition, act in the indicated population/setting, or both, e.g., in a significant number of patients in such studies). In aspects, compositions provided by the invention are not suitable for administration to children. In aspects, compositions provided by the invention are suitable for administration to children for whom other interventions are unsuitable, undesirable, or insufficient. Determinations of suitable and efficacy in such aspects can be determined by, e.g., scientific evidence, such as, for example, determination of bioequivalence to a product having such effects, or determination of such effectives through one or more scientific studies, such as one or more adequate, well-controlled, studies, which would be suitable for submission to US FDA in connection with approval of a pharmaceutical product, wherein a suitably significant effect is observed.

Method of Modulating Physiological Properties of the Eye: Reducing Intraocular Pressure: Treating Glaucoma In one aspect, the invention provides a method of detectably or significantly modulating one or more physiological properties of a mammalian eye comprising administering a therapeutically effective amount of any one or more compositions described herein. In aspects, the invention provides a method of detectably or significantly reducing intraocular pressure in a mammalian eye comprising administering a therapeutically effective amount of any one or more compositions described herein. In aspects, the invention provides a method of detectably or significantly slowing the rate of increase of intraocular pressure in a mammalian eye comprising administering to a patient benefitting therefrom a therapeutically effective amount of any one or more compositions described herein. In aspects, the invention provides methods of detectably or significantly slowing glaucoma progression, e.g., open-angle glaucoma progression or, e.g., improving or slowing the progression of one or more symptoms related to glaucoma, e.g., open angle glaucoma, such as, e.g., elevated intraocular pressure, vision impairment, vision loss, seeing halos around lights, rainbow-colored circles around lights, light sensitivity, ocular redness, hazy appearance of the eye (e.g., whitening of the cornea), upset stomach or vomiting, eye pain, loss of peripheral or side vision, patchy blind spots inside or central vision, tunnel vision, headaches, and any other symptoms related to glaucoma comprising administering a therapeutically effective amount of any one or more compositions described herein. In aspects, the invention provides methods of treating glaucoma, e.g., open-angle glaucoma, in a mammalian eye comprising administering to a patient diagnosed with glaucoma or suffering from clinical symptom(s) of glaucoma a therapeutically effective amount of any one or more compositions described herein.

In aspects, the invention provides the methods described above comprising administering to the recipient/patient a therapeutically effective amount of a pharmaceutically acceptable and ophthalmologically suitable ophthalmic composition, e.g. provided in the form of a solution, comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; and (4) about 0.25% w/v-about 2.5% w/v of a penetration enhancer component. In aspects, the ratio of the quaternary ammonium salt to the penetration enhancer component in the composition is about 1:35-about 1:840. In aspects, the ratio of the bimatoprost compound to the penetration enhancer component is about 1:12.5-about 1:500. In aspects, the ratio of the timolol compound to the penetration enhancer component is between about 3.2:1-1:6.3. In aspects, compositions can comprise any combination of such ratios described here. In aspects, the composition is stable when stored at about 25° C.+/−2° C. and about 40%+/−5% relative humidity; about 40° C.+/−2° C. and not more than about 25% relative humidity; about 15° C.-about 27° C. and about 60% relative humidity; about 38° C.-about 42° C. and 75% relative humidity; or when stored under any such condition, or a sequential combination of such conditions, for at least about 1 month, e.g., at least about 2 months, at least about 3 months, at least about 2-about 6 months, about 3-about 9 months, about 6-about 12 months, about 9-about 18 months, about 12-about 24 months, about 18-about 30 months, about 24-about 36 months, or, e.g., for at least about 36 months.

In aspects, the invention provides the methods described above comprising administering to the recipient/patient a therapeutically effective amount of a pharmaceutically acceptable and ophthalmologically suitable ophthalmic composition, e.g., provided in the form of a gel. In aspects, such composition(s) are composition(s) comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; and (4) about 0.25% w/v-about 2.5% w/v of a penetration enhancer component. In aspects the ratio of the quaternary ammonium salt to the penetration enhancer component in the composition is about 1:35-about 1:840. In aspects, the ratio of the bimatoprost compound to the penetration enhancer component in the composition is about 1:12.5-about 1:500. In aspects, the ratio of the timolol compound to the penetration enhancer component in the composition is between about 3.2:1-1:6.3. In aspects, the ratio of bimatoprost compound, e.g., bimatoprost base, to the viscosity enhancer component in the composition is about 1:2 to about 1:1000. In aspects, the ratio of timolol compound, e.g., a salt of timolol, e.g., timolol maleate, to the viscosity enhancer component in the composition is about 10:1 to about 1:10. In aspects, the ratio of the total amount of API consisting of the bimatoprost compound, e.g., bimatoprost base, and the timolol compound, e.g., salt of timolol, e.g., timolol maleate, to the viscosity enhancer component in the composition is about 10.5:1 to about 1:9.9. In aspects, composition(s) comprise any one or more such ratio(s) described here. In aspects, the composition is stable when stored at about 25° C.+/−2° C. and about 40%+/−5% relative humidity; about 40° C.+/−2° C. and not more than about 25% relative humidity; about 15° C.-about 27° C. and about 60% relative humidity; about 38° C.-about 42° C. and 75% relative humidity; or when stored under any such condition, or a sequential combination of such conditions, for at least about 1 month, e.g., at least about 2 months, at least about 3 months, at least about 2-about 6 months, about 3-about 9 months, about 6-about 12 months, about 9-about 18 months, about 12-about 24 months, about 18-about 30 months, about 24-about 36 months, or, e.g., for at least about 36 months.

In aspects, the invention provides the methods described above comprising administering to the recipient/patient a therapeutically effective amount of a pharmaceutically acceptable and ophthalmologically suitable ophthalmic composition, e.g., provided in the form of a gel comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt. In aspects, the viscosity of the composition detectably or significantly increases (a) upon exposure to the environment of the mammalian eye to which it is administered, (b) upon exposure to temperatures of at least about 32 degrees Celsius (° C.), (c) upon exposure to an environment having an ionic strength detectably or significantly greater than that of one or more gelling agents present in the composition (e.g., gellan gum), (d) exposure to an environment having a pH of greater than about 6.2, or (e) any combination of (a)-(e), over the viscosity of the composition while stored prior to administration at a temperature of between about 15° C. to about 25° C.+/−2° C.). In aspects, (a) the ratio of bimatoprost compound, e.g., bimatoprost base, to the viscosity enhancer component is about 1:2 to about 1:1000; (b) the ratio of timolol compound, e.g., a salt of timolol, e.g., timolol maleate, to the viscosity enhancer component is about 10:1 to about 1:10; (c) the ratio of the total amount of API consisting of the bimatoprost compound, e.g., bimatoprost base, and the timolol compound, e.g., salt of timolol, e.g., timolol maleate, to the viscosity enhancer component is about 10:1 to about 1:10; or (d) any combination of (a)-(c) are true. In aspects, compositions comprise any combination of such characteristics described in this paragraph. In aspects, the composition is stable when stored at about 25° C.+/−2° C. and about 40%+/−5% relative humidity; about 40° C.+/−2° C. and not more than about 25% relative humidity; about 15° C.-about 27° C. and about 60% relative humidity; about 38° C.-about 42° C. and 75% relative humidity; or when stored under any such condition, or a sequential combination of such conditions, for at least about 1 month, e.g., at least about 2 months, at least about 3 months, at least about 2-about 6 months, about 3-about 9 months, about 6-about 12 months, about 9-about 18 months, about 12-about 24 months, about 18-about 30 months, about 24-about 36 months, or, e.g., for at least about 36 months.

In aspects, a physiological property of a mammalian eye that is treated/modified or modulated by methods of the invention can be any physiological property participating in, affecting, contributing to, affected by, impaired by, damaged by, or otherwise associated with an ophthalmic condition treatable with the compositions herein, e.g., ocular conditions comprising as an element of its clinical presentation, elevated intraocular pressure, such as, e.g., glaucoma (for example, open-angle glaucoma).

In one specific aspect, the invention provides pharmaceutically acceptable and ophthalmologically suitable compositions comprising bimatoprost compound(s) and timolol compound(s), wherein the compositions are used in methods described herein, e.g., in a method of reducing elevated IOP in adult patients with open-angle glaucoma or ocular hypertension who have demonstrated an insufficient response to topical beta-blockers or prostaglandin analogues when administered alone, or, e.g., in a method of treating glaucoma, e.g., open-angle glaucoma, in adult patients who have demonstrated an insufficient response to topical beta-blockers or prostaglandin analogues when administered alone, wherein the method(s) comprise(s) administering to the patient a composition described herein in an effective amount for an effective administration period, e.g., 1-2 drops once or twice daily for a period of at least 1 day, e.g., at least one week, at least one month, at least one year, at least 2 years, at least 3 years, at least 4 years, or 5 years or longer.

Exemplary Improvement(s)

In aspects, the invention provides a method of detectably or significantly reducing elevated intraocular pressure, the method comprising administering an effective amount, e.g., 1-2 drops of composition provided once or twice daily, the composition being any one or more of the compositions described herein, for an effective treatment period, e.g., about 1 day to about 5 years or longer. In aspects, the degree or extent of intraocular pressure elevation is improved after a treatment period of at least about 24 hours, e.g., ≥~2 days, ≥~3 days, ≥~4 days, ≥~5 days, ≥~6 days, ≥~1 week, ≥~2 weeks, ≥~3 weeks, ≥~1 months, ≥~6 weeks, ≥~2 months, ≥~10 weeks, or ≥~3 months is about 95%, ~90%, ~85%, ~80%, ~75%, ~70%, ~60%, ~55%, ~50%, ~45%, ~40%, ~35%, ~30%, ~25%, ~20%, ~15%, or ~10% (or, in aspects, less) compared to the degree or extent of elevated intraocular pressure at the start of treatment (or, e.g., the degree of intraocular pressure present without treatment).

In aspects, the invention provides a method of detectably or significantly slowing the rate of intraocular pressure increase, the method comprising administering an effective amount, e.g., 1-2 drops of composition provided once or twice daily, the composition being any one or more of the compositions described herein, for an effective treatment period, e.g., about 1 day to about 5 years or longer. In aspects, the rate of intraocular pressure elevation is improved (e.g., rate of intraocular pressure is slowed or reduced) after a treatment period of at least about 24 hours, e.g., ≥~2 days, ≥~3 days, ≥~4 days, ≥~5 days, ≥~6 days, ≥~1 week, ≥~2 weeks, ≥~3 weeks, ≥~1 months, ≥~6 weeks, ≥~2 months, ≥~10 weeks, or ≥~3 months is about 95%, ~90%, ~85%, ~80%, ~75%, ~70%, ~60%, ~55%, ~50%, ~45%, ~40%, ~35%, ~30%, ~25%, ~20%, ~15%, or ~10% (or, in aspects, less) compared to the rate of intraocular pressure increase being experienced at the start of treatment (or, e.g., the rate of intraocular pressure increase present without treatment).

In certain aspects, a single administration of a composition provided by the invention detectably or significantly reduces intraocular pressure for a period of at least about 1 hour, such as, e.g., ≥~2 hours, ≥~4 hours, ≥~6 hours, ≥~8 hours, ≥~10 hours, ≥~12 hours, ≥~14 hours, ≥~16 hours, ≥~18 hours, ≥~20 hours, ≥~22 hours, ≥~24 hours, ≥~26 hours, ≥~28 hours, ≥~30 hours, ≥~32 hours, ≥~34 hours, ≥~36 hours, ≥~38 hours, ≥~40 hours, ≥~42 hours, ≥~44 hours, ≥~46 hours, or ≥~48 hours. In aspects, such improvement is in a significant number of patients, as determined by one or more adequate and well-controlled clinical studies. This principle can be applied to any other clinical/therapeutic improvement/effect described in this disclosure.

In aspects, the invention provides a method of treating glaucoma, e.g., open-angle glaucoma, the method comprising administering an effective amount, e.g., 1-2 drops of composition provided once or twice daily, the composition being any one or more of the compositions described herein, for an effective treatment period, e.g., about 1 day to about 5 years or longer. In aspects, the degree or extent of glaucoma is improved after a treatment period of at least about 24 hours, e.g., ≥~2 days, ≥~3 days, ≥~4 days, ≥~5 days, ≥~6 days, ≥~1 week, ≥~2 weeks, ≥~3 weeks, ≥~1 months, ≥~6 weeks, ≥~2 months, ≥~10 weeks, or ≥~3 months is about 95%, ~90%, ~85%, ~80%, ~75%, ~70%, ~60%, ~55%, ~50%, ~45%, ~40%, ~35%, ~30%, ~25%, ~20%, ~15%, or ~10% (or, in aspects, less) compared to the degree or extent of glaucoma at the start of treatment (or, e.g., the degree of intraocular pressure present without treatment).

In aspects, the invention provides a method of detectably or significantly slowing the progression of glaucoma, the method comprising administering an effective amount, e.g., 1-2 drops of composition provided once or twice daily, the composition being any one or more of the compositions described herein, for an effective treatment period, e.g., about 1 day to about 5 years or longer. In aspects, the rate of glaucoma progression is improved (e.g., rate of glaucoma progression is slowed or reduced) after a treatment period of at least about 24 hours, e.g., ~2 days, ≥~3 days, ≥~4 days, ≥~5 days, ≥~6 days, ≥~1 week, ≥~2 weeks, ≥~3 weeks, ≥~1 months, ≥~6 weeks, ≥~2 months, ≥~10 weeks, or ≥~3 months is about 95%, ~90%, ~85%, ~80%, ~75%, ~70%, ~60%, ~55%, ~50%, ~45%, ~40%, ~35%, ~30%, ~25%, ~20%, ~15%, or ~10% (or, in aspects, less) compared to the rate of glaucoma progression being experienced at the start of treatment (or, e.g., the rate of intraocular pressure increase present without treatment).

In certain aspects, a single administration of a composition provided by the invention detectably or significantly reduces or improves (as applicable) one or more clinical indicators of glaucoma for a period of at least about 1 hour, such as, e.g., ≥~2 hours, ≥~4 hours, ≥~6 hours, ≥~8 hours, ≥~10 hours, ≥~12 hours, ≥~14 hours, ≥~16 hours, ≥~18 hours, ≥~20 hours, ≥~22 hours, ≥~24 hours, ≥~26 hours, ≥~28 hours, ≥~30 hours, ≥~32 hours, ≥~34 hours, ≥~36 hours, ≥~38 hours, ≥~40 hours, ≥~42 hours, ≥~44 hours, ≥~46 hours, or ≥~48 hours. In aspects, such improvement is in a significant number of patients, as determined by one or more adequate and well-controlled clinical studies. This principle can be applied to any other clinical/therapeutic improvement/effect described in this disclosure.

In aspects, the invention provides methods of using the compositions described herein, e.g., within the "Methods of Use" section of this detailed description of the invention, wherein the methods comprise administration of an effective amount of the composition, wherein the effective amount about 1-about 2 drops, such as, e.g., about 1 drop, of the composition administered to a mammalian eye once or twice daily, e.g., for example once daily, over an effective treatment period (e.g., exemplary effective treatment periods disclosed elsewhere herein), and the method is optionally repeated for a number of times demonstrated to provide a significant clinical effect in a significant number of patients in a well-controlled and adequate study or that is shown to be bioequivalent to a product that has been demonstrated to achieve the at least substantially the same, generally the same, or effectively the same clinical effect.

In aspects, the invention provides the methods described herein, wherein the method comprises the administration of a composition comprising both a bimatoprost compound and a timolol compound and the method is capable of detectably or significantly reducing elevated intraocular pressure in a recipient suffering therefrom but who was previously demonstrated as being insufficiently responsive to a topical beta-blocker administered alone, a prostaglandin analogue administered alone, or both.

Comparable or Improved Effects/Reduced Side Effects

In aspects, compositions described herein can be characterized in reference to a reference composition. In aspects, references to comparator compositions relative to a comparison of effect(s) should be interpreted as being demonstrated by one or more well-controlled and adequate clinical studies performed in compliance with generally prevailing regulatory authority standards. Herein, a prevailing regulatory authority standard can be established by, e.g., a recognized regulatory authority such as, e.g., the United States Food and Drug Administration (US FDA).

In aspects compositions herein, methods of using compositions herein, or both, are clinically demonstrated to be as effective or detectably or significantly more effective than treatment of the same or at least essentially the same, generally the same, or the same condition with a composition (e.g., a reference composition) or method comprising use of a composition (e.g., a reference composition), as determined by one or more well-controlled and adequate clinical studies performed in compliance with generally prevailing regulatory authority standards. In aspects, reference to a "reference composition" herein includes any composition demonstrating bioequivalence to that reference composition. In aspects, a reference composition herein includes any composition demonstrating clinical equivalence to that reference composition.

In aspects, compositions described herein, methods of using compositions herein, or both, demonstrate clinical equivalence as measured by any one or more clinical parameters known in the art for the target indication to any reference composition described herein or any composition having demonstrated bioequivalence to any reference composition described herein.

In aspects, compositions described herein, methods of using compositions herein, or both, demonstrate clinical superiority as measured by any one or more clinical parameters known in the art for the target indication to any reference composition described herein or any composition having demonstrated bioequivalence to any reference composition described herein.

In aspects, compositions herein, methods of using compositions herein, or both, demonstrate at least equivalent or, in aspects, detectably or significantly greater biological effect, to one or more reference compositions described herein, or e.g., to any composition or methods of their use having demonstrated bioequivalence to any reference composition described herein, as measured by one or more bioequivalence indicators (such as, e.g., one or more pharmacokinetic data parameters known in the art).

In aspects, compositions described herein, methods of using compositions herein, or both, demonstrate bioequivalence as measured by any one or more pharmacokinetic parameters known in the art for the target indication to any reference composition described herein or to any composition having demonstrated bioequivalence to any reference composition described herein.

In aspects, compositions described herein, methods of using compositions herein, or both, demonstrate bioequivalence as determined by applicable United States Food and Drug Administration (US FDA) standards to any reference composition described herein or to any composition having demonstrated bioequivalence to any reference composition described herein.

In aspects, compositions described herein, methods of using compositions herein, or both, demonstrate superior biological effect as measured by any one or more pharmacokinetic parameters known in the art for the target indication to any reference composition described herein or to any composition having demonstrated bioequivalence to any reference composition described herein.

In aspects, one reference composition is a composition comprising, e.g., consisting of, 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide, and water, a composition approved as European Medicines Agency product number EMEA/H/C/000668 (first granted marketing authorization valid throughout the European Union on May 19, 2006), having the marketed product name "GANFORT®". See, e.g., the website ema.europa.eu/en/medicines/human/EPAR/ganfort #product-information-section. Herein, reference to GANFORT® should be interpreted as the product approved as European Medicines Agency product number EMEA/H/C/000668, having receive such first granted marketing authorization valid throughout the European Union on May 19, 2006; the product described in "Ganfort: EPAR—Product Information", first published on May 3, 2010 and last updated on Sep. 1, 2021 (available via the website cited above); the product marked in Europe as GANFORT® as of the date of this filing, or any combination thereof.

In aspects, one reference composition is a composition comprising, e.g., consisting of, 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water. In aspects, such a composition is identifiable as, e.g., "Bimat LS™ Eye Drops" by Ajanta Pharma. In aspects, such a composition is a composition equivalent to the composition identifiable as "Bimat LS™ Eye Drops" by Ajanta Pharma.

In aspects, the invention provides methods of treatment provided herein, such as, e.g., a method of improving vision in a mammalian eye, a method of modulating one or more physiological properties of a mammalian eye, a method of reducing intraocular pressure, a method of treating glaucoma or one or more symptoms related thereto, or any combination thereof, wherein the method is clinically demonstrated to be as effective or detectably or significantly more effective than treatment of the same or at least essentially the same, generally the same, or the same condition with about the same amount of a composition (e.g., a reference composition) comprising or, e.g., consisting of, 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide, and water for the same or similar indication (e.g., reducing IOP) and for at least substantially the same administration period as determined by one or more well-controlled and adequate clinical studies performed in compliance with generally prevailing regulatory authority standards. In aspects, the invention provides methods of treatment provided herein, such as, e.g., a method of improving vision in a mammalian eye, a method of modulating one or more physiological properties of a mammalian eye, a method of reducing intraocular pressure, a method of treating glaucoma, or any combination thereof, wherein the method is clinically demonstrated to be as effective or detectably or significantly more effective than treatment of the same condition with about the same amount of a reference composition consisting of 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide, and water for the same or similar indication (e.g., reducing IOP) and for at least substantially the same administration period as determined by one or more well-controlled and adequate clinical studies performed in compliance with generally prevailing regulatory authority standards.

In aspects, the invention provides methods of treatment provided herein, such as, e.g., a method of improving vision in a mammalian eye, a method of modulating one or more physiological properties of a mammalian eye, a method of reducing intraocular pressure, a method of treating glaucoma, or any combination thereof, wherein the method is clinically demonstrated to be as effective or detectably or significantly more effective than treatment of the same or at least essentially the same, generally the same, or the same condition with about the same amount of the product approved as European Medicines Agency product number EMEA/H/C/000668 for the same or similar indication (e.g., reducing IOP) and for at least substantially the same administration period.

In aspects, the invention provides methods of treatment provided herein, such as, e.g., a method of improving vision in a mammalian eye, a method of modulating one or more physiological properties of a mammalian eye, a method of reducing intraocular pressure, a method of treating glaucoma, or any combination thereof, wherein the method is clinically demonstrated to be as effective or detectably or significantly more effective than treatment of the same or at least essentially the same, generally the same, or the same condition with about the same amount of a composition, e.g., a reference composition, comprising, or, e.g., consisting of, 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water for the same or similar indication (e.g., reducing TOP) and for at least substantially the same administration period. In aspects, the invention provides methods of treatment provided herein, such as, e.g., a method of improving vision in a mammalian eye, a method of modulating one or more physiological properties of a mammalian eye, a method of reducing intraocular pressure, a method of treating glaucoma, or any combination thereof, wherein the method is clinically demonstrated to be as effective or detectably or significantly more effective than treatment of the same condition with about the same amount of a composition consisting of, 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water for the same or similar indication (e.g., reducing IOP) and for at least substantially the same administration period.

In aspects, the invention provides methods of treatment provided herein, such as, e.g., a method of improving vision in a mammalian eye, a method of modulating one or more physiological properties of a mammalian eye, a method of reducing intraocular pressure, a method of treating glaucoma, or any combination thereof, wherein the method comprises use of a composition described herein, and the method results in a population of treated subjects, on average, maintaining a longer course of therapy than the course of therapy tolerated by a comparable population of treated subjects, on average, treated with (1) the product approved as European Medicines Agency product number EMEA/H/C/000668; (2) a composition comprising, consisting at least generally of, substantially of, essentially of, or consisting of, 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide, and water (3) a composition comprising or, e.g., consisting at least generally of, substantially of, essentially of, or consisting of, 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water; (4) an ophthalmic composition demonstrating essentially the same, generally the same, or the same intraocular pressure reduction capability, (5) ophthalmic compositions comprising a higher amount of benzalkonium chloride, bimatoprost compound, timolol compound, or any combination thereof, or (6) any combination thereof, as determined by one or more well-controlled and adequate clinical studies performed in compliance with generally prevailing regulatory authority standards.

In aspects, the invention provides methods of treatment provided herein, such as, e.g., a method of improving vision in a mammalian eye, a method of modulating one or more physiological properties of a mammalian eye, a method of reducing intraocular pressure, a method of treating glaucoma, or any combination thereof, wherein the method comprises administration of an effective amount of a composition described herein, and wherein an effective amount is, e.g., about 1-about 2 drops of the composition administered once or twice daily over an effective treatment period, and wherein the method results in detectably or significantly reduced frequency of (as experienced by a single user, reported as an average of a population of users, or both), one or more of hyperemia, ocular redness, ocular burning, ocular itching, ocular stinging, conjunctival irritation (irritation of the conjunctiva), sensitivity to light, eye pain, sticky eye(s), dry eye(s), sensation that something is in the recipient's eye(s), detectable or significant breaks in the surface of the eye either with or without associated inflammation, detectable or significant reduction in clear vision, redness and itching of the eyelid(s), hair growth around treated eye(s), darkening of the eyelid(s), darkening of the skin color around the treated eye(s), eyelash lengthening, ocular irritation, eye watering, swollen eyelid(s), reduced vision, runny nose, headache, abnormal sensation(s) in the eye(s), iris inflammation, swollen conjunctiva, painful eyelid(s), tired eye(s), ingrown (in-growing) eyelash(es), darkening iris color, sunken eye appearance, separation of the eyelid from the surface of the eye, eyelash darkening, shortness of breath, conjunctival hyperemia, tear film instability, loss of goblet cells, conjunctival squamous metaplasia and apoptosis, disruption of the corneal epithelium barrier, damage to deep ocular tissue, cystoid macular oedema (retinal swelling leading to worsening vision), eye swelling, blurred vision, ocular discomfort, difficulty breathing/wheezing, symptoms of allergic reaction (swelling, redness of the eye and rash of the skin) or hypersensitivity, changes in taste sensation, dizziness, slowing of heart rate, high blood pressure, difficulty sleeping, nightmare, asthma, hair loss, periocular skin discoloration, and tiredness, or detectably or significantly reduced absorption of BKC by soft contact lenses, compared to treatment of the same or at least essentially the same, generally the same, or the same condition with about the same amount of (1) the product approved as European Medicines Agency product number EMEA/H/C/000668; (2) a composition comprising, consisting at least generally of, substantially of, essentially of, or consisting of, 0.3 mg/mL (0.03% w/v) bimatoprost, 6.8 mg/mL (0.68% w/v) timolol maleate (an amount equivalent to 5 mg/mL or 0.5% w/v timolol), 0.05 mg (0.005% w/v) benzalkonium chloride, sodium chloride, sodium phosphate dibasic heptahydrate, citric acid monohydrate, hydrochloric acid and/or sodium hydroxide, and water; (3) a composition comprising, consisting at least generally of, substantially of, essentially of, or consisting of, 0.1 mg/mL (0.01% w/v) bimatoprost; timolol maleate in an amount equivalent to 5 mg/mL (0.5% w/v) timolol; 0.1 mg/mL (0.01% w/v) benzalkonium chloride; optionally one or more of sodium chloride, sodium phosphate dibasic heptahydrate, citric acid monohydrate, hydrochloric acid and/or sodium hydroxide; and water, or (4) any combination thereof, for at least substantially the same administration period, such as that which may be reported by one or more users or determined by an appropriately controlled clinical trial recognized by a prevailing regulatory authority, such as the United States Food and Drug Administration (US FDA).

Methods of Manufacturing

In one aspect, the invention provides a process for preparing a pharmaceutically acceptable and ophthalmologically suitable composition in the form of a solution. In aspects, the method of manufacture/manufacturing comprises a process for preparing a pharmaceutically acceptable and ophthalmologically suitable composition in the form of a solution comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; and (4) about 0.25% w/v-about 2.5% w/v of a penetration enhancer component. In aspects, the invention provides a process for preparing a pharmaceutically acceptable and ophthalmologically suitable composition in the form of a gel comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt; (4) about 0.25% w/v-about 2.5% w/v of a penetration enhancer component; and (5) about 0.1% w/v-about 1% w/v of a viscosity enhancer component. In aspects, the invention provides a process for preparing a pharmaceutically acceptable and ophthalmologically suitable composition in the form of a gel comprising (1) about 0.005% w/v-about 0.02% w/v of a bimatoprost compound; (2) about 0.4% w/v-about 0.8% w/v of a timolol compound; (3) about 0.003%-about 0.007% of a quaternary ammonium salt and (4) about 0.1% w/v-about 1% w/v of a viscosity enhancer component.

In aspects, such composition(s) and related method(s) of their manufacture is/are characterized by lacking one, two, or more of elements or steps provided here, comprising such elements but in different effective amounts, or, e.g., comprising such recited elements however providing such elements in a different order than described here. In certain aspects, one or more steps provided here may be eliminated.

In aspects, compositions are prepared by using any suitable technique, many of which are known to those skilled in the art, the steps of which can be combined in any order. In describing methods of manufacturing provided by the invention, references to order of operations/steps may be present. It should be understood that steps of described manufacturing process(es) can be performed in any suitable order, provided that the end product is at least substantially, at least generally, or essentially the same.

According to certain aspects, the invention provides a method of manufacturing (e.g., a manufacturing process) for compositions described herein, wherein the process is a non-aseptic process, and wherein the method of manufacturing comprises a terminal sterilization step. In aspects, compositions are terminally sterilized using moist heat. Terminal sterilization can be used to destroy all viable microorganisms within the final, sealed container containing the pharmaceutical composition. In aspects, an autoclave is used to accomplish terminal heat-sterilization of compositions in their final packaging. Typical autoclave cycles in the pharmaceutical industry to achieve terminal sterilization of the final product are about 121° C. for at least about 10 minutes. In aspects, facilities, equipment, procedures, and personnel participating in the method of manufacturing, e.g., participating in the processing, meet GMP rules and guidelines for non-aseptic processes.

According to alternative aspects, the invention provides a method of manufacturing (e.g., a manufacturing process) for compositions described herein, wherein the process is an aseptic process. In aspects, sterility is maintained during the manufacturing process by use of sterile materials and a controlled working environment. In aspects, all containers and apparatus utilized in the process are sterilized, preferably by heat sterilization, prior to use, e.g., prior to filling. In aspects, a sterilized container is filled under aseptic conditions, such as by passing the composition through a filter, e.g., a sterilizing filter. Therefore, in aspects, the compositions can be sterile filled into a container to avoid the heat stress of terminal sterilization. In aspects, facilities, equipment, procedures, and personnel participating in the method of manufacturing, e.g., participating in the processing, meet GMP rules and guidelines for aseptic processing.

In aspects, the invention provides a method of manufacturing a composition described herein, wherein the method comprises (1) preparation of a bulk composition, (2) offline filtration of the bulk composition, (3) online filtration of the bulk composition, and (4) final packaging of the composition. In aspects, composition(s) resulting from the method can be used in any one or more of the methods of treatment described herein.

In aspects, the invention provides a method of manufacturing a composition described herein, wherein the method comprises (1) preparation of a polymer phase, (2) preparation of a drug phase, (3) filtration of the drug phase into the polymer phase, (4) filtering the composition resulting from (3), and (5) final packaging of the composition. In aspects, composition(s) resulting from the method can be used in any one or more of the methods of treatment described herein.

In aspects, the invention provides pharmaceutically acceptable and ophthalmologically suitable compositions comprising bimatoprost compound(s), bimatoprost base, and timolol compound(s), e.g., a salt of timolol, e.g., timolol maleate, and methods of their manufacture, wherein the composition resulting from the method of manufacturing is aseptically distributed into single-dose or multidose containers. Further, in aspects, the invention provides packaging of such single or multidose containers into kits for distribution to an end user.

Specific examples of manufacturing process(es) suitable for manufacturing compositions provided by the invention are found in, e.g., Example 3 and Example 4 of this disclosure.

According to some aspects, the invention provides a first method of manufacturing a composition described herein comprising the following steps.

In aspects, the invention provides a manufacturing process comprising the preparation of a bulk solution.

In aspects, preparation of a bulk solution comprises collecting water, e.g., WFI, in a manufacturing vessel at a temperature of about 65° C. to about 85° C., such as, e.g., about 70° C.-about 80° C., or, e.g., not less than about 70° C. In aspects, the method comprises cooling the water for injection to about 15° C. to about 30° C., such as about 20° C.-about 25° C. In aspects, the method comprises bubbling 0.2 μm filtered nitrogen through the WFI. In aspects, the method comprises bubbling 0.2 μm filtered nitrogen through the WFI until the dissolved oxygen content of the WFI is less than or equal to about 2 ppm, such as, e.g., ≤~1.5 ppm, ≤~1 ppm, or, e.g., ≤~0.5 ppm. In aspects, the manufacturing process comprises continuing to bubble 0.2 μm filtered nitrogen through the WFI during bulk solution manufacturing.

In aspects, preparation of a/the bulk solution comprises transferring an amount, e.g., an amount of about 60-about 80 Kg, of WFI, e.g., about 70 Kg of WFI, into a separate holding vessel. In aspects, this reserved WFI can be used in other manufacturing steps, such as, e.g., the preparation of pH adjusting agents (such as, e.g., 0.1N hydrochloric acid, 0.1N sodium hydroxide, or both), and for, e.g., bringing the final composition up to a final target volume.

In aspects, bulk solution preparation comprises mixing the WFI with a suitable mixing device/stirrer, set at a speed appropriate for attaining sufficient mixing. In aspects, mixing speed can be adjusted according to the vessel geometry and mixing/stirring dynamics exhibited by the solution/composition throughout manufacture.

In aspects, bulk solution preparation comprises adding the required quantity of a preservation agent, e.g., benzalkonium chloride. In aspects, the container comprising the preservation agent, e.g., benzalkonium chloride to be added is rinsed one or more times, e.g., once, twice, three times, four times, or, e.g., five times, with a sufficient amount of WFI sufficient to rinse the container, e.g., an amount such as, e.g., about 30 mL to about 70 mL, or, e.g., about 50 mL each time. In aspects, mixing/stirring is continued during the addition of the rinse solution back into the vessel after each rinse.

In aspects, bulk solution preparation comprises adding the required quantity of solubilizer, penetration enhancer, or compound(s) providing both a solubilization and penetration enhancement effect, e.g., polysorbate 80, tocopherol polyethylene glycol succinate (TPGS), polyoxyl castor oil (e.g., polyethyoxylated castor oil, such as polyoxyl 35 castor oil, or, e.g., protein/peptide penetration enhancer(s) such as poly-arginine or polyserine). In aspects, such ingredient(s) is/are added, and the container(s) used to add the ingredient(s) is/are rinsed one or more times, e.g., once, twice, three times, four times, or, e.g., five times, with an amount of WFI sufficient to rinse the container, e.g., an amount such as, e.g., about 30 mL to about 70 mL, or, e.g., about 50 mL each time. In aspects, mixing/stirring is continued during the addition of the rinse solution back into the vessel after each rinse.

In aspects, the total required quantity of PAC, e.g., a bimatoprost compound, such as bimatoprost base, is added. In aspects, such ingredient(s) is/are added, and the container(s) used to add the ingredient(s) is/are rinsed one or more times, e.g., once, twice, three times, four times, or, e.g., five times, with an amount of WFI sufficient to rinse the container, e.g., an amount such as, e.g., about 20 mL to about 70 mL, or, e.g., about 25 mL or about 50 mL each time. In aspects, mixing/stirring is continued during the addition of the rinse solution back into the vessel after each rinse. In aspects, stirring is continued for at least about 15 minutes, such as at least about 30 minutes, at least about 45 minutes, at least about 60 minutes, or at least about 65 minutes, or for a sufficient time to ensure complete dissolution of the timolol compound and composition uniformity.

In aspects, the total required quantity of BBC, such as, e.g., timolol compound, e.g., a salt of timolol, e.g., timolol maleate, is added. In aspects, such ingredient(s) is/are added, and the container(s) used to add the ingredient(s) is/are rinsed one or more times, e.g., once, twice, three times, four times, or, e.g., five times, with an amount of WFI sufficient to rinse the container, e.g., an amount such as, e.g., about 20 mL to about 70 mL, or, e.g., about 25 mL or about 50 mL each time. In aspects, mixing/stirring is continued during the addition of the rinse solution back into the vessel after each rinse. In aspects, stirring is continued for at least about 15 minutes, such as at least about 30 minutes, at least about 45 minutes, at least about 60 minutes, or at least about 65 minutes, or for a sufficient time to ensure complete dissolution of the timolol compound and composition uniformity.

In aspects, the volume of the composition in the manufacturing vessel is brought up to about 90 L (e.g., about 90 Kg) using previously reserved WFI. In aspects, the resulting solution is stirred for at least about 15 minutes, such as at least about 20 minutes, at least about 25 minutes, at least about 30 minutes, or, e.g., at least about 35 minutes or for a sufficient time to ensure composition uniformity.

In aspects, bulk solution preparation comprises adding the required amount of a first buffer agent(s), such as, e.g., a phosphate buffer, e.g., dibasic sodium phosphate (heptahydrate), citrate buffer (e.g., citric acid monohydrate), borate buffer or, e.g., acetate buffer. In aspects, dibasic sodium phosphate is added. In aspects, mixing/stirring is continued during the addition of the components, and is continued for a sufficient period of time to ensure the buffer constituents are completely dissolved, such as, for example, a period of time of, e.g., about 5 minutes, about 10 minutes, about 15 minutes, about 20 minutes, about 25 minutes, about 30 minutes, etc. In aspects, additional manufacturing step(s) continue once composition uniformity is ensured by visual inspection of the bulk solution for clarity.

In aspects, bulk solution preparation comprises adding a required amount of a second buffer agent(s), such as, e.g., a phosphate buffer, e.g., dibasic sodium phosphate (heptahydrate), citrate buffer (e.g., citric acid monohydrate), borate buffer or, e.g., acetate buffer. In aspects, citric acid monohydrate is added. In aspects, mixing/stirring is continued during the addition of the components, and is continued for a sufficient period of time to ensure the buffer constituents are completely dissolved, such as, for example, a period of time of, e.g., about 5 minutes, about 10 minutes, about 15 minutes, about 20 minutes, about 25 minutes, about 30 minutes, etc. In aspects, additional manufacturing step(s) continue once composition uniformity is ensured by visual inspection of the bulk solution for clarity.

In aspects, bulk solution preparation can continue by adding the required amount of tonicity agent(s), such as, e.g., sodium chloride. In aspects, mixing/stirring is continued during the addition of the components and is continued for a sufficient period of time to ensure the buffer constituents are completely dissolved, such as, for example, a period of time of, e.g., about 5 minutes, about 10 minutes, about 15 minutes, about 20 minutes, about 25 minutes, or at least about 30 minutes or more. In aspects, composition uniformity is ensured by inspecting for visual clarity of the solution.

In aspects, preparation of the bulk solution is pH adjusted using one or more pH adjusting agents. In aspects, pH of the solution is adjusted by the addition or one or more pH adjusting agents, with the solution sufficiently mixed after each addition such that the composition has a uniform pH prior to (1) sampling for pH, and (2) applying further pH adjustment as needed. In aspects, pH is adjusted to a pH of about 6.9-about 7.5, such as, e.g., about 7-about 7.4, e.g., about 7.1 to about 7.3 using the pH adjusting agent(s).

In aspects, preparation of the bulk solution comprises bringing up the volume of the solution to a final volume of, e.g., about 100 L, with WFI reserved as described above. In aspects, the resulting solution is mixed for a sufficient period of time to ensure composition uniformity, such as, e.g., a period of at least about 10 minutes, at least about 15 minutes, at least about 20 minutes, at least about 25, or at least about 30 minutes. In aspects, a final pH check is performed to ensure that the composition pH is about 6.9-about 7.5, such as, e.g., about 7-about 7.4, e.g., about 7.1 to about 7.3.

In aspects, once preparation of a/the bulk solution is complete, offline filtration is performed. In aspects, the filtration is performed under laminar air flow.

In aspects, after completion of the preparation of the bulk solution, the filtration process is initiated under controlled conditions, such as, e.g., under laminar air flow (LAF). In aspects, prior to initiation of the filtration process, a cartridge filter, e.g., a 0.2 μm capsule or cartridge filter, is integrity tested using an industry standard integrity test, such as, e.g., a water bubble point test, against the filter manufacturer's specification. In one aspect, an exemplary acceptable result is a pressure of not less than about 46 psi under a filtration pressure limit of about 0.8 kg/cm$^2$ to about 1.8 kg/cm$^2$.

In aspects, prior to the start of filtration activity, the filtration unit is flushed with a sufficient amount of bulk solution to flush the unit, such as, e.g., about 200-250 mL, e.g., about 180 mL, about 200 mL, about 210 mL, about 220 mL, or e.g., about 230 mL of the bulk solution. In aspects, the bulk solution can be held inside of the filtration unit for a period of time during the flush, such as about 1.5 minutes, about 2 minutes, about 2.5 minutes, or about 3 minutes during the flush. In aspects, the bulk solution used for the flush is discarded after the flush. In aspects, the flushing procedure is repeated a number of times, such as one more time, two more times, three more times, four more times, or five or more times. In aspects, flushing is conducted a total of about 3 times.

In aspects, upon completion of flushing, filtration of a/the bulk solution is initiated. In aspects, the bulk solution is filtered through the pre-sterilized, tested, and flushed 0.2 μm capsule or cartridge filter, e.g., a polyethersulfone (PES) capsule filter. In aspects, all filtrate is collected in a sterile receiving vessel.

In aspects, upon completion of filtration, the filtrate within the sterile receiving vessel is overlayed with nitrogen, such as, e.g., 0.2 µm-filtered nitrogen.

In aspects, the receiving vessel can be transferred to a storage area, e.g., a sterile storage area, and stored under controlled conditions, e.g., controlled temperature and air flow conditions (e.g., under laminar air flow) until initiation of the filling activity.

In aspects, a post-filtration integrity test of the filter can be performed. In aspects, the post-filtration integrity test of the filter can be a water bubble point test. In aspects, an acceptable result is a pressure of not less than 39.2 psi under a filtration pressure limit of about 0.8 kg/cm$^2$ to about 1.8 kg/cm$^2$.

In certain aspects, completion of a/the first filtration process is followed by a second filtration, wherein, prior to the initiation of filling and capping activity, the bulk solution is filtered through another filter, e.g., another 0.2p pre-sterilized capsule or cartridge filter, e.g., a polyethersulfone (PES) capsule filter.

In aspects, pre-integrity filter testing is performed using an industry-accepted standard integrity test, such as, e.g., a water bubble point test, against the filter manufacturer's specification. In aspects, an acceptable result is a pressure of not less than about 46 psi under a filtration pressure limit of about 0.8 kg/cm$^2$ to about 1.8 kg/cm$^2$. Upon passing the integrity test, in aspects the filter is then connected to the filling line through a pre-sterilized vessel, e.g., buffer tank.

In aspects, prior to the initiation of filtration activity, the filter/filtration unit is flushed with a sufficient volume of water to flush the filter, such as, e.g., about 200-about 250 mL of bulk solution, such as, e.g., about 180 mL, about 190 mL, about 200 mL, about 210 mL, about 220 mL, or, e.g., about 230 mL of the bulk solution. In aspects, the bulk solution is held within the filtration unit for a period of time during flushing, such as about 1.5 minutes, about 2 minutes, about 2.5 minutes, or, e.g., about 3 minutes, during this flushing process. In aspects, the flush and is then discarded. In aspects, the flushing process is repeated a number of times, such as at least one more time, at least two more times, at least 3 more times, at least four more times, or, e.g., at least five more times. In aspects, the flushing process is performed at least two additional times for a total of at least about 3 flushes, with the bulk solution used for flushing discarded after each flush.

In aspects, after discarding the filter flush solution, the entire quantity of remaining bulk solution is filtered into the sterile vessel, e.g., the sterile buffer tank.

In aspects, upon completing the filtration, the filling activity is then initiated. In aspects, upon the completion of the filling activity, a post-filtration integrity test of the filter is performed using an industry standard integrity test, such as, e.g., a water bubble point test. In aspects, an acceptable result is a pressure of not less than about 39.2 psi under a filtration pressure limit of about 0.8 kg/cm$^2$ to about 1.8 kg/cm$^2$.

In aspects, the final step of a method of manufacturing composition(s) described herein is the process of filling and capping the composition(s).

In aspects, suitable sterile containers, such as, e.g., sterile vials, bottles such as, e.g., dropper bottles, are each filled to a target fill volume. In aspects, single-dose bottles can be used. In aspects, multi-dose bottles can be used. In aspects, suitable containers are Abak® or Comod® bottles, or, e.g., similar or equivalent packaging, e.g., other bottles allowing compositions contained therein to be provided as drops administered over several days. In aspects, a suitable single-dose or multi-dose container is made of EP-quality LDPE. In aspects, a suitable single-dose or multi-dose container contains no additives. In aspects, an exemplary filling volume is, e.g., a volume of between about 1 mL and about 10 mL, such as a volume of between about 1 mL and about 5 mL, or, e.g., a volume of between about 1 mL and about 3 mL, such as a volume of about 2 mL to about 3 mL, e.g., a target volume of about 2.6 mL to about 2.8 mL (about 2.62 g to about 2.82 g), such as about 2.7 mL (about 2.72 g).

In aspects, after filling, the head space of each container is flushed with nitrogen, e.g., filtered nitrogen. In aspects, a minimum nitrogen flow is established, such as, e.g., a minimum nitrogen flow of about 1.5 L/min, about 2 L/min, about 2.5 L/min, or, e.g., about 3 L/min. In aspects, this step comprises placing associated container (e.g., vial, bottle, etc.), such as the nozzle of the bottle, and capping the bottle.

In aspects, a first set of vials filled, e.g., the first about 20, about 25, about 30, about 35, or, e.g., about 40 vials filled are collected and identified as the initial system flush.

In aspects, checks for proper processing, e.g., proper filling volume and vial sealing, are performed intermittently (e.g., at least 2 times, at least 5 times, at least 10 times, at least 20 times, at least 50 times or more) during any single batch filling procedure. In aspects, the filling process is stopped, adjusted, or otherwise corrected if filling processes do not meet previously defined standards (e.g., of fill volume, air-tight sealing of vials, etc.). Packaged product identified as not meeting predefined acceptance criteria are rejected.

According to some aspects, the invention provides a second method of manufacturing a composition described herein comprising the following steps.

In aspects, a first ("filter number 1") and a second ("filter number 2") filter, e.g., 0.2 µm capsule filter, are each integrity-tested using an industry standard filter integrity test, e.g., a water bubble point test, against the filter manufacturer's specification(s). In aspects, an acceptable result of each test is a pressure of not less than about 46.0 psi under a filtration pressure limit of about 0.8 kg/cm$^2$ to about 1.8 kg/cm$^2$. In aspects, upon completion of integrity testing, filters are flushed with a sufficient amount of nitrogen to remove any residual water from the filter pores.

In aspects, upon passing the integrity test, the outlet of filter number 2 is connected to the inlet of filter number 1 using a suitable connection mechanism, such as tubing, e.g., Pharma 50 silicone tubing, of a suitable length. Such length can be any suitable length for the manufacturing configuration, such as, e.g., a length of about 40 cm, about 50 cm, about 60 cm, about 70 cm, or about 80 cm. In aspects, the outlet of filter number 1 is connected to a valve, e.g., a diaphragm valve. In aspects, the inlet of filter number 2 is connected to a suitable connection mechanism, such as, e.g., tubing, for example Pharma 50 silicone tubing, of suitable length for the manufacturing configuration, such as, for example, a length of about 1.5 meters, 2 meters, 2.5 meters, 3 meters, or, e.g., about 3.5 meters, e.g., in aspects, about 2.30 meters. In aspects, the entire assembly is sterilized using a suitable sterilization method, e.g., autoclaving. During sterilization, e.g., while autoclaving, in aspects, the diaphragm valve is maintained in an open position. In aspects, upon completion of sterilization, e.g., after autoclaving, the diaphragm valve is closed under aseptic conditions. In aspects, the entire assembly is then connected to an empty manufacturing vessel (e.g., a "reactor vessel").

In aspects, the manufacturing vessel/reactor vessel is sterilized with a sufficient amount of water, e.g., water for injection (WFI), such as, e.g., about 100 Kg, about 110 Kg, about 120 Kg, about 130 Kg, about 140 Kg, or, e.g., about 150 Kg of WFI. In aspects, this establishes a sterilized "reactor vessel" or "SIP vessel".

In aspects, a sufficient amount of WFI, e.g., about 120 Kg of WFI, at a temperature of not less than about 70° C., e.g., a temperature of about 70° C.-about 80° C., is collected in a manufacturing vessel, such as, e.g., a stainless-steel (SS) manufacturing vessel.

In aspects, the WFI is cooled, for example to a temperature of about 20° C.-about 25° C., such as, e.g., by circulating the water through a water jacket. In aspect, while cooling, e.g., simultaneously with cooling, nitrogen, e.g., 0.2µ-filtered nitrogen, is passed (e.g., bubbled) through the WFI, with all WFI collected in the manufacturing vessel.

In aspects, the dissolved oxygen content of the WFI is tested one or more times, e.g., the WFI is routinely tested, to ensure that the WFI reaches a dissolved oxygen content of no more than about 2 ppm, e.g., no more than about 1.5 ppm, no more than about 1 ppm, or, e.g., no more than about 0.5 ppm.

In aspects, nitrogen bubbling is continued throughout the manufacturing process of one or more solutions of the method.

After completion of empty reactor sterilization, about 50 Kg, e.g., about 50 Kg to about 70 Kg, of the about 120 Kg of WFI is transferred to a second manufacturing vessel, e.g., a stainless-steel manufacturing vessel. In aspects, this reserved WFI is used for one or more steps of the method, such as, e.g., used in the preparation of a drug phase, bringing composition(s) up to volume, or both, as is described further below.

In aspects, the establishment of a polymer phase is a first step(s) of the method of manufacturing.

In aspects, while maintaining the temperature of the remaining about 70 Kg (e.g., about 50 to about 70 Kg) of WFI in the reactor vessel at about 70° C. to about 80° C., such as about 73° C. to about 78° C., a suitable stirrer (mixer) is established in the reactor vessel. In aspects, the suitable stirrer can be any stirrer suitable for the manufacturing configuration. In aspects, the stirrer/mixer is set to a stirrer speed of about 50 rpm to about 200 rpm, such as, e.g., about 75 rpm to about 175 rpm, or, e.g., about 100-about 150 rpm. In aspects, the mixing speed can be adjusted as necessary based on/according to the equipment being used in the manufacturing process, the batch volume, etc., e.g., according to the vessel geometry and the stirring dynamics during manufacture of the batch.

In aspects, the required quantity of a viscosity enhancer component, e.g., a gelling agent, e.g., gellan gum NF (national formulary), is added to the reactor vessel. In aspects, stirring is maintained at a sufficient speed, e.g., about 125 rpm± about 50 rpm, for a sufficient time, e.g., for at least about 30 minutes, such as about 60 mins, or for a sufficient time to ensure complete dissolution of the gellan gum. In aspects, the solution is maintained at a temperature of between about 70° C. and about 80° C., such as, e.g., 73° C. and about 78° C., during continuous stirring.

In aspects, the total required quantity of a preservative component, e.g., benzalkonium chloride, is added. In aspects, the resulting composition is mixed for a sufficient period of time to ensure that the preservative component constituent(s) are completely dissolved.

In aspects, after complete dissolution of all previously added ingredients, the solution is cooled to a temperature of between about 20° C. and about 25° C. In aspects, cooling is conducted under constant stirring. In aspects, this establishes the "polymer phase."

In aspects, the polymer phase is sterilized at set temperature, such as, e.g., a temperature of about 122.0° C., or a period of time, e.g., for at least about 20 minutes. In aspects, constant stirring continues during this period, e.g., at a suitable speed, such as a speed of about 125 rpm± about 50 rpm.

In aspects, upon completion of sterilization, the polymer phase is cooled, such as, e.g., to a temperature of about 20° C. to about 30° C., e.g., 25° C. In aspects, while cooling, when the temperature of the polymer phase reaches a set temperature, such as, e.g., a temperature of about 50° C. to about 70° C., such as, e.g., about 60° C., the stirring speed is increased to a suitable increased mixing speed, e.g., a stirring speed of about 250 rpm±50 rpm.

In aspects, the method of manufacturing continues with a second step(s) of preparing a drug phase solution.

In aspects, an amount of reserved WFI, e.g., about 50 kg of the reserved, cooled WFI, is collected in a suitable manufacturing vessel. In aspects, a suitable stirrer/mixer is established in the manufacturing vessel. In aspects, the mixer is set to a suitable stirring speed for the manufacturing configuration being used, e.g., a stirring speed of, e.g., about 200 rpm to about 400 rpm, such as, e.g., about 250 rpm to about 350 rpm. In aspects, the mixing speed can be adjusted as necessary based on/according to the equipment being used in the manufacturing process, the batch size being manufactured, or both, e.g., according to the vessel geometry and the stirring dynamics during the manufacture of the batch.

In aspects, the total quantity of solubilizing component, penetration enhancer component, or compound(s) providing both solubilization and penetration enhancement effect, e.g., polysorbate 80, tocopherol polyethylene glycol succinate (TPGS), polyoxyl castor oil (e.g., polyethoxylated castor oil, such as polyoxyl 35 castor oil), or, e.g., protein/peptide enhancers (e.g., poly-arginine or polyserine) is optionally added to the manufacturing vessel. In aspects, in certain formulations, such one or more ingredients is absent from the composition (e.g., is/are not added). The container(s) used to add each ingredient is/are rinsed multiple times, e.g., about 5 times, with approximately 50 mL of WFI each time. The rinses are added to the manufacturing vessel under stirring. Stirring is continuous from the beginning of the process to the end of the process, unless otherwise indicated.

In aspects, the total required quantity of PAC, e.g., bimatoprost compound(s), e.g., bimatoprost base, is added to the manufacturing vessel. The container(s) used to add the PAC constituent(s) is/are rinsed multiple times, e.g., about 2, about 3, about 4, or, e.g., about 5 times, with approximately 25 mL of WFI each time. The rinses are added to the manufacturing vessel. Stirring is continued for at least about 15 minutes, such as at least about 30 minutes, at least about 45 minutes, at least about 60 minutes, or at least about 65 minutes, or for a sufficient time to ensure complete dissolution of the PAC constituent(s) and composition uniformity.

In aspects, the total required quantity of BBC, e.g., timolol compound(s), e.g., salt(s) of timolol, e.g., timolol maleate, is added to the manufacturing vessel. The container(s) used to add the BBC constituent(s) is/are rinsed multiple times, e.g., about 2, about 3, about 4, or, e.g., about 5 times, with approximately 25 mL of WFI each time. The rinses are added to the manufacturing vessel. Stirring is continued for at least about 15 minutes, such as at least about 30 minutes, at least about 45 minutes, at least about 60 minutes, or at least about 65 minutes, or for a sufficient time to ensure complete dissolution of the BBC constituent(s) and composition uniformity.

In aspects, upon the complete dissolution of all previously added ingredients, the total required quantity of a tonicity component, e.g., mannitol, is added to the solution. In aspects, the resulting composition is mixed for a suitable period of time to allow the tonicity component, e.g., mannitol, to completely dissolve.

Upon the complete dissolution of the mannitol, the total required quantity of a second solubilizer (if, e.g., a prior solubilizer was optionally added), e.g., a solubilizer which in aspects may also be characterizable as a penetration enhancer, e.g., tromethamine, is added to the solution. In aspects, the resulting composition is mixed for a sufficient period of time to ensure complete dissolution of the component, e.g., tromethamine. In aspects, such a period of time can be, e.g., at least about 5 minutes, at least about 10 minutes, at least about 15 minutes, or, e.g., at least about 20 min.

In aspects, the composition is then checked for clarity. In aspects, clarity is evaluated using visual inspection. In aspects, stirring/mixing is continued until visual clarity of the solution is achieved.

In aspects, the volume of the composition is then brought to between about 50 L and about 60 L, e.g., to about 55 L (if, e.g., an exemplary batch size of about 100 L is being manufactured; it should be understood that this and other steps of the methods of manufacturing described here can be adjusted as needed for the batch size being manufactured) using, e.g., previously reserved WFI. In aspects, the composition is then stirred for a sufficient period of time to ensure composition uniformity, such as for at least about 5 minutes, at least about 10 minutes, at least about 15 minutes, at least about 20 minutes, at least about 25 minutes, or, e.g., at least about 30 minutes. In aspects, this establishes the "drug phase".

In aspects, an industry standard sampling protocol is used to sample and test the drug phase to ensure that the phase meets pre-established specification(s). Upon acceptance, in aspects, the drug phase is transferred to the sterilized polymer phase via aseptic filtration (see below).

In aspects, the method of manufacture/manufacturing comprises or next comprises a step of aseptic filtration. As has been previously stated, references to order of operation, e.g., "next" as used here, should not be interpreted as limiting. In aspects, manufacturing steps/processes described can be performed in any suitable order provided the resulting composition comprises the characteristic(s) described herein.

In aspects, aseptic filtration of the drug phase into the sterile polymer phase is performed at a filtration pressure of, e.g., about 0.8 Kg/cm$^2$-about 1.8 Kg/cm$^2$ In aspects, prior to beginning the aseptic filtration, the weight of the drug phase is noted. In aspects, an amount of drug phase, e.g., about 50 Kg to ~60 Kg, e.g., about 55 Kg of the drug phase (which can be referred to as the "concentrated drug phase"), is filtered into the reactor vessel containing the polymer phase through 2 sterilized 0.2 μm filters connected in series.

In aspects, WFI is passed through the filters a number of times, such as about two times or about three times with, e.g., between about 2 L and about 3 L of WFI used each time, such as, e.g., about 2.5 L of WFI each time. In aspects, the filtrate added to the reactor vessel each time to ensure all required drug phase is added into the reactor vessel. In aspects, the resulting composition is then stirred for a sufficient period of time and at a suitable speed to ensure composition uniformity. In aspects for example, the composition is mixed for at least about 45 minutes, at least about 50 minutes, at least about 55 minutes, at least about 60 minutes, at least about 65 minutes, at least about 75 minutes, at least about 80 minutes, or, e.g., at least about 85 minutes, such as, e.g., about 1 hour, at a suitable speed, such as, e.g., a speed of about 150 rpm-about 350 rpm, or, e.g., a speed of about 200 rpm to about 300 rpm, to ensure composition uniformity.

In aspects, a post-filtration integrity test of the filter is performed using an industry standard filter integrity test, e.g., a water bubble point test. In aspects, an acceptable result is a pressure of not less than about 34.8 psi under a filtration pressure limit of about 0.8 kg/cm$^2$ to about 1.8 kg/cm$^2$.

In aspects, the composition is pH adjusted using one or more pH adjusting agents. In aspects, pH of the solution is adjusted by the addition or one or more pH adjusting agents, with the solution sufficiently mixed after each addition such that the composition has a uniform pH prior to (1) sampling for pH, and (2) applying further pH adjustment as needed. In aspects, pH is adjusted to a pH of 6-about 7.5, such as, e.g., about 6.1-about 7.2, e.g., about 6.2 to about 7 using the pH adjusting agent(s).

In aspects, the method of manufacturing further comprises a final combined composition (bulk solution) filtration step.

In aspects, filtration of the final combined composition (bulk solution) is then performed using a suitable filter, e.g., such as an 8 μm filter, such as, e.g., an 8 μm PP2 MidiCap® filter (Sartorius).

In aspects, prior to initiating filtration activity, a sterilized filter, e.g., a sterilized 8.0 μm filter, e.g. a sterilized 8 μm polypropylene filter, is flushed with a sufficient amount of bulk solution, such as, e.g., about 80 mL to about 140 mL of bulk solution, e.g., about 100 mL to about 120 mL of bulk solution, a number of times such as about 2 times, about 3 times, about 4 times, or, e.g., about 5 times. In aspects, during each flush, the composition is held in the filtration unit for an extended period of time, such as about 1 minute, about 2 minutes, about 3 minutes, about 4 minutes, or, e.g., about 5 minutes, prior to discarding each flush. In aspects, upon completion of the flushing process, filtration of the bulk solution is performed. In aspects, the filtrate collected in a sterile receiving vessel.

In aspects, a final step of the method is filling and capping step(s).

In aspects, suitable sterile containers, such as, e.g., sterile vials, bottles such as, e.g., dropper bottles, are each filled to a target fill volume. In aspects, single-dose bottles can be used. In aspects, multi-dose bottles can be used. In aspects, suitable containers are Abak® or Comod® bottles, or, e.g., other bottles allowing compositions contained therein to be provided as drops administered over several days. In aspects, a suitable single-dose or multi-dose container is made of EP-quality LDPE. In aspects, a suitable single-dose or multi-dose container contains no additives. In aspects, an exemplary filling volume is, e.g., a volume of between about 1 mL and about 10 mL, such as a volume of between about 1 mL and about 5 mL, or, e.g., a volume of between about 1 mL and about 3 mL, such as a volume of about 2 mL to about 3 mL, e.g., a target volume of about 2.6 mL to about 2.8 mL (about 2.62 g to about 2.82 g), such as about 2.7 mL (about 2.72 g).

In aspects, after filling, the head space of each container is flushed with nitrogen, e.g., filtered nitrogen. In aspects, a minimum nitrogen flow is established, such as, e.g., a minimum nitrogen flow of about 1.5 L/min, about 2 L/min, about 2.5 L/min, or, e.g., about 3 L/min. In aspects, this step comprises placing associated container (e.g., vial, bottle, etc.), such as the nozzle of the bottle, and capping the bottle.

In aspects, a first set of vials filled, e.g., the first about 20, about 25, about 30, about 35, or, e.g., about 40 vials filled are collected and identified as the initial system flush.

In aspects, checks for proper processing, e.g., proper filling volume and vial sealing, are performed intermittently (e.g., at least 2 times, at least 5 times, at least 10 times, at least 20 times, at least 50 times or more) during any single batch filling procedure. In aspects, the filling process is stopped, adjusted, or otherwise corrected if filling processes do not meet previously defined standards (e.g., of fill volume, air-tight sealing of vials, etc.). Packaged product identified as not meeting predefined acceptance criteria are rejected.

Product-by-Process Aspects

In aspects, the invention provides compositions comprising (1) a PAC, e.g., bimatoprost, e.g., bimatoprost base in an amount of, for example, about 0.005% w/v-about 0.02% w/v or other amount(s) disclosed herein; (2) a BBC, e.g., a timolol compound, e.g., a salt of timolol, e.g., timolol maleate, in an amount of, for example, about 0.4% w/v-about 0.8% w/v or other amount(s) disclosed herein; (3) a quaternary ammonium salt, e.g., benzalkonium chloride, in an amount of, for example, about 0.003% w/v-about 0.005% w/v or other amount(s) disclosed herein; (4) a penetration enhancer component, e.g., polysorbate 80, TPGS, cremophor EL, or one or more other penetration enhancer component constituents disclosed herein in an amount of, for example, about 0.25% w/v-about 2.5% w/v; (5) a tonicity agent, e.g., sodium chloride, in an amount of, for example, about 0.05% w/v-about 1.5% w/v or other amount(s) disclosed herein; (6) a buffer component comprising one or more buffer constituents, such as, e.g., a phosphate buffer, a citrate buffer, or both, in an amount of, for example, about 0.015% w/v-about 0.6% w/v or other amount(s) disclosed herein, and (7) a sufficient amount of pH adjusting agent(s) to establish the pH of the composition at about 6-about 8, such as, e.g., about 6.9-about 7.5, e.g., about 7.1-about 7.3, and water, the composition made by a process comprising (1) preparing a bulk composition, (2) offline filtering the bulk composition, (3) online filtering the bulk composition, and (4) packaging of the final composition, wherein the process is either an aseptic process or a non-aseptic process. In aspects, such compositions can be manufactured by a process comprising any one or more manufacturing steps described in the "Methods of Manufacturing" section herein. In aspects, compositions can lack one or more of the constituents described above (e.g., in this paragraph). In aspects, a composition resulting from such process(es) maintains its established pH within acceptable limits (e.g., about 6 to about 8, e.g., about 6.2-about 7 or about 6.9-about 7.5, according to its established pH during its manufacture). In aspects, a composition resulting from such process(es) retains at least about 95%, such as, e.g., at least about 97%, about 98%, or, e.g., at least about 99% of the original PAC, BBC, or both when stored at about 25° C.+/−2° C. and about 40%+/−5% relative humidity; about 40° C.+/−2° C. and not more than about 25% relative humidity; about 15° C.-about 27° C. and about 60% relative humidity; about 38° C.-about 42° C. and 75% relative humidity; or when stored under any such condition, or a sequential combination of such conditions. In aspects, a composition resulting from such process(es) comprises less than about 2.5% total impurities, e.g., less than about 2%, less than about 1.5%, less than about 1%, or, e.g., less than about 0.5% total impurities after storage at about 25° C.+/−2° C. and about 40%+/−5% relative humidity; about 40° C.+/−2° C. and not more than about 25% relative humidity; about 15° C.-about 27° C. and about 60% relative humidity; about 38° C.-about 42° C. and 75% relative humidity; or when stored under any such condition, or a sequential combination of such conditions. In aspects, a composition resulting from such process(es) comprises or maintains any one or more such feature(s) described in this paragraph for a period of at least about 1 month, such as, e.g., ≥~3 months, ≥~6 months, ≥~9 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months.

In aspects, the invention provides compositions comprising (1) a PAC, e.g., bimatoprost, e.g., bimatoprost base in an amount of, for example, about 0.005% w/v-about 0.02% w/v or other amount(s) disclosed herein; (2) a BBC, e.g., a timolol compound, e.g., a salt of timolol, e.g., timolol maleate, in an amount of, for example, about 0.4% w/v-about 0.8% w/v or other amount(s) disclosed herein; (3) a quaternary ammonium salt, e.g., benzalkonium chloride, in an amount of, for example, about 0.003% w/v-about 0.005% w/v or other amount(s) disclosed herein; (4) optionally a penetration enhancer component, e.g., polysorbate 80, TPGS, cremophor EL, or one or more other penetration enhancer component constituents disclosed herein in an amount of, for example, about 0.25% w/v-about 2.5% w/v; (5) a solubilizing component, e.g., tromethamine, in an amount of, for example, about 0.05% w/v-about 1% w/v or other amount(s) disclosed herein; (6) a viscosity enhancer component, e.g., gellan gum, in an amount of, for example, about 0.1% w/v-about 1% w/v or other amount(s) disclosed herein; (7) a tonicity agent, e.g., mannitol, in an amount of, for example, about 2% w/v-about 6% w/v or other amount(s) disclosed herein; (8) a buffer component comprising one or more buffer constituents, such as, e.g., a phosphate buffer, a citrate buffer, or both, in an amount of, for example, about 0.015% w/v-about 0.6% w/v or other amount(s) disclosed herein, and (9) a sufficient amount of pH adjusting agent(s) to establish the pH of the composition at about 6-about 8, more specifically between about 6.1-about 7.5, or, e.g., about 6.2-about 7, and water, the composition made by a process comprising (1) preparing a polymer phase, (2) preparing a drug phase, (3) filtering the drug phase into the polymer phase, (4) filtering the composition resulting from (3), and (5) packaging the final composition, wherein the process is either an aseptic process or a non-aseptic process. In aspects, such compositions can lack one or more of the constituents described above. In aspects, the composition, e.g., the composition of this paragraph, maintains its established pH within acceptable limits (e.g., about 6.2-about 7, according to its established pH during its manufacture); retains at least about 95%, such as, e.g., at least about 97%, about 98%, or, e.g., at least about 99% of the original PAC, BBC, or both when stored at about 25° C.+/−2° C. and about 40%+/−5% relative humidity; about 40° C.+/−2° C. and not more than about 25% relative humidity; about 15° C.-about 27° C. and about 60% relative humidity; about 38° C.-about 42° C. and 75% relative humidity; or when stored under any such condition, or a sequential combination of such conditions; comprises less than about 2.5% total impurities, e.g., less than about 2%, less than about 1.5%, less than about 1%, or, e.g., less than about 0.5% total impurities after storage at about 25° C.+/−2° C. and about 40%+/−5% relative humidity; about 40° C.+/−2° C. and not more than about 25% relative humidity; about 15° C.-about 27° C. and about 60% relative humidity; about 38° C.-about 42° C. and 75% relative humidity; or when stored under any such condition, or a sequential combination of such conditions; or any combination of or all of such characteristic(s) for a period of at least about 1 month, such as, e.g., ≥~3 months, ≥~6 months, ≥~9 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months.

In one aspect, the invention provides a pharmaceutically acceptable and ophthalmologically suitable composition comprising bimatoprost in an amount of about 0.005% to about 0.02% by weight and timolol in an amount of about 0.25% to about 0.5% by weight, benzalkonium chloride in an amount of about 0.003% to about 0.007% by weight, and/or a penetration enhancer other than benzalkonium chloride, wherein the compositions are capable of reducing intraocular pressure in a mammalian eye suffering from increased intraocular pressure and are further capable of maintaining the stability of drug when stored up to at least 3 months at 40° C. and 75% relative humidity, at 25° C. and 60% relative humidity, or under either condition, or a sequential combination of such conditions, made by a process comprising one or more heat sterilization steps, gas sterilization steps, filtration sterilization steps, radiation sterilization steps, or any combination thereof.

Packaging/Delivered Form and Kits

In aspects, compositions provided by the invention can be provided with, e.g., contained within, a delivery device suitable for administering the composition. In aspects, such a delivery device can be any suitable delivery device capable of maintaining the compositions therein in sterile form prior to administration. In aspects, such a delivery device can be capable of preventing detectable or significant degradation of the compositions during shipping or storage. In aspects, compositions can be provided with, e.g., contained within, dropper bottle(s), squeeze bottle(s), vials, and the like which are commonly known in the art.

According to certain embodiments, pharmaceutically acceptable and ophthalmologically suitable compositions provided by the invention can be packaged in any suitable packaging, such suitability being at least in part defined by protecting the compositions held therein from degradation, contamination, or both. In certain aspects, suitable packaging materials are materials which exhibit less than about 20%, such as <~18%, <~16%, <~14%, <~12%, <~10%, <~8%, <~6%, <~4%, <~2% or even less sorption of a PAC constituent, such as, e.g., a bimatoprost compound, or more specifically bimatoprost base, a BBC constituent, such as, e.g., a timolol compound, or more specifically timolol maleate, or both. In some respects, suitable materials include but may not be limited to packaging material made of select polyolefins, such as, e.g., DuPont® 20 LDPE, Chevron 5502 HDPE, Atofina 3020 PP, polypropylene homopolymers, low ethylene content (<8%) polypropylenes, and polymers (HDPE, PP) with low content of additives (<5%) and with low flexural modulus (<200 kpsi). In some respects, a suitable material is an EP-quality LDPE which, in further aspects, may contain no additives. In aspects, suitable packaging can comprise a polypropylene container provided that that polypropylene container is not packaged in a bag/container containing an iron oxide oxygen scavenger. In aspects, suitable packaging can be, e.g., single-dose or multi-dose bottles such as, e.g., those identifiable in the art as Abak© or Comod© packaging, or, e.g., equivalent such bottles allowing the compositions to be applied in the form of eye drops. In aspects, suitable packaging can allow the compositions to be applied in the form of eye drops over the course of several days, e.g., 2+ days or more, such as, e.g., more than 7 days, ore more than 14 days or more, e.g., more than 21 days or more than about 30 days. In aspects, suitable packaging provides for compositions to be applied in the form of eye drops over the course of several days without the presence of one or more preservatives. In aspects, suitable packaging allows for compositions to remain stable, e.g., maintaining one or more characteristics of stability described elsewhere herein, when stored at controlled room temperature (15° C. to 25° C.+/−2° C.), when stored at about 25° C.+/−2° C. and about 40%+/−5% relative humidity; about 40° C.+/−2° C. and not more than about 25% relative humidity; about 15° C.-about 27° C. and about 60% relative humidity; about 38° C.-about 42° C. and 75% relative humidity; or when stored under any such condition, or a sequential combination of such conditions, for a period of at least about 1 month, such as, e.g., at least about 1, ~2, ~4, ~6, ~8, ~10, ~12, ~14, ~16, ~18, ~20, ~22, ~24, ~26, ~28, ~30, ~32, ~34, or, e.g., ~36 months or longer.

In certain aspects, the packaging can comprise or can be mostly comprised of (e.g., comprise in an amount ≥~10%, ≥~20%, ≥~30%, ≥~40%, or ≥~50%, such as, e.g., comprise in an amount ≥~60%, ≥~70%, ≥~80%, ≥~90% or more) an ultraviolet-light blocking agent or material, e.g., a material comprising ultraviolet-light blocking agent(s). In aspects, such a material can be capable of blocking ≥~1%, ≥~5%, ≥~10%, ≥~20%, ≥~30%, ≥~40%, or ≥~50%, such as, e.g., ≥~60%, ≥~70%, ≥~80%, ≥~90% or more of the ultraviolet light in the environment from entering the container. In aspects, compositions described herein can be packaged in, stored, in, or both packaged and stored in a container wherein the container significantly reduces exposure of the composition to UV B radiation, such as by at least about 50%, at least about 65%, at least about 75%, at least about 90%, at least about 95%, or at least 99%. In some aspects, the packaging material of a composition described herein is semi- or completely opaque, while in alternative aspects, the packaging is semi- or completely clear. In aspects, packaging can comprise different parts wherein one component of the packaging comprises a first material and one or more components of the packaging contain a second (or more) material(s).

In certain aspects, packaging can be selected based on the method of delivery of the compositions herein (e.g., compositions provided as a gel can be provided in suitable packaging for gels wherein compositions provided as a liquid can be provided in suitable packaging for liquids, e.g., in a user-friendly dropper bottle; in aspects, a composition in gel form can also or alternatively be provided in a dropper bottle for drop-by-drop administration.) In aspects, the compositions of the invention are stored in a packaging that facilitates the delivery of the composition as eye drops.

In one aspect, ophthalmic compositions provided by the invention comprise a bimatoprost compound, e.g., bimatoprost base, a timolol compound, e.g., timolol maleate, and one or more pharmaceutically acceptable excipient(s), and are provided in single-dose bottles. In an alternative aspect, such compositions are provided in multi-dose bottles, such as multi-dose eye dropper bottles. In aspects, such multi-dose bottles allow for the composition, e.g., provided as a solution to be dropped into the recipient's eye(s), to be applied as liquid drops over a course of treatment, such as, e.g., over the course of many days, several weeks, months, or longer.

In aspects, the average force required to release one or more drops of the compositions described herein from a dropper bottle (a standard bottle common in the art for dispensing liquid in droplet form), by compressing the middle section of the storage body of such a dropper bottle, ranges between ~1.7-~2.8 Kg for release of the first drop, e.g., ~1.7-~2.6, ~1.7-~2.4, ~1.7-~2.2, or ~1.7-~2.0 Kg. In aspects, successive drops can require more tension, such as can require an additional ~20-30% of force for release of the second drop, and, e.g., an additional force of ~24-~50% for release of the third drop.

In aspects, compositions are provided in single-dose or multi-dose packaging.

In aspects, a single-dose package comprises a single-dose of composition within a single-dose administration container. In aspects, a multi-dose package comprises a plurality of single-dose administration containers. In aspects, a multi-dose package comprises a plurality of doses within a single administration container. For example, a multi-dose package can be, e.g., a single dropper bottle comprising sufficient volume of composition to administer the composition multiple times over the course of an administration period, such as (but certainly not limited to) administration of about 1-3x/day over a period of about 1-7 days, ~1 week-~1 month, ~1 month-~3 months, ~3 months-~6 months, or, e.g., ~6 months-~1 year.

In aspects, packaging of compositions is any suitable packaging which effectively provides compositions with a shelf life of at least about 1 month, such as, e.g., ≥~3 weeks, ≥~4 weeks (1 month), ≥~5 weeks, ≥~6 weeks, ≥~7 weeks, ≥~8 weeks (2 months), ≥~9 weeks, ≥~10 weeks, ≥~11 weeks, ≥~12 weeks (3 months), ≥~13 weeks, ≥~14 weeks, ≥~15 weeks, ≥~16 weeks (4 months), or more, such as ≥~5 months, ≥~6 months, ≥~7 months, ≥~8 months, ≥~9 months, ≥~10 months, ≥~11 months, or ≥~12 months (1 year), or even longer, such as, ≥~18 months, ≥~24 months (2 years), ≥~30 months, or, e.g., ≥~36 months (3 years) or longer. The term "shelf life" has been described elsewhere herein. In aspects, shelf life refers to a period of time wherein any API of the composition loses more than about 10%, such as, e.g., ≤~9%, ≤~8%, ≤~7%, ≤~6%, ≤~5%, ≤~4%, ≤~3%, ≤~2%, or, e.g., ≤~1%, of the potency while in storage after manufacturing and prior to use.

Kits (Collections of Compositions and Administration Devices)

In aspects, the invention provides kits comprising one or more bimatoprost and timolol compound compositions described herein and one or more delivery devices for such compounds. In aspects, a kit provided by the invention can comprise a single delivery device comprising a single composition, the composition present in an amount representative of a single dose. In aspects, a kit provided by the invention can comprise a single delivery device comprising a single composition, the composition present in an amount representative of multiple doses, e.g., 2 or more, 3 or more, 5 or more, 10 or more 20 or more, 30 or more, or, e.g., 50 or more doses. In aspects, a kit provided by the invention can comprise a plurality of delivery devices comprising a single composition, the composition present in an amount representative of a single dose. In aspects, a kit provided by the invention can comprise a plurality of delivery devices comprising a single composition, the composition present in an amount representative of a multiple doses, e.g., 2 or more, 3 or more, 5 or more, 10 or more 20 or more, 30 or more, or, e.g., 50 or more doses. In aspects, a kit provided by the invention can comprise multiple compositions in multiple delivery devices, wherein at least one ingredient of at least one composition varies from that of at least one other composition in either presence or amount. In aspects, a kit provided by the invention can comprise multiple compositions in multiple delivery devices, wherein the amount of at least one composition in one delivery device varies from the amount of at least one other composition in at least one other delivery device. In aspects, a dose can be a single drop. In aspects, a dose can be 2 drops. In aspects, a dose can be 3 drops. Typically, a dose is one or two drops, e.g., a single drop.

In aspects, the invention provides a kit wherein compositions are pre-filled in a delivery device, and a kit comprises one or more pre-filled delivery devices and one or more additional components to facilitate administration of the composition(s). For example, in aspects, the invention provides a kit wherein composition(s) are provided in one or more pre-filled containers which facilitate administration of the compositions by drops, such as, e.g., one or more pre-filled dropper bottles as described herein.

In aspects, the invention provides for a kit as described in this section, wherein the kit has a shelf life when stored at about room temperature, such as, e.g., about 25° C.+/-~2° C., for at least about 1 month, e.g., ~2, ~3, ~4, ~5, or at least ~6 months (e.g., 6-36 months).

Stored at Room Temperature

In aspects, compositions provided by the invention, e.g., compositions in final packaged form, such as, e.g., compositions provided as a component of a kit, are stable when stored at standard room temperature, that is, controlled room temperature of about 15° C. to 27° C., e.g., about 25° C.+/-2° C. for a period of at least about 1 month, e.g., ≥~3, ≥~6, ≥~9, ≥~12, ≥~18, ≥~24, ≥~28, ≥~33, or, e.g., ≥~36 months.

REPRESENTATIVE EXPERIMENTS/EMBODIMENTS ("EXAMPLES")

The following detailed exemplary expository descriptions or experiments involving embodiments, applications, or related principles, of or otherwise related to the invention ("Examples") are provided to assist readers in further understanding aspects of the invention or principles related to the invention or practice of aspects of the invention.

Any particular materials, methods, steps, and conditions employed/described in the following Examples, and any results thereof, are merely intended to further illustrate aspects of the invention. These Examples reflect exemplary embodiments of the invention, and the specific methods, findings, principles of such Examples, and the general implications thereof, can be combined with any other part of this disclosure. However, readers should understand that the invention is not limited by these Examples or any part thereof.

Example 1

Table 3 below provides an exemplary formulation (Formulation A), providing a list of ingredients suitable for compositions of the present invention provided in the form of a solution.

TABLE 3

Exemplary Formulation A.
Bimatoprost, Timolol, & Penetration Enhancer (Solution).

| MATERIALS | Qty./mL | % w/v |
|---|---|---|
| Bimatoprost | 0.05-0.2 mg | 0.005-0.02 |
| Timolol Maleate (equiv. to timolol) | 4-8 mg (2.9-5.9 mg) | 0.4-0.8 |
| Solubilizers and penetration enhancers (such as PS-80, TPGS, Cremophor EL, etc.) | 2.5-25 mg | 0.25-2.5 |
| Benzalkonium chloride NF (added as 10% w/v solution) | 0.03-0.07 mg | 0.003-0.007 |
| Sodium chloride USP | 0.5-15 mg | 0.05-1.5 |
| Dibasic sodium phosphate USP (Heptahydrate) | 0.1-5 mg | 0.01-0.5 |
| Citric acid monohydrate USP | 0.05 mg-0.9 mg | 0.005-0.09 |
| Sodium hydroxide NF | q.s. to adjust pH 7.1 to 7.3 | q.s. to adjust pH 7.1 to 7.3 |
| Hydrochloric acid NF | q.s. to adjust pH 7.1 to 7.3 | q.s. to adjust pH 7.1 to 7.3 |
| Water for Injection USP | q.s. to 1 mL | q.s. to 1 mL |

Table 4 below provides an exemplary composition (Composition A), providing a list of ingredients in exemplary amounts according to Formulation A, suitable for compositions of the present invention provided in the form of a solution.

TABLE 4

Exemplary Composition A.
Bimatoprost, Timolol, & Penetration Enhancer (Solution).

| MATERIALS | Qty./mL | % |
|---|---|---|
| Bimatoprost | 0.10 mg | 0.01 |
| Timolol Maleate (equiv. to timolol) | 6.8 mg (5.0 mg) | 0.68 |
| Solubilizers and penetration enhancers (such as PS-80, TPGS, Cremophor EL, etc.) | 10.0 mg | 1 |
| Benzalkonium chloride NF (added as 10% w/v solution) | 0.05 mg | 0.005 |
| Sodium chloride USP | 8.0 mg | 0.8 |
| Dibasic sodium phosphate USP (Heptahydrate) | 2.68 mg | 0.268 |
| Citric acid monohydrate USP | 0.14 mg | 0.014 |
| Sodium hydroxide NF | q.s. to adjust pH 7.1 to 7.3 | q.s. to adjust pH 7.1 to 7.3 |
| Hydrochloric acid NF | q.s. to adjust pH 7.1 to 7.3 | q.s. to adjust pH 7.1 to 7.3 |
| Water for Injection USP | q.s. to 1 mL | q.s. to 1 mL |

Example 2

Table 5 below provides two exemplary formulations (Formulation B and Formulation C), providing a list of ingredients suitable for compositions of the present invention provided in the form of a gel.

TABLE 5

Exemplary Formulation B and Formulation C.
Bimatoprost & Timolol with and without Penetration Enhancer (Gel).

| MATERIALS | Qty./mL | % | Qty./mL | % |
|---|---|---|---|---|
| Bimatoprost | 0.05-0.2 mg | 0.005-0.02 | 0.05-0.2 mg | 0.005-0.02 |
| Timolol Maleate (equiv. to timolol) | 4-8 mg (2.9-5.9 mg) | 0.4-0.8 | 4-8 mg (2.9-5.9 mg) | 0.4-0.8 |
| Solubilizers and penetration enhancers (such as PS-80, TPGS, Cremophor EL, etc.) | — | — | 2.5-25 mg | 0.25-2.5 |
| Tromethamine | 0.5-10 mg | 0.05-1 | 0.5-10 mg | 0.05-1 |
| Benzalkonium chloride NF (added as 10% w/v solution) | 0.03-0.07 mg | 0.003-0.007 | 0.03-0.07 mg | 0.003-0.007 |
| Mannitol | 20-60 mg | 2-6 | 20-60 mg | 2-6 |
| Gellan Gum | 1-10 mg | 0.1-1 | 1-10 mg | 0.1-1 |
| Sodium hydroxide NF | q.s. to adjust pH 6.2 to 7 | q.s. to adjust pH 6.2 to 7 | q.s. to adjust pH 6.2 to 7 | q.s. to adjust pH 6.2 to 7 |
| Hydrochloric acid NF | q.s. to adjust pH 6.2 to 7 | q.s. to adjust pH 6.2 to 7 | q.s. to adjust pH 6.2 to 7 | q.s. to adjust pH 6.2 to 7 |
| Water for Injection USP | q.s. to 1 mL | q.s. to 1 mL | q.s. to 1 mL | q.s. to 1 mL |

Table 6 below provides two exemplary compositions (Composition B and Composition C), providing a list of ingredients in exemplary amounts according to Formulations B and Formulation C, suitable for compositions of the present invention provided in the form of gel.

TABLE 6

Exemplary Composition B and Composition C.
Bimatoprost & Timolol with and without Penetration Enhancer (Gel).

| MATERIALS | Bimatoprost + Timolol (no penetration enhancer) | | Bimatoprost + Timolol (with penetration enhancer) | |
|---|---|---|---|---|
| | Qty./mL | % | Qty./mL | % |
| Bimatoprost | 0.10 mg | 0.01 | 0.10 mg | 0.01 |
| Timolol Maleate (equiv. to timolol) | 6.8 mg (5.0 mg) | 0.068 | 6.8 mg (5.0 mg) | 0.68 |
| Solubilizers and penetration enhancers (such as PS-80, TPGS, Cremophor EL, etc.) | — | — | 10.0 mg | 1 |
| Tromethamine | 1.85 mg | 0.185 | 1.85 mg | 0.185 |
| Benzalkonium chloride NF (added as 10% w/v solution) | 0.05 mg | 0.005 | 0.05 mg | 0.005 |
| Mannitol | 40.5 mg | 4.05 | 40.5 mg | 4.05 |

TABLE 6-continued

Exemplary Composition B and Composition C.
Bimatoprost & Timolol with and without Penetration Enhancer (Gel).

|  | Bimatoprost + Timolol (no penetration enhancer) | | Bimatoprost + Timolol (with penetration enhancer) | |
| --- | --- | --- | --- | --- |
| MATERIALS | Qty./mL | % | Qty./mL | % |
| Gellan Gum | 6.0 mg | 0.6 | 6.0 mg | 0.6 |
| Sodium hydroxide NF | q.s. to adjust pH 6.2 to 7 | q.s. to adjust pH 6.2 to 7 | q.s. to adjust pH 6.2 to 7 | q.s. to adjust pH 6.2 to 7 |
| Hydrochloric acid NF | q.s. to adjust pH 6.2 to 7 | q.s. to adjust pH 6.2 to 7 | q.s. to adjust pH 6.2 to 7 | q.s. to adjust pH 6.2 to 7 |
| Water for Injection USP | q.s. to 1 mL | q.s. to 1 mL | q.s. to 1 mL | q.s. to 1 mL |

Example 3

The following manufacturing process can be used to manufacture a composition according to Formulation A of Table 3, e.g., Composition A, of Table 4 (Example 1).

Part 1. Bulk Solution Manufacturing (100 L):

The manufacturing vessel/reactor vessel is sterilized with about 120 Kg of water for injection (WFI), accomplished by collection of about 120 Kg of WFI in the vessel at a temperature of at least about 70° C.

The WFI is cooled to about 20° C.-about 25° C., such as by circulating the water through a water jacket. While cooling, e.g., simultaneously with cooling, 0.2µ-filtered nitrogen is bubbled through the WFI, with all WFI collected in the manufacturing vessel.

The dissolved oxygen content of the WFI is routinely tested to ensure that the WFI reaches a dissolved oxygen content of no more than 2 ppm.

Nitrogen bubbling is continued throughout bulk solution manufacturing.

About 70 Kg of WFI is transferred into a separate holding vessel. This WFI is used for rinsing, preparation of 0.1N hydrochloric acid (for pH adjustment), and preparation of 0.1N sodium hydroxide solution (for pH adjustment), and for bringing the final composition up to a target final volume.

A suitable stirrer is set to a speed of about 400 rpm± about 100 rpm within the manufacturing vessel containing about 50 Kg of WFI. The mixing speed is adjusted as necessary based on/according to the equipment and batch, e.g., vessel geometry and the stirring dynamics.

The total required quantity of benzalkonium chloride (BKC) solution is added to the manufacturing vessel. The container used to add the BKC is rinsed multiple times, e.g., about 5 times, with approximately 50 mL of WFI each time. The rinses are added to the manufacturing vessel. Stirring is continued for at least about 10 minutes, such as for about 15 to 17 minutes, or for a sufficient time to ensure complete dissolution and composition uniformity.

The total required quantity of solubilizer, penetration enhancer, or compound(s) providing both solubilization and penetration enhancement effect, e.g., polysorbate 80, tocopherol polyethylene glycol succinate (TPGS), polyoxyl castor oil (e.g., polyethoxylated castor oil, such as polyoxyl 35 castor oil), or, e.g., protein/peptide enhancers (e.g., poly-arginine or polyserine) is added to the manufacturing vessel. The container used to add the polysorbate 80 is rinsed multiple times, e.g., about 5 times, with approximately 50 mL of WFI each time. The rinses are added to the manufacturing vessel under stirring. Stirring is continuous from the beginning of the process to the end of the process, unless otherwise indicated.

The total required quantity of bimatoprost compound is added to the manufacturing vessel. The container used to add the bimatoprost compound is rinsed multiple times, e.g., about 3 times, with approximately 25 mL of WFI each time. The rinses are added to the manufacturing vessel. Stirring is continued for at least about 15 minutes, such as at least about 30 minutes, at least about 45 minutes, at least about 60 minutes, or at least about 65 minutes, or for a sufficient time to ensure complete dissolution of the bimatoprost compound and composition uniformity.

The total required quantity of timolol compound is added to the manufacturing vessel. The container used to add the timolol compound is rinsed multiple times, e.g., about 3 times, with approximately 25 mL of WFI each time. The rinses are added to the manufacturing vessel. Stirring is continued for at least about 15 minutes, such as at least about 30 minutes, at least about 45 minutes, at least about 60 minutes, or at least about 65 minutes, or for a sufficient time to ensure complete dissolution of the timolol compound and composition uniformity.

The volume of the composition in the manufacturing vessel is brought up to about 90 L (e.g., about 90 Kg) using previously reserved WFI. The resulting solution is stirred for at least about 15 minutes, such as at least about 20 minutes, at least about 25 minutes, at least about 30 minutes, or, e.g., at least about 35 minutes or for a sufficient time to ensure composition uniformity.

The total required quantity of a first buffer, e.g., dibasic sodium phosphate (heptahydrate), is added to the manufacturing vessel. Stirring is continued for at least about 5 minutes, such as at least about 10 minutes or at least about 15 minutes, or for a sufficient time to ensure complete dissolution of the buffer component/ingredient and composition uniformity. Composition uniformity is ensured by inspecting for visual clarity of the solution.

The total required quantity of a second buffer, e.g., citric acid monohydrate, is added to the manufacturing vessel. Stirring is continued for at least about 5 minutes, such as at least about 10 minutes or at least about 15 minutes, or for a sufficient time to ensure complete dissolution of the buffer component/ingredient and composition uniformity. Composition uniformity can be ensured by inspecting for visual clarity of the solution.

The total required quantity of sodium chloride (e.g., sodium chloride USP) is added to the manufacturing vessel and stirring is continued to ensure its complete dissolution. Composition uniformity can be ensured by inspecting for visual clarity of the solution.

The pH of the bulk solution is checked. If required, the pH of the bulk solution is adjusted to about 7.2 (e.g., to a pH within a range limited to about 6.9-about 7.5, such as, e.g., about 7.1-about 7.3, e.g., about 7.2) using 0.1N sodium hydroxide solution or 0.1N hydrochloric acid solution. The bulk solution is mixed for at least about 3 minutes, such as at least about 5 minutes, at least about 10 minutes, or for a sufficient amount of time to ensure uniformity of the solution after each addition of sodium hydroxide or hydrochloric acid before measuring or repeating the measurement of the pH during pH adjustment.

The final volume of the bulk solution in the manufacturing vessel is brought up to a final volume of about 100 L (e.g., about 100 Kg), using reserved WFJ. The resulting bulk solution is stirred for at least about 10 minutes such as about 15 minutes, at least about 30 minutes, or, e.g., at least about 40 minutes or for a sufficient time to ensure uniformity of the bulk solution. The final bulk solution is checked to confirm that the pH of the solution is about 7.2, e.g., about 6.9-about 7.5, such as, e.g., about 7.1-about 7.3, e.g., about 7.2. The pH of the solution is adjusted, if necessary, with stirring and final pH confirmation repeated, as necessary.

Part 2. Filtration 2.1 Offline Filtration

After completion of the preparation of the bulk solution (e.g., compounding activity), the filtration process is initiated under laminar air flow (LAF).

Prior to initiation of the filtration process, a 0.2 μm capsule or cartridge filter is integrity tested using a water bubble point test against the filter manufacturer's specification. The result should be a pressure of not less than 46 psi under a filtration pressure limit of about 0.8 Kg/cm² to about 1.8 Kg/cm².

Prior to the start of filtration activity, the filtration unit is flushed with about 200 mL to about 220 mL of the bulk solution. The bulk solution is held inside of the filtration unit for about 1 minute, about 1.5 minutes, about 2 minutes, about 2.5 minutes, or, e.g., about 3 minutes during the flush. The bulk solution used for the flush is then discarded. The flushing procedure is repeated two additional times for a total of 3 flushes.

After flushing, filtration of the bulk solution is initiated. The bulk solution is filtered through the pre-sterilized, tested, and flushed 0.2 μm capsule or cartridge filter, e.g., a polyethersulfone (PES) capsule filter. All filtrate is collected in a sterile receiving vessel (filtrate receiving vessel).

Upon completion of filtration, the filtrate within the sterile receiving vessel is overlayed with 0.2 μm-filtered nitrogen.

The receiving vessel is transferred to a sterile storage area and stored under laminar air flow until initiation of the filling activity.

A post-filtration integrity test of the filter is performed using a water bubble point test. The result should be a pressure of not less than 39.2 psi under a filtration pressure limit of about 0.8 Kg/cm² to about 1.8 Kg/cm².

2.2 Online Filtration

Prior to the initiation of filling and capping activity, the bulk solution is filtered through another 0.2μ pre-sterilized capsule or cartridge filter, e.g., a polyethersulfone (PES) capsule filter.

Pre-integrity filter testing is performed using a water bubble point test against the filter manufacturer's specification. The result should be a pressure of not less than 46 psi under a filtration pressure limit of about 0.8 Kg/cm² to about 1.8 Kg/cm². The filter is then connected to the filling line through a pre-sterilized vessel, e.g., buffer tank.

Prior to the initiation of filtration activity, the filter/filtration unit is flushed with about 200 to about 220 mL of the bulk solution. The bulk solution is held within the filtration unit for about 1 minute, such as about 2 minutes, about 2.5 minutes, or, e.g., about 3 minutes during this flushing process and is then discarded. The flushing process is repeated at least two additional times for a total of at least about 3 flushes, with the bulk solution used for flushing discarded after each flush.

After completely discarding the filter flush solution, the entire quantity of remaining bulk solution is filtered into the sterile vessel, e.g., the sterile buffer tank.

The filling activity is then initiated.

Upon the completion of the filling activity, a post-filtration integrity test of the filter is performed using a water bubble point test. The result should be a pressure of not less than 39.2 psi under a filtration pressure limit of about 0.8 Kg/cm² to about 1.8 Kg/cm².

Part 3. Filling and Capping

Suitable sterile containers, such as sterile vials, are each filled to a volume of about 2.6 mL to about 2.8 mL (~2.62 g-~2.82 g), such as about 2.7 mL (about 2.72 g).

After filling, the head space of each vial is flushed with filtered nitrogen, e.g., using a minimum nitrogen flow of about 2 L/min.

The first about 30 vials are collected and identified as the initial system flush.

Checks for proper processing, e.g., proper filling volume and vial sealing, are performed intermittently (e.g., at least 2 times, at least 5 times, at least 10 times, at least 20 times, at least 50 times or more) during any single batch filling procedure. The filling process is stopped, adjusted, or otherwise corrected if filling processes do not meet previously defined standards (e.g., of fill volume, air-tight sealing of vials, etc.). Packaged product identified as not meeting predefined acceptance criteria are rejected.

Example 4

The following manufacturing process can be used to manufacture a composition according to Formulation B or Formulation C of Table 5, e.g., Composition B or Composition C of Table 6 (Example 2).

Part 1. Bulk Solution Manufacturing (100 L)

1.1 Preparation of Polymer Phase Solution

A first (filter no. 1) and a second (filter no. 2) 0.2 μm capsule filter are each integrity-tested using a water bubble point test against the filter manufacturer's specification(s). The result of each test should be a pressure of not less than 46.0 psi under a filtration pressure limit of about 0.8 Kg/cm² to about 1.8 Kg/cm². Upon completion of integrity testing, filters are flushed with nitrogen to remove any residual water from the filter pores.

The outlet of filter no. 2 is connected to the inlet of filter No. 1 using a suitable connection mechanism, such as Pharma 50 silicone tubing of a suitable length, such as about 60 cm. The outlet of filter no. 1 is connected to a diaphragm valve. The inlet of filter no. 2 is connected to a suitable connection mechanism, such as Pharma 50 silicone tubing of suitable length, such as about 2.30 meters. The entire assembly is sterilized using a suitable sterilization method such as autoclaving. During sterilization, e.g., while autoclaving, the diaphragm valve is maintained in an open position. Upon completion of sterilization, e.g., after autoclaving, the diaphragm valve is closed under aseptic conditions. The entire assembly is then connected to an empty manufacturing vessel (e.g., a "reactor vessel").

The manufacturing vessel/reactor vessel is sterilized with about 120 Kg of water for injection (WFJ). This establishes a sterilized "reactor vessel" or "SIP vessel".

About 120 Kg of water for injection (WFI) at a temperature of not less than about 70° C. is collected in a manufacturing vessel, such as, e.g., a stainless-steel (SS) vessel.

The WFI is cooled to about 20° C.-about 25° C., such as by circulating the water through a water jacket. While cooling, e.g., simultaneously with cooling, 0.24μ-filtered nitrogen is bubbled through the WFI, with all WFI collected in the manufacturing vessel.

The dissolved oxygen content of the WFI is routinely tested to ensure that the WFI reaches a dissolved oxygen content of no more than 2 ppm.

Nitrogen bubbling is continued throughout bulk solution manufacturing.

After completion of empty reactor sterilization, about 50 Kg of the 120 Kg of WFI is transferred to a second manufacturing vessel, e.g., a stainless-steel manufacturing vessel, to be used in the preparation of a drug phase and bringing composition(s) up to volume.

While maintaining the temperature of the remaining about 70 Kg WFI in the reactor vessel between about 73° C. and 78° C., a suitable stirrer in the reactor vessel is set to a stirrer speed of about 125 rpm± about 50 rpm. The mixing speed is adjusted as necessary based on/according to the equipment and batch, e.g., vessel geometry and the stirring dynamics during the manufacture of the batch.

The required quantity of gellan gum NF (national formulary) is added to the reactor vessel and stirring is maintained at about 125 rpm± about 50 rpm for at least about 30 minutes, such as about 60 mins, or for a sufficient time to ensure complete dissolution of the gellan gum. The solution is maintained at a temperature of between about 73° C. and about 78° C. during the continuous stirring.

Optionally, the total required quantity of a preservative component, e.g., benzalkonium chloride is added. In aspects, the resulting composition is mixed for a sufficient period of time to ensure that the preservative component constituent(s) are completely dissolved.

After complete dissolution, the solution is cooled to between about 20° C. and about 25° C. under constant stirring. This establishes the "polymer phase".

The polymer phase is sterilized at set temperature of about 122.0° C. for about 20 minutes while constantly stirring at speed of about 125 rpm± about 50 rpm.

Upon completion of sterilization, the polymer phase is cooled to about 25° C. While cooling, when the temperature of the polymer phase reaches about 60° C., the stirring speed is increased to a stirring speed of about 250 rpm±50 rpm.

1.2 Preparation of Drug Phase Solution

About 50 Kg of the reserved, cooled WFI is collected in a suitable manufacturing vessel. A suitable stirrer in the manufacturing vessel is set to a stirring speed of about 300 rpm±50 rpm. The mixing speed is adjusted as necessary based on/according to the equipment and batch, e.g., vessel geometry and the stirring dynamics during the manufacture of the batch.

The total required quantity of solubilizer, penetration enhancer, or compound(s) providing both solubilization and penetration enhancement effect, e.g., polysorbate 80, tocopherol polyethylene glycol succinate (TPGS), polyoxyl castor oil (e.g., polyethoxylated castor oil, such as polyoxyl 35 castor oil), or, e.g., protein/peptide enhancers (e.g., poly-arginine or polyserine) is optionally added to the manufacturing vessel. In certain formulations, such one or more ingredients is absent from the composition (e.g., is/are not added). The container(s) used to add each such ingredient is/are rinsed multiple times, e.g., about 5 times, with approximately 50 mL of WFI each time. The rinses are added to the manufacturing vessel under stirring. Stirring is continuous from the beginning of the process to the end of the process, unless otherwise indicated.

The total required quantity of bimatoprost compound is added to the manufacturing vessel. The container used to add the bimatoprost compound is rinsed multiple times, e.g., about 3 times, with approximately 25 mL of WFI each time. The rinses are added to the manufacturing vessel. Stirring is continued for at least about 15 minutes, such as at least about 30 minutes, at least about 45 minutes, at least about 60 minutes, or at least about 65 minutes, or for a sufficient time to ensure complete dissolution of the bimatoprost compound and composition uniformity.

The total required quantity of timolol compound is added to the manufacturing vessel. The container used to add the timolol compound is rinsed multiple times, e.g., about 3 times, with approximately 25 mL of WFI each time. The rinses are added to the manufacturing vessel. Stirring is continued for at least about 15 minutes, such as at least about 30 minutes, at least about 45 minutes, at least about 60 minutes, or at least about 65 minutes, or for a sufficient time to ensure complete dissolution of the timolol compound and composition uniformity.

The total required quantity of mannitol is added to the solution in the manufacturing vessel. The resulting composition is mixed for a suitable period of time to allow the mannitol to completely dissolve.

Upon the complete dissolution of the mannitol, the total required quantity of tromethamine is added to the solution. The resulting composition is mixed for a sufficient period of time, such as about 10 minutes, to ensure complete dissolution of the tromethamine.

The composition is checked for clarity. Stirring is continued until visual clarity is achieved.

The volume is brought to about 55 L using previously reserved WFJ. The composition is stirred for at least about 10 minutes, e.g., at least about 15 minutes, at least about 20 minutes, or for a sufficient period of time to ensure composition uniformity. This establishes the "drug phase".

An industry standard sampling protocol is used to sample and test the drug phase to ensure that the phase meets pre-established specification(s). Upon acceptance, the drug phase is transferred to the sterilized polymer phase via aseptic filtration (see below).

1.3 Aseptic Filtration of Drug Phase into Sterile Polymer Phase

Aseptic filtration of the drug phase into the sterile polymer phase is performed at a filtration pressure of about 0.8 Kg/cm²-about 1.8 Kg/cm².

Prior to beginning the aseptic filtration, the weight of the drug phase is noted. About 55 Kg of the drug phase (which can be referred to as the "concentrated drug phase") is filtered into the reactor vessel containing the polymer phase through the two sterilized 0.2 μm filters connected in series.

WFI is then passed through the filters a number of times, such as about two times with about 2.5 L of WFI each time, and the filtrate added to the reactor vessel each time to ensure all required drug phase is added into the reactor vessel. The resulting composition is then stirred for about 1 hour at a speed of about 250 rpm± about 50 rpm, or for a sufficient period of time (and at a suitable speed) to ensure composition uniformity.

A post-filtration integrity test of the filter is performed using a water bubble point test. The result should be a pressure of not less than 34.8 psi under a filtration pressure limit of about 0.8 Kg/cm² to about 1.8 Kg/cm².

The pH of the composition is adjusted using one or more pH adjusting agents. The pH of the solution is adjusted by the addition or one or more pH adjusting agents, with the solution sufficiently mixed after each addition such that the composition has a uniform pH prior to (1) sampling for pH, and (2) applying further pH adjustment as needed. Composition pH is adjusted to a pH of about 6.2 to about 7, such as, e.g., ~6.3, ~6.4, ~6.5, ~6.6, ~6.7, ~6.8, or ~6.9, using the pH adjusting agent(s).

Part 2. Filtration

Filtration of the final combined composition (bulk solution) is then performed using a suitable filter such as an 8 μm PP2 MidiCap® filter (Sartorius).

Before initiating filtration activity, a sterilized 8.0 μm polypropylene filter is flushed with about 100 mL to about 120 mL of bulk solution a number of times such as about 3 times. During each flush, the composition is held in the filtration unit for an extended period of time, such as about 2 minutes, prior to discarding each flush. Upon completion of flushing, filtration of the bulk solution is performed with the filtrate collected in a sterile receiving vessel.

Part 3. Filling and Capping

Suitable sterile containers, such as sterile vials, are each filled to a volume of about 2.6 mL to about 2.8 mL (about 2.62 g to about 2.82 g), such as ~2.7 mL (about 2.72 g).

After filling, the head space of each vial is flushed with filtered nitrogen, e.g., using a minimum nitrogen flow of about 2 L/min.

What is claimed is:

1. A pharmaceutically acceptable and ophthalmologically suitable composition for treating an ocular condition in a mammalian eye consisting of (1) 0.01% w/v of a bimatoprost compound; (2) about 0.4% w/v-about 0.8% w/v of a timolol compound; (3) about 0.005%-about 0.007% of benzalkonium chloride; and (4) about 0.25% w/v-about 2.5% w/v of a penetration enhancer component wherein the penetration enhancer component comprises one or more compounds selected from the group consisting of a polyoxyethylene sorbitan fatty acid ester, a tocopheryl polyethylene glycol succinate, a polyoxyl hydrogenated castor oil, a poly-arginine, and a polyserine, wherein the ratio of the benzalkonium chloride to the penetration enhancer component is between about 1: about 35-about 1: about 500; and wherein bimatoprost and timolol are the only active pharmaceutical ingredients present in the composition.

2. The composition of claim 1, wherein the ratio of the benzalkonium chloride to the penetration enhancer component is between about 1: about 100-about 1: about 300.

3. The composition of claim 2, wherein the ratio of the benzalkonium chloride to the penetration enhancer component is between about 1: about 200.

4. The composition of claim 2, wherein the bimatoprost compound is bimatoprost base.

5. The composition of claim 2, wherein the timolol compound is a salt of timolol.

6. The composition of claim 5, wherein the salt of timolol is timolol maleate, and the timolol maleate makes up about 0.68% w/v of the composition.

7. The composition of claim 1, wherein the penetration enhancer component comprises at least one constituent which provides further detectable or significant activity as a solubilizer, a demulcent, or both.

8. The composition of claim 1, wherein the composition is stable when stored at about 25° C.+/−2° C. and about 40%+/−5% relative humidity, about 40° C.+/−2° C. and not more than about 25% relative humidity, or when stored under either condition, for a period of at least about 1 month.

9. The composition of claim 1, wherein the composition is provided as a solution, suspension, ointment, cream, gel, spray, or other dosage form suitable for topical ophthalmic administration.

10. The composition of claim 9, wherein the composition is provided as a solution.

11. A pharmaceutically acceptable and ophthalmologically suitable composition for treating an ocular condition in a mammalian eye consisting of (1) 0.01% w/v of a bimatoprost compound; (2) about 0.4% w/v-about 0.8% w/v of a timolol compound; (3) about 0.005%-about 0.007% of a quaternary ammonium salt benzalkonium chloride; and (4) about 0.25% w/v-about 2.5% w/v of a penetration enhancer component wherein the penetration enhancer component comprises one or more compounds selected from the group consisting of a polyoxyethylene sorbitan fatty acid ester, a tocopheryl polyethylene glycol succinate, a polyoxyl hydrogenated castor oil, a poly-arginine, and a polyserine, wherein the (a) the ratio of the timolol compound to the penetration enhancer component is between about 3.2: about 1 and about 1: about 6.3, (b) the ratio of the bimatoprost compound to the penetration enhancer component is about 1: about 25-about 1: about 250, or (c) both (a) and (b) are true; and wherein bimatoprost and timolol are the only active pharmaceutical ingredients present in the composition.

12. The composition of claim 11, wherein the ratio of the bimatoprost compound to the penetration enhancer component is about 1: about 25-about 1: about 250.

13. The composition of claim 12, wherein the ratio of the bimatoprost compound to the penetration enhancer component is about 1: about 40-about 1: about 200.

14. The composition of claim 13, wherein the ratio of the bimatoprost compound to the penetration enhancer component is about 1: about 100.

15. The composition of claim 11, wherein the ratio of the timolol compound to the penetration enhancer component is between about 3.2: about 1-about 1: about 6.3.

16. The composition of claim 15, wherein ratio of the timolol maleate to the penetration enhancer component is between about 2: about 1-about 1: about 3.

17. The composition of claim 16, wherein the ratio of the timolol maleate to the penetration enhancer component is about 1: about 1.5.

18. The composition of claim 1, wherein the bimatoprost compound is bimatoprost base and the timolol compound is timolol maleate, and the timolol maleate makes up about 0.68% w/v of the composition.

19. The composition of claim 18, wherein the composition is provided as a solution for topical ophthalmic administration.

* * * * *